United States Patent
Broenstrup et al.

(10) Patent No.: US 9,422,566 B2
(45) Date of Patent: Aug. 23, 2016

(54) GENE CLUSTER FOR BIOSYNTHESIS OF GRISELIMYCIN AND METHYLGRISELIMYCIN

(71) Applicant: SANOFI, Paris (FR)

(72) Inventors: Mark Broenstrup, Frankfurt (DE); Claudia Koenig, Frankfurt (DE); Luigi Toti, Frankfurt (DE); Joachim Wink, Frankfurt (DE); Wulf Leuschner, Frankfurt (DE); Johann Gassenhuber, Frankfurt (DE); Rolf Müller, Saarbrücken (DE); Silke Wenzel, Saarbrücken (DE); Tina Binz, Zürich (CH); Carsten Volz, Saarbrücken (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/351,255

(22) PCT Filed: Oct. 11, 2012

(86) PCT No.: PCT/EP2012/070213
§ 371 (c)(1),
(2) Date: Apr. 11, 2014

(87) PCT Pub. No.: WO2013/053857
PCT Pub. Date: Apr. 18, 2013

(65) Prior Publication Data
US 2014/0295457 A1    Oct. 2, 2014

(30) Foreign Application Priority Data

Oct. 12, 2011 (EP) ..................................... 11306321
Oct. 28, 2011 (EP) ..................................... 11306400

(51) Int. Cl.
| | |
|---|---|
| *G01N 33/573* | (2006.01) |
| *C12N 15/52* | (2006.01) |
| *C12R 1/465* | (2006.01) |
| *C12P 13/24* | (2006.01) |
| *C07K 14/36* | (2006.01) |
| *C07K 7/64* | (2006.01) |
| *C07K 16/40* | (2006.01) |
| *C12N 9/00* | (2006.01) |
| *C12Q 1/18* | (2006.01) |
| *C12Q 1/25* | (2006.01) |

(52) U.S. Cl.
CPC . *C12N 15/52* (2013.01); *C07K 7/64* (2013.01); *C07K 14/36* (2013.01); *C07K 16/40* (2013.01); *C12N 9/93* (2013.01); *C12P 13/24* (2013.01); *C12Q 1/18* (2013.01); *C12Q 1/25* (2013.01); *C12R 1/465* (2013.01)

(58) Field of Classification Search
None
See application file for complete search history.

(56) References Cited

U.S. PATENT DOCUMENTS 3,857,937 A    12/1974 Mancy et al.

FOREIGN PATENT DOCUMENTS

| WO | 00/24775 A1 | 5/2000 |
| WO | 2013053857 A2 | 4/2013 |

OTHER PUBLICATIONS

Altschul S. F. et al., "Gapped Blast and PSI-BLAST: A New Generation of Protein Database Search Programs" Nucleic Acids Res., 1997, 25, 3389-3402.
Barry S. M. and Challis G. L., "Recent advances in siderophore biosynthesis" Curr. Opin. Chem. Biol., 2009, 13, 205-215.
Becker D. et al., "Two-Component flavin-dependent pyrrole-2-carboxylate monooxygenase from *Rhodococcus Ap*." Eur. J. Biochem. 1997, 249, 739-747.
Bibb, M. J. et al., "Cloning and analysis of the promoter region of the erythromycin resistance gene (ermE) of *Streptomyces erythraeus*" Gene 1985, 38, 215-266.
Bibb, M. J. et al., "The mRNA for the 23S rRNA methylase encoded by the ermE gene of *Saccharopolyspora erythraea* is translated in the absence of a conventional ribosome-binding site" Molecular Microbiology 1994, 14, 533-545.
Bierman M. et al., "Plasmid cloning vectors for the conjugal transfer of DNA from *Escherichia coli* to *Streptomyces spp*." Gene 1992, 116, 43-49.
Bignell Dawn R D et al.: "*Streptomyces scabies* 87-22 Contains a Coronafacic Acid-Like Biosynthetic Cluster That Contributes to Plant-Microbe Interactions", Molecular Plant-Microbe Interactions, American Phytopathological Society, United States, vol. 23, No. 2, Feb. 1, 2010, pp. 161-175.
Challis G. L et al., "Predictive, structure-based model of amino acid recognition by nonribosomal peptide synthetase adenylation domains" Chem. Biol. 2000, 7, 211-224.
Fernandez-Moreno M. A. et al., "The act Cluster Contains Regulatory and Antibiotic Export Genes, Direct Targets for Translational Control by the b/dA tRNA Gene of Streptomyces" Cell, 1991, 66, 769-780.
Finking R. and Marahiel M. A., "Biosynthesis of Nonribosomal Peptides" Annu. Rev. Microbiol., 2004; 58, 453-488.
Gaitatzis N. et al., "In vitro reconstitution of the myxochelin biosynthetic machinery of *Stigmatella aurantiaca* Sga15: Biochemical characterization of a reductive release mechanism from nonribosomal peptide synthetases" Proc. Natl. Acad. Sci. USA, 2001, 98, 11136-11141.
Gust B et al.,"PCR-targeted Streptomyces gene replacement identifies a protein domain needed for biosynthesis of the sesquiterpene soil odor geosmin" Proc. Natl. Acad. Sci. USA, 2003, 100, 1541-1546.

(Continued)

*Primary Examiner* — J. Hines
*Assistant Examiner* — Khatol Shannan Shah
(74) *Attorney, Agent, or Firm* — Lathrop & Gage LLP; James H. Velema

(57) ABSTRACT

The present invention refers to the gene cluster and genes comprised by the gene cluster which are involved in the biosynthesis of griselimycin and methylgriselimycin and to the use of the gene cluster, genes comprised thereby and proteins encoded thereby for the production of antibiotic agents.

26 Claims, 13 Drawing Sheets

(56) References Cited

OTHER PUBLICATIONS

Hahn M. and Stachelhaus T., "Selective interaction between nonribosomal peptide synthetases is facilitated by short communication-mediating domains" Proc. Natl. Acad. Sci. USA, 2004, 101, 15585-15590; Epub Oct. 21, 2004.
Herai S. et al., "Hyper-inducible expression system for streptomycetes" Proc. Natl. Acad. Sci. USA 2004, 101, 14031-14035.
Hoffmann D. et al., "Sequence analysis and biochemical characterization of the nostopeptolide A biosynthetic gene cluster from *Nostoc sp.* GSV224" Gene, 2003, 311, 171-180.
Katz E et al. "Novel actinomycins formed by biosynthetic incorporation of cis-and-trans-4-methylproline" Antimicrobial Agents and Chemotherapy. American Society for Microbiology. Washington. DC. US. vol. 11. No. 6. Jun. 1, 1977, pp. 1056-1063.
Li W. et al., "Biosynthesis of Sibiromycin, a Potent Antitumor Antibiotic" Appl. Environ. Microbiol., 2009, 75, 2869-2878.
Luesch H. et al., "Biosynthesis of 4-Methylproline in Cyanobacteria: Cloning of nosE and nosF Genes and Biochemical Characterization of the Encoded Dehydrogenase and Reductase Activities" J. Org. Chem., 2003, 68, 83-91.
Marahiel M. A., "Working outside the protein-synthesis rules: insights into non-ribosomal peptide synthesis" J. Pept. Sci., 2009, 15, 799-807.
Mervyn J. et al., "The mRNA for the 23S rRNA methylase encoded by the ermE gene of *Saccaropolyspora arythraea* is translated in the absence of a conventional ribosome-binding site" Molecular Microbiology, 1994, 14(3), 533-545.
Mootz H. D. and Marahiel M. k, The Tyrocidine Biosynthesis Operon of *Bacillus brevis*: Complete Nucleotide Sequence and Biochemical Characterization of Functional Internal Adenylation Domains J. Bacteriol., 1997, 179, 6843-6850.
Muller C. et al., "Sequencing and Analysis of the Biosynthetic Gene Cluster of the Lipopeptide Antibiotic Friulimicin in *Actinoplanes friuliensis*" Antimicrob. Agents Chemother., 2007, 51, 1028-1037.
Murakami, T. et al., "Thiostrepton-Induced Gene Expression in *Streptomyces lividans*" J. Bacteriol., 1989, 171, 1459-1466.
PCT/EP2012/070213 International Search Report and Written Opinion, mailed Jun. 20, 2013, 14 pages.
PCT/EP2012/070213 International Preliminary Report on Patentability, dated Apr. 15, 2014, 9 pages.
Peschke U. et al., "Molecular characterization of the lincomycin-production gene cluster of *Streptomyces lincolnensis* 78-11" Mol. Microbiol., 1995, 16, 1137-1156.
Takano, E et al., "Construction of the thiostrepton-inducible, high-copy-number expression vectors for use in *Streptomyces spp.*" Gene, 1995, 166, 133-137.
Tao, M. et al. "The tallysomycin biosynthetic gene cluster from *Streptoalloteichus hindustanus* E465-94 ATCC 31158 unveiling new insights into the biosynthesis of bleomycin family of antitumor antibiotics", Molecular Biosystems, Royal Society of Chemistry, GB, vol. 3, No. 1, Jan. 1, 2007; pp. 60-74.
Terlain B et al. "Structure of Griselimycin, Polypeptide Antibiotic Extracted From Streptomyces Cultures. 3. Products Related to Griselimycin", Bulletin de la Societe Chimique de France, Societe Francaise de Chimie. Paris France, vol. 6, Jun. 1971; pp. 2363-2365.
Thomas M. G. et al., "Conversion of L-Proline to Pyrrolyl-2-Carboxyl-S-PCP during Undecylprodigiosin and Pyoluteorin Biosynthesis" Chem. Biol. 2002, 9, 171-184.
Toyohara et al: 11 Aspects Of The Antituberculous Activity of 27753-RP. A New Semisynthetic Derivative of Griselimycine. Annales de L'institut Pasteur/Microbiologie. Paris. FR. vol. 138. No. 6. Nov. 1, 1987; pp. 737-744.
Nehmeier U. F., "New multifunctional *Escherichia coli-streptomyces* shuttle vectors allowing blue-white screening on XGal plates" Gene, 1995, 165, 149-150.
Yin X. et al., "VioC is a Non-Heme Iron a-Ketoglutarate-Dependent Oxygenase that Catalyzes the Formation of 3S-Hydroxy-I-Arginine during Viomycin Biosynthesis" Chem. Biol. Chem. 2004, 5, 1274-1277.

SEQUENCE LISTING

```
<160> NUMBER OF SEQ ID NOS: 31

<210> SEQ ID NO 1
<211> LENGTH: 66868
<212> TYPE: DNA
<213> ORGANISM: Streptomyces DSM 22643
<220> FEATURE:
<221> NAME/KEY: misc_feature
<222> LOCATION: (837)..(2075)
<223> OTHER INFORMATION: ORF 1, positive strandedness
<220> FEATURE:
<221> NAME/KEY: misc_feature
<222> LOCATION: (2185)..(2625)
<223> OTHER INFORMATION: ORF 2, positive strandedness
<220> FEATURE:
<221> NAME/KEY: misc_feature
<222> LOCATION: (2625)..(2819)
<223> OTHER INFORMATION: ORF 3, positive strandedness
<220> FEATURE:
<221> NAME/KEY: misc_feature
<222> LOCATION: (3033)..(4037)
<223> OTHER INFORMATION: ORF 4, positive strandedness
<220> FEATURE:
<221> NAME/KEY: misc_feature
<222> LOCATION: (4110)..(5630)
<223> OTHER INFORMATION: ORF 5, positive strandedness
<220> FEATURE:
<221> NAME/KEY: misc_feature
<222> LOCATION: (5627)..(7066)
<223> OTHER INFORMATION: ORF 6, positive strandedness
<220> FEATURE:
<221> NAME/KEY: misc_feature
<222> LOCATION: (7240)..(8133)
<223> OTHER INFORMATION: ORF 7, positive strandedness
<220> FEATURE:
<221> NAME/KEY: misc_feature
<222> LOCATION: (31885)..(8501)
<223> OTHER INFORMATION: ORF 8, negative strandedness
<220> FEATURE:
<221> NAME/KEY: misc_feature
<222> LOCATION: (33102)..(32770)
<223> OTHER INFORMATION: ORF 9, negative strandedness
<220> FEATURE:
<221> NAME/KEY: misc_feature
<222> LOCATION: (33187)..(33726)
<223> OTHER INFORMATION: ORF 10, positive strandedness
<220> FEATURE:
<221> NAME/KEY: misc_feature
<222> LOCATION: (34127)..(33567)
<223> OTHER INFORMATION: ORF 11, negative strandedness
<220> FEATURE:
<221> NAME/KEY: misc_feature
<222> LOCATION: (36172)..(37314)
<223> OTHER INFORMATION: ORF 13, positive strandedness
<220> FEATURE:
<221> NAME/KEY: misc_feature
<222> LOCATION: (36300)..(34648)
<223> OTHER INFORMATION: ORF 12, negative strandedness
<220> FEATURE:
<221> NAME/KEY: misc_feature
<222> LOCATION: (39032)..(37746)
<223> OTHER INFORMATION: ORF 14, negative strandedness
```

```
<220> FEATURE:
<221> NAME/KEY: misc_feature
<222> LOCATION: (39643)..(52149)
<223> OTHER INFORMATION: ORF 15, positive strandedness
<220> FEATURE:
<221> NAME/KEY: misc_feature
<222> LOCATION: (52146)..(56120)
<223> OTHER INFORMATION: ORF 16, positive strandedness
<220> FEATURE:
<221> NAME/KEY: misc_feature
<222> LOCATION: (56117)..(56335)
<223> OTHER INFORMATION: ORF 17, positive strandedness
<220> FEATURE:
<221> NAME/KEY: misc_feature
<222> LOCATION: (56434)..(57246)
<223> OTHER INFORMATION: ORF 18, positive strandedness
<220> FEATURE:
<221> NAME/KEY: misc_feature
<222> LOCATION: (57243)..(58418)
<223> OTHER INFORMATION: ORF 19, positive strandedness
<220> FEATURE:
<221> NAME/KEY: misc_feature
<222> LOCATION: (58445)..(59245)
<223> OTHER INFORMATION: ORF 20, positive strandedness
<220> FEATURE:
<221> NAME/KEY: misc_feature
<222> LOCATION: (59242)..(60141)
<223> OTHER INFORMATION: ORF 21, positive strandedness
<220> FEATURE:
<221> NAME/KEY: misc_feature
<222> LOCATION: (61680)..(61144)
<223> OTHER INFORMATION: ORF 22, negative strandedness
<220> FEATURE:
<221> NAME/KEY: misc_feature
<222> LOCATION: (62170)..(62820)
<223> OTHER INFORMATION: ORF 23, positive strandedness
<220> FEATURE:
<221> NAME/KEY: misc_feature
<222> LOCATION: (62824)..(63939)
<223> OTHER INFORMATION: ORF 24, positive strandedness
<220> FEATURE:
<221> NAME/KEY: misc_feature
<222> LOCATION: (63969)..(65165)
<223> OTHER INFORMATION: ORF 25, positive strandedness
<220> FEATURE:
<221> NAME/KEY: misc_feature
<222> LOCATION: (66108)..(65206)
<223> OTHER INFORMATION: ORF 26, negative strandedness

<400> SEQUENCE: 1
tgccccacct caacgctgtt gtgtgctggt gcctccgtac ggctatggga atgacgctat      60
gtcacatagc ttgtatgaca cgggtggttg accgccagca agcggtgcgt acgtggccct     120
ccgagtagca ggatgcacca acggccgacc ggcatcagct ttggaagagg aattttcgac     180
ggtccaggct cagctgcgag tgttcaccac tgccatggtg cccaaacggg gtggctcgct     240
gcgaggtgtg ccgctgtggt cggcggctgc gatgctccaa ccgacgatgt gctgctccgc     300
ctccccggtg aggaagtgcg gtgggttcat cccgtggagc cgcggttctc ggcgatcagg     360
ggactctggt ggtgttcttc cgaggttcgc aacaacgcga gaggccccga tcaaggtcag     420
gcaggttcca tgcggaggcg gcgcccgcag cgagaggcac tccttctggc cagtatgtct     480
gtgaccggcg gaggcggtgg gattcgacca acgggaacgc ttccacgtcc ttagggcctt     540
ccggcgagtg caggattcgc gcggacaatc tgtccgtagg tacttccacg cccacctctt     600
gactggtggg cgatgacgct actcactctg cgcccgcttc gctacgacat gcctgcttc      660 ggccgtgcgg tcacaggtcc aggagggaac aacaaggtgc ctgtggcccg tgctgtagat     720
ccacctcgtg ggcgcgggc catcgactct gttaacagtt ggcgaccaag ggcgcaggct      780
tggacattat ccgtactctg atccaagtgc ttcatcgcga agggacaggt ccaccgatga     840
```

-continued

```
gtgaaaacct gacgctggga gaccgtctcc gtatcgctcg taggacacgg aaactgtctg    900
ccgcccaact ggcacagaag gtcgcggtct ccccgagcta cgtgcagaag ttggagtcgg    960
gcgcgcgcaa ggcttcaccc tcgttggtcc tggcgctcgc caaggcgctg cgcttcggtc   1020
ccgaggtcct gaccggccag ccgtactacg gtgagccgga agcggaggac ggcgtccacg   1080
ccgtcatacc cgagctccgt cgcctcctgc tctgctacga cagccccgac gacctggaga   1140
tcgctccgcg ggcgcttccc gtgctcgcct cggaggtcga ccaggtggcg ccctacgcc    1200
gcgacgcccg ctacgccccg atgggcccgc tgctgccgcc gatcatcacc gaactgaccc   1260
acgtcgccct cggcgggaac aacgcgacc ggggcaaggc gttctggcac ctggcacgcg    1320
cctatcgcgc cgtgaactcc ctggcccaca agatgggcca ccacgacctg tcgaacacgg   1380
ctctggagcg cgtccgttgg gcggccgacc gctccggcga cccgctgatg cagttcacgg   1440
ccggctacct cgtcgcaggg gcgatgctgc gccaaggcgc gtactcgccg gcccgccgca   1500
agctccttgg gctgcggacc gagttggagc ggttccagcc ggagcactcc ttcacggagg   1560
acgcgctcgc ggtcgacggc gcgcttctgc tgaagctggg ggttctcgaa gcccgcgaga   1620
acaactccga tcgcgccgac gcgtacctgc gggaggcgga gcaggtcgcg accatggcag   1680
gcaaccgtga ctccctcgca tacgagatgt cgttcgggcc gacgaacatc cgcatccatg   1740
aggtgcacgc gatgatcgac acgggtgaca ccgagcaggc cctcgcccgc ctcgtcgaat   1800
ggtctccggt ctccggcggc gagtgggcgc cgcccagtac gaccgtcggc gagcggtcga   1860
gccaccactt catcgacgtg gcgtccgcga agctcgcaga gggcgaccgg acggtgcct    1920
tcgcggacct caagcgcgca cggaaggtcg cgcccaacca cacgcgattc cacccgtccg   1980
ttcgcgagac cactgcggca ctgctcagga tggatgcaca ccctccaac gagctgtctg    2040
cttttggag ttggacgggc attagcacaa cctgagccct tgtcaagggc tttggcgatc    2100
ggagcccacg gacagactgt ccgtgcagga caccttgctg aatggaatgg tctcttcaca   2160
cgcagtggtg aggaggcctt ttccatgtcc gacgacaatc ccgcagctcg cgcgaacccg   2220
ccgcgctgga tgcccatcgg cgaggagccc gagctgtgct ccgcggggga gtggtgggac   2280
gccgtacgcg ccgtagaggc cgtgggccgg cgcgcgatcg agatcctcgg cgagggtgac   2340
gaaccggtcg gcccggtgat cctggaccac ggaggcccgg agcctcggct gtacttcctg   2400
gttcccgtgg gtaccgcggc tcgctgggag gagccgggga ccgtagcgct ggggcagaag   2460
tgccacgtcg tcgtgccgtc cgcggagagc acgacgcctc cggggatgca ctggcacgtc   2520
tttccccagg gtccgcgatc gctgacgcga cctgacgcgc tgcgccgcgc gctgagccag   2580
gctcgccggg agcggcgagg gcccgcagag gaagcagcct gctgatggcc ttgagcatct   2640
ccctcgtgct ggtactcggg atcgtcgtgg tgctcctggt ccgaagcaaa gccgtgaaac   2700
ccggacccgc gatcgtctgc gtgcttttcg ggttcttcct ggcgagcacg tccatcgccc   2760
cgaacatcaa ccggttcgtg accggcgtcg ccgacatgat cggacagatt agcttctagg   2820
cggcgcgacg cggcatccga atccccttta cctgccaggc cggcggtcca ccccgatcac   2880
ttcgcggccc cgcaccccc aacttgcctg aggcccctga tgacattcat gttcagctcg    2940
gagagcacat ccccccgtac agtgcgcgcg catcggacga acggcccccga tcccgttcgc   3000
cggcggcgcc tgatccgcgc cgagggactc tgatgcgtct cgtctaccac ccggctggcc   3060
atgacgacga cctacgtacg gccctggtcg aactgcaggc ggggcgttgg aagtcggcgc   3120
gggggctgct ctgggagacg ggcacgcact ggccgttgcg aacgtcacgc actcagttgc   3180
tggccgtggc agccgcccga tcagacgtgg tcgacgtctg gctcgtcgag gagccggaca   3240
```

```
gctacgacgc gcagctgatg gctgttcgtg tagccgtcga gagagcgctg cgtgctcaac    3300
gtcaacaaca tcctcggacc ttggagttcg agacgagggc gcgacgtgcc gcgctcctgg    3360
cagctcgtcg tgcgccgcac gatcccgtgc cgtgggtgtg cctcgttgcg ctggcgcaga    3420
tcgacacgca gcaactgcgt caggaacaca ggatgaggcc caacgagccg atgctgccca    3480
gcggtccgtg ggggttgttg tacgaggtca accagcgtga tccgtacaac cgcgaggcct    3540
accaccgtgt gctgcagttc ctgctcgccc ttgaggggcc gtgggcgct tctttggcgg     3600
cggtcttcga cttcggccga tccgtggcct cgcagcgtcc cgtcggatcg cctctgctgc    3660
ttctgccggc gtacgcacag atcgagcagc gtcggcaatc gcgcgccgat ccactgtggc    3720
ggcggcagtg ggcgcaggag tcgacactcg actacacact ggccgccttt cacgactggt    3780
tccacaaggc gcccgtcggg cagcactcgg tggccgatct gaacctcctg gcctacgcgt    3840
tgtgggcagg agcccagtac ctggaggccg ccgaggtgtt cgaggtgatg ggcccgtacg    3900
cggcccgtga gccgtgggcg tcggtgcacg aggggggccgc agggccggac cccggcgagg    3960
cactgctcct tcgggcgcgc gccgaatccc tctcgtacgc ccgtaaccat aggccgcgcg    4020
ccgggccgca cctgtgatcg gcatccgcca gcagccaagc taattggcat gaacctgtcc    4080
agatcgtctt gagttttgga ggctgacccg tgtctcgttt gagtccgaac catcgcgcga    4140
cgtcccggaa gcccgatgac gcgtacctgc gggagctggg ctacgagccc gtgctgaccc    4200
ggcgcatggg gccgttcggg aacttcgcga tttccttcag cgtcatcagt gtcttgtccg    4260
gctgcatgac cttgtacggc ttcggcctga acactggcgg cccgtcggtg atgctgtggg    4320
gctggctgat cgtcggcgcc atggtgacgt tcatcggcgc cgcactcgcc gaggtgacct    4380
ccgcctatcc gacctccgga gccctgtact accaggcaga gcagctcggc gggcggaagt    4440
ggggctggta cacaggctgg ctcaacttgt tgggcctgct cggcgcgatc gccggcatcg    4500
actacgggc cgcgctgttc acgggcgccc tgttaaacct gcagtggggc ttcgagccga     4560
cgccgggcgg gaccatggtg atcttcctgt gcatcctcgc cctgaacctg ttcggggtcc    4620
ggctggtcag cattctcaac agcatcagcg tctggtggca cctcggcggc gtcacggtga    4680
tcgttgggc actggcgatc gtgccctctc atcaccagtc cgcagacttc gtgttcggcg    4740
agttcgtcaa caacaccggc tggtccagcc ccttgtacgt ggcagtgctc ggtctgctgc    4800
tggcccagta cacgttctgc ggttacgacg cctccgcgca cctgtcggag gagaccaccg    4860
acgcccaggt ctccgcatcc cgcggcatca tccacgcgat cgggtggtcg tggctggccg    4920
ggttcgtcct gctggcaggg ctcacgttcg cgatccagga ctacgcgggc accgtgggca    4980
ccgcgacggg ggtgccgccg gcgcagatct tcctggatgc tctgggcgtg gcggggcga    5040
aggcactgct cctggtggtg atcatcgcgc agttgtgctg tggcaacgcc gagaccgccg    5100
cggccagccg gatggtgttc gcgttctcgc gcgacgggc gctgccgggc tcgcacctgt    5160
ggcgtcaggt tgaccgacgc actggcaccc cgcgcatggc cgtgctgctg gcggtcgtgt    5220
gcgccgccgt gcttgccctg ccgagcctgt acagccccgt cgcgtacgcg gcgatcacca    5280
gcatcaacgt ggtcggcatc accccggcct acgcgatccc gatctacttg cgcatcaaga    5340
accatgatcg cttccggccc ggcccttgga acctcggcaa ctggggtgtg gccgtcggca    5400
cgatcgccgt tgtctgggtg gtgttcgtga cggtgctgtt ctgtctgccg cagacacgcc    5460
ccgcggaagg cggcctcgtg tccgtggaga ccttcaacta cgcgccgatc gctctgctcg    5520
tcgtcctggt ccttgcctgg gggtggtggc ggaagcaggg cagctcctat gaagtgccgg    5580
```

```
cccagaactt cgaccgctcg acggctacgt acgaagacga ggtcgtgtga tgacgagaac    5640
cacgaccggc aacggcaccg tggcccgatt ggccgccgca cctggccccg agcagggcgg    5700
gcgctccggg aagggcatct ccctgtccga cctgcggaac ctcgtaaagg cgggtgcgat    5760
cgacacagtg ttgctcgccg tccctgacct gcagggagg ctgaagggga agcgttacga    5820
cgccaaccac ttcctcaagc gcgtcgcgca tgacggcgcc gaggtgtgcg cctacgtcct    5880
ggcaaccgac gtcgacatga gccggcgga cggcttcgcc ctgacctcgt gggagaccgg    5940
ctaccaggac ctgtccgtgc aaccggccct gtcgaccctg tgcgtcgtgc cgtggctgcc    6000
gcgcaccgtt gccgtgctcg gcgatgcggt gcaccacgac gggacgctga tcgacatcgc    6060
gccccgccag atcctcctcc agcagttgac ccgactgtcg cggcacgggc tgcatcccaa    6120
ggtggggatc gagaccgagt tcgtcctcta aagggcacg tacgcggacg cggaacaggc    6180
tggctatcag ggtctacggc cgttgacgac ggagaacctg gactacgccc tcgaccacga    6240
ccccgtgtct gaccggtact tgcgccgtct tcagcgggcg ctcgccgggg cggggatgcc    6300
cgtggaagcg atcaagaccg aagcaggccc cggccaggtc gaggtgacct tcccgtacgg    6360
tggtgctctc accgcctgcg accggcaccc gctcttcaag cacgccgtgc gcaccctggg    6420
ctcgcgagcc ggtctggcac ccacgttcat ggcagcccg gagaccggcc gagccaatgg    6480
cctgcacctg cacgtgtcgc tgtggtcgaa ggccatcagc caactccacg agcccggcac    6540
cgagcacgaa ctgtcccagg tcggtcagca cgccatcgcg ggtctgctcg ccggcctgcc    6600
cgagctgggc ccgttctacg cacccagcgt caactcctac aagcggttca cgcccggctc    6660
cttcgcgccg accacgttca cctggggccg cgacaaccgc acctgcgccg tccgcgtcgt    6720
cggccgcggc gaagggctgc acctggagat ccgtgtgccg ggtgcggacg ccaatccgta    6780
tctggcgctg tcggcggtgc tggccgccat ggaccacggt ctggaacgga agcccgccct    6840
tggtcccgaa gcgaccggca acgcctaccg cgcgagtgga acagaagccc cagtgccatc    6900
caccctcggc ttggccctga ccgtattcca ggacagcgcg ctcgcgcggc aggccttcgg    6960
caccgaggtg gtcgagcact acgcccgcct cgccgggctc gaactcgccc acgacgagcg    7020
cctcgtcacc gatgccgagc gtcagcggtg gctggcccgt gcctgaccgg tccgcttccc    7080
aggagggaac tatcgccgtg agcgtccgca gatgaccagc tcaggccgca ttgtcagtgg    7140
cccttggcaa gctacccacc cacgacagga cactgagcgc gtccgatccg tcacccatcg    7200
tggcgtggtc gggcggccaa gcgagcggaa gggcgccctg tgaccgacat gcccagtgcg    7260
ctccaccaac tggtggagtc ggtgaccgac atgtacgagg tggtcgccga gcacgcccgg    7320
cccggagcca tccggccttc cgtctgggag gtcaacggcc cggcggcca aggtggttc    7380
gggaaggttc acgcgggccc gaagctccac cggcgcgagg tgacggcgta ccagaagtgg    7440
accgtggccc tgcgcgcgga ccatgcaccc gaactggtcg ccgcggacac gctgacgcgc    7500
accgttctgg tcaccgccgt gcccggacac ggtctcgaca cgctgcgcct gcccgccgag    7560
caggaacatg cggcttacgt ccaggccggc gaactgctcg cccggttcca caccgcggca    7620
gccgacgagc cgatgccgga aacggccgat gaggcatggg acgaggcggt cgcccgattg    7680
ctggaccgta cggcgacgca cgcgtcggaa acgatctcg cgttggtgcg cacgctggcg    7740
aaggaggctc ctccacgcct gccccggta tcccagcacg gcgactacat gcccaagaac    7800
tggatgtggg acgagacaga gcagcgccta cgggtcatcg acttcgaacg ggccgaactc    7860
cggacccccg cctaccggga cctgagtcgg ctgcgctacc ggatcctgtg ccaccgcccc    7920
gacctcgacg ccgccttcca ccacggatac ggccgtcccc tcaccgagga ggaacagatc    7980
```

```
gcgtgccggg cctacggggc gcttgatgcc ctggactccc tggactgggg gatcaagcac    8040
cgcgacatcg gactggtcga cgaggcgcag accatgctgg agaacctgcg ccgggagacc    8100
ggcaagaggg tgtggggcgg gtggcgcgcg tgaacgcctt cgccgtcctc acgacccgcc    8160
gtccgtccgt acacggcggc gacggaaaag ccgaaggaca tgcgctgccg caataaagcg    8220
actcgcatca gccgatgggg ccgaccaacg atcgaggtca aggtcctcca gggagcggcc    8280
acggtctccg agtcgaatca cctgccgatc gtcccacaga cctcaaacgc ggcctgacgc    8340
ggagcatgcg ggtgaagcct ccagtaaggc acatcctgga ggcttcacgg ggcaccgatc    8400
ggatgtcggt cccggactcc acctacggtt tgagcgggct tgaatggcgc tcacatcaac    8460
ggattcagcc cgccgagtgc cggttaccca aagggtgacg tcacgagtct cccccggacc    8520
acttgttgag gttgtcaaga agcttcatac gttcctgctg ggtcagcacc tcgatacgtc    8580
gcagacgctt gtcaggattc gcaatcacct ccctcagtac gcgcagtagg cgctcagtca    8640
gcttttctac tgtggccaca ctgaaaagag acgagtcata ctcaattact ccgttaattc    8700
cccgtgctga attattctcg gcgcgatact cgctgaaatt gaagaacagg tcgaacttcg    8760
cggtctgcgt gtgagtggtc tcaaagcgtg cttgcaggcc tggaagtttg aactgccctt    8820
cgggggtgtt ttggagggcg agcatgactt ggaagagggg gtggtgggcg agggagcgtt    8880
cggggttgag gatttcgacg aggtgttcga aggggacgtc ctggtgggcg taggcggcca    8940
ggtcggtctc gcgtacccgg gccaggagtt cacggaaggt ggggttgccg gaagtatccg    9000
tgcgcaggac gagggtgttg acgaagaacc cgaccaggtc gtcgagggcc tcgtcggtgc    9060
ggccggcgat cgggctgccc aggggatgt cgtcccccgc acccagacgg ctcatcaacg    9120
ccgccaagcc ggcctgcagc accatgaaca cggtcgtacc ggtggaacgt gccaggtcta    9180
tcaggccttg gtggagttcg gcgtcccatt tgaagtacag ggagtcgcct tggtaggtgg    9240
ctgtggcggg gcggggccgg tcggtgggca gggtgacctg ttcgggcagg ccggtgaggg    9300
tggtgcgcca gtactccagc tgccgggcga tcaggctgcc cgtgtcggag tggtcgccga    9360
ggagatcgtt ctgccagagg gtgtagtccg cgtactgcac cggcagcgcc gaccagcccg    9420
gcgtgcggcc gtcggcccgg gccgcatacg ccaccgtcag gtcacggaac aagggggaca    9480
gtgaccagcc gtctcctgcg atgtggtgca cgacgagcac cagcacgtgc tcctcggggg    9540
cgagtgcgaa cagccacgcc cgcactggca actccgcgga gagatcgaag gcatactgcg    9600
atgctgccga gaccgcttcg gccagcccct cctcgctcgt ttggacgacg tgcagcaccg    9660
gccgggcctc cacctcggca agaacgtgct gatagggaac gctgtcggtt ccgggaagaa    9720
cggtccgcag gctttcgtgc cgctccacca cgtcggtgag tgccgtgtgc agggcctccc    9780
ggtccagccg ccccgacaac cgcagcgcca tcgggatgtt gtaggtcgca ctcggccctt    9840
ccaaacggtg gaggaaccac aggcggctct gcgcggagga caaaggtatc cgctccggac    9900
gcaccgcggg gaccagcgtc gagcgcaccg tctcaccgtt gctggtctcc agcagcacag    9960
tcagtgcggc gacggtgggg gcttcgaaga gggcgcggac ggggacttcg gtgttgaggg   10020
tggcgcggat gcggctgatg aggcgggtgg cgaggaggga gtgtccgccg aggtcgaaga   10080
agctgtcgtc gatgccgacg gcgggcaggc ccaggacttc ggcgaacagg ccggcgagga   10140
tctcctcgcg ggggctgcgt gcggtgcgtc cggcgggttc ggcagcgaac tccggtgtgg   10200
gcagggcccg gcggtcgagc ttcccgctcg cggtcagtgg cagccgctcc agcaccacca   10260
ccgcggcggg caccatgtag tccggcagcc tggtgcgcag gtactcccgg accgtacccg   10320
```

```
catccaccac caccacccgag gcggggacgt caccggaggt gatgccggtg ggcacgatat   10380
agagggcgag ctgtttgccg cgggtgtcgt cctcatgcac ggtggccgcg gcctgcgcga   10440
cggcgggatg gccggcggcg gtggtctcga tctcgccgag ttcgatccgg aacccgcgga   10500
tcttgacctg gtcgtcggcg cgtccgacga actccagctc accggaggtg ttccagcgca   10560
ccacgtcccc ggtccggtac atgcgtgaac ccgccggccc gtacggatcc gccacgaacc   10620
gcgacgcggt cagaccagca cggttcacat acccacgcgc cagacccgca cccgccacat   10680
acaactcacc cgcaacaccc accggcacca cacgcaaccc cgcatccagg acgtagacgc   10740
gggtgttggg cagcggacgg ccgatggggg cggtgtcctg ggtgagggga tcgctccagg   10800
tggcgacgac gctggcttcg gtggggccgt aggcgttgat gaagcgcctg ccgggcgacc   10860
agcgggccac cagttccggc gggcaggctt ccgctccggt cagcagtgtc cgcaggtgcg   10920
gcaggtccgt ttcgggcagg gtggcgagcg cgctgggggt gatcagtgtg tgggtgatct   10980
cctggcgggc gaggagcgcg gccaggtcgt cgcccagcag ccggccttgt ggcgcgatga   11040
ccagggtggc gccgctgccg aacgccatgc tcagttccag caccgccgcg tcgaatccga   11100
ccgaggccag ttgcaggacc cggctgccgg cggacaggtc cagcgcagcc cgttccgctg   11160
ccgtcaggtt cgccagtccc gcatgggaa ccagcactcc cttcggcaca cccgtcgaac   11220
cggaggtgta gatcacatac gccggatgcg acccctccag caccacaccc cgctcggaat   11280
cggtgggatc cgacaccgca cacgcgcga cggtctcggt gacagccggg tcgtccagga   11340
ggacggaggt gacgccttcg gtgcggggca ggccggccgc gacatcggag gtggtcagca   11400
ggagtgtggg gcgggtgtcg gtgagcatgt gggtgatgcg ttcggccggg tagtccggat   11460
ccacgggcag atacgccgcg ccggccttga gtaccgccag gaccgcgatc accaggtcgg   11520
tgccgcgggg cagggccagc gccacgatcc gttccggtcc cgcgccctgc ccaatcagat   11580
agtgcgccag ccggttcgcc cgctcgttca gctcgcggta ggagagtcgc tcggtctcga   11640
agacgaccgc ggtcgcctcc ggcgcctcgg cagcctgggc ctggaacagt ccggcaggc   11700
tggccggcgg cacctccagg gcggtgtcgt tccactccgc caccagccgg tgctcctcct   11760
gcccgctcag caccggcaga gcacccaccg tcacatccgg atcggccgcc accgacacca   11820
gcacccgccg caaccgctcc agcaccacct ccaccgacac ccggtcaaac agatccgtac   11880
tgaactccac agaaccatgg agccccccag gccaccgct gtctcccaca agccgtaga   11940
agttcagggc cagatcgaat cggacgtac gcgtgccgac tggctcaaca ctgatctcca   12000
ggccgtccag ttcaagccga tggccaggag tgttgtccag cgtcaccgat acctggaaga   12060
gggggtggtg ggcgagggag cgttcggggt tgaggatttc gacgaggtgt tcgaaggga   12120
cgtcctggtg ggcgtaggcg gccaggtcgg tctcgcgtac ccgggccagg agctcacgga   12180
aggtgggtt gccggaagta tccgtgcgca ggacgagggt gttgacgaag aacccgacca   12240
ggtcgtcgag ggcctcgtcg gtacggccgg cgatcgggct gcccaggggg atgtcgtccc   12300
ccgcacccag acggctcatc aacgccgcca agccggcctg cagcaccatg aacacggtcg   12360
taccggtgga acgtgccaga tccaccagac cctgatgcaa ctcagcatcc cagctgaact   12420
cgaacacctc accctctgc gacgccatcg ccggccgcgg gcggtccgtc ggcaacgtga   12480
cctgctccgg caggccggtg agggtggtgc gccagtactc cagctgccgg gcgatcaggc   12540
tgccggtgtc ggagtggtcg ccgaggaggt cgttctgcca cagcgtgtag tccgcgtact   12600
gcaccggcag cggcgcccag cccggcacac ggccgtcggc ccgggccgcg taagcggtga   12660
ccaggtcacg ggagagaggt gccagcgacc agccgtcact cgcgatgtgg tgcaccacca   12720
```

```
gcacgagcac gtgctcctca cgggcgagtg cgaacagcca cgcccgcacc ggcaactcaa   12780
ccgacaggtc gaacgggtag cgggcagcac cggccagcgc ctgatccagc tggtcttctg   12840
caatgtcggc aacctccagc acgggctggg cttcggcccc ggccaggatc tgctgacagg   12900
gcaccccgtc ggtttcgggg aagacggtcc gcagactctc gtgccgctcc actacatcgg   12960
cgagtgccgt gtgcagggcc tcccggtcca gccgccccga caaccgcagc gccatcggca   13020
tgttgtaggt cgcactcggc ccctcaagcc ggtggaggaa ccacaggcgg ctctgcgccg   13080
acgacagcgg catccgctcc ggacgcgtca cggggaccag cgccgagcgc accgactcgc   13140
tgctggtctc caggagtgcg gcgaggccgg cgacggtggg ggtctcgaac agagcccgga   13200
tcggtatctc cgcaccaaga atggcgcgga tgcggctgat gaggcgggtg gcgaggaggg   13260
agtgtccgcc gaggtcgaag aagctgtcgt cgatgccgac ggcgggcagg ccgaggactt   13320
cggcgaacag gccggcgagg atctcctcgc gggggctgcg tgcggtgcgt ccggcgggtt   13380
cggcagcgaa ctccggtgtg ggcagggccc ggcggtcgag cttcccgctc gcggtcagtg   13440
gcagctgctc cagcaccacc accgccgccg gcaccatgta gtcgggcagt tcgtgcgca   13500 ggtactcccg gaccgtaccc gcatccacca caccaccggt gccggtgggc acgatataga   13560
gggcgagctg tttgccgcgg gtgtcgtcct catgcacggt ggccgcggcc tgcgcgacgg   13620
cgggatggcc ggcggcggtg gtctcgatct cgccgagttc gatccggaac ccgcggatct   13680
tgacctggtc gtcggcgcgt ccgacgaact ccagctcacc ggaggtgttc cagcgcacca   13740 cgtcccggt ccggtacatg cgtgaacccg caggcccgta cggatccgcc acgaaccgcg   13800
acgcggtcag accagcacgg ttcacatacc cacgcgccag accgcacccc gccacataca   13860
actcacccgc aacacccacc ggcaccgcac gtagagcagc atccaggaca tatacacggt   13920
cgttagctac cggaccgcct actggagccg ccgacaccgg ccagtcagcc accgctccg   13980 gcaacacata cgcagtcacc gcatgcgtct ccgtaggccc gtagtggttg tgcagccgga   14040
tgtgcggacg ctcccggaag aaccggcgca tcgccgcccc cggcaccagc gcctcaccac   14100
cctgggccac atgccgcagc gcgggcagga ccagccccag ctcaccggcc gctgcgcga   14160 ccgcgtcaat caccagcgcc ggagcgaaca actcctcgac cgcatgctcc tgcagccacc   14220
gcgccagccc ctccccactg cgccggacct cctcacccgg aacccacaac tccttgccga   14280
acaccagcgc cgacaagatc tcctgcgccg acacatcgaa actgatcgtc gtgaactgcg   14340
ccgtccgcgc accgcccgc cccgcaatca ccgagggatg ccagtgcagc agattcacca   14400
gaccacccga cggcatcacc acccccttcg gcacacccgt cgaacggag gtgtagatca   14460 catacgccgg atgcgacccc tccagcacca caccccgctc ggaatcggtg ggatccgaca   14520
ccgcacacag cgccgacggtc tcggtgacag ccgggtcgtc caggaggacg gaggtgacgc   14580
cttcggtgcg gggcaggccg gccgcgacat cggaggtggt cagcaggagt gtggggcggg   14640
tgtcggtgag catgtgggtg atgcgttcgg ccgggtagtc cggatccacg ggcagatacg   14700
ccgcgccggc cttgagtacc gccagcaccg cgatcaccag gtcggtgccg cggggcaggg   14760
ccagcgccac gatccgttcc ggtcccgcgc cctgcccaat cagatagtgc gccagccggt   14820
tcgcccgctc gttcagctcg cggtaggaga gtcgctcggt ctcgaagacg accgcggtcg   14880
cctccggtgt ggcggcagcc tgggcctgga acagttccgg caggctggcc ggcggcacct   14940
ccagggcggt gtcgttccac tccgccacca gccggtgctc ctcctgcccg ctcagcaccg   15000
gcagagcacc caccgtcaca tccggatccg ccgccaccga caccagcacc cgccgcaacc   15060
```

```
gctccagcac cacctccacc gacacccggt caaacagatc cgtactgaac tccacagaac    15120
catggagccc cccaggccca ccgctgtctc ccacaagccc gtagaagttc agggccagat    15180
cgaatcggga cgtacgcgtg ccgactggct caacactgat ctccaggccg tccagttcaa    15240
gccgatggcc aggagtgttg tccagcgtca ccgatacctg aagaggggg tggtgggcga    15300 gggagcgttc ggggttgagg atttcgacga ggtgttcgaa ggggacgtcc tggtgggcgt    15360
aggcggccag gtcggtctcg cgtacccggg ccaggagttc acggaaggtg gggttgccgg    15420
aagtatccgt gcgcaggacg agggtgttga cgaagaaccc gaccaggtcg tcgagggcct    15480
cgtcggtgcg gccggcgatc gggctgccca ggggatgtc gtccccgca cccagacggc     15540 tcatcaacgc cgccaagccg gcctgcagca ccatgaacac ggtcgtaccg gtggaacgtg    15600
ccaggtctat caggccttgg tggagttcgg cgtcccattt gaagtacagg gagtcgcctt    15660
ggtaggtggc tgtggcgggg cggggccggt cggtgggcag ggtgacctgt tcgggcaggc    15720
cggtgagggt ggtgcgccag tactccagct gccgggcgat caggctgccg gtgtcggagt    15780
ggtcgccgag gagatcgttc tgccagaggg tgtagtccgc gtactgcacc ggcagcgccg    15840
accagcccgg cgtgcggccg tcggcccggg ccgcatacgc caccgtcagg tcacggaaca    15900 aggggggacag tgaccagccg tctcctgcga tgtggtgcac gacgagcacc agcacgtgct    15960 cctcggggc gagtgcgaac agccacgccc gcaccggcaa ctccgcggag agatcgaacg     16020
ggtagcgggc ggcaccagcc agtgcttctt cgagtccgtc ctcaccgacc tcggcgacct    16080
ccagcactgg ccgggcctcg gccccggtca ggatgcgctg gtgggaatt ccgtcggttt     16140 cggggaagac ggtccgcagg ctttcgtgcc gctccaccac atcggcgagt gccagacgca    16200
ggacctcagg catgaccgga ccggtcagcc gcaacgccat cggaacgttg taggtcgcac    16260
tcggcccctc caaacggtgg aggaaccaca ggcggctctg cgccgacgac agcggcatcc    16320
gctccggacg cgtcacgggg accagcgccg agcgcaccga ctcgctgctg gtctccagga    16380
gtgcggcgag gccggcgacg gtgggggtct cgaacagagc ccggatcggt atctccgcac    16440
caagaatggc gcggatgcgg ctgatgaggc gggtggcgag gagggagtgt ccgccgaggt    16500
cgaagaagct gtcgtcgatg ccgacggcgg gcaggcccag gacttcggcg aacaggccgg    16560
cgaggatctc ctcgcggggg ctgcgtgcgg tgcgtccggc gggttcggca gcgaactccg    16620
gtgtgggcag ggcccggcgg tcgagcttcc cgctcgcgt cagtggcagc cgctccagca    16680
ccaccaccgc ggcgggcacc atgtagtccg gcagcctggt gcgcaggtac tcccggaccg    16740
tacccgcatc caccacacca cccgaggcgg ggacgtcacc ggaggtgatg ccggtgggca    16800
cgatatagag ggcgagctgt tgccgcgggg tgtcgtcctc atgcacggtg gccgcggcct    16860
gcgcgacggc gggatggccg gcggcggtgg tctcgatctc gccgagttcg atccggaacc    16920
cgcggatctt gacctggtcg tcggcgcgtc cgacgaactc cagctcaccg gaggtgttcc    16980
agcgcaccac gtccccggtc cggtacatgc gtgaacccgc cggcccgtac ggatccgcca    17040
cgaaccgcga cgcggtcaga ccagcacggt tcacatacccc acgcgccaga cccgcacccg    17100
ccacatacaa ctcacccgca acacccaccg gcaccacacg caaccccgca tccaggacgt    17160
agacgcgggt gttgggcagc ggacggccga tgggggcggt gtcctgggtg agggatcgc    17220 tccaggtggc gacgacgctg gcttcggtgg ggccgtaggc gttgatgaag cgcctgccgg    17280
gcgaccagcg ggccaccagt tccggcgggc aggcttccgc tccggtcagc agtgtccgca    17340
ggtgcggcag gtccgtttcg ggcagggtgg cgagcgcgct gggggtgatc agtgtgtggg    17400
tgatctcctg gcgggcgagg agcgcggcca ggtcgtcgcc cagcagccgg ccttgtggcg    17460
```

```
cgatgaccag ggtggcgccg ctgccgaacg ccatgctcag ttccagcacc gccgcgtcga    17520
atccgaccga ggccagttgc aggacccggc tgccggcgga caggtccagc gcagcccgtt    17580
ccgctgccgt caggttcgcc agtcccgcat ggggaaccag cactcccttc ggcacacccg    17640
tcgaaccgga ggtgtagatc acgtatgccg gatgcgaccc ctccagcacc acaccgcggt    17700
ccgtgtccga cggatcatcc gccgacaaca ccgccaccgc ctcgacgacg gccggagcat    17760
ccacgaggac ggaggtgacg ccttcggtgt ggggcaggcc ggcggccacg ccgctggtgg    17820
tgaccatgag ggccggggcg gcatcgtgca gcatgtgggt gatgcgttcg gcggggtagt    17880
ccgggtccac gggcagatac gccgctccgg ccttgagtac cgccaggacc gcgatcacca    17940
ggtcggtgcc gcggggcagg gccagcgcca cgatccgttc cggtcccgcg ccctgtttga    18000
tcaggtagtg cgccagccgg ttcgcccgct cgttcagctc gcggtaggag agtcgctcgg    18060
tctcgaagac gaccgcggtc gcctccggcg cctcggcagc ctgggcctgg aacagttccg    18120
gcaggctggc cggcggcacc tccagcacgg tgtcgttcca ctccgccacc agccggtgct    18180
cctcctgccc gctcagcacc ggcagagcac ccaccgtcac atccggatcc gccgccaccg    18240
acaccagcac ccgccgcaac cgctccagca ccacctccac cgacacccgg tcaaacagat    18300
ccgtactgaa ctccacgaag ccaccaagcc ccgaagccgc accatcctca cgctgccact    18360
cgacaaaatg cagcgacaca tcaaaccgcg acgtaccagt cggcgccacg ggtactgcac    18420
cgacgttcac cgtcccaggt agggcgaagc tccgctctgg ggtgttttgg agggcgagca    18480
tgacttggaa gaggggtgg tgggcgaggg agcgttcggg gttgaggatt tcgacgaggt    18540
gttcgaaggg gacgtcctgg tgggcgtagg cggccaggtc ggtctcgcgt acccgggcca    18600
ggagttcacg gaaggtgggg ttgccggaag tatccgtgcg caggacgagg gtgttgacga    18660
agaacccgac caggtcgtcg agggcctcgt cggtacggcc ggcgatcggg ctgcccaggg    18720
ggatgtcgtc ccccgcaccc agacggctca tcaacgccgc caagccgcc tgcagcacca    18780 tgaacacggt cgtaccggtg gaacgtgcca gatccaccag accctgatgc aactcagcat    18840
cccagctgaa ctcgaacacc tcacccctct gcgacgccat cgccggccgc gggcggtccg    18900
tcggcaacgt gacctgctcc ggcaggccgg tgagggtggt gcgccagtac tccagctgcc    18960
gggcgatcag gctgccggtg tcggagtggt cgccgaggag gtcgttctgc cacagcgtgt    19020
agtccgcgta ctgcaccggc agcggcgccc agcccgcac acggccgtcg gcccgggccg    19080
cgtaagcggt gaccaggtca cgggagagag gtgccagcga ccagccgtca ctcgcgatgt    19140
ggtgcaccac cagcacgagc acgtgctcct cacgggcgag tgcgaacagc cacgcccgca    19200
ccggcaactc aaccgacagg tcgaacgggt agcgggcagc accggccagc gcctgatcca    19260
gctggtcttc tgcaatgtcg gcaacctcca gcacgggctg ggcttcggcc ccggccagga    19320
tctgctgaca gggcaccccg tcggtttcgg ggaagacggt ccgcagactc tcgtgccgct    19380
ccactacatc ggcgagtgcc gtgtgcaggg cctcccggtc cagccgcccc gacaaccgca    19440
gcgccatcgg catgttgtag gtcgcactcg gcccctcaag ccggtggagg aaccacaggc    19500
ggctctgcgc ggaggacagg ggtattcgtt ccggacgggc tgcgggggta agtgtcgggc    19560
ggacggcccg gttctcgtcc aggagggtgg ccaggccggc gacggtgggg gcttcgaaga    19620
ggtcacggac ggggacttcg gtgttgaggg tggcgcggat gcggctgatg aggcgggtgg    19680
cgaggaggga gtgccgccg aggtcgaaga agctgtcgtc gatgccgacg gcgggcaggc    19740
cgaggacttc ggcgaacagg ccggcgagga tttcctcgcg ggggctgcgg ggggcgcggc    19800
```

```
cggtggtgtg ggtgccgagg tcgggtgcgg gcagggcccg gcggtcgagt ttgccgctgg   19860
cggtcagcgg gagccgttcg aggacgacga tggcggcggg caccatgtgg tcggggagtt   19920
tggtgcgcag gtggtcacgg acctgtgtga tcagtgtgct ggtgtcccgg gaggcggccg   19980
ggttgttcgc cagtgcctgg aaggacgtct ccgcggtgtg gtccggggcg gaggtttccc   20040
ggagatcggt ggcggtggcg gtggcggtgg cggaccatgc cgtgccgtcg aaaatatcga   20100
ggggcaggag gagggtgttg taggtgtcgg gggcggggge gggctggagc acggcgtggt   20160
agccggtggc ggcggcgagc tggtggaggt gttcggggtc gatgccgcgg gggccggcca   20220
gcgcggtgac ggcctcggtg agggtgccgc cgttctccag gacccgcagc gcggcgtact   20280
cgcccgccag ccgggcgttg ggtatacccg tcacccgcaa cggcgcagcc ccacgagacc   20340
gcagcaggtc atcgaggccg tccagaccac cggacagagt gttccagctg atccgttcga   20400
ccagtgccgg cgtttctgcc tctgccttcg tgggccgcgc tgcctctgct tcttcctctg   20460
ttgctgtgtc tgtttctgtg tttgtggtgt ggaggatgac gtcgtagcgg tggcgggtga   20520
gttcgttgtg ggcctggccg tgtttgaggc gcacctcgac cgccgacacc gcgggcagcg   20580
tgcggcccac ggcggtgaag aactccgggt ccagcagcag ttcgttctcc agcagcagtc   20640
cctgttcgac cgcccgccgc agtccgcccg cgtccatccc gtcaccagcc ctgccgccgg   20700
tggtgcgggt gagctggaca gcggtgtgga acgcgcgcag agtacgcagg tcacgcacgt   20760
caccgatgaa gacccggcca ccggcgccag ccgggacac cgcggcctcg atcaccgacg   20820
ccagatactg cgcaccgggg aagtactgca ccaccgagtt gatcaccacg gtgtcgaagt   20880
agccctccgg caggccccgc gtgtcatcgg cccgctggca ggcgagccgc accgttccc    20940 gcagcaccgg atcggcctgc acatgcccgt ccagcgcatc gatcaccaca cccgacagat   21000
cggtggccca gtactcctca cacccggccg ccagacgcga catcagcaga ccggtcccca   21060
ccccgatctc cagaacccgc cgcccgccca gaccccggat ccgctccacc gtggcatcac   21120
gccactcccg catctcctcc agcgggatcg ccgcaccgtc ataactgctg tcccagcccg   21180
agaaatcctc cccgaacaca gaagaccccg gcccgccata caacgagtca taaatctccc   21240
gccactcacc cacctgctca tccaccacac ccgacacacc accgtcagga acagcccat    21300 caccggagac agagccggag acgtcaccgg aggtgagacc ggtgggcacg acatacaggg   21360
cgagctgttt gccgcgggtg tcgtcctcat gcacggtggc cgcggcctgc gcgacggcgg   21420
gatggccggc ggcggtggtc tcgatctcgc cgagttcgat ccggaacccg cggatcttga   21480
cctggtcgtc ggcgcgcccg acgaactcca gctcaccgga ggtgttccag cgcaccacgt   21540
ccccggtccg gtacatgcgt gaacccgccg gcccgtacgg atccgccacg aaccgcgacg   21600
cggtcagacc agcacggttc acatacccac gcgccagacc cgcacccgcc acatacaact   21660
cacccgcaac acccaccggc accacacgca accccgcatc caggacatag acacgaaggt   21720
cagggatcgt tgtaccaatt gcgctgctgc cgtcagaggc gaaagcagag ccacggttca   21780
attccctgta cgtcacgtgg accgtggtct cggtgatccc gtacatgttg accaggacag   21840
gctctgtgtc gagatgcgct tcgaaccagg gcttcaacct gcttgtgtcc agggcctcac   21900
cgccgaagac gactcggcgc aatgaaagac gccggtcgag agcagagttc tcctgggcag   21960
cctgctgcaa ttggctgaag gccgacgggg tctggttgag gacagtcaca ccttctgcca   22020
ccagcagacg caacaactcc accggcgacc gactcgtcag atgcgacacg atgaccaacc   22080
gcccaccgtg cagaagcgca ccccacaact cccacaccga gaaatcgaag gcataggaat   22140
gaaagagcgt ccatacgtca tcggctccga atccgaacca gtgatcagtt gcggcaaaca   22200
```

```
accgagtcac gttctgatgc ggtatcaaca ctcccttgg ctgccctgtg gagccggagg   22260
tgtagatcac gtaggcggga tgcgacgcgt ccagcacacc gcggtccgtg tccgacggat   22320
catccgccga caacaccgcc accgcctcga cgacgaccgg gtcgtccagg agaacctggg   22380
ggatcccttc gatgtggggt aggtcggctg tcgcgtcgga ggtggtcagc agcagtgtgg   22440
ggcgggtgtc ggtgagcatg tgggtgatgc gttcggccgg gtagtccgga tccaccggca   22500
gatacgccgc gcccgctttc agtaccgcca gcaccgcgat caccaggtcg gtgccgcggg   22560
gcagggccag cgccacgatc cgttccggtc ccgcgccctg tttgatcagg tagtgcgcca   22620
gccggttcgc ccgctcgttc aacacccgat acgagatgcg gacatcctcg aagacgaccg   22680
cggtcgcctc cggtgtggcg gcagcctggg cctggaacag ttccggcagg ctggccggcg   22740
gcacctccag ggcggtgtcg ttccactccg ccaccagccg gtgctcctcc tgcccgctca   22800
gcaccggcag agcacccacc gtcacatccg gatccgccgc caccgacacc agcacccgcc   22860
gcaaccgctc cagcaccacc tccaccgaca cccggtcaaa caaatccgta ctgaactcca   22920
cgaagccacc aagacctgcg ggcaggtcac ctagctcgtt ggactcaaag aagtggaaag   22980
acagatcaaa ccgcgaagtc ctggtctcgg cccgttcact tcgcatgttg atgtcaggga   23040
gggtgaagtt gcgggtggt gtgttgtgga gggcgagggc cacctggaag aggggggtggt   23100
gtgccggaga gcgttcgggg ttgaggattt cgacgaggtg ttcgaagggg acgtcctggt   23160
gggcgtaggc ggccaggtcg gtctcgcgta cccgggccag gagttcacgg aaggtggggt   23220
tgccggaagt atccgtgcgc aggacgaggg tgttgacgaa gaacccgacc aggtcgtcga   23280
gggcctcgtc ggtgcggccg gcgatcggac tgccgagggg gatgtcgtcc cccgcaccca   23340
gacggctcat caacgccgcc aacccgcct gcagcaccat gaacacgtc gtgccggtgg   23400
aacgtgccag gtctatcagg ccttggtgga gttcggcgtc ccaggcgaag tcgtgcaggg   23460
cgccttggta ggtggcggtg gccggccgcg gccggtcggt gggcagggtg acctgttcgg   23520
gcaggccggt gagggtggtg cgccagtact ccagctgccg ggcgaccaga ctgtccccat   23580
cggactggtc gccgaggagg tcgttctgcc agagggtgta gtcggcatac tgcaccggca   23640
gcgccgacca gcccggcgtg cggccgtcgg cccgggccgc atacgccacc gtcaggtcac   23700
ggaacaaggg ggacagtgac cagccgtctc ctgcgatgtg gtgcacgacg aggacgagca   23760
cgtgctcctc gggggcgagt gcgaacagcc acgcccgcac cggcaactcc gcggagagat   23820
cgaacgggta gcgggcagca ccggccagcg cctcgtccag ctggtcctct gcaatgtcgg   23880
caacctccag cacgggctgg gcttcggccc cggccaggat gtgctggcag ggcacgccgt   23940
cggtttcggg gaagacggtc cgcaggctct cgtgccgctc cgctacatcg gcgagtgccg   24000
tgtgcagggc ctcccggtcc agccgccccg acaaccgcag cgccatcggc atgttgtagg   24060
tcgcactcgg cccctccagc cggtggagga accacaggcg gttctgtgcg gaggacaggg   24120
gtattcgttc cggacgggct gcggggtaa gtgtcgggcg gacggcccgg ttctcgtcca   24180
ggagggtggc caggccggcg acggtggggg cttcgaagag ggcgcggacg gggacttcgg   24240
tgttgagggt ggcgcggatg cggctgatga ggcgggtggc gaggagggag tgtccgccga   24300
ggtcgaagaa gctgtcgtcg atgccgacgg cgggcaggcc gaggacttcg gcgaacaggc   24360
cggcgaggat ctcctcgcgg gggctgcgtg cggtgcgtcc ggcgggttcg gcagcgaact   24420
ccggtgtggg cagggcccgg cggtcgagct tcccgctcgc ggtcagtggc agctgctcca   24480
gcaccaccac cgccgccggc accatgtagt cgggcagttt cgtgcgcagg tactcccgga   24540
```

-continued

```
ccgtacccgc atccaccaca ccaccggtgc cggtgggcac gatatagagg gcgagctgtt    24600
tgccgcgggt gtcgtcctca tgcacggtgg ccgcggcctg cgcgacggcg ggatggccgg    24660
cggcggtggt ctcgatctcg ccgagttcga tccggaaccc gcggatcttg acctggtcgt    24720
cggcgcgtcc gacgaactcc agctcaccgg aggtgttcca gcgcaccacg tccccggtcc    24780
ggtacatgcg tgaacccgcc ggcccgtacg gatccgccac gaaccgcgac gcggtcagac    24840
cagcacggtt cacataccca cgcgccagac ccgcacccgc cacatacaac tcacccgcaa    24900
cacccaccgg caccgcacgt agagcagcat ccaggacata tacacggtcg ttagctaccg    24960
gaccgcctac tggagccgcc gacaccggcc agtcagccac ccgctccggc aacacatacg    25020
cagtcaccgc atgcgtctcc gtaggcccgt agtggttgtg cagccggatg tgcggacgct    25080
cccggaagaa ccggcgcatc gccgcccccg gcaccagcgc ctcaccaccc tgggccacat    25140
gccgcagcgc gggcaggacc agcccagct caccggccgc ctgcgcgacc gcgtcaatca     25200
ccagcgccgg agcgaacaac tcctcgaccg catgctcctg cagccaccgc gccagcccct    25260
ccccactgcg ccgacctcc tcacccgaa cccacaactc cttgccgaac accagcgccg      25320
acaagatctc ctgcgccgac acatcgaaac tgatcgtcgt gaactgcgcc gtccgcgcac    25380
ccgcccgccc cgcaatcacc gagtgatgcc agtgcagcag attcaccaga ccacccgacg    25440
gcatcaccac ccccttcggc acaccgtcg aaccggaggt gtagatcaca tacgccggat     25500
gcgacccctc cagcaccaca ccccgctcgg aatcggtggg atccgacacc gcacacagcg    25560
cgacggtctc ggtgacagcc gggtcgtcca ggaggacgga ggtgacgcct tcggtgcggg    25620
gcaggccggc cgcgacatcg gaggtggtca gcaggagtgt ggggcgggtg tcggtgagca    25680
tgtgggtgat gcgttcggcc gggtagtccg gatccaccgg cagatacgcc gcgccggcct    25740
tgagtaccgc cagcaccgcg atcaccaggt cggtgccgcg gggcagggcc agcgccacga    25800
tccgttccgg acccgcgccc tgcccaatca gatagtgcgc cagccggttc gcccgctcgt    25860
tcagctcgcg gtaggagagt cgctcggtct cgaagacgac cgcggtcgcc tccggcgcct    25920
cggcagcctg ggcctggaac agttccggca ggctggccgg cggcacctcc agggcggtgt    25980
cgttccactc cgccaccagc cggtgctcct cctgcccgct cagcaccggc agagcaccca    26040
ccgtcacatc cggatccgcc gccaccgaca ccagcacccg ccgcaaccgc tccagcacca    26100
cctccaccga cacccggtca aacagatccg tactgaactc cacgaagact tcgaggccac    26160
ctgggagccc ggactcgcta cgacgttcgg tcaatccgag gaagagatca aagcgagcag    26220
tgtgggtcgc gatcggccat tccttcgcct ccagtccgct cagagcaaac cggcgctctg    26280
gggtgttttg gagggcgagc atgacttgga agaggggtg gtgtgcgagg gagcgttcgg     26340
ggttgaggat ttcgacgagg tgttcgaagg ggacgtcctg gtgggcgtag gcggccaggt    26400
cggtctcgcg tacccgggcc aggagttcac ggaaggtggg gttgccggaa gtatccgtgc    26460
gcaggacgag ggtgttgacg aagaacccga ccaggtcgtc gagggcctcg tcggtgcggc    26520
cggcgatcgg gctgccgagg gggatgtcgt ccccgcacc cagacggctc atcaacgccg      26580
ccaagccggc ctgcagcacc atgaacacgg tcgtaccggt ggaacgtgcc aggtctatca    26640
gaccctgatg caactcagca tcccagctga actcgaacac ctcacccctc tgcgacgcca    26700
tcgccggccg cgggcggtcc gtcggcaacg tgacctgctc cggcaggccg gtgagggtgg    26760
tgcgccagta ctccagctgc cgggcgacca gactgccggt gtcggactgg tcgccgagga    26820
ggtcgttctg ccacagcgtg tagtccgcgt actgcaccgg cagcgccgac cagcccggca    26880
ccccgccctc ggcccggggcc gcatacgcca ccgtcagatc acggaacaac ggggacagtg    26940
```

```
accagccgtc cccgcgatg tgatgcacca ccagcaccag cacatgctcc tcgggagcaa   27000
gcgcgaacaa ccacgcccgc accggcaact cggtggagag atcgaaggca tgcctcgaaa   27060
cgatcaggat ggtgtctgct agttcttcct cactcgtctg cctcgtctcc agcacgggct   27120
gggcttcggc cccggccagg atgtgctgac agggcacccc gtcggtttcg gggaagacgg   27180
tccgcaggct ctcgtgccgc tccaccacat cggcgagtgc cgtctgcagg gcctcccggt   27240
ccagccgccc cgacaaccgc agcgccatcg ggatgttgta ggtcgcactc ggcccctcaa   27300
gccggtggag gaaccacagg cggctctgcg ccgacgacag cggtattcgt tccggacgag   27360
ctgcgggagt cagcttcctg cggaccacgt cgctgctgcc ggtctccagc agcacagcca   27420
gccccgccac agtcggcgct tcgaatagat cccggatcgg tatctccacg ccaagaatgg   27480
cgcggatgcg gctgatgagg cgggtggcga ggagggagtg cccgccgagg tcgaagaagc   27540
tgtcgtcgat gccgacggcg ggcaggccga ggacttcggc gaacaggccg gcgaggattt   27600
cctcgcgggg gctgcggggg gcgcggccgg tggtgtgggt gccgaggtcg ggtgcgggca   27660
gggcccggcg gtcgagtttg ccgctggcgg tcagcgggag ccgttcgagg acgacgatgg   27720
cggcgggcac catgtggtcg gggagttggg tgcgcaggtg gtcacggacc tgtgtgatca   27780
gtgtgctggt gtcccgggag gcggccgggt tgttcgccag tgcctggaag gacgtctccg   27840
cggtgtggtc cggggcggag gtttcccgga gatcggtggc ggtggcggtg gcggtggcgg   27900
accatgccgt gccgtcgaaa atatcgaggg gcaggaggag ggtgttgtag gtgtcggggg   27960
cggggcggg ctggagcacg gcgtggtagc cggtggcggc ggcgagctgg tggaggtgtt   28020
cggggtcgat gccgcggggg ccggccagcg cggtgacggc ctcggtgagg gtgccgccgt   28080
tctccaggac ccgcagcgcg gcgtactcgc ccgccagccg ggcgttgggt atacccgtca   28140
cccgcaacgg cgcagcccca cgagaccgca ggatctcctc cagccctgtg agctggcccg   28200
gaacactgtt ccagctgatc ccttccaccg gcgcaggcgt cggagctggt gcttctgtgt   28260
ctgtttctgt gtttgtggtg tggaggatga cgtcgtagcg gtggcgggtg agttcgttgt   28320
gggcctggcc gtgtttgagg cgcacctcga ccgccgacac cgcgggcagc gtgcggccca   28380
cggcggtgaa gaactccggg tccagcagca gttcgttctc cagcagcagt ccctgttcga   28440
ccgcccgccg cagtccgccc gcgtccatcc cgtcaccagc cctgccgccg gtggtgcggg   28500
tgagctggac agcggtgtgg aacgcgcgca gagtacgcag gtcacgcacg tcaccgatga   28560
agacccggcc accggcgcc agccgggaca ccgcggcctc gatcaccgac gccagatact   28620
gcgcaccggg gaagtactgc accaccgagt tgatcaccac ggtgtcgaag tagccctccg   28680
gcaggccccg cgtgtcatcg gcccgctggc aggcgagccg caccgttcc cgcagcaccg   28740
gatcggcctg cacatgcccg tccagcgcat cgatcaccac acccgacaga tcggtggccc   28800
agtactcctc acacccggcc gccagacgcg acatcagcag accggtcccc accccgatct   28860
ccagaacccg ccgcccgccc agaccccgga tccgctccac cgtggcatca cgccactccc   28920
gcatctcctc cagcgggatc gccgcaccgt cataactgct gtcccagccc gagaaatcct   28980
cccccgaacac agaagacccc ggcccgccat acaacgagtc ataaatctcc cgccactcac   29040
ccacctgctc atccaccaca cccgacacac caccgtcagg aacagcccca tcaccggaga   29100
cagagccgga gacgtcaccg gaggtgagac cggtgggcac gacatacagg gcgagctgtt   29160
tgccgcgggt gtcgtcctca tgcacggtgg ccgcggcctg cgcgacggcg ggatggccgg   29220
cggcggtggt ctcgatctcg ccgagttcga tccggaaccc gcggatcttg acctggtcgt   29280
```

```
cggcgcgccc gacgaactcc agctcaccgg aggtgttcca gcgcaccacg tccccggtcc    29340
ggtacatgcg tgaacccgcc ggcccgtacg gatccgccac gaaccgtgac gcggtcagac    29400
cagcacggtt cacataccca cgcgccagac ccgcacccgc cacatacaac tcacccgcaa    29460
cacccaccgg caccacacgc aacccagcat ccaggacata tcccagcgcc ctatctacgg    29520
gtcggccgat ggataccacc gggtttccgc cactgacact gtcgacgtga cacgtcgtgg    29580
cgtgcaccgt cgtctccgtc ggcccgtaga tattgaccac ccggacaccc ggaaccagcc    29640
cggacgccag ctcagcagtc cgcgccggca acgcctcacc accgaacacc acccggcgca    29700
gcaccaaacc ctcagccccc gccggatcct cgcgccaccac acccgccaac gcgtcaaaag    29760
ccgacggcgt ctggcacagc accgtcacct gctcagccac cagcagacgc aacaactcca    29820
ccggcgaccg actcgtcaga tgcggcacca ccaccagaca cccgccatgc agcaacgccc    29880
cccacaactc aaacaccgag aagtcgaacg tgtacgaatg gaacaaagcc cacacatcat    29940
ccggcgcaaa cccgaaccag tgcccgcccc cacccacgtc gaaaagccgc accacatttc    30000
cgtgcgacgt catcacgccc ttcgggcgcc ccgtcgaacc cgacgtataa atcacatgca    30060
ccggatgcgc cggcgacaac accgcacccc gatccgcatc cgacggatcc gacaccccgc    30120
acccggccag ctcacccagc accgccgggt catccagcga cacgtactcg acatcatcga    30180
caaccggcag accagccacg accgcagagg acgtcaaagc caacacggga cggctgtcct    30240
cgagcatgta ggcgacgcgt tcggccgggt agtccggatc caccggcaga tacgccgccc    30300
ccgccttcac caccgccagc accgccacca ccagatcgac accacgcggc aacgccagag    30360
cgaccacccg ctccggaccc acaccacgcc ccagcaacca atgcgccagc cggttcgccc    30420
gctcgttcaa caccccatac gacacacgaa catccccgaa aacaaccgca gtcgccccg    30480 gaacagacgc agcacacacc tcaaaaagcc cagggagggt cgccgtcgat atcgcatcgg    30540
tggcaccact ccattccgtc aaaattcgac gctcttcctc tgcgtccaaa aactccagca    30600
ggctaatcgc tgggaggaa cgactcggat ccgtgaactc cttcaggagg cgcatgaacc    30660
tctcgctgtg agcctggagt tcttgatagc tatagaggtc ggaattcgcc tctatatcga    30720
tacgaagctc gcttccgtcc cgcctgtcgt aaatggcgat ggtgaggtca tcaacaactc    30780
ccagagacag attcttcgct actgcattag cgtcaccgaa agttatattg tagtcgaacg    30840
gcatgaagtt gacccgtggg ccaatcattc ctcgaatgcc cgccggaaga ccagatctc    30900 gcgcaatatc ctcgctgcgg tagcgctgat gcctgagcag atctgctatc tcgcggcaca    30960
cttgcccctc aagatcagaa acagttgttt cctgactcac agtcaattg aggggaagca    31020 ggttggacat cattcccgcg acctgcttca aatccgcacc gggacgcgct gcggcagcaa    31080
atccgaggag gaaatcaacc tgccctgtgg ccctgtaaac gtaagctgcc gccgccgcc    31140 tcagagttac agcccatcct cggagatccc ggtcacctcg gaccgcgtcg ccgccatgga    31200
catcagagaa agtcatgctt acacggtgga actttccaga ggccggtgcg gtacgtcccg    31260
ccaactccac gggttccggg aggtcagcaa ggcgccccat ccagaattcg cggtcccgcg    31320
caaggtcctc ggaggctcgg taggaggcat cgtcgtccag cagcagcgcg acagagtcgt    31380
cgccaccaag aactccctcg ttgcgagaaa ggcgattata gctgtctgcc acccttctgg    31440
cgacgactcc catggcaaag gcgtccatgg cgatgtggtg gtatccctga taccaaacaa    31500
ccctgttccg ggaaatccgg aacagggcgt atgagaaaac aggaccgaca gttatatcta    31560
tggaccgccc caggtcttcc ctcatccacc gctctgcgac ggaaagcgga tcatcaacat    31620
cacttaaatc aataaccgga agatcccagt cctccttgcg ctcaactacc tgctcgggcc    31680
```

```
cttcttgccc ttccgtgaat cgaacgtgca acgtttcagt ctgtgcgacc acggtgcgca   31740
gcgccctttc gaaaagggtc aggtcaatgt cgcccgaaat atccaggtac tcaccgactc   31800
gataaagagg gttctcaagg tcctgctgct gactgaacca gatctcacgc tgagcggcag   31860
acaaaagttt cgagttgatc tgcatgactg aaaagccccc tgtgccaatt tgacggtgca   31920
gtcatttggt caactcgggc gcatccccga gcaacacgac agggctcacc cctctgccgc   31980
gccgaagatc atcatcacaa ggccagccac catcacacca ccctttccca gccaacctgc   32040
gaaatgtcac aggggatgc gatcaagcca atcctggttc tgatggttaa ctggcgacgg   32100
tatgtggaag ccgcttgccg tagtacccgt agcaggtgcg gaccttccct gcacgccacc   32160
atccggttct gcggaccatg tcggtcacag cagacatgga aaatctgcca ggaatggcca   32220
tagctcagcc cggcccatag tcatccacag cagatgagcc ccagctggat gtaactcaac   32280
cctcccgaac ggaggcggta tcgagagact gcaacgctag caacgttggc ttgattgccc   32340
aggaccacag tgtcaggatc gccgtggcgt cgtgcctgtt cagggaaaca acatggggat   32400
agtgaagcgg gggcatcagc caaggggggcc ctactgccac gctggttaga cgcctcacgg   32460
tttcaagctg tcagcgatga ggtcaacggc catttgtaat ccccagtggc ggccaaatgt   32520
tctacgccct catggccgaa tcggcgtccc cagcggcggg acggtctgtc ccagggcctc   32580
cgtgaagtgc aacttcccag tgcgggacgg gtgcagatgc agaggttttc ccgacgcccg   32640
acccactcca gtgtctccag cgagtcctgg acctgacggg ttatggagga ctgggtctcc   32700
tcccaatcgc cgaacgtctt gtccgcgggg tactcggccc gcttgcgtcg gccccgtagg   32760
ttcgcggcat cacgtccggt tcgccgaggt gggcaccagg tccgccttgg cgatgcgaac   32820
cgtcgcctcg ctgccgccct tggcctcggg atccgctggc agacaggtgt ggatcgttat   32880
gccgtagtgc cggccgactt cgacgatctc agggttgcgg accgcgatgt tcgcaatgtg   32940
ctcggtcgtg acgatcttct cgttgtccgt cagcgcatag ctcgggaccc ctccgatccg   33000
ccgcaaagtg gcatccagac aagccacgat cgtcggcagc gccttttcga acaccgggat   33060
gaccacccgg aatctcgacc aggccagccg agcgcaccac aaagacgtac gtcttccgcc   33120
aatgcgtggc ccttcacccc agtcctactg cagccagagg ccggctcggc gatcttctct   33180
gatgcgatga aaggagcggg acctcccact cctgccgggc gcgcaggatg ctcggctgag   33240
gcagaagtcc gaactcgggg agccctcgat tggtactggg ccgttgacgt actcaccgag   33300
gccggagccg gggttcacct cacccacccc ctgggggtga aggcgtttgc gtaccgccgg   33360
gtcaagaatg atgagcgaga cgccgccgac ctgaccgacc tgctgcggct gggccggcta   33420
ccggttgcgg gttcgatgct ggcagtgtac gtgcggcagt gcttgaagaa cggcgacacc   33480
gtggaagtca gcgcttcgtg ctggtggaag ttctcggcgg acaccatcac ccagcacggc   33540
gagtacctgt tggccttcgt cgatggtcac gtgtgtgtcg gcgccttcga gatcgttggg   33600
gcggagcccg atgagaccga aggcgagaag tacgtcttcg atcttcttcg ccctgcagca   33660
cggttccagt gggcgctggg gaggaagctt ccactgccgc ccggtcgcaa cccgtgcgca   33720
ttctgaccgg ccaggccctg cgcgagttcc tcgtccgacc cgcggtaagg gatctggggc   33780
ggctgcgccg gcggtgagct cgatggaacc cggtgatgtc tcgagcgcat cctcgccttc   33840
accttgacga ccgcgcggcg ggtggtgcga tccccgccgg tcaagcccgc cgcagtgatc   33900
cgccggtgca cgatgtccgc acctatccgc cctttcgagg cggtcagcaa ctcctcgatc   33960
ttgtccatga attcgtcgat cgggcgggcc cggtgctgac gctccgcggg acgctcgccc   34020
```

```
gcctcacgca acttcacata gcgagccacc gtgtggtggt cgacgccagc cagctcggcc   34080
gcggcgcggt gactccccgt gaggtgatac gcccccaagc ttgccactgc ggtccggccg   34140
caagcgcggc gtcgaggccg aggagctgtg cggctttggc aggggtgggt gccagctaag   34200
gggtcacggg tctcgggctc acacaggccg ttggtccagg tggcataggc gctcagcgct   34260
gcggggtagt actcgcgcag cagagaccgg agctggttgg aggtcagcgc cggtcccagg   34320
tcgcgtcctg ctgggccagg acggcgatgg cgcgggccat gtcggagtcg ttagggaggg   34380
ggcggcggcg tgcatgtcgg ttcgcagaag gttcgccagg gtcagggcgc cgccggggcg   34440
gttttcttgc gggagacaga gtgccggtcg cggtagcggg ccgcagctag gcccgtgacc   34500
ggctggcctc ctgggtgtcg ggtgaactca ccgacaatga ggcggtgttg gtggtcgatg   34560
agacggggga cgaggagtcc tccaccgact gcgtgggcgc cgcccgccag tactccggcg   34620
cgctgggggc ttgtacgtga ataactgtca gtcttgatct gtggggtcgt cctccgcaga   34680
tgcaaggcgg gctctcagct gctcaagtgt gcgtgcgggg gctccgggta tcggcgtgac   34740
ggcgatccgg tagaggtcga ggatccggtg gccatcctgg aactggttgg acaggttggt   34800
gcgtgtgacg cccagcagtt gggccaggag agtgctggtc gccgccttgc ggcggcgcag   34860
cagggctgtg aggagccggt ggaagtggtc caggctgctg gtttgcgggt gaaggtagct   34920
gcgcgggcgg tggaaacggc gctggaaggc cgcctcggcc agggcgtccc agtacggctc   34980
cgagactgcc gcgaggtgcg cgaagtccgc gcgtggcata ccggtcaggg ccgggtcgat   35040
gagcattgtg gtcagggcgg gatcgatggg ccgacgggtc gtgggagctt cggcaggact   35100
gggcggggca ggagccaagg tgtagttcca gtctccgtgg aatgcctctg gcgcgatcgg   35160
cagggcctgg aactcggcgg gtgtgacagt cgtgccgagc gggtagctgc cggtgtccag   35220
ctcggcgccc atggacagtc cgttcgcggt cgtcgtcgcg gcgatggtct ccacgacgac   35280
ctggtagctg gtcagtggct ggccgcgcca gttggcggtg atgtggcaga acatccggtg   35340
ctcgatcttg ttccacttcg aagtgcccgg tgggaagtga cagaccgtga tttccaggcc   35400
gctctcctgc gcgaaggcgt gaaggtattt cttccatgtc cagcggcggg catcgttgga   35460
gccgccggca tccgcagtga tcagtaaccg ggttgcgttc gggtggtcgg tccgtccgcg   35520
gcgccgccac cagcggcgga tggactccac cgcgaactcg gcggtgtcgt ggtcggtgcc   35580
gacgttgacc cagccggtgt tggtggccag gtcgtagatc ccgtagggga tggcgaccgg   35640
catttcgtcg gtgacgaagg tgtggcagtc caccttgatc gggcccttgc cggggcgcca   35700
ggtgcgtccg ggccggtcgc ggttgccgat ccactccttg gccttggtgt cgacgctgat   35760
caccggctgg tggctgtcga ggaaggcggt ggcggtggcg tcgcggtccg ggtggcgggc   35820
gccctccgtg gtcttggcgg tgccctgcag gctgtagccc atcgcatgca gcaggcgccc   35880
gacggtcgtt gcgccgaccg ggtgtccctg tgcggtcagt gtcgaggcaa gcgtccgcag   35940
cgaaagcgtg gtccagcgca gcggggagac cgggtcgcca cgggtacgcg gctcgatcag   36000
ggcctccaac gccggccgca gtccggtgtc ggtcgtcgtc agcggcttgc gtccagcccc   36060
tagagcccgg ttgcggcacg tcgtcgccgg atgcgcgtcc agctcggcga tgccacgtgc   36120
gatggtggcg gtgctcgtgc cggaagcggc agccaccgcg gcgattccgc cgtggccgag   36180
cgcaacagcc tcgctggcca ggtagaaccg tcgacgccgc tcgtcgaggt ggggcaggat   36240
ccgatcgaac ttggccttca accgggctgt ggggatgcga agttgcggaa ccggagtcat   36300
gctccagcct cccaccacgg ctcacccac agatcaagtc tgacagttat tcacgtacaa   36360
gccctgggcg gaatcgggct gtgccaggtc gccgtgcacc tcacctacgc cacgccgcgc   36420
```

```
ggccacgcgc tgatcgaccg ggagttgtac ctgcccgccg cctgggcgca ggacgaggag   36480
cgccgcctgc tgcggcacgt gcccgacgag gtcttttcg ccaccaagcc ccagctcgcc    36540
gccgtcatgc tcacccgtgc ccgcgaactg ggcgtgtgcg cccgctggtt cgccggcgac   36600
gaggtctacg gcagcctcga gctgcgacga accgcccgga tgctcggctt cgactacgcc   36660
ctggccgtca aggccgacca caccgccacc acctccgcgg gccgcttcac cgccgcccga   36720
ctcgcggcga aggtcccggc gaagtcctgg atgcggatgc gcaccggaca cgggttgaag   36780
ggcgaccggc actacgactg ggcgctgatc gaggtccgcc ccgacgacac ccccaccgac   36840
agtgaggccg gcgggcacgc cttcctcgtc atccgccgcc accgctacac ccgcgaactg   36900
tccttctacc gctgccactc caccaccccc atcagcctcg ccgacctcgt caacatcatc   36960
tgcaccaggt ggaagatcga agaggacttc cagggcgcaa agggcctcac cggcctcgac   37020
cagggccagg tcgcctgctg gaactcctgg atgcactgga gcctgatcag cctgatcgcc   37080
gccgcggtcc tggccatcac ccgcgcccgc accgccgccc cggccgccgg catcgcgctc   37140
gtccccgcca gccccgcga actgctcgcc gtgctccgcg ccacggccct tccggcgccc    37200
cgccgccacc tcgggcacgt cctgcactgg tccgcctggc gccgccatca ccagcaccaa   37260
gccgtccagg cccaccgccg ctggaacaac gtcaccgcag aagcgacaag gtgacccac    37320 gacgaagatc acgacttaca gcgactgagc gtcagtgctc tagccagagg atcgcggccg   37380
gggcggcttt atatccgccc ggcctctact cggctgccat gacgagcccc acgaccatac   37440
acgtgtctat ccggaggcct cagtggcctg atggcagatg tcatagcccc aggctcaaac   37500
agaaccagcg gaaccaccca gtgggtctga tccgtcgacc ctgcgggcac gcgacatccg   37560
cctcgccagt gcggtctcgt cgatccgagg atcctgcgcg gcgtacgcga ttgacttgcc   37620
cgtggcgatg acgatctgca cagccacctc atggaactcc gcctcgaagt cccgtcscat   37680
cttgcctaca atgatcctcc acttccctg caaccagaat ttctatgagg gaagctctct    37740
tcgaatcacc gatggaaccg tacaggcatg accagatatc gagctgacgt atcggcttcg   37800
gcgtctacag acgacttccc catgattaca gccttcccgt tggaactggt gaatgagaac   37860
tgggcccagg aggcatccaa gttcgtgagc ccgtcaagaa ggaaggatgg gttgaacgcg   37920
atgtcgatac tttcaccttc aagtgaagct gccatgcgcg acgtggctcg atcgtcatct   37980
gccccaccag cttgtagaac caattctccg tcggtgaaat caagcgcaac cgagctgttt   38040
cgctccagga cgagagaaac cctcttcaat gcctcaacaa ggcgagagac ctcaaccgcc   38100
ccgaaagatg tgaactcctt ggggaacaac ttttcatagt ctgggagggt ccctccagt    38160 aggcggcaag tcatctgccg tgtacccgca tggagcccga aagattccc ttcatcgctc    38220 aatgcaattt ttactaggtc tcccttgttg agggattttg caaaatccag gagtgtccga   38280
gccggcacca ataccgaact agatgatggt gtgccttcag gcttccatgc gagctctcga   38340
atcgcgaagc ggtagcggtc ggtggcattc agcttcatga tctccccatc gaaattcact   38400
ccgatgccag tgaggactgg cagggcatca tcgcggctag ccacgacggc aacctgagag   38460
acagcgcgtg cgaactggtc accttctacc gatccacaga cggtgggcag cttcgggagc   38520
gttggatact catccaatgg cagcgcgttg aggacaaagc tgttcgagtc gcattgcacg   38580
tacaccttgg tctggtcaac attgaactca atcggcacat ctggaagaac tttcgcgatg   38640
tccgcgagtc ggcgacctgg aatcaggacc gttcccgatt cctccacatt cgctttgagc   38700
tcaaccctcg tggataccte atagtcgaaa cctgacaacg tcagtgtgtc accttcggca   38760
```

```
tttaccacga caccagagag gatagggaca gacggccgga cggcgagccc acgggcaacc   38820
cagccgattc cctccgccag aacttcccgc tcgacctgaa accgcatgga atacgcctcc   38880
gatggcttgc tgcacgtcgc gacggagtcc gctccgccgc ctgcggccca gtatggcgca   38940
tcacaccgtc cacaggcggt gccgcggggg gccagcctcc agggatcatc agccacccgg   39000
gccggataat cgcctgcgct gcagcacttc atggtcgcgc tcgctccatg gacggcacct   39060
tttcgcgcct accggttcat tttcggccat agttgaatgc atacaccatg gtcccccat   39120
gcgcttccat ccgcacgaca gcggctctgt agacccctca accggacgtc tggtcggagg   39180
gtcgaccctc gcagagcggc ggctgaaaat acccccttcaa gaggcggccg catcggcttg   39240
gctgaaaaga agtggttgag cccgatgcga tttggcgacg atcatcttga tcgccggggc   39300
gacgctgctt gctgtctcac ccctcacggt ccctgcacaa tccatgcccg atccttttgt   39360
tcgggatccg ccccagggag tgcgttcttc atgcctgcca gctcgacatc atcgccggat   39420
tcgcgacatg aggtgtgagt ccactgggct ggctcacttc acgtcacgtc ccgacatggc   39480
ggccctaggc ggccgcagca ggcgatggag tatctccgac gacgtgccct atcaaaaact   39540
ctgacgacga gcaaaatgcc gccacatgca gatcactctc gattttccat ggcctttgac   39600
tgcgccatga tcttgcgacc aaccttttcg gggagctgag ccgtgttcga tcgcatatcc   39660
cacgacaaca ggaaaattcc cacagcaggt accctccctg gcttttttga ggtgtgtgct   39720
gcgtctgttc cggggcgac tgcggttgtt ttcggggatg ttcgtgtgtc gtatggggtg   39780
ttgaacgagc gggcgaaccg gctggcgcat tggttgctgg ggcgtggtgt gggtccggag   39840
cgggtggtcg ctctggcgtt gccgcgtggt gtcgatctgg tggtggcggt gctggcggtg   39900
gtgaaggcgg gggcggcgta tctgccggtg gatccggact acccggccga acgcgtcgcc   39960
tacatgctcg aggacagccg tcccgtgttg gctttgacgt cctctgcggt cgtgctggt   40020
ctgccggttg tcgatgatgt cgagtacgtg tcgctggatg accggcggt gctgggtgag   40080
ctggccgggt gcggggtgtc ggatccgtcg gatgcggatc ggggtgcggt gttgtcgccg   40140
gcgcatccgg tgcatgtgat ttatacgtcg ggttcgacgg ggcgcccgaa gggcgtgatg   40200
acgtcgcacg gaaatgtggt gcggcttttc gacgtgggtg agggcgggca ctggttcggg   40260
tttgcgccgg atgatgtgtg ggctttgttc cattcgtaca cgttcgactt ctcggtgttt   40320
gagttgtggg gggcgttgct gcatggcggg tgtctggtgg tggtgccgca tctgacgagt   40380
cggtcgccgg tggagttgtt gcgtctgctg gtggctgagc aggtgacggt gctgtgccag   40440
acgccgtcgg cttttgacgc gttggcgggt gtggtggcgc aggatccggc gggggctgag   40500
ggtttggtgc tgcgccgggt ggtgttcggt ggtgaggcgt tgccggcgcg gactgctgag   40560
ctggcgtccg ggctggttcc gggtgtccgg gtggtcaata tctacgggcc gacggagacg   40620
acggtgcacg ccacgacgtg tcacgtcgac agtgtcagtg gcggaaaccc ggtggtatcc   40680
atcggccgac ccgtggacaa agcccgtgcc tacgtgttgg acgacgagct ctttcccgtg   40740
gctcctggtg ttgcgggtga gttgtatgtg gcgggtgcgg gtctggcgcg tgggtatgtg   40800
aaccgtgctg gtctgaccgc gtcgcggttc gtggcggatc cgtacgggcc ggcgggttca   40860
cgcatgtacc ggaccgggga cgtggtgcgc tggaacacct ccggtgagct ggagttcgtc   40920
gggcgcgccg acgaccaggt caagatccgc gggttccgga tcgaactcgg cgagatcgag   40980
accaccgccg ccggccatcc cgccgtcgcg caggccgcgg ccaccgtgca tgaggacgac   41040
acccgcggca aacagctcgc cctgtatgtc gtgcccaccg gtctcacctc cggtgacgtc   41100
tccggctctg tctccggtga tggggctgtt cctgacggtg gtgtgtcggg tgtggtggat   41160
```

```
gagcaggtgg gtgagtggcg ggaratttat gactcgttgt atggcgggcc ggggtcttct   41220
gtgttcgggg aggatttctc gggctgggac agcagttatg acggtgcggc gatcccgctg   41280
gaggagatgc gggagtggcg tgatgccacg gtggagcgga tccggggtct gggcgggcgg   41340
cgggttctgg agatcggggt ggggaccggt ctgctgatgt cgcgtctggc ggccgggtgt   41400
gaggagtact gggccaccga tctgtcgggt gtggtgatcg atgcgctgga cgggcatgtg   41460
caggccgatc cggtgctgcg ggaacgggtg cggctcgcct gccagcgggc cgatgacacg   41520
cggggcctgc cggagggcta cttcgacacc gtggtgatca actcggtggt gcagtacttc   41580
cccggtgcgc agtatctggc gtcggtgatc gaggccgcgg tgtcccggct ggcgccgggt   41640
ggccgggtct tcatcggtga cgtgcgtgac ctgcgtactc tgcgcgcgtt ccacaccgct   41700
gtccagctca cccgcaccac cggcggcagg gctggtgacg ggatggacgc gggcggactg   41760
cggcgggcgg tcgaacaggg actgctgctg gagaacgaac tgctgctgga cccggagttc   41820
ttcaccgccg tggccgcac gctgcccgcg gtgtcggcgg tcgaggtgcg cctcaaacac   41880
ggccaggccc acaacgaact caccgccac cgctacgacg tcatcctcca caccacaaac   41940
acagaaacag acacagcaac agaggaagaa gcagaggcag cgcggcccac gaaggcagag   42000
gcagaaacgc cggcactggt cgaacggatc agctggaaca ctctgtccgg tggtctggac   42060
ggcctcgatg acctgctgcg gtctcgtggg gctgcgccgt tgcgggtgac gggtataccc   42120
aacgcccggc tggcgggcga gtacgccgcg ctgcgggtcc tggagaacgg cggcacccct   42180
accgaggccg tcaccgcgct ggccggcccc cgcggcatcg accccgaaca cctccaccag   42240
ctcgccgccg ccaccggcta ccacgccgtg ctccagcccg cccccgcccc cgacacctac   42300
aacaccctcc tcctgcccct cgatattttc gacggcacgg catggtccgc caccgccacc   42360
gccaccgcca ccgatctccg ggaaacctcc gccccggacc acaccgcgga gacgtccttc   42420
caggcactgg cgaacaaccc ggccgcctcc cgggacacca gcacactgat cacacaggtc   42480
cgtgaccacc tgcgcaccaa actccccgac cacatggtgc ccgccgccat cgtcgtcctc   42540
gaacggctcc cgctgaccgc cagcggcaaa ctcgaccgcc gggccctgcc cgcacccgac   42600
ctcggcaccc acaccaccgg ccgcgccccc cgcagccccc gcgaggaaat cctcgccggc   42660
ctgttcgccg aagtcctcgg cctgcccgcc gtcggcatcg acgacagctt cttcgacctc   42720
ggcgggcact ccctcctcgc caccgcctc atcagccgca tccgcgccat tcttggcgtg   42780
gagataccga tccgggatct attcgaagcc cccaccgtcg ccggcctggc caccctcctg   42840
gacgagaacc gggccgtccg cccgacactt acccccgcag cccgtccgga acgaataccc   42900
ctgtcctccg cgcagaaccg cctgtggttc ctccaccgcc tcgaaggtat gggtgcagcc   42960
gcgtacaacg ttccgatggc gttgcggctg accggttcgg tcatgcccga ggtgctgcgt   43020
ctggcgctgg ctgatgtggt ggagcggcac gagagcctgc ggaccgtctt ccccgaaacc   43080 gacgggggtgc cctgtcagca catcctgtct gtggtggagg cccggccggt gctgcacgtc   43140
gtccaaacga gcgaggaagg gctggccgaa gcggtctcga cagcatcgca gtatgccttc   43200
gatctctctg cggagttgcc ggtgcgggcg tggctgttcg cactcgcccc cgaggagcac   43260
gtgctcgtgc tggtggtgca ccacatcgca ggagacggct ggtcactgtc ccccttgttc   43320
cgtgacctga cgaccgccta cgcagcccgg gccgacggcc gcacgccggg ctgggcgccg   43380
ctgccggtgc agtacgcgga ctacacgctg tggcagaacg acctcctcgg cgaccactcc   43440
gacaccggca gcctgatcgc ccggcagctg gagtactggc gcaccaccct caccggcctg   43500
```

```
cccgaacagg tcaccctgcc caccgaccgg ccgcggccgg ccaccgccac ctaccaaggc    43560
gccctgcacg acttcgcctg ggacgccgaa ctccaccaag gcctgataga cctggcgcgt    43620
tccaccggta cgacggtgtt catggtgctg caggcggggt tggcggcgtt gatgagccgt    43680
ctgggtgcgg gggacgacat cccctcggc agtccgatcg ccggccgtac cgacgaggcc     43740
ctcgacgacc tggtcgggtt cttcgtcaac accctcgtcc tgcgcacgga tacttccggc    43800
aaccccacct tccgtgaact cctggcccgg gtacgcgaga ccgacctggc cgcctacgcc    43860
caccaggacg tccccttcga cacctcgtc gaaatcctca accccgaacg ctccctcgcc      43920
caccaccccc tcttccaagt catgctgccc ctccaaaacg ccccgaagg gcagttcaaa     43980
cttcctggcc tgcaagcacg ctttgagacc acccacacgc agaccgcgaa gttcgacctg    44040
ttcttcaacg tccacgaata ccgcgcaacg acggcgggc ctgggggct ctatggttct       44100
gtggagttca gtacggatct gtttgaccgg gtgtcggtgg aggtggtgct ggagcggttg    44160
cggcgggtgc tggtgtcggt ggcggcggat ccggatgtga cggtgggtgc tctgccggtg    44220
ctgagcgggc aggaggagca ccggctggtg gcggagtgga acgacaccgc cctggaggtg    44280
ccgccggcca gcctgccgga actgttccag gcccaggctg ccgccacacc ggaggcgacc    44340
gcggtcgtct tcgaggatgt ccgcatctcg tatgggagt tgaacgagcg gcgaaccgg      44400
ctggcgcact atctgattgg gcagggcgcg ggtccggaac ggatcgtggc gctggccctg    44460
ccccgcggca ccgacctggt gatcgcggtg ctggcggtac tcaaggccgg cgcggcgtat   44520
ctgccggtgg atccggacta cccggccgaa cgcatcaccc acatgctcac cgacacccgc    44580
cccacactcc tgctgaccac ctccgacgcg acagccggcc tgccccacac cgaagggatc    44640
ccccaggttc tcctggacga ctcggccgtc atcgagaccg tggcggtgtt gtcggcggat    44700
gatccgtcgg acacggaccg cggtgtggtg ctggagggt cgcatccggc gtatgtgatc     44760
tacacctccg gttcgacggg tgtgccgaag ggggtggtga tgccgtcggg tggtctggtg    44820
aatctgctgc actggcatca ctcggtgatt gcggggcggg cgggtgcgcg gacggcgcag    44880
ttcacgacga tcagtttcga tgtgtcggcg caggagatct tgtcggcgct ggtgttcggc    44940
aaggagttgt gggttccggg tgaggaggtc cggcgcagtg gggagggct ggcgcggtgg      45000
ctgcaggagc atgcggtcga ggagttgttc gctccggcgc tggtgattga cgcggtcgcg    45060
caggcggccg gtgagctggg gctggtcctg cccgcgctgc ggcatgtggc ccaggcaggt    45120
gaggcgctgg tgccggggc ggcgatgcgc cggttcttcc gggagcgtcc gcacatccgg      45180
ctgcacaacc actacgggcc tgccgaaaca cacgttgtaa ctgctcaccc cctgccaaac    45240
cgaattgcag actgggcaac ttcagtcccc atcggccgtc cgctgccaa cacccgcgtc     45300
tacgtgctgg atgcgggtt gcgtgtggtg ccggtgggtg ttgcgggtga gttgtatgtg    45360
gcgggtgcgg gtctggcgcg tgggtatgtg aaccgtgctg gtctgaccgc gtcgcggttc    45420
gtggcggatc cgtacgggcc ggcgggttca cgcatgtacc ggaccgggga cgtggtgcgc    45480
tggaacacct ccggtgagct ggagttcgtc gggcgcgccg acgaccaggt caagatccgc    45540
gggttccgga tcgaactcgg cgagatcgag accaccgccg ccgagcatcc cgccgtcgcg    45600
caggccgcgc ccaccgtgca tgaggacgac cccgcggca aacagctcgc cctctatgtc     45660
gtacccaccg gcatcacctc cggtgacgtc cccgcctcgg gtggtgtggt ggatgcgggt    45720
acggtccggg agtacctgcg cacgaaactg cccgactaca tggtgcccgc cgcggtggtg    45780
gtgctggagc agctgccact gaccgcgagc gggaagctcg accgccgggc cctgcccaca    45840
ccggagttcg ctgccgaacc cgccggacgc accgcacgca gccccgcga ggagatcctc       45900
```

```
gccggcctgt tcgccgaagt cctcggcctg cccgccgtcg gcatcgacga cagcttcttc   45960
gacctcggcg gacactccct cctcgccacc cgcctcatca gccgcatccg cgccaccctc   46020
aacaccgaag tccccgtccg cgccctcttc gaagccccca ccgtcgccgc actgactgtg   46080
ctgctggagg ctggcagcag cgacgtggtc cgcaggaaac tgactcccgc agcccgtccg   46140
gagcggatac cgctgtcctc cgcgcagagc cgcctgtggt tcctccaccg cctcgagggg   46200
ccgagtgcga cctacaacat gccgatggcg ttgcggctga ccggtccggt catgcctgag   46260
gtcctgcgtc tggcgctggc tgatgtggtg gagcggcacg agagcctgcg gaccgtcttc   46320
cccgaaaccg acggcgtgcc ctgccagcac atcctggccg gggccgaagc ccaacccgtg   46380
ctggaggttg tagaggtcgg tgaggacgga ctcgaagaag cactggccgg tgccgcccgc   46440
tacccgctcg atctctccgc cgagttgccg gtgcgtggct ggttgttcgg gttggggccg   46500
accgagcacg tgctcgttct ggtagtgcat cacattgcgg gggatggctg gtcgctggca   46560
cctctctccc gtgacctggt caccgcttac gcggcccgtg ccgacggccg cacgccgggc   46620
tgggcgccgc tgccggtgca gtacgcggac tacacgctgt ggcagaacga cctcctcggc   46680
gaccagtccg atggggacag tctggtcgcc cggcagctgg agtactggcg caccaccctc   46740
accggcctgc ccgaacaggt caccctgccc accgaccggc cgcggccggc caccgccacc   46800
taccaaggcg ccctgcacga cttcgcctgg gacgccgaac tccaccaagg cctgatagac   46860
ctggcgcgtt ccaccggtac gaccgtgttc atggtgctgc aggcggggtt ggcggcgttg   46920
atgagccgtc tgggtgcggg ggacgacatc cccctcggca gtccgatcgc cggccgtacc   46980
gacgaggccc tcgacgacct ggtcgggttc ttcgtcaaca ccctcgtcct gcgcacggat   47040
acttccggca accccacctt ccgtgaactc ctggcccggg tacgcgagac cgacctggcc   47100
gcctacgccc accaggacgt ccccttcgaa cacctcgtcg aaatcctcaa ccccgaacgc   47160
tccctcgccc accacccct cttccaggtg gccctcgccc tccacaacac accacccggc   47220
aacttcaccc tccccgacat caatattcat ggtcagcgcc tctcgactgg tacgtcgcgg   47280
tttgatgtgt cgctgcattt tgtcgagtgg cagcgtgagg atggtgcggc ttcggggctt   47340
ggtggcttcg tggagttcag tacgcgatctg tttgaccggg tgtcggtgga ggtggtgctg   47400
gagcggttgc ggcgggtgct ggtgtcggtg gcggcggatc cggatgtgac ggtgggtgct   47460
ctgccggtgc tgagcgggca ggaggagcac cggctggtgg cggagtggaa cgacaccgtg   47520
ctggaggtgc cgccggccag cctgccggaa ctgttccagg cccaggctgc cgaggcgccg   47580
gaggcgaccg cggtcgtctt cgagaccgag cgactctcct accgcgagct gaacgagcgg   47640
gcgaaccggc tggcgcacta cctgatcaaa cagggcgcgg gaccggaacg gatcgtggcg   47700
ctggccctgc cccgcggcac cgacctggtg atcgcggtcc tggcggtact caaggccgga   47760
gcggcgtatc tgcccgtgga cccggactac cccgccgaac gcatcaccca catgctgcac   47820
gatgccgccc cggccctcat ggtcaccacc agcggcgtgg ccgccggcct gccccacacc   47880
gaaggcgtca cctccgtcct cgtggatgct ccggccgtcg tcgaggcggt ggcggtgttg   47940
tcggcggatg atccgtcgga cacggaccgc ggtgtggtgc tggagggggtc gcatccggca   48000 tacgtgatct acacctccgg ttcgacgggt gtgccgaagg gagtgctggt tccccatgcg   48060
ggactggcga acctgacggc agcggaacgg gctgcgctgg acctgtccgc cggcagccgg   48120
gtcctgcaac tggcctcggt cggattcgac gcggcggtgc tggaactgag catggcgttc   48180
ggcagcggcg ccaccctggt catcgcgcca caaggccggc tgctgggcga cgacctggcc   48240
```

```
gcgctcctcg cccgccagga gatcacccac acactgatca ccccagcgc gctcgccacc      48300 ctgcccgaaa cggacctgcc gcacctgcgg acactgctga ccggagcgga agcctgcccg      48360
ccggaactgg tggcccgctg gtcgcccggc aggcgcttca tcaacgccta cggccccacc      48420
gaagccagcg tcgtcgccac ctggagcgat cccctcaccc aggacaccgc ccccatcggc      48480
cgtccgctgc ccaacacccg cgtctacgtc ctggatgcgg ggttgcgtgt ggtgccggtg      48540
ggtgttgcgg gtgagttgta tgtggcgggt gcgggtctgg cgcgtgggta tgtgaaccgt      48600
gctggtctga ccgcgtcgcg gttcgtggcg gatccgtacg ggccggcggg ttcacgcatg      48660
taccggaccg gggacgtggt gcgctggaac acctccggtg agctggagtt cgtcgggcgc      48720
gccgacgacc aggtcaagat ccgcgggttc cggatcgaac tcggcgagat cgagaccacc      48780
gccgccggcc atcccgccgt cgcgcaggcc gcggccaccg tgcatgagga cgacacccgc      48840
ggcaaacagc tcgccctgta tgtcgtgccc accggtctca cctccggtga cgtctccggc      48900
tctgtctccg gtgatgggc tgttcctgac ggtggtgtgt cgggtgtggt ggatgagcag      48960
gtgggtgagt ggcgggagat ttatgactcg ttgtatggcg ggccggggtc ttctgtgttc      49020
ggggaggatt tctcgggctg ggacagcagt tatgacggtg cggcgatccc gctggaggag      49080
atgcgggagt ggcgtgatgc cacggtggag cggatccggg gtctgggcgg gcggcgggtt      49140
ctggagatcg gggtggggac cggtctgctg atgtcgcgtc tggcggccgg gtgtgaggag      49200
tactgggcca ccgatctgtc gggtgtggtg atcgatgcgc tggacgggca tgtgcaggcc      49260
gatccggtgc tgcgggaacg ggtgcggctc gcctgccagc gggccgatga cacgcggggc      49320
ctgccggagg gctacttcga caccgtggtg atcaactcgg tggtgcagta cttccccggt      49380
gcgcagtatc tggcgtcggt gatcgaggcc gcggtgtccc ggctggcgcc gggtggccgg      49440
gtcttcatcg gtgacgtgcg tgacctgcgt actctgcgcg cgttccacac cgctgtccag      49500
ctcacccgca ccaccggcgg cagggctggt gacgggatgg acgcgggcgg actgcggcgg      49560
gcggtcgaac agggactgct gctggagaac gaactgctgc tggacccgga gttcttcacc      49620
gccgtgggcc gcacgctgcc cgcggtgtcg gcggtcgagg tgcgcctcaa acacggccag      49680
gcccacaacg aactcacccg ccaccgctac gacgtcatcc tccacaccac aaacacagaa      49740
acagacacag caacagagga agaagcagag gcagcgcggc ccacgaaggc agaggcagaa      49800
acgccggcac tggtcgaacg gatcagctgg aacactctgt ccggtggtct ggacggcctc      49860
gatgacctgc tgcggtctcg tggggctgcg ccgttgcggg tgacgggtat acccaacgcc      49920
cggctggcgg gcgagtacgc cgcgctgcgg gtcctggaga acggcggcac cctcaccgag      49980
gccgtcaccg cgctggccgg cccccgcggc atcgaccccg aacacctcca ccagctcgcc      50040
gccgccaccg gctaccacgc cgtgctccag cccgccccg ccccgacac ctacaacacc      50100 ctcctcctgc ccctcgatat tttcgacggc acggcatggt ccgccaccgc caccgccacc      50160
gccaccgatc tccgggaaac ctccgccccg gaccacaccg cggagacgtc cttccaggca      50220
ctggcgaaca cccggccgc ctcccgggac accagcacac tgatcacaca ggtccgtgac      50280
cacctgcgca ccaaactccc cgaccacatg gtgcccgccg ccatcgtcgt cctcgaacgg      50340
ctcccgctga ccgccagcgg caaactcgac cgccgggccc tgcccgcacc cgacctcggc      50400
acccacacca ccggccgcgc ccccgcagc ccccgcgagg aaatcctcgc cggcctgttc      50460
gccgaagtcc tcggcctgcc cgccgtcggc atcgacgaca gcttcttcga cctcggcggg      50520
gacagcatca tttcgatcca gctggtcagc cgagcccgca aggcagggct gaaggtctcg      50580
gccggtgacg tgctccgcta caagaccgtc tcggcactcg ctgccgtcgc ccaagatcta      50640
```

```
cacgctgagg cctcctacat cagcgatgac ggacttggtg acgttcctca gacccccatc   50700
atgcgttggg cgttcaaaca agaagacctc gttcatgggc tacatcaggc gatgctcttg   50760
gagacgcccg ccggtctgca gcaagctcag ctggtcgcca tcacccagac gctcctggac   50820
catcacgaaa tgcttcgtgc ccgtttagtc gtgaggagag cgaagaaag cgtcctgcgg   50880 gtggccgaag ccggggcagt ccgcgcggat gacctcattc agcaagtggc cgtcgccgca   50940 aactccgag aaaatctgcg cgattcgata tccgcagagt tctctgccgc acgggatcgc   51000 cttccccgg aatccggcag catgctccag ttggtgtggt tcaacagtgg acccaatcac   51060
gctggtaggc tgctcatcgt gatacaccat ctggtcgtcg acggcgtatc atggcgcatc   51120
ctcctttctg acgtggcaga cgcctgggaa gacatctcgg cggggcgtgc acccgttctc   51180
gaaccacgtc gcacgtcgtt caagcgctgg gcaaatgccc tgatctcgga ggcacatgcc   51240
cctaaacgtg ttgaggagat gcctctatgg atgggaaccc tcaccgattc tgggtgggaa   51300
tttgcttcga agcctaagga cgaaaaggaa gcgagtacgt ccgcgcagct caccctcact   51360
ctttcccctg agaagacaat tccgatcctc acagaggtcc ctgcggtctt ccacgggaaa   51420
atcaacgacg tcttgctaac agcctttacg atcgccgccg tcgaatggcg aagggtccac   51480
cgagcgacgt acgccggcac cgatgtactg ctgaatctgg aaggacacgg acgggagcac   51540
ttcgctgaag gtttcgatgt ttcccggact gtgggctggt ttaccagtat gtttcctgtg   51600
cggctcgacc caggcgaata cgatcgcgat gaggtccgga tcggcgggcc tgcactcggt   51660
aaagtcctga agaccgtcaa ggagcagttg cgatcccagc cggacaacgg cctcgggttc   51720
ggcctcctcc gttacctcaa taccgagact gcaacgaaac tgtgcggact tgcagtgccg   51780
caggtcagct tcaactacct cgggcgtttc ggcgcctccg tggtgccgg atgggtccag   51840 gcacccgaga gtgacatcgt ggccaacggg cagcacggcc cgctcgctca cctgctggag   51900
gtgaatgcgc tgactcgtga cggcgtagac ggaccagagt tgatcgcgac atggtcgtgg   51960
actcctggga ggttcacgga agctgaggtc ctagatttcg cggagaggtg gttcagcgtt   52020
ctgggttctc tcacaatcca cgcgtcggcc ccagacgcag gcggatacac accatccgat   52080 gtaccctcg tctcactatc gcaagaacaa atcgaactgc tcgaatccga atggaggca   52140 tcggaatgaa ggatccaggc ctggaggata ttcttccact cactcccctc caagaaggaa   52200
tattattcca tgcagccttc gatgccgagg acaggatcc gtacgtcata cagttgacac   52260
tcgaatttca aggcccattg aaggccaagg atctgcggtc agcggcacag tcgttgctgg   52320
agcggcattc aaacctccgt gccagctttc gctaccacgg cctggaccgc cctgtccaac   52380
tcatacctcg gcatgccgaa gcccctggg aggagatcga cctcagcaac ctgtccgccg   52440
cccttcgtga ccaggaggta tcgaaagctg tcgctgctga cctgcagcgc cggttcgatc   52500
tcaccaaagg gccgtccatc cgcttcacct tggtccgact cgcagaagac ctccacaagt   52560
tcgtgatcac ctctcaccac atcctcatgg atggctggtc gataccggtg ctgtttcgcg   52620
agttgttcgc ttgttatgca gccggaggcg caacgtcgat gcttccccg gcgcagccct   52680 tccgtaacta cctcgcgtgg tcggccaagc aggaccgcag ctccgcggag caagcctgga   52740
aggaagctct ttccggcctc gatcatccca cccgtctcgc tccccacagt cctgcacgca   52800
gtgttctgct accgcagcag gtgtctctca gcctgggtga ggaccttacg gagcagttgg   52860
gggcctgggc ccgcagtcga gacttcactc tgagccaggt tgtgcaggga gcttggggcg   52920
tgctactggg caggctcacc ggccagagcg atgttgtgtt cggtgccacg gtcgctgggc   52980
```

```
gcccgccgga agtagccgga gtggaatcga tgatcggtct cttcatcaac actctgcccg   53040
tcagactacg catcgttccc gacgaatcgt ttacggtatt gctgcgccgt catcagcgcg   53100
accaggagcg cctttttccc caccatcacc tcggcctcac tgatattcag cacgcagcag   53160
gcgtcggtca gttattcgac agtatcgtta tttttgagaa ctaccccaca aaaatcggct   53220
ccgaaaaaac aggcagcggt tcgctccgtg tgaccggatt cgaggcacac gacgccactc   53280
actatccgat aacgctgttc gtcattccag gtaagcgact gaacttccgt ttggactaca   53340
atgcggagta tttcgaccac gccacagtcc agacgatgct agaacggtta cgtcgtctac   53400
tggcatcggt agtgtccgat cccgaaccac aactaagcgg tctcaccttg ctcggcacgg   53460
aggaggaaca ccgcatactg acggagtgga acgacactcg actagaggtg ccggcggcgt   53520
ctctgttcga actgttccaa gcgcaggcgg tatccactcc ggatgcgacg gcagtcgtct   53580
ttgaggacac gagcgtcacc tacgaggagc tgaatgcgcg ggccaaccga cttgcgcact   53640
ggctgattgg ggagggcgtc ggaccagagc gagtggtcgc tctggccatc ccccggagtg   53700
tcgacctggt cgtggcggtg ctggcggtgt gaaggccgg agcggcctac ctaccgatcg   53760
atccggagta tccgcctgag cgcatcgcgc acatgctgac agactctcgt cccacgatgc   53820
tggtgacctc gtccaaagcg cgcaggacc tgccgaccgt ctctggcact cggtcagtgt   53880
gtctggatgg ccctgccctg atgtggtctc ttggaaccag caaggcgacg aatccgaccc   53940
acgtcgaccg cggcaaagcg gtcgatgccc ggcatccggc gtatgtgatc tacacgtcgg   54000
gctcgacggg gcggccgaag ggagtggtcg tacccacagg cagcgtggtt aacctgctca   54060
ccgccatggg cgattggttt cccgtgaccg gcaaggactg cctgcttgcc gtcacgacgt   54120
tcgccttcga catcgctact ctcgaattac ttctcccccct gctcaacggt gcccggctgg   54180
tgctgacgaa ccgtgaaacg gtgctggaat cgtccgcatt ggcagaagtg atcgcacggc   54240
acagcgtgac gatcatgcag gcaaccccca cttctggaa tgaattcgcc gccaacgagc   54300
ccgaagcact cacaggcatt cggattctca ccggcggtga agccttgagc gaaggtctgg   54360
ccggcagact ccaggcattg gccgacgatg tcaccaacgt gtacgggccc acggagacca   54420
ccatctggtc aacggccgcg gcgatcaccg cagctactgg cgttccgccg atcgggcgtc   54480
ccctggcgaa cacccaggca tatgtgctgg acgaaagcct tcggccagtg ccacccggtg   54540
ttcccgggga cctgtacctg gccggcgccg gtgtgggccca gggatatcac aaccgccccg   54600
ggctaactgc gcaacgtttt gttgccaatc cctatggccc aataggcgcc cggatgtacc   54660
agacgggaga cgtggttcgg tgggatctcg acggctacct ggagttcctc ggtcggtctg   54720
acaaccagat aaagattcgc ggttttcgca tcgaacctgg agagatcgtc gcagcgcttg   54780
agaggcatcc acatgttgcc gaggcggccg tcgcggtgca ggaaagaaag aggaatcaga   54840
agggcctggt cgcctacgtc actgccagtg atgggcaaga aattgacacc actgaattac   54900
gcaatcacct gtcggatatc ctagcccgac acgccatacc ttccgccttc gttgtcatga   54960
gtgaactgcc gcgcacttcg aacgggaaac tcgacagttc ggctctacca gcacctacgc   55020
aagaggcaac agcacaagga agagcccctc gaagccctca ggaagaaatc ctgtgtgaac   55080
ttttcgctga ggtgctggag attcctcgcg tcggagtcga cgatgacttc ttcgaactcg   55140
gcggtcactc cctcctggct attcggctca tcagtcgcat tcgcgatgcc ctcggtagta   55200
atctgacgat acgaagcctc ttcgaagcac ccacggtact ggcactcgcg cagcgcctag   55260
acatggacac cgcagacaat gcgttcgacg tgatgcttcc gatgaagtcc aacgcagca   55320
acccaccaat cttctgcata catcccggcg gtggaatcgg atggatttac gcccggctga   55380
```

```
tcgcgtttct cgggcacgaa cagccagtct acgcgattca agctcggggg ctggccaagg     55440
aggaaccgct ccctgagaca atcgaggaaa tggctgagga ctacgtcagg gagatccggt     55500
ctatccaggc atctggtccg taccatcttg tcggatactc cttcggcggt ttggtggcgc     55560
aggccatcgc aacgagactt cagcaggacg gagacaaggt cggagtactg ggcttgatcg     55620
aggcgtatcc cgccgaagga atggccggca gtgaacgtcc agagatttca gagcaagaaa     55680
tcctggaagt gatcgcagag agcattgaca aggccgagga aattaaggcg aaagatcgcg     55740
cctttgagcg gatggagacg gaaggcatca ccttcgagca actcattgaa ggtgctcgcg     55800
cccgcggtag tgtcctgtcg gctttggata ggcgccatgt cacggccatg ccgacatcc      55860 atgccaactg tctacatctc aggcacaact tcaccccttc ctgttacgac ggtgatgcac     55920
ttctcttcag gtcgacactg actccgaata caccttcccc ggatacatgg cgaccgttta     55980
tcggcggccg gatcgaaacg agggaaatcg ccgccctaca ccaccagatg cttcatcctg     56040
aaccactcgc tgccataggg aaaatcctgg cggaagagct ccgaaaaacc caccacgaat     56100
acgaggaaaa atcgaaatga acaacccatt cgaagaccct gaaggcacct acaaggtact     56160
gatcaacgga gaggcccagt attcgctatg ccaacgtcg atcgacgtcc ctgcgggttg       56220
gaccatcgtt catggtccgg acagtcagca ggcctgcctc gatttcgtcg aggaaaactg     56280
gactgacatg cgccccaaga gcctaatcga agctatgaac gacacggtca gctgatcgct     56340
cgtgatacct gggccgggtc ggcccgcggg ctcacgctcc cggccggacc cggcctctct     56400
ggctagcgac catcccactg aaaggaacag attatgcagc tcacggccga tcaggtcgaa     56460
aagtacaaga gtgacggtta cgtccttctt gaaggtgcct tctctccgga ggaggtgcat     56520
gtcatgaggc aagccctgaa gaaggaccag gaggtgcagg gaccccatcg aattttggag      56580
gaagacggcc gcaccgtacg agcgctgtac gcttcgcaca cacggcagtc agtattcgac     56640
cagctcagcc gctcggatcg actgcttgga cccgcgacgc agctcttaga gtgcgacctc     56700
tacatacatc agttcaagat aaatacgaag cgggcgttcg gtggtgattc ctgggcctgg     56760
catcaggact tcatcgtctg gcgggatacg gatgggctgc cggcgccacg cgccgtgaat     56820
gtcggagtat tcctcagtga cgtcaccgag ttcaacggac cggtagtgtt cctcagtggc     56880
tcgcatcaac gcggcactgt cgagcgcaag gctcgggaaa cgtctcgatc cgaccaacat     56940
gtcgacccgg acgactactc gatgacacca gccgagctat cacagatggt ggaaaagcat     57000
ccaatggtga gcccgaaggc cgcctctggt tcagtcatgc ttttcatcc ggagatcatc       57060 cacggatcgg ctcccaacat ctctcccttc gcgagggatc tgctgatcat cacgtacaac     57120
gacgtcgcga atgcaccgaa gcccgcaggt gagccgcgtc ctgagtacgt catcgggcga     57180
gacaccacgc ctctggtctc caggagcgga ccgctgcatg aggccgccga atcgaggctg     57240
gcatgagcga taggtctccg tctgtggtaa ccctggtgt ggcgtccggc ggcatcactg       57300
ccagagccgc ggtcctggaa tccttccaga agccgcttac cgtacgacag tttcccgtac     57360
ctgcccccag tccgggagaa atcctggtcg acgtacgtta cggcgggatc tgcggaacag     57420
acctccacct gcagctaggg caccttccga tccctgttcc gcttgttctg ggccatgaag     57480
ggttgggcag catccggagg ctcggacgg aaggtctcac ggacgccaat gggaccgaac       57540
tgcgtatcgg cgacacggtg atgtgggcct cgtccatcgc ctgcggctct tgtggcccat     57600
gtcggcaaca tcgagagccc acgctctgcg aatcacgccg acatatggag tcaatcggc       57660 aagtcgaggg cgattccggt ctgttcggcg cctggtccga aaccattctt ctccatccag     57720
```

-continued

```
gcgcgacagt ggtgcggctt ccgcagtctg tggatcccct tggctgccatg tctctggcct   57780
gcgccggccc cacgctaatc cacgccctt  acgaacgccg acccgtaaga gtaggagaga   57840
ccgtcatcgt tcagggcagt ggccccgtcg gcatggcagc cgccgcgctg gctcaactgt   57900
ccggcgccgc catggtcatc ctgctcggtg gccacaaca  gcgtctggac ctcgcccgac   57960
agtgcggtat cggggacgtc cacctgaaca tcgccgatag gtcggacacc acatcggcac   58020
tcaacgaggc ccgcgagatg acgcgaggag gactcggtgc cgatttggtc atcgagtgtg   58080
caggtgtacc tgaggccgtc gcccaggggg tctatctggc ccggcgcggt gggtcctatc   58140
tcgtcgtggg ccagtacacg gacagcggag agacgctgtt caaccctcat cagttggtct   58200
accggcaact agaggtcgtg ggttcgtggg ccttcaccgg agctcacctg gtccactacg   58260
tcaatctcct gccctctctg ctcgagcgat tcgatctacg ccgtctggtg acggagttcc   58320
ctctcggtga ggtaaacgac gcgatggtag ctgtcggcac cggcgaggtg gtgaaggcag   58380
tactggaaag ccggcacctt cccacggtcg ataccctgagc agtgatcact ttggaggcag   58440
aaatatgcca attgccacgg tgaacgagac ccaattgcgc tacgacatcc acgggtcggg   58500
agagcccgtc gtgatggtga tgggcagcgg aagcggcggc cgtgtttggg agatgcatca   58560
ggtgcctgct ctggtggccg acggctacca ggtcgttaca ttcgacgatc gcggcgtctc   58620
gcaaccggag gatatcgagc cctacggtct cgacgacatg gtggccgacg tggcagcgct   58680
cgtcgatcac ctgagtctcg ggccctgtcg attcgttggt acgtctctcg gagcgctgac   58740
cgtgcaggaa ctggccatac ggcgtccgga cctggtatcc gagtctgttt tgatggccac   58800
tcgcggacgt actgacacac tgagcggggc catctccaag gccgagatcg atctcatcga   58860
tgagagtgca aagattcccg ttcgctatca ggcagttgtt caggctttgc tgaacctgtc   58920
gcggaaaact ctacgaaacg aacaagaact gcgggactgg atcgacatcc tggagatgtc   58980
ggggcctcag ccctcagggc tgcggtcaca actggaggca tcgttgatcg aggaccgact   59040
ggaggctctc aggtctacgc gtgctcagac tctggtcatt gggttccagg acgacctcat   59100
cactccgcca cacctcaacc gccaagtggc tgaggccatc cccggtagta cctacatcga   59160
agtggccgat tgcggccatt acggatacct ggagcaacct gatgtcgtca acaagcacat   59220
actcgacttc ttctccaagg gatgactcga aggatgcgct atggcgtcgt gattctccct   59280
gaacacagct gggccagagc ccaggacctg tggcgaaacg tggaggatct tggtttcgat   59340
cacgcttgga catatgacca tttgcagtgg cgatggctga gcgacaggcc ctggtttggc   59400
gccataccga ccttgaccgc cgcagccgtg gtcacatcac ggatcggact gggcacactc   59460
gtggccagca ccaaactgcg ggacccagtc atgctcgcca aggagatcat gacccttgac   59520
gacatctcgg gcgccgaat  gctgtgcggc gtaggttcag gcggcccga  tcggatctc   59580
ttgcaggcct acgaactcac gcgacgccag ttgaccgccc gctacgggga gttcatagag   59640
ttgttggact cactgctgcg ccaggagcca gtagtcttcg agggcaccta ttacacgtgc   59700
cgcaacacgt tgctgcagcc agcctgcctc cagcgacctc gcgcccctct ctgtgtggcg   59760
gcggccggcc cgcagggaat gcggctcgca gctcggttcg cggatatctg ggtgacgatg   59820
ggggcgccga acatgttcga cgaggctccg tatgccgact cggccatgct catcaaggat   59880
caggtcgctg cgctggagca gacgtgccac gaggttggac gtgatcctgc gagtctcagg   59940
aggctcctgg tcaccggccc ctcgatcggg ggcgtcctcg actcggtcgg ctcttttccag   60000
gacgcggcgg ggactttcca ggaggtaggt atcaccgacc tcgtcgtcca ctggcccgcg   60060
cctgactttc cataccgagg cgaccccgcg gtcatggagg acatcgcaag tatcctgccg   60120
```

```
accgcaccag ggaaattgta aacccgcagg ggtgtgcgga attcctccca tcaagtggaa    60180
agcagagcaa ggtcggggcc ttgccggcag acggatcggg caatataccg gacttcaccc    60240
cgggccacgt cgcgctggcc ggagaaacag tcatccgcga atggcgcagt actcagccct    60300
caagtcgatc ggggcgcatc tgctccggcc atccggggcg gccaggctcg cgaacagtcc    60360
agtcaagttg gggagtggag caacaccgcc cacgtctgtg gcaccgtcg atatgtccac     60420 catcttcggc tctggcgtcc aagccgtcga cagcagatgg atgactcttg atccatacag    60480
agccctccga ggtccagctg acgccgggtg cgagtgacgg ccacgtaggc gaggcgtgcg    60540
tccgtgtcgc tcaccgcttc cgggagcggg cggccgctgg cgtcctgctg gtcgctgtcc    60600
ggcggtgggg gaagtcgtcg gcggttctga cttcgggtca ctcccggccc tttgccttgt    60660
gagccgtgga caccgtcacc tcggcgttgt tctcgtcggt cagcgcgtcg acggcggcga    60720
tgacagcttc gggaccatgg gtgtcgacga gttcaacgaa cggctggagg tctcggccga    60780
cgggatcgta ctcggcgtag tcttccaact cgccccagga ggcgaagagg accagtcagg    60840
aggggaggtg cgacggccgt cttttgaggtc cctggcggcg agcgccagtg caacgagtgt    60900
ctgtccgccc ctggccagag ccaccggacg gccaggctgc tcggtgatca ggcagggtcg    60960
ggagacaggc acctactgcc tgtgtccgcc tggtatgcga gagttcagga cctggtcgtg    61020
agcagccgcg cgagggcatg accctcggta ctccgagatc cgacgccggc tccgtgtgtg    61080 gtggggtcg agcgccgccg cgtgccggac gtctgttccg cccttcccgg ggcccctgcg     61140
cggtcaggcc gcagtgctcg cggccttcgg ccgggcggcg ttcacctggc ccatggctcg    61200
gtcgatcgtg atctcgatga ccacccgctc cgggtccgga gccggcgtcc gcccgtaccg    61260
gtccgcgtag cgggccacgg cgtcggcgac cgctgccgcg tcggtcagga cttcggccgt    61320
gccttccagg gtggcccagc ggcccccatc gacctgacag acggctgcgc gggcttcgcc    61380
ggggcgggac gcctgatgt tggcgaccttt cctgcttgat ttgcgtgtga taacgcgtgc    61440
gactcccgcg tcgacatcaa gggtcacgcc gacgggcact catgcgcgac ttccgtcgga    61500
gcgaagcgtg gtgagggtgc acaagtggta ctcattccag aacgctgagt actcagggat    61560
ctggctgaat atgtcgctag gcatacccgt gagcgtaacg cggactactg cacagattgg    61620
cgcagaagtg acctcttcca cacacctgcc cgcaagacca tgcctcggtg agatgcgcac    61680
tttgcggctg aatgcccacg ttatgatccc gctaaatatc tcaaaaacat aacggaagcg    61740
tgtgtcggtc gggttggcat gaccaatatg accgcaagtg aatcagcagt tcagcgccgt    61800
gatcgggaat cgggaatggt cgatttgatg agttttgcca gaggtggcga agtcttcctg    61860
tcgtgccttg aggtgtagct tttcggcctt gatctcatgc gggcctgacg tagggtccaa    61920
gactgttccc acagggcttc attcgttcgc ttgaccgttc cgctagcga tttcacgagt     61980 tcggagaggc tcttgcgtgt cctcgcggct cgctagccga ggtcggcgtg caccgtgtgc    62040
ggtgcacctc tcggtgcttg cgatcaccte catgagcgcc gtttgggac tcgaacatcg     62100 ttgaccgtg gtgctggcg cccggctctc agcaagagcc ccgatcggcc ggtacgaagg      62160
gattgctcaa tgtctccggg agacagtcgt cgcgtcgctg cggaatccac ggttcccgcg    62220
cgggagaagg taagctgtcg gcggttgggg cgtggcgta cagctgcgag gcggaccgtg     62280
gagcgcgacc tccaccgccg actgcggcag gagctgcgcg acctcggcat ccacccaccc    62340
ctggacgtag aggaactggc caaggcgctc ggcgagaggc gcgacgccc gatcgtcctg     62400 cgtcccttcc cgctggagaa gccagggccc tcggggctgt ggatcgatac gccgcagatg    62460
```

```
gacgtgatcc tctaccagca ggagacgacc cggctgcacc agcggcagat catcctccac   62520
gagatcctcc acatcctcgt cgccgagtgg gaagaggacc aggccgagga ggcgcccgag   62580
gaatccccgg acgacttcgt cgagggttgg gcgaccctca ttcccgtact cgatcccaaa   62640
ctgatccggc gggtcgcccg ccgttgctcc tatgaggacg aagaggagtg ctcggtcgag   62700
ctcgcggcca cgatcatcct cgagtggtcc tcagtgctcg acgaactccc tccgctctcg   62760
gaagacccgg aggtacgtcg tgtgcagtcc gccctgggcg accggcgagg gtggctgtag   62820
tccgtgagcg agatactcct gctggtcatc gcggccgccg tcgtgtggag gctctacctg   62880
tggtcccggg ccccgcatga cgctcccacg aggtcggtcg ccctctgcct gctgagtgcg   62940
gggctgtcgt accccgtggc catgccgggc ggcaccaccg gcatcgacac cgtggccggg   63000
cacggcacgg cgaagctgct gcagaacgtc cttctcctgc tgacggtcta cttcctgatg   63060
tgcttctacc tgtactcggc cgacgggtcg gtggcgcgac gacgtgcgcg gtgggaagcc   63120
gtcgtcgtgt ccgtggtcgc tgtggcgatc atcctggcgg ccgtgaccgt gccgcacgag   63180
gacttcgccg gctcgttcag cacgcggac atgacgatcc cgcagatcgc cttcttctac   63240
gccggcgcgg gtctgtacct gatgtacgcg ctcggcgctg cgggacggtg gaccgtccgt   63300
tatgcccgca tgtcgagcag gccgcacgcc accgggctgt ggatgaccgc gatcggtctc   63360
ggcgccatgg cggtggcctg cgccgtccgc gcggtcttcg tcgccgtccg gtggagcggc   63420
ggaaccgttc cggaccgact catggctggc gtggcgttct ggctcgtcgt gtcgatcctg   63480
ctcttcgtcg cgggtgtcac ctattcggcg acccgctcca ggatcacggc cacccggctg   63540
tggctacggc gtcgccgtga tcaccgtcgg cttagcccgc tgtggcaact gctggccgag   63600
gtctacccgg agaacgaact gcgccccgcc tcccgagggc tgtgggaccg gtggcgtgcg   63660
cgcggcgtgc accgtcgcta ccaccggcgg atagtggaat gccgggacgg tctggtcgac   63720
atcagcccct atctggtcga cgagaacggc gacgccgacc tgctccgcct ggagccggcg   63780
gaactcgcga gcagactgcg gcaggccgcc gacatgatcc ggcagggttc ccggcgcct   63840 ggacaggcgg tgccgctcgc ggtgccgaag gaggacgacc gggacgcgga cgtccgtcag   63900 ctgatcgcg tgtcggaagc actccggctg accgcgtgac cggggaagaa cgagggagac   63960
gtaacgagat gctgatcacc gccagccggg tcctgaccgg ctccgggacg cacctggagg   64020
acggcgccgt cctcgtcgaa ggcgactcga tcgccgcagt cgggcggcgc gcagaacttg   64080
ccgaccgcgt cggcgcggat gggaagcacc tggcgttttcc cgacgcgaca ctgctgcccg   64140
gactgatcga cgcccacgtg catctcgcgt tcgacggcgg cggcgacccg gtggccaccc   64200
tcgacgagtc gagcgacgag aagctgttgg aggacatgcg ccgacgcgcg gagcaactcc   64260
tgtccagcgg ggtgacgacg gtccgggacc tgggcgaccg ccacggcctg gccctccgcc   64320
tggatgaaga gatcagccag ggcggcactt ccggcccgcg catcgtggcc gcgggcacac   64380
cggccactcc tcctggaggg cattgtcact tcctgggtgg cgaggtctca ggcgtggacc   64440
aggtccgcga tctcgtacgg cgcaacatcg cggcgggcgc cggcgtgatc aaggcgatgg   64500
tcaccggagg cggcctgacc aaggacgggc cgaagagctg gcagagccag ttcagtccgg   64560
acgaactcca ggccttggtc gacgaggccc accaggccga cgtgccggtg gccgctcacg   64620
cgcacggtac ggacggcatc accgcggcag tcgaagcagg cgtcgacacg atcgagcact   64680
gcacctggat gaccgccgac ggctttgacc tccgccagga cgtcctgaag cagatcatcg   64740
atcgggacat cgcggtctgc ccggccgtca gccctcactg ggagatgctg ccccgcttct   64800
tcggggagga gcgggcggcg gccatgttcg atctcgtacg gcagatggcg gaggccggcg   64860
```

```
ccaagctcat cgctggcacc gacgcagggg tccagcgcgc cgggttcgac ggcctggtcc    64920
ccgccctttc cttctacgcg caccttggcc tgtcgaacag caggatcctc gacatggcga    64980
ccgccgacgc ggccggtgca ctagggctgg gcgagacgac gggccggatc gctccgaggt    65040
tccgcgcgga cctgctggtg atcgacgag accctctgga agacctcagt gcgctaaaga    65100
tggtccgggc cgtggtcgcc gctggccgcc tcctcgagcc gggcaggacg gcagaacagc    65160
agtagcaacc gtgcctgtcc gcaggccgtg agctgcggac aggcgctact cgttcgcgcc    65220
cgtttccttc tcctccagtt ccgccaccaa ctcgttgacg agtgccatcg ccttcggcga    65280
caggccctgc gcgcccaggc cacgagcctt gacccggccc acggccccct tcttggcggc    65340
tgccagtagc tggaggccct catagacctg agcggccacg gcgtcgtccg gcttgaagta    65400
catcctcgag acaccgatga cgtcggccag tgcgtccaga acctcagggg cagcggtctc    65460
agccacgccc gtacggagat gccggaagcc ctcctcggtg aggatctgct ccccggcgct    65520
ggcgttcacc gcgcttgcca tctccgcatc cgacggtggc cctggaggac tgggatacga    65580
gctgttcagc agcagggtga tcttctcggt cagcgatccc ggagcagcgt cagcggctgg    65640
ggccctcttc gcctccgacg gcgcagatcc ctcgaccggc ataccctgcg ccttggcgat    65700
cgaccggtct tccgcccgcc gcagttcgac ctcgctgacg ccgtatgccg cagccagagc    65760
cgggatgtac ttgtccttga gccgccgctc accgcgctcg gcgcctgcca ctggcccggc    65820
gctcttggtt ccgatcagcg tggccgtctc gtactggtag tagccggcat cgcaccgcag    65880
atcagtcaga tcgggcggcc cggaccgcgg aacagatca tctacatcgt ggccgacagc    65940
acgcgccagt gcaggcagct tctcagggtc cggagtctgg gcaccgcttt cccagctagc    66000
gaccgccgag tcggatacgc ccagcacctc gcccacggca gcttgggatt tctcggcggc    66060
tcgccgcacc gtacgtagac ggctccggtc gaagtgacga gcagacatcg aaccctcgtt    66120
ttttgtgcaa gctggaggtc gtccagtgtg ttgactttt cttcaggcgg gaatagcttc    66180
agcttagcga agggcgggtg tggtttgcac ccctgctcga tcttcgtgtt cgcgccctgt    66240
cgaggctctc gggctgaggg agggagcgag gggagcgcaa ccgtgacgtc ctgtgcgtga    66300
agcgcctcag tgggaagcgg cgccggcgag ttcgcctctc gggcgtcgga aagtgcgcga    66360
cttcgctccg gaagagggcg gagtcgtact tcggtcactc catgcccttg aacggtacgc    66420
gcgagtggct gtcgcgtgag gagtgtcgta tgtctctgct tcaccaaacg gtcgtcggta    66480
aagccgtccg gctcgaatgc aaggcgcctg cagagattcc gtcgacgctg atcctcatgc    66540
tctgcagcag cttagaaaac aggtgcgggc gtggattccc gtcgaggact gtgtcctgac    66600
gcccaccaac ccagcgatgt atgtcgagtt ggcgtcgaat cggctcagta cccgctgtca    66660
gctggagtgt taaccatcct ctgcatatgt tgctgctccc tcggcggaac agccgaaccg    66720
aagcctctca agggagaaac gcgaaaaccc catccaacgt caagtccgcg gatttcaggg    66780
ggaaatgacg cggcgcccag gagttagcag ctcccgggcg ccaagcccgc caccctgagg    66840
gcgcggattc ataaccgggg cgagtcgg                                       66868
```

<210> SEQ ID NO 2
<211> LENGTH: 412
<212> TYPE: PRT
<213> ORGANISM: Streptomyces DSM 22643

<400> SEQUENCE: 2

Met Ser Glu Asn Leu Thr Leu Gly Asp Arg Leu Arg Ile Ala Arg Arg
1               5                   10                  15

```
Thr Arg Lys Leu Ser Ala Ala Gln Leu Ala Gln Lys Val Ala Val Ser
         20                  25                  30

Pro Ser Tyr Val Gln Lys Leu Glu Ser Gly Ala Arg Lys Ala Ser Pro
             35                  40                  45

Ser Leu Val Leu Ala Leu Ala Lys Ala Leu Arg Phe Gly Pro Glu Val
 50                  55                  60

Leu Thr Gly Gln Pro Tyr Tyr Gly Pro Glu Ala Glu Asp Gly Val
 65                  70                  75                  80

His Ala Val Ile Pro Glu Leu Arg Arg Leu Leu Cys Tyr Asp Ser
                 85                  90                  95

Pro Asp Asp Leu Glu Ile Ala Pro Arg Ala Leu Pro Val Leu Ala Ser
                100                 105                 110

Glu Val Asp Gln Val Ala Ala Leu Arg Arg Asp Ala Arg Tyr Ala Pro
            115                 120                 125

Met Gly Pro Leu Leu Pro Pro Ile Ile Thr Glu Leu Thr His Val Ala
130                 135                 140

Leu Gly Gly Asn Asn Gly Asp Arg Gly Lys Ala Phe Trp His Leu Ala
145                 150                 155                 160

Arg Ala Tyr Arg Ala Val Asn Ser Leu Ala His Lys Met Gly His His
                165                 170                 175

Asp Leu Ser Asn Thr Ala Leu Glu Arg Val Arg Trp Ala Ala Asp Arg
            180                 185                 190

Ser Gly Asp Pro Leu Met Gln Phe Thr Ala Gly Tyr Leu Val Ala Gly
        195                 200                 205

Ala Met Leu Arg Gln Gly Ala Tyr Ser Pro Ala Arg Arg Lys Leu Leu
    210                 215                 220

Gly Leu Arg Thr Glu Leu Glu Arg Phe Gln Pro Glu His Ser Phe Thr
225                 230                 235                 240

Glu Asp Ala Leu Ala Val Asp Gly Ala Leu Leu Leu Lys Leu Ala Val
                245                 250                 255

Leu Glu Ala Arg Glu Asn Asn Ser Asp Arg Ala Asp Ala Tyr Leu Arg
            260                 265                 270

Glu Ala Glu Gln Val Ala Thr Met Ala Gly Asn Arg Asp Ser Leu Ala
        275                 280                 285

Tyr Glu Met Ser Phe Gly Pro Thr Asn Ile Arg Ile His Glu Val His
    290                 295                 300

Ala Met Ile Asp Thr Gly Asp Thr Glu Gln Ala Leu Ala Arg Leu Val
305                 310                 315                 320

Glu Trp Ser Pro Val Ser Gly Gly Glu Trp Ala Pro Pro Ser Thr Thr
                325                 330                 335

Val Gly Glu Arg Ser Ser His His Phe Ile Asp Val Ala Ser Ala Lys
            340                 345                 350

Leu Ala Glu Gly Asp Arg Asp Gly Ala Phe Ala Asp Leu Lys Arg Ala
        355                 360                 365

Arg Lys Val Ala Pro Asn His Thr Arg Phe His Pro Ser Val Arg Glu
    370                 375                 380

Thr Thr Ala Ala Leu Leu Arg Met Asp Ala His Pro Ser Asn Glu Leu
385                 390                 395                 400

Ser Ala Phe Gly Ser Trp Thr Gly Ile Ser Thr Thr
                405                 410

<210> SEQ ID NO 3
<211> LENGTH: 146
```

-continued

<212> TYPE: PRT
<213> ORGANISM: Streptomyces DSM 22643

<400> SEQUENCE: 3

Met Ser Asp Asp Asn Pro Ala Arg Ala Asn Pro Pro Arg Trp Met
1               5                   10                  15

Pro Ile Gly Glu Glu Pro Glu Leu Cys Ser Ala Gly Glu Trp Trp Asp
                20                  25                  30

Ala Val Arg Ala Val Glu Ala Val Gly Arg Arg Ala Ile Glu Ile Leu
            35                  40                  45

Gly Glu Gly Asp Glu Pro Val Gly Pro Val Ile Leu Asp His Gly Gly
        50                  55                  60

Pro Glu Pro Arg Leu Tyr Phe Leu Val Pro Val Gly Thr Ala Ala Arg
65                  70                  75                  80

Trp Glu Glu Pro Gly Thr Val Ala Leu Gly Gln Lys Cys His Val Val
                85                  90                  95

Val Pro Ser Ala Glu Ser Thr Thr Pro Pro Gly Met His Trp His Val
                100                 105                 110

Phe Pro Gln Gly Pro Arg Ser Leu Thr Arg Pro Asp Ala Leu Arg Arg
            115                 120                 125

Ala Leu Ser Gln Ala Arg Arg Glu Arg Arg Gly Pro Ala Glu Glu Ala
        130                 135                 140

Ala Cys
145

<210> SEQ ID NO 4
<211> LENGTH: 64
<212> TYPE: PRT
<213> ORGANISM: Streptomyces DSM 22643

<400> SEQUENCE: 4

Met Ala Leu Ser Ile Ser Leu Val Leu Val Leu Gly Ile Val Val Val
1               5                   10                  15

Leu Leu Val Arg Ser Lys Ala Val Lys Pro Gly Pro Ala Ile Val Cys
                20                  25                  30

Val Leu Phe Gly Phe Pro Leu Ala Ser Thr Ser Ile Ala Pro Asn Ile
            35                  40                  45

Asn Arg Phe Val Thr Gly Val Ala Asp Met Ile Gly Gln Ile Ser Phe
        50                  55                  60

<210> SEQ ID NO 5
<211> LENGTH: 334
<212> TYPE: PRT
<213> ORGANISM: Streptomyces DSM 22643

<400> SEQUENCE: 5

Met Arg Leu Val Tyr His Pro Ala Gly His Asp Asp Leu Arg Thr
1               5                   10                  15

Ala Leu Val Glu Leu Gln Ala Gly Arg Trp Lys Ser Ala Arg Gly Leu
                20                  25                  30

Leu Trp Glu Thr Gly Thr His Trp Pro Leu Arg Thr Ser Arg Thr Gln
            35                  40                  45

Leu Leu Ala Val Ala Ala Arg Ser Asp Val Val Asp Val Trp Leu
        50                  55                  60

Val Glu Glu Pro Asp Ser Tyr Asp Ala Gln Leu Met Ala Val Arg Val
65                  70                  75                  80

Ala Val Glu Arg Ala Leu Arg Ala Gln Arg Gln Gln His Pro Arg Thr

```
            85                  90                  95
Leu Glu Phe Glu Thr Arg Ala Arg Ala Ala Leu Leu Ala Ala Arg
            100                 105                 110

Arg Ala Pro His Asp Pro Val Pro Trp Val Cys Leu Val Leu Ala
            115                 120                 125

Gln Ile Asp Thr Gln Gln Leu Arg Gln Glu His Arg Met Arg Pro Asn
130                 135                 140

Glu Pro Met Leu Pro Ser Gly Pro Trp Gly Leu Leu Tyr Glu Val Asn
145                 150                 155                 160

Gln Arg Asp Pro Tyr Asn Arg Glu Ala Tyr His Arg Val Leu Gln Phe
                165                 170                 175

Leu Leu Ala Leu Glu Gly Pro Trp Gly Ala Ser Leu Ala Ala Val Phe
            180                 185                 190

Asp Phe Gly Arg Ser Val Ala Ser Gln Arg Pro Val Gly Ser Pro Leu
            195                 200                 205

Leu Leu Leu Pro Ala Tyr Ala Gln Ile Glu Gln Arg Arg Gln Ser Arg
210                 215                 220

Ala Asp Pro Leu Trp Arg Arg Gln Trp Ala Gln Glu Ser Thr Leu Asp
225                 230                 235                 240

Tyr Thr Leu Ala Ala Phe His Asp Trp Phe His Lys Ala Pro Val Gly
                245                 250                 255

Gln His Ser Val Ala Asp Leu Asn Leu Leu Ala Tyr Ala Leu Trp Ala
            260                 265                 270

Gly Ala Gln Tyr Leu Glu Ala Ala Glu Val Phe Glu Val Met Gly Pro
            275                 280                 285

Tyr Ala Ala Arg Glu Pro Trp Ala Ser Val His Glu Gly Ala Ala Gly
290                 295                 300

Pro Asp Pro Gly Glu Ala Leu Leu Leu Arg Ala Arg Ala Glu Ser Leu
305                 310                 315                 320

Ser Tyr Ala Arg Asn His Arg Pro Arg Ala Gly Pro His Leu
                325                 330

<210> SEQ ID NO 6
<211> LENGTH: 506
<212> TYPE: PRT
<213> ORGANISM: Streptomyces DSM 22643

<400> SEQUENCE: 6

Val Ser Arg Leu Ser Pro Asn His Arg Ala Thr Ser Arg Lys Pro Asp
1               5                   10                  15

Asp Ala Tyr Leu Arg Glu Leu Gly Tyr Glu Pro Val Leu Thr Arg Arg
            20                  25                  30

Met Gly Pro Phe Gly Asn Phe Ala Ile Ser Phe Ser Val Ile Ser Val
            35                  40                  45

Leu Ser Gly Cys Met Thr Leu Tyr Gly Phe Gly Leu Asn Thr Gly Gly
        50                  55                  60

Pro Ser Val Met Leu Trp Gly Trp Leu Ile Gly Ala Met Val Thr
65                  70                  75                  80

Phe Ile Gly Ala Ala Leu Ala Glu Val Thr Ser Ala Tyr Pro Thr Ser
                85                  90                  95

Gly Ala Leu Tyr Tyr Gln Ala Glu Gln Leu Gly Gly Arg Lys Trp Gly
            100                 105                 110

Trp Tyr Thr Gly Trp Leu Asn Leu Leu Gly Leu Leu Gly Ala Ile Ala
            115                 120                 125
```

```
Gly Ile Asp Tyr Gly Ala Ala Leu Phe Thr Gly Ala Leu Leu Asn Leu
            130                 135                 140

Gln Trp Gly Phe Glu Pro Thr Pro Gly Gly Thr Met Val Ile Phe Leu
145                 150                 155                 160

Cys Ile Leu Ala Leu Asn Leu Phe Gly Val Arg Leu Val Ser Ile Leu
                165                 170                 175

Asn Ser Ile Ser Val Trp Trp His Leu Gly Gly Val Thr Val Ile Val
            180                 185                 190

Gly Ala Leu Ala Ile Val Pro Ser His His Gln Ser Ala Asp Phe Val
        195                 200                 205

Phe Gly Glu Phe Val Asn Asn Thr Gly Trp Ser Ser Pro Leu Tyr Val
210                 215                 220

Ala Val Leu Gly Leu Leu Leu Ala Gln Tyr Thr Phe Cys Gly Tyr Asp
225                 230                 235                 240

Ala Ser Ala His Leu Ser Glu Glu Thr Thr Asp Ala Gln Val Ser Ala
                245                 250                 255

Ser Arg Gly Ile Ile His Ala Ile Gly Trp Ser Trp Leu Ala Gly Phe
            260                 265                 270

Val Leu Leu Ala Gly Leu Thr Phe Ala Ile Gln Asp Tyr Ala Gly Thr
        275                 280                 285

Val Gly Thr Ala Thr Gly Val Pro Pro Ala Gln Ile Phe Leu Asp Ala
290                 295                 300

Leu Gly Val Ala Gly Ala Lys Ala Leu Leu Val Val Ile Ile Ala
305                 310                 315                 320

Gln Leu Cys Cys Gly Asn Ala Glu Thr Ala Ala Ser Arg Met Val
                325                 330                 335

Phe Ala Phe Ser Arg Asp Gly Ala Leu Pro Gly Ser His Leu Trp Arg
            340                 345                 350

Gln Val Asp Arg Arg Thr Gly Thr Pro Arg Met Ala Val Leu Leu Ala
        355                 360                 365

Val Val Cys Ala Ala Val Leu Ala Leu Pro Ser Leu Tyr Ser Pro Val
370                 375                 380

Ala Tyr Ala Ala Ile Thr Ser Ile Asn Val Val Gly Ile Thr Pro Ala
385                 390                 395                 400

Tyr Ala Ile Pro Ile Tyr Leu Arg Ile Lys Asn His Asp Arg Phe Arg
                405                 410                 415

Pro Gly Pro Trp Asn Leu Gly Asn Trp Gly Val Ala Val Gly Thr Ile
            420                 425                 430

Ala Val Val Trp Val Val Phe Val Thr Val Leu Phe Cys Leu Pro Gln
        435                 440                 445

Thr Arg Pro Ala Glu Gly Gly Leu Val Ser Val Glu Thr Phe Asn Tyr
450                 455                 460

Ala Pro Ile Ala Leu Leu Val Val Leu Val Leu Ala Trp Gly Trp Trp
465                 470                 475                 480

Arg Lys Gln Gly Ser Ser Tyr Glu Val Pro Ala Gln Asn Phe Asp Arg
                485                 490                 495

Ser Thr Ala Thr Tyr Glu Asp Glu Val Val
            500                 505

<210> SEQ ID NO 7
<211> LENGTH: 479
<212> TYPE: PRT
<213> ORGANISM: Streptomyces DSM 22643

<400> SEQUENCE: 7
```

-continued

```
Val Met Thr Arg Thr Thr Thr Gly Asn Gly Thr Val Ala Arg Leu Ala
1               5                   10                  15

Ala Ala Pro Gly Pro Glu Gln Gly Gly Arg Ser Gly Lys Gly Ile Ser
            20                  25                  30

Leu Ser Asp Leu Arg Asn Leu Val Lys Ala Gly Ala Ile Asp Thr Val
        35                  40                  45

Leu Leu Ala Val Pro Asp Leu Gln Gly Arg Leu Lys Gly Lys Arg Tyr
50                  55                  60

Asp Ala Asn His Phe Leu Lys Arg Val Ala His Asp Gly Ala Glu Val
65              70                  75                  80

Cys Ala Tyr Val Leu Ala Thr Asp Val Asp Met Ser Pro Ala Asp Gly
                85                  90                  95

Phe Ala Leu Thr Ser Trp Glu Thr Gly Tyr Gln Asp Leu Ser Val Gln
            100                 105                 110

Pro Ala Leu Ser Thr Leu Cys Val Val Pro Trp Leu Pro Arg Thr Val
            115                 120                 125

Ala Val Leu Gly Asp Ala Val His His Asp Gly Thr Leu Ile Asp Ile
        130                 135                 140

Ala Pro Arg Gln Ile Leu Leu Gln Gln Leu Thr Arg Leu Ser Arg His
145                 150                 155                 160

Gly Leu His Pro Lys Val Gly Ile Glu Thr Glu Phe Val Leu Tyr Lys
                165                 170                 175

Gly Thr Tyr Ala Asp Ala Glu Gln Ala Gly Tyr Gln Gly Leu Arg Pro
            180                 185                 190

Leu Thr Thr Glu Asn Leu Asp Tyr Ala Leu Asp His Asp Pro Val Ser
            195                 200                 205

Asp Arg Tyr Leu Arg Arg Leu Gln Arg Ala Leu Ala Gly Ala Gly Met
        210                 215                 220

Pro Val Glu Ala Ile Lys Thr Glu Ala Gly Pro Gly Gln Val Glu Val
225                 230                 235                 240

Thr Phe Pro Tyr Gly Gly Ala Leu Thr Ala Cys Asp Arg His Pro Leu
                245                 250                 255

Phe Lys His Ala Val Arg Thr Leu Gly Ser Arg Ala Gly Leu Ala Pro
            260                 265                 270

Thr Phe Met Ala Ala Pro Glu Thr Gly Arg Ala Asn Gly Leu His Leu
            275                 280                 285

His Val Ser Leu Trp Ser Lys Ala Ile Ser Gln Leu His Glu Pro Gly
        290                 295                 300

Thr Glu His Glu Leu Ser Gln Val Gly Gln His Ala Ile Ala Gly Leu
305                 310                 315                 320

Leu Ala Gly Leu Pro Glu Leu Gly Pro Phe Tyr Ala Pro Ser Val Asn
                325                 330                 335

Ser Tyr Lys Arg Phe Thr Pro Gly Ser Phe Ala Pro Thr Thr Phe Thr
            340                 345                 350

Trp Gly Arg Asp Asn Arg Thr Cys Ala Val Arg Val Val Gly Arg Gly
            355                 360                 365

Glu Gly Leu His Leu Glu Ile Arg Val Pro Gly Ala Asp Ala Asn Pro
370                 375                 380

Tyr Leu Ala Leu Ser Ala Val Leu Ala Met Asp His Gly Leu Glu
385                 390                 395                 400

Arg Lys Pro Ala Leu Gly Pro Glu Ala Thr Gly Asn Ala Tyr Arg Ala
                405                 410                 415
```

```
Ser Gly Thr Glu Ala Pro Val Pro Ser Thr Leu Gly Leu Ala Leu Thr
            420                 425                 430

Val Phe Gln Asp Ser Ala Leu Ala Arg Gln Ala Phe Gly Thr Glu Val
        435                 440                 445

Val Glu His Tyr Ala Arg Leu Ala Gly Leu Glu Leu Ala His Asp Glu
    450                 455                 460

Arg Leu Val Thr Asp Ala Glu Arg Gln Arg Trp Leu Ala Arg Ala
465                 470                 475

<210> SEQ ID NO 8
<211> LENGTH: 297
<212> TYPE: PRT
<213> ORGANISM: Streptomyces DSM 22643

<400> SEQUENCE: 8

Val Thr Asp Met Pro Ser Ala Leu His Gln Leu Val Glu Ser Val Thr
1               5                   10                  15

Asp Met Tyr Glu Val Val Ala Glu His Ala Arg Pro Gly Ala Ile Arg
            20                  25                  30

Pro Ser Val Trp Glu Val Asn Gly Pro Gly Gln Arg Trp Phe Gly
        35                  40                  45

Lys Val His Ala Gly Pro Lys Leu His Arg Arg Glu Val Thr Ala Tyr
50                  55                  60

Gln Lys Trp Thr Val Ala Leu Arg Ala Asp His Ala Pro Glu Leu Val
65                  70                  75                  80

Ala Ala Asp Thr Leu Thr Arg Thr Val Leu Val Thr Ala Val Pro Gly
                85                  90                  95

His Gly Leu Asp Thr Leu Arg Leu Pro Ala Glu Gln Glu His Ala Ala
            100                 105                 110

Tyr Val Gln Ala Gly Glu Leu Leu Ala Arg Phe His Thr Ala Ala Ala
        115                 120                 125

Asp Glu Pro Met Pro Glu Thr Ala Asp Glu Ala Trp Asp Glu Ala Val
    130                 135                 140

Ala Arg Leu Leu Asp Arg Thr Ala Thr His Ala Ser Glu His Asp Leu
145                 150                 155                 160

Ala Leu Val Arg Thr Leu Ala Lys Glu Ala Pro Pro Arg Leu Pro Pro
                165                 170                 175

Val Ser Gln His Gly Asp Tyr Met Pro Lys Asn Trp Met Trp Asp Glu
            180                 185                 190

Thr Glu Gln Arg Leu Arg Val Ile Asp Phe Glu Arg Ala Glu Leu Arg
        195                 200                 205

Thr Pro Ala Tyr Arg Asp Leu Ser Arg Leu Tyr Arg Ile Leu Cys
    210                 215                 220

His Arg Pro Asp Leu Asp Ala Ala Phe His His Gly Tyr Gly Arg Pro
225                 230                 235                 240

Leu Thr Glu Glu Glu Gln Ile Ala Cys Arg Ala Tyr Gly Ala Leu Asp
                245                 250                 255

Ala Leu Asp Ser Leu Asp Trp Gly Ile Lys His Arg Asp Ile Gly Leu
            260                 265                 270

Val Asp Glu Ala Gln Thr Met Leu Glu Asn Leu Arg Arg Glu Thr Gly
        275                 280                 285

Lys Arg Val Trp Gly Gly Trp Arg Ala
    290                 295

<210> SEQ ID NO 9
```

-continued

```
<211> LENGTH: 7794
<212> TYPE: PRT
<213> ORGANISM: Streptomyces DSM 22643
<220> FEATURE:
<221> NAME/KEY: DOMAIN
<222> LOCATION: (9)..(1493)
<223> OTHER INFORMATION: Module 1
<220> FEATURE:
<221> NAME/KEY: DOMAIN
<222> LOCATION: (9)..(336)
<223> OTHER INFORMATION: Module 1; domain C1
<220> FEATURE:
<221> NAME/KEY: DOMAIN
<222> LOCATION: (481)..(939)
<223> OTHER INFORMATION: Module 1; domain A1'
<220> FEATURE:
<221> NAME/KEY: DOMAIN
<222> LOCATION: (940)..(1365)
<223> OTHER INFORMATION: Module 1; domain MT in domain A1
<220> FEATURE:
<221> NAME/KEY: DOMAIN
<222> LOCATION: (1366)..(1406)
<223> OTHER INFORMATION: Module 1; domain A1''
<220> FEATURE:
<221> NAME/KEY: DOMAIN
<222> LOCATION: (1429)..(1493)
<223> OTHER INFORMATION: Module 1; domain T1
<220> FEATURE:
<221> NAME/KEY: DOMAIN
<222> LOCATION: (1517)..(2569)
<223> OTHER INFORMATION: Module 2
<220> FEATURE:
<221> NAME/KEY: DOMAIN
<222> LOCATION: (1517)..(1858)
<223> OTHER INFORMATION: Module 2; domain C2
<220> FEATURE:
<221> NAME/KEY: DOMAIN
<222> LOCATION: (2003)..(2482)
<223> OTHER INFORMATION: Module 2; domain A2
<220> FEATURE:
<221> NAME/KEY: DOMAIN
<222> LOCATION: (2505)..(2569)
<223> OTHER INFORMATION: Module 2; domain T2
<220> FEATURE:
<221> NAME/KEY: DOMAIN
<222> LOCATION: (2591)..(4102)
<223> OTHER INFORMATION: Module 3
<220> FEATURE:
<221> NAME/KEY: DOMAIN
<222> LOCATION: (2591)..(2932)
<223> OTHER INFORMATION: Module 3; domain C3
<220> FEATURE:
<221> NAME/KEY: DOMAIN
<222> LOCATION: (3077)..(3536)
<223> OTHER INFORMATION: Module 3; domain A3'
<220> FEATURE:
<221> NAME/KEY: DOMAIN
<222> LOCATION: (3537)..(3974)
<223> OTHER INFORMATION: Module 3; domain MT3 in domain A3
<220> FEATURE:
<221> NAME/KEY: DOMAIN
<222> LOCATION: (3975)..(4015)
<223> OTHER INFORMATION: Module 3; domain A3''
<220> FEATURE:
<221> NAME/KEY: DOMAIN
<222> LOCATION: (4038)..(4102)
<223> OTHER INFORMATION: Module 3; domain T3
<220> FEATURE:
<221> NAME/KEY: DOMAIN
<222> LOCATION: (4124)..(5170)
<223> OTHER INFORMATION: Module 4
<220> FEATURE:
<221> NAME/KEY: DOMAIN
<222> LOCATION: (4124)..(4465)
<223> OTHER INFORMATION: Module 4; domain C4
<220> FEATURE:
<221> NAME/KEY: DOMAIN
<222> LOCATION: (4612)..(5083)
<223> OTHER INFORMATION: Module 4; domain A4
```

```
<220> FEATURE:
<221> NAME/KEY: DOMAIN
<222> LOCATION: (5106)..(5170)
<223> OTHER INFORMATION: Module 4; domain T4
<220> FEATURE:
<221> NAME/KEY: DOMAIN
<222> LOCATION: (5193)..(6245)
<223> OTHER INFORMATION: Module 5
<220> FEATURE:
<221> NAME/KEY: DOMAIN
<222> LOCATION: (5193)..(5534)
<223> OTHER INFORMATION: Module 5; domain C5
<220> FEATURE:
<221> NAME/KEY: DOMAIN
<222> LOCATION: (5679)..(6158)
<223> OTHER INFORMATION: Module 5; domain A5
<220> FEATURE:
<221> NAME/KEY: DOMAIN
<222> LOCATION: (6181)..(6245)
<223> OTHER INFORMATION: Module 5; domain T5
<220> FEATURE:
<221> NAME/KEY: DOMAIN
<222> LOCATION: (6268)..(7312)
<223> OTHER INFORMATION: Module 6
<220> FEATURE:
<221> NAME/KEY: DOMAIN
<222> LOCATION: (6268)..(6609)
<223> OTHER INFORMATION: Module 6; domain C6
<220> FEATURE:
<221> NAME/KEY: DOMAIN
<222> LOCATION: (6754)..(7225)
<223> OTHER INFORMATION: Module 6; domain A6
<220> FEATURE:
<221> NAME/KEY: DOMAIN
<222> LOCATION: (7248)..(7312)
<223> OTHER INFORMATION: Module 6; domain T6
<220> FEATURE:
<221> NAME/KEY: DOMAIN
<222> LOCATION: (7336)..(7677)
<223> OTHER INFORMATION: Module 7
<220> FEATURE:
<221> NAME/KEY: DOMAIN
<222> LOCATION: (7336)..(7677)
<223> OTHER INFORMATION: Module 7; domain C7

<400> SEQUENCE: 9

Met Gln Ile Asn Ser Lys Leu Leu Ser Ala Ala Gln Arg Glu Ile Trp
1               5                   10                  15

Phe Ser Gln Gln Gln Asp Leu Glu Asn Pro Leu Tyr Arg Val Gly Glu
                20                  25                  30

Tyr Leu Asp Ile Ser Gly Asp Ile Asp Leu Thr Leu Phe Glu Arg Ala
            35                  40                  45

Leu Arg Thr Val Val Ala Gln Thr Glu Thr Leu His Val Arg Phe Thr
        50                  55                  60

Glu Gly Gln Glu Gly Pro Glu Gln Val Val Glu Arg Lys Glu Asp Trp
65                  70                  75                  80

Asp Leu Pro Val Ile Asp Leu Ser Asp Val Asp Pro Leu Ser Val
                85                  90                  95

Ala Glu Arg Trp Met Arg Glu Asp Leu Gly Arg Ser Ile Asp Ile Thr
            100                 105                 110

Val Gly Pro Val Phe Ser Tyr Ala Leu Phe Arg Ile Ser Arg Asn Arg
        115                 120                 125

Val Val Trp Tyr Gln Gly Tyr His His Ile Ala Met Asp Ala Phe Ala
    130                 135                 140

Met Gly Val Val Ala Arg Arg Val Ala Asp Ser Tyr Asn Arg Leu Ser
145                 150                 155                 160

Arg Asn Glu Gly Val Leu Gly Gly Asp Asp Ser Val Ala Leu Leu Leu
                165                 170                 175
```

```
Asp Asp Asp Ala Ser Tyr Arg Ala Ser Glu Asp Leu Ala Arg Asp Arg
            180                 185                 190

Glu Phe Trp Met Gly Arg Leu Ala Asp Leu Pro Glu Pro Val Glu Leu
            195                 200                 205

Ala Gly Arg Thr Ala Pro Ala Ser Gly Lys Phe His Arg Val Ser Met
            210                 215                 220

Thr Phe Ser Asp Val His Gly Asp Ala Val Arg Gly Asp Arg Asp
225                 230                 235                 240

Leu Arg Gly Trp Ala Val Thr Leu Thr Ala Ala Ala Ala Tyr Val
                245                 250                 255

Tyr Arg Ala Thr Gly Gln Val Asp Phe Leu Leu Gly Phe Ala Ala Ala
            260                 265                 270

Ala Arg Pro Gly Ala Asp Leu Lys Gln Val Ala Gly Met Met Ser Asn
            275                 280                 285

Leu Leu Pro Leu Lys Leu Thr Val Ser Gln Glu Thr Thr Val Ser Asp
            290                 295                 300

Leu Glu Gly Gln Val Cys Arg Glu Ile Ala Asp Leu Leu Arg His Gln
305                 310                 315                 320

Arg Tyr Arg Ser Glu Asp Ile Ala Arg Asp Leu Gly Leu Pro Ala Gly
                325                 330                 335

Ile Arg Gly Met Ile Gly Pro Arg Val Asn Phe Met Pro Phe Asp Tyr
            340                 345                 350

Asn Ile Thr Phe Gly Asp Ala Asn Ala Val Ala Lys Asn Leu Ser Leu
            355                 360                 365

Gly Val Val Asp Asp Leu Thr Ile Ala Ile Tyr Asp Arg Arg Asp Gly
            370                 375                 380

Ser Glu Leu Arg Ile Asp Ile Glu Ala Asn Ser Asp Leu Tyr Ser Tyr
385                 390                 395                 400

Gln Glu Leu Gln Ala His Ser Glu Arg Phe Met Arg Leu Leu Lys Glu
                405                 410                 415

Phe Thr Asp Pro Ser Arg Ser Ser Gln Pro Ile Ser Leu Leu Glu Phe
            420                 425                 430

Leu Asp Ala Glu Glu Arg Arg Ile Leu Thr Glu Trp Ser Gly Ala
            435                 440                 445

Thr Asp Ala Ile Ser Thr Ala Thr Leu Pro Gly Leu Phe Glu Val Cys
450                 455                 460

Ala Ala Ser Val Pro Gly Ala Thr Ala Val Phe Gly Asp Val Arg
465                 470                 475                 480

Val Ser Tyr Gly Val Leu Asn Glu Arg Ala Asn Arg Leu Ala His Trp
                485                 490                 495

Leu Leu Gly Arg Gly Val Gly Pro Glu Arg Val Val Ala Leu Ala Leu
            500                 505                 510

Pro Arg Gly Val Asp Leu Val Val Ala Val Leu Ala Val Val Lys Ala
            515                 520                 525

Gly Ala Ala Tyr Leu Pro Val Asp Pro Asp Tyr Pro Ala Glu Arg Val
            530                 535                 540

Ala Tyr Met Leu Glu Asp Ser Arg Pro Val Leu Ala Leu Thr Ser Ser
545                 550                 555                 560

Ala Val Val Ala Gly Leu Pro Val Val Asp Val Glu Tyr Val Ser
                565                 570                 575

Leu Asp Asp Pro Ala Val Leu Gly Glu Leu Ala Gly Cys Gly Val Ser
            580                 585                 590
```

```
Asp Pro Ser Asp Ala Asp Arg Gly Ala Val Leu Ser Pro Ala His Pro
        595                 600                 605

Val His Val Ile Tyr Thr Ser Gly Ser Thr Gly Arg Pro Lys Gly Val
610                 615                 620

Met Thr Ser His Gly Asn Val Val Arg Leu Phe Asp Val Gly Glu Gly
625                 630                 635                 640

Gly His Trp Phe Gly Phe Ala Pro Asp Val Trp Ala Leu Phe His
                645                 650                 655

Ser Tyr Thr Phe Asp Phe Ser Val Phe Glu Leu Trp Gly Ala Leu Leu
                660                 665                 670

His Gly Gly Cys Leu Val Val Pro His Leu Thr Ser Arg Ser Pro
        675                 680                 685

Val Glu Leu Leu Arg Leu Val Ala Glu Gln Val Thr Val Leu Cys
690                 695                 700

Gln Thr Pro Ser Ala Phe Asp Ala Leu Ala Gly Val Val Ala Gln Asp
705                 710                 715                 720

Pro Ala Gly Ala Glu Gly Leu Val Leu Arg Arg Val Val Phe Gly Gly
                725                 730                 735

Glu Ala Leu Pro Ala Arg Thr Ala Glu Leu Ala Ser Gly Leu Val Pro
                740                 745                 750

Gly Val Arg Val Val Asn Ile Tyr Gly Pro Thr Glu Thr Thr Val His
                755                 760                 765

Ala Thr Thr Cys His Val Asp Ser Val Ser Gly Gly Asn Pro Val Val
                770                 775                 780

Ser Ile Gly Arg Pro Val Asp Arg Ala Leu Gly Tyr Val Leu Asp Ala
785                 790                 795                 800

Gly Leu Arg Val Val Pro Val Gly Val Ala Gly Glu Leu Tyr Val Ala
                805                 810                 815

Gly Ala Gly Leu Ala Arg Gly Tyr Val Asn Arg Ala Gly Leu Thr Ala
                820                 825                 830

Ser Arg Phe Val Ala Asp Pro Tyr Gly Pro Ala Gly Ser Arg Met Tyr
        835                 840                 845

Arg Thr Gly Asp Val Val Arg Trp Asn Thr Ser Gly Glu Leu Glu Phe
850                 855                 860

Val Gly Arg Ala Asp Asp Gln Val Lys Ile Arg Gly Phe Arg Ile Glu
865                 870                 875                 880

Leu Gly Glu Ile Glu Thr Thr Ala Ala Gly His Pro Ala Val Ala Gln
                885                 890                 895

Ala Ala Ala Thr Val His Glu Asp Asp Thr Arg Gly Lys Gln Leu Ala
        900                 905                 910

Leu Tyr Val Val Pro Thr Gly Leu Thr Ser Gly Asp Val Ser Gly Ser
        915                 920                 925

Val Ser Gly Asp Gly Ala Val Pro Asp Gly Gly Val Ser Gly Val Val
930                 935                 940

Asp Glu Gln Val Gly Glu Trp Arg Glu Ile Tyr Asp Ser Leu Tyr Gly
945                 950                 955                 960

Gly Pro Gly Ser Ser Val Phe Gly Glu Asp Phe Ser Gly Trp Asp Ser
                965                 970                 975

Ser Tyr Asp Gly Ala Ala Ile Pro Leu Glu Glu Met Arg Glu Trp Arg
        980                 985                 990

Asp Ala Thr Val Glu Arg Ile Arg  Gly Leu Gly Gly Arg  Arg Val Leu
        995                 1000                1005

Glu Ile  Gly Val Gly Thr Gly  Leu Leu Met Ser Arg  Leu Ala Ala
```

```
            1010                1015                1020
Gly Cys Glu Glu Tyr Trp Ala Thr Asp Leu Ser Gly Val Val Ile
        1025                1030                1035

Asp Ala Leu Asp Gly His Val Gln Ala Asp Pro Val Leu Arg Glu
        1040                1045                1050

Arg Val Arg Leu Ala Cys Gln Arg Ala Asp Asp Thr Arg Gly Leu
        1055                1060                1065

Pro Glu Gly Tyr Phe Asp Thr Val Val Ile Asn Ser Val Val Gln
        1070                1075                1080

Tyr Phe Pro Gly Ala Gln Tyr Leu Ala Ser Val Ile Glu Ala Ala
        1085                1090                1095

Val Ser Arg Leu Ala Pro Gly Gly Arg Val Phe Ile Gly Asp Val
        1100                1105                1110

Arg Asp Leu Arg Thr Leu Arg Ala Phe His Thr Ala Val Gln Leu
        1115                1120                1125

Thr Arg Thr Thr Gly Gly Arg Ala Gly Asp Gly Met Asp Ala Gly
        1130                1135                1140

Gly Leu Arg Arg Ala Val Glu Gln Gly Leu Leu Leu Glu Asn Glu
        1145                1150                1155

Leu Leu Leu Asp Pro Glu Phe Phe Thr Ala Val Gly Arg Thr Leu
        1160                1165                1170

Pro Ala Val Ser Ala Val Glu Val Arg Leu Lys His Gly Gln Ala
        1175                1180                1185

His Asn Glu Leu Thr Arg His Arg Tyr Asp Val Ile Leu His Thr
        1190                1195                1200

Thr Asn Thr Glu Thr Asp Thr Glu Ala Pro Ala Pro Thr Pro Ala
        1205                1210                1215

Pro Val Glu Gly Ile Ser Trp Asn Ser Val Pro Gly Gln Leu Thr
        1220                1225                1230

Gly Leu Glu Glu Ile Leu Arg Ser Arg Gly Ala Ala Pro Leu Arg
        1235                1240                1245

Val Thr Gly Ile Pro Asn Ala Arg Leu Ala Gly Glu Tyr Ala Ala
        1250                1255                1260

Leu Arg Val Leu Glu Asn Gly Gly Thr Leu Thr Glu Ala Val Thr
        1265                1270                1275

Ala Leu Ala Gly Pro Arg Gly Ile Asp Pro Glu His Leu His Gln
        1280                1285                1290

Leu Ala Ala Thr Gly Tyr His Ala Val Leu Gln Pro Ala Pro
        1295                1300                1305

Ala Pro Asp Thr Tyr Asn Thr Leu Leu Leu Pro Leu Asp Ile Phe
        1310                1315                1320

Asp Gly Thr Ala Trp Ser Ala Thr Ala Thr Ala Thr Ala Thr Asp
        1325                1330                1335

Leu Arg Glu Thr Ser Ala Pro Asp His Thr Ala Glu Thr Ser Phe
        1340                1345                1350

Gln Ala Leu Ala Asn Asn Pro Ala Ala Ser Arg Asp Thr Ser Thr
        1355                1360                1365

Leu Ile Thr Gln Val Arg Asp His Leu Arg Thr Lys Leu Pro Asp
        1370                1375                1380

His Met Val Pro Ala Ala Ile Val Val Leu Glu Arg Leu Pro Leu
        1385                1390                1395

Thr Ala Ser Gly Lys Leu Asp Arg Arg Ala Leu Pro Ala Pro Asp
        1400                1405                1410
```

-continued

```
Leu Gly Thr His Thr Thr Gly Arg Ala Pro Arg Ser Pro Arg Glu
1415                1420                1425

Glu Ile Leu Ala Gly Leu Phe Ala Glu Val Leu Gly Leu Pro Ala
    1430                1435                1440

Val Gly Ile Asp Asp Ser Phe Phe Asp Leu Gly Gly His Ser Leu
1445                1450                1455

Leu Ala Thr Arg Leu Ile Ser Arg Ile Arg Ala Ile Leu Gly Val
    1460                1465                1470

Glu Ile Pro Ile Arg Asp Leu Phe Glu Ala Pro Thr Val Ala Gly
1475                1480                1485

Leu Ala Val Leu Leu Glu Thr Gly Ser Ser Asp Val Val Arg Arg
    1490                1495                1500

Lys Leu Thr Pro Ala Ala Arg Pro Glu Arg Ile Pro Leu Ser Ser
1505                1510                1515

Ala Gln Ser Arg Leu Trp Phe Leu His Arg Leu Glu Gly Pro Ser
    1520                1525                1530

Ala Thr Tyr Asn Ile Pro Met Ala Leu Arg Leu Ser Gly Arg Leu
1535                1540                1545

Asp Arg Glu Ala Leu Gln Thr Ala Leu Ala Asp Val Val Glu Arg
    1550                1555                1560

His Glu Ser Leu Arg Thr Val Phe Pro Glu Thr Asp Gly Val Pro
1565                1570                1575

Cys Gln His Ile Leu Ala Gly Ala Glu Ala Gln Pro Val Leu Glu
    1580                1585                1590

Thr Arg Gln Thr Ser Glu Glu Glu Leu Ala Asp Thr Ile Leu Ile
1595                1600                1605

Val Ser Arg His Ala Phe Asp Leu Ser Thr Glu Leu Pro Val Arg
    1610                1615                1620

Ala Trp Leu Phe Ala Leu Ala Pro Glu Glu His Val Leu Val Leu
1625                1630                1635

Val Val His His Ile Ala Gly Asp Gly Trp Ser Leu Ser Pro Leu
    1640                1645                1650

Phe Arg Asp Leu Thr Val Ala Tyr Ala Ala Arg Ala Glu Gly Gly
1655                1660                1665

Val Pro Gly Trp Ser Ala Leu Pro Val Gln Tyr Ala Asp Tyr Thr
    1670                1675                1680

Leu Trp Gln Asn Asp Leu Leu Gly Asp Gln Ser Asp Thr Gly Ser
1685                1690                1695

Leu Val Ala Arg Gln Leu Glu Tyr Trp Arg Thr Thr Leu Thr Gly
    1700                1705                1710

Leu Pro Glu Gln Val Thr Leu Pro Thr Asp Arg Pro Arg Pro Ala
1715                1720                1725

Met Ala Ser Gln Arg Gly Glu Val Phe Glu Phe Ser Trp Asp Ala
    1730                1735                1740

Glu Leu His Gln Gly Leu Ile Asp Leu Ala Arg Ser Thr Gly Thr
1745                1750                1755

Thr Val Phe Met Val Leu Gln Ala Gly Leu Ala Ala Leu Met Ser
    1760                1765                1770

Arg Leu Gly Ala Gly Asp Asp Ile Pro Leu Gly Ser Pro Ile Ala
1775                1780                1785

Gly Arg Thr Asp Glu Ala Leu Asp Asp Leu Val Gly Phe Phe Val
    1790                1795                1800
```

-continued

```
Asn Thr Leu Val Leu Arg Thr Asp Ser Gly Asn Pro Thr Phe
    1805                1810                1815

Arg Glu Leu Leu Ala Arg Val Arg Glu Thr Asp Leu Ala Ala Tyr
    1820                1825                1830

Ala His Gln Asp Val Pro Phe Glu His Leu Val Glu Ile Leu Asn
    1835                1840                1845

Pro Glu Arg Ser Leu Ala His His Pro Leu Phe Gln Val Met Leu
    1850                1855                1860

Ala Leu Gln Asn Thr Pro Glu Arg Arg Phe Ala Leu Ser Gly Leu
    1865                1870                1875

Glu Ala Lys Glu Trp Pro Ile Ala Thr His Thr Ala Arg Phe Asp
    1880                1885                1890

Leu Phe Leu Gly Leu Thr Glu Arg Arg Ser Glu Ser Gly Leu Pro
    1895                1900                1905

Gly Gly Leu Glu Val Phe Val Glu Phe Ser Thr Asp Leu Phe Asp
    1910                1915                1920

Arg Val Ser Val Glu Val Val Leu Glu Arg Leu Arg Arg Val Leu
    1925                1930                1935

Val Ser Val Ala Ala Asp Pro Asp Val Thr Val Gly Ala Leu Pro
    1940                1945                1950

Val Leu Ser Gly Gln Glu Glu His Arg Leu Val Ala Glu Trp Asn
    1955                1960                1965

Asp Thr Ala Leu Glu Val Pro Pro Ala Ser Leu Pro Glu Leu Phe
    1970                1975                1980

Gln Ala Gln Ala Ala Glu Ala Pro Glu Ala Thr Ala Val Val Phe
    1985                1990                1995

Glu Thr Glu Arg Leu Ser Tyr Arg Glu Leu Asn Glu Arg Ala Asn
    2000                2005                2010

Arg Leu Ala His Tyr Leu Ile Gly Gln Gly Ala Gly Pro Glu Arg
    2015                2020                2025

Ile Val Ala Leu Ala Leu Pro Arg Gly Thr Asp Leu Val Ile Ala
    2030                2035                2040

Val Leu Ala Val Leu Lys Ala Gly Ala Ala Tyr Leu Pro Val Asp
    2045                2050                2055

Pro Asp Tyr Pro Ala Glu Arg Ile Thr His Met Leu Thr Asp Thr
    2060                2065                2070

Arg Pro Thr Leu Leu Leu Thr Thr Ser Asp Val Ala Ala Gly Leu
    2075                2080                2085

Pro Arg Thr Glu Gly Val Thr Ser Val Leu Leu Asp Asp Pro Ala
    2090                2095                2100

Val Thr Glu Thr Val Ala Leu Cys Ala Val Ser Asp Pro Thr Asp
    2105                2110                2115

Ser Glu Arg Gly Val Val Leu Glu Gly Ser His Pro Ala Tyr Val
    2120                2125                2130

Ile Tyr Thr Ser Gly Ser Thr Gly Val Pro Lys Gly Val Val Met
    2135                2140                2145

Pro Ser Gly Gly Leu Val Asn Leu Leu His Trp His His Ser Val
    2150                2155                2160

Ile Ala Gly Arg Ala Gly Ala Arg Thr Ala Gln Phe Thr Thr Ile
    2165                2170                2175

Ser Phe Asp Val Ser Ala Gln Glu Ile Leu Ser Ala Leu Val Phe
    2180                2185                2190

Gly Lys Glu Leu Trp Val Pro Gly Glu Glu Val Arg Arg Ser Gly
```

```
            2195                2200                2205

Glu Gly Leu Ala Arg Trp Leu Gln Glu His Ala Val Glu Glu Leu
    2210                2215                2220

Phe Ala Pro Ala Leu Val Ile Asp Ala Val Ala Gln Ala Ala Gly
    2225                2230                2235

Glu Leu Gly Leu Val Leu Pro Ala Leu Arg His Val Ala Gln Gly
    2240                2245                2250

Gly Glu Ala Leu Val Pro Gly Ala Ala Met Arg Arg Phe Phe Arg
    2255                2260                2265

Glu Arg Pro His Ile Arg Leu His Asn His Tyr Gly Pro Thr Glu
    2270                2275                2280

Thr His Ala Val Thr Ala Tyr Val Leu Pro Glu Arg Val Ala Asp
    2285                2290                2295

Trp Pro Val Ser Ala Ala Pro Val Gly Gly Pro Val Ala Asn Asp
    2300                2305                2310

Arg Val Tyr Val Leu Asp Ala Ala Leu Arg Ala Val Pro Val Gly
    2315                2320                2325

Val Ala Gly Glu Leu Tyr Val Ala Gly Ala Gly Leu Ala Arg Gly
    2330                2335                2340

Tyr Val Asn Arg Ala Gly Leu Thr Ala Ser Arg Phe Val Ala Asp
    2345                2350                2355

Pro Tyr Gly Pro Ala Gly Ser Arg Met Tyr Arg Thr Gly Asp Val
    2360                2365                2370

Val Arg Trp Asn Thr Ser Gly Glu Leu Glu Phe Val Gly Arg Ala
    2375                2380                2385

Asp Asp Gln Val Lys Ile Arg Gly Phe Arg Ile Glu Leu Gly Glu
    2390                2395                2400

Ile Glu Thr Thr Ala Ala Gly His Pro Ala Val Ala Gln Ala Ala
    2405                2410                2415

Ala Thr Val His Glu Asp Asp Thr Arg Gly Lys Gln Leu Ala Leu
    2420                2425                2430

Tyr Ile Val Pro Thr Gly Thr Gly Gly Val Val Asp Ala Gly Thr
    2435                2440                2445

Val Arg Glu Tyr Leu Arg Thr Lys Leu Pro Asp Tyr Met Val Pro
    2450                2455                2460

Ala Ala Val Val Val Leu Glu Gln Leu Pro Leu Thr Ala Ser Gly
    2465                2470                2475

Lys Leu Asp Arg Arg Ala Leu Pro Thr Pro Glu Phe Ala Ala Glu
    2480                2485                2490

Pro Ala Gly Arg Thr Ala Arg Ser Pro Arg Glu Glu Ile Leu Ala
    2495                2500                2505

Gly Leu Phe Ala Glu Val Leu Gly Leu Pro Ala Val Gly Ile Asp
    2510                2515                2520

Asp Ser Phe Phe Asp Leu Gly Gly His Ser Leu Leu Ala Thr Arg
    2525                2530                2535

Leu Ile Ser Arg Ile Arg Ala Thr Leu Asn Thr Glu Val Pro Val
    2540                2545                2550

Arg Ala Leu Phe Glu Ala Pro Thr Val Ala Gly Leu Ala Thr Leu
    2555                2560                2565

Leu Asp Glu Asn Arg Ala Val Arg Pro Thr Leu Thr Pro Ala Ala
    2570                2575                2580

Arg Pro Glu Arg Ile Pro Leu Ser Ser Ala Gln Asn Arg Leu Trp
    2585                2590                2595
```

-continued

```
Phe Leu His Arg Leu Glu Gly Pro Ser Ala Thr Tyr Asn Met Pro
    2600              2605              2610
Met Ala Leu Arg Leu Ser Gly Arg Leu Asp Arg Glu Ala Leu His
    2615              2620              2625
Thr Ala Leu Ala Asp Val Ala Glu Arg His Glu Ser Leu Arg Thr
    2630              2635              2640
Val Phe Pro Glu Thr Asp Gly Val Pro Cys Gln His Ile Leu Ala
    2645              2650              2655
Gly Ala Glu Ala Gln Pro Val Leu Glu Val Ala Asp Ile Ala Glu
    2660              2665              2670
Asp Gln Leu Asp Glu Ala Leu Ala Gly Ala Ala Arg Tyr Pro Phe
    2675              2680              2685
Asp Leu Ser Ala Glu Leu Pro Val Arg Ala Trp Leu Phe Ala Leu
    2690              2695              2700
Ala Pro Glu Glu His Val Leu Val Leu Val Val His His Ile Ala
    2705              2710              2715
Gly Asp Gly Trp Ser Leu Ser Pro Leu Phe Arg Asp Leu Thr Val
    2720              2725              2730
Ala Tyr Ala Ala Arg Ala Asp Gly Arg Thr Pro Gly Trp Ser Ala
    2735              2740              2745
Leu Pro Val Gln Tyr Ala Asp Tyr Thr Leu Trp Gln Asn Asp Leu
    2750              2755              2760
Leu Gly Asp Gln Ser Asp Gly Asp Ser Leu Val Ala Arg Gln Leu
    2765              2770              2775
Glu Tyr Trp Arg Thr Thr Leu Thr Gly Leu Pro Glu Gln Val Thr
    2780              2785              2790
Leu Pro Thr Asp Arg Pro Arg Pro Ala Thr Ala Thr Tyr Gln Gly
    2795              2800              2805
Ala Leu His Asp Phe Ala Trp Asp Ala Glu Leu His Gln Gly Leu
    2810              2815              2820
Ile Asp Leu Ala Arg Ser Thr Gly Thr Thr Val Phe Met Val Leu
    2825              2830              2835
Gln Ala Gly Leu Ala Ala Leu Met Ser Arg Leu Gly Ala Gly Asp
    2840              2845              2850
Asp Ile Pro Leu Gly Ser Pro Ile Ala Gly Arg Thr Asp Glu Ala
    2855              2860              2865
Leu Asp Asp Leu Val Gly Phe Phe Val Asn Thr Leu Val Leu Arg
    2870              2875              2880
Thr Asp Thr Ser Gly Asn Pro Thr Phe Arg Glu Leu Leu Ala Arg
    2885              2890              2895
Val Arg Glu Thr Asp Leu Ala Ala Tyr Ala His Gln Asp Val Pro
    2900              2905              2910
Phe Glu His Leu Val Glu Ile Leu Asn Pro Glu Arg Ser Pro Ala
    2915              2920              2925
His His Pro Leu Phe Gln Val Ala Leu Ala Leu His Asn Thr Pro
    2930              2935              2940
Pro Arg Asn Phe Thr Leu Pro Asp Ile Asn Met Arg Ser Glu Arg
    2945              2950              2955
Ala Glu Thr Arg Thr Ser Arg Phe Asp Leu Ser Phe His Phe Phe
    2960              2965              2970
Glu Ser Asn Glu Leu Gly Asp Leu Pro Ala Gly Leu Gly Gly Phe
    2975              2980              2985
```

-continued

| | | | | | | | | | | | |
|---|---|---|---|---|---|---|---|---|---|---|---|
| Val | Glu | Phe | Ser | Thr | Asp | Leu | Phe | Asp | Arg | Val | Ser | Val | Glu | Val |
| | 2990 | | | | | 2995 | | | | | 3000 | | | |
| Val | Leu | Glu | Arg | Leu | Arg | Arg | Val | Leu | Val | Ser | Val | Ala | Ala | Asp |
| | 3005 | | | | | 3010 | | | | | 3015 | | | |
| Pro | Asp | Val | Thr | Val | Gly | Ala | Leu | Pro | Val | Leu | Ser | Gly | Gln | Glu |
| | 3020 | | | | | 3025 | | | | | 3030 | | | |
| Glu | His | Arg | Leu | Val | Ala | Glu | Trp | Asn | Asp | Thr | Ala | Leu | Glu | Val |
| | 3035 | | | | | 3040 | | | | | 3045 | | | |
| Pro | Pro | Ala | Ser | Leu | Pro | Glu | Leu | Phe | Gln | Ala | Gln | Ala | Ala | Ala |
| | 3050 | | | | | 3055 | | | | | 3060 | | | |
| Thr | Pro | Glu | Ala | Thr | Ala | Val | Val | Phe | Glu | Asp | Val | Arg | Ile | Ser |
| | 3065 | | | | | 3070 | | | | | 3075 | | | |
| Tyr | Arg | Val | Leu | Asn | Glu | Arg | Ala | Asn | Arg | Leu | Ala | His | Tyr | Leu |
| | 3080 | | | | | 3085 | | | | | 3090 | | | |
| Ile | Lys | Gln | Gly | Ala | Gly | Pro | Glu | Arg | Ile | Val | Ala | Leu | Ala | Leu |
| | 3095 | | | | | 3100 | | | | | 3105 | | | |
| Pro | Arg | Gly | Thr | Asp | Leu | Val | Ile | Ala | Val | Leu | Ala | Val | Leu | Lys |
| | 3110 | | | | | 3115 | | | | | 3120 | | | |
| Ala | Gly | Ala | Ala | Tyr | Leu | Pro | Val | Asp | Pro | Asp | Tyr | Pro | Ala | Glu |
| | 3125 | | | | | 3130 | | | | | 3135 | | | |
| Arg | Ile | Thr | His | Met | Leu | Thr | Asp | Thr | Arg | Pro | Thr | Leu | Leu | Leu |
| | 3140 | | | | | 3145 | | | | | 3150 | | | |
| Thr | Thr | Ser | Asp | Ala | Thr | Ala | Asp | Leu | Pro | His | Ile | Glu | Gly | Ile |
| | 3155 | | | | | 3160 | | | | | 3165 | | | |
| Pro | Gln | Val | Leu | Leu | Asp | Asp | Pro | Val | Val | Glu | Ala | Val | Ala |
| | 3170 | | | | | 3175 | | | | | 3180 | | | |
| Val | Leu | Ser | Ala | Asp | Asp | Pro | Ser | Asp | Thr | Asp | Arg | Gly | Val | Leu |
| | 3185 | | | | | 3190 | | | | | 3195 | | | |
| Asp | Ala | Ser | His | Pro | Ala | Tyr | Val | Ile | Tyr | Thr | Ser | Gly | Ser | Thr |
| | 3200 | | | | | 3205 | | | | | 3210 | | | |
| Gly | Gln | Pro | Lys | Gly | Val | Leu | Ile | Pro | His | Gln | Asn | Val | Thr | Arg |
| | 3215 | | | | | 3220 | | | | | 3225 | | | |
| Leu | Phe | Ala | Ala | Thr | Asp | His | Trp | Phe | Gly | Phe | Gly | Ala | Asp | Asp |
| | 3230 | | | | | 3235 | | | | | 3240 | | | |
| Val | Trp | Thr | Leu | Phe | His | Ser | Tyr | Ala | Phe | Asp | Phe | Ser | Val | Trp |
| | 3245 | | | | | 3250 | | | | | 3255 | | | |
| Glu | Leu | Trp | Gly | Ala | Leu | Leu | His | Gly | Gly | Arg | Leu | Val | Ile | Val |
| | 3260 | | | | | 3265 | | | | | 3270 | | | |
| Ser | His | Leu | Thr | Ser | Arg | Ser | Pro | Val | Glu | Leu | Leu | Arg | Leu | Leu |
| | 3275 | | | | | 3280 | | | | | 3285 | | | |
| Val | Ala | Glu | Gly | Val | Thr | Val | Leu | Asn | Gln | Thr | Pro | Ser | Ala | Phe |
| | 3290 | | | | | 3295 | | | | | 3300 | | | |
| Ser | Gln | Leu | Gln | Gln | Ala | Ala | Gln | Glu | Asn | Ser | Ala | Leu | Asp | Arg |
| | 3305 | | | | | 3310 | | | | | 3315 | | | |
| Arg | Leu | Ser | Leu | Arg | Arg | Val | Val | Phe | Gly | Gly | Glu | Ala | Leu | Asp |
| | 3320 | | | | | 3325 | | | | | 3330 | | | |
| Thr | Ser | Arg | Leu | Lys | Pro | Trp | Phe | Glu | Ala | His | Leu | Asp | Thr | Glu |
| | 3335 | | | | | 3340 | | | | | 3345 | | | |
| Pro | Val | Leu | Val | Asn | Met | Tyr | Gly | Ile | Thr | Glu | Thr | Thr | Val | His |
| | 3350 | | | | | 3355 | | | | | 3360 | | | |
| Val | Thr | Tyr | Arg | Glu | Leu | Asn | Arg | Gly | Ser | Ala | Phe | Ala | Ser | Asp |
| | 3365 | | | | | 3370 | | | | | 3375 | | | |
| Gly | Ser | Ser | Ala | Ile | Gly | Thr | Ala | Ile | Pro | Asp | Leu | Arg | Val | Tyr |

-continued

```
            3380              3385              3390

Val Leu Asp Ala Gly Leu Arg Val Val Pro Val Gly Val Ala Gly
    3395              3400              3405

Glu Leu Tyr Val Ala Gly Ala Gly Leu Ala Arg Gly Tyr Val Asn
    3410              3415              3420

Arg Ala Gly Leu Thr Ala Ser Arg Phe Val Ala Asp Pro Tyr Gly
    3425              3430              3435

Pro Ala Gly Ser Arg Met Tyr Arg Thr Gly Asp Val Val Arg Trp
    3440              3445              3450

Asn Thr Ser Gly Glu Leu Glu Phe Val Gly Arg Ala Asp Asp Gln
    3455              3460              3465

Val Lys Ile Arg Gly Phe Arg Ile Glu Leu Gly Glu Ile Glu Thr
    3470              3475              3480

Thr Ala Ala Gly His Pro Ala Val Ala Gln Ala Ala Ala Thr Val
    3485              3490              3495

His Glu Asp Asp Thr Arg Gly Lys Gln Leu Ala Leu Tyr Val Val
    3500              3505              3510

Pro Thr Gly Leu Thr Ser Gly Asp Val Ser Gly Val Ser Gly
    3515              3520              3525

Asp Gly Ala Val Pro Asp Gly Gly Val Ser Gly Val Val Asp Glu
    3530              3535              3540

Gln Val Gly Glu Trp Arg Glu Ile Tyr Asp Ser Leu Tyr Gly Gly
    3545              3550              3555

Pro Gly Ser Ser Val Phe Gly Glu Asp Phe Ser Gly Trp Asp Ser
    3560              3565              3570

Ser Tyr Asp Gly Ala Ala Ile Pro Leu Glu Glu Met Arg Glu Trp
    3575              3580              3585

Arg Asp Ala Thr Val Glu Arg Ile Arg Gly Leu Gly Gly Arg Arg
    3590              3595              3600

Val Leu Glu Ile Gly Val Gly Thr Gly Leu Leu Met Ser Arg Leu
    3605              3610              3615

Ala Ala Gly Cys Glu Glu Tyr Trp Ala Thr Asp Leu Ser Gly Val
    3620              3625              3630

Val Ile Asp Ala Leu Asp Gly His Val Gln Ala Asp Pro Val Leu
    3635              3640              3645

Arg Glu Arg Val Arg Leu Ala Cys Gln Arg Ala Asp Asp Thr Arg
    3650              3655              3660

Gly Leu Pro Glu Gly Tyr Phe Asp Thr Val Val Ile Asn Ser Val
    3665              3670              3675

Val Gln Tyr Phe Pro Gly Ala Gln Tyr Leu Ala Ser Val Ile Glu
    3680              3685              3690

Ala Ala Val Ser Arg Leu Ala Pro Gly Gly Arg Val Phe Ile Gly
    3695              3700              3705

Asp Val Arg Asp Leu Arg Thr Leu Arg Ala Phe His Thr Ala Val
    3710              3715              3720

Gln Leu Thr Arg Thr Thr Gly Gly Arg Ala Gly Asp Gly Met Asp
    3725              3730              3735

Ala Gly Gly Leu Arg Arg Ala Val Glu Gln Gly Leu Leu Leu Glu
    3740              3745              3750

Asn Glu Leu Leu Leu Asp Pro Glu Phe Phe Thr Ala Val Gly Arg
    3755              3760              3765

Thr Leu Pro Ala Val Ser Ala Val Glu Val Arg Leu Lys His Gly
    3770              3775              3780
```

-continued

Gln Ala His Asn Glu Leu Thr Arg His Arg Tyr Asp Val Ile Leu
3785                3790                3795

His Thr Thr Asn Thr Glu Thr Asp Thr Ala Thr Glu Glu Glu Ala
3800                3805                3810

Glu Ala Ala Arg Pro Thr Lys Ala Glu Ala Glu Thr Pro Ala Leu
3815                3820                3825

Val Glu Arg Ile Ser Trp Asn Thr Leu Ser Gly Gly Leu Asp Gly
3830                3835                3840

Leu Asp Asp Leu Leu Arg Ser Arg Gly Ala Ala Pro Leu Arg Val
3845                3850                3855

Thr Gly Ile Pro Asn Ala Arg Leu Ala Gly Glu Tyr Ala Ala Leu
3860                3865                3870

Arg Val Leu Glu Asn Gly Gly Thr Leu Thr Glu Ala Val Thr Ala
3875                3880                3885

Leu Ala Gly Pro Arg Gly Ile Asp Pro Glu His Leu His Gln Leu
3890                3895                3900

Ala Ala Ala Thr Gly Tyr His Ala Val Leu Gln Pro Ala Pro Ala
3905                3910                3915

Pro Asp Thr Tyr Asn Thr Leu Leu Leu Pro Leu Asp Ile Phe Asp
3920                3925                3930

Gly Thr Ala Trp Ser Ala Thr Ala Thr Ala Thr Ala Thr Asp Leu
3935                3940                3945

Arg Glu Thr Ser Ala Pro Asp His Thr Ala Glu Thr Ser Phe Gln
3950                3955                3960

Ala Leu Ala Asn Asn Pro Ala Ala Ser Arg Asp Thr Ser Thr Leu
3965                3970                3975

Ile Thr Gln Val Arg Asp His Leu Arg Thr Lys Leu Pro Asp His
3980                3985                3990

Met Val Pro Ala Ala Ile Val Val Leu Glu Arg Leu Pro Leu Thr
3995                4000                4005

Ala Ser Gly Lys Leu Asp Arg Arg Ala Leu Pro Ala Pro Asp Leu
4010                4015                4020

Gly Thr His Thr Thr Gly Arg Ala Pro Arg Ser Pro Arg Glu Glu
4025                4030                4035

Ile Leu Ala Gly Leu Phe Ala Glu Val Leu Gly Leu Pro Ala Val
4040                4045                4050

Gly Ile Asp Asp Ser Phe Phe Asp Leu Gly Gly His Ser Leu Leu
4055                4060                4065

Ala Thr Arg Leu Ile Ser Arg Ile Arg Ala Thr Leu Asn Thr Glu
4070                4075                4080

Val Pro Val Arg Asp Leu Phe Glu Ala Pro Thr Val Ala Gly Leu
4085                4090                4095

Ala Thr Leu Leu Asp Glu Asn Arg Ala Val Arg Pro Thr Leu Thr
4100                4105                4110

Pro Ala Ala Arg Pro Glu Arg Ile Pro Leu Ser Ser Ala Gln Ser
4115                4120                4125

Arg Leu Trp Phe Leu His Arg Leu Glu Gly Pro Ser Ala Thr Tyr
4130                4135                4140

Asn Met Pro Met Ala Leu Arg Leu Ser Gly Arg Leu Asp Arg Glu
4145                4150                4155

Ala Leu His Thr Ala Leu Ala Asp Val Val Glu Arg His Glu Ser
4160                4165                4170

-continued

```
Leu Arg Thr Val Phe Pro Glu Thr Asp Gly Val Pro Cys Gln Gln
    4175                4180                4185

Ile Leu Ala Gly Ala Glu Ala Gln Pro Val Leu Glu Val Ala Asp
    4190                4195                4200

Ile Ala Glu Asp Gln Leu Asp Gln Ala Leu Ala Gly Ala Ala Arg
    4205                4210                4215

Tyr Pro Phe Asp Leu Ser Val Glu Leu Pro Val Arg Ala Trp Leu
    4220                4225                4230

Phe Ala Leu Ala Arg Glu Glu His Val Leu Val Leu Val Val His
    4235                4240                4245

His Ile Ala Ser Asp Gly Trp Ser Leu Ala Pro Leu Ser Arg Asp
    4250                4255                4260

Leu Val Thr Ala Tyr Ala Ala Arg Ala Asp Gly Arg Val Pro Gly
    4265                4270                4275

Trp Ala Pro Leu Pro Val Gln Tyr Ala Asp Tyr Thr Leu Trp Gln
    4280                4285                4290

Asn Asp Leu Leu Gly Asp His Ser Asp Thr Gly Ser Leu Ile Ala
    4295                4300                4305

Arg Gln Leu Glu Tyr Trp Arg Thr Thr Leu Thr Gly Leu Pro Glu
    4310                4315                4320

Gln Val Thr Leu Pro Thr Asp Arg Pro Arg Pro Ala Met Ala Ser
    4325                4330                4335

Gln Arg Gly Glu Val Phe Glu Phe Ser Trp Asp Ala Glu Leu His
    4340                4345                4350

Gln Gly Leu Val Asp Leu Ala Arg Ser Thr Gly Thr Thr Val Phe
    4355                4360                4365

Met Val Leu Gln Ala Gly Leu Ala Ala Leu Met Ser Arg Leu Gly
    4370                4375                4380

Ala Gly Asp Asp Ile Pro Leu Gly Ser Pro Ile Ala Gly Arg Thr
    4385                4390                4395

Asp Glu Ala Leu Asp Asp Leu Val Gly Phe Phe Val Asn Thr Leu
    4400                4405                4410

Val Leu Arg Thr Asp Thr Ser Gly Asn Pro Thr Phe Arg Glu Leu
    4415                4420                4425

Leu Ala Arg Val Arg Glu Thr Asp Leu Ala Ala Tyr Ala His Gln
    4430                4435                4440

Asp Val Pro Phe Glu His Leu Val Glu Ile Leu Asn Pro Glu Arg
    4445                4450                4455

Ser Leu Ala His His Pro Leu Phe Gln Val Met Leu Ala Leu Gln
    4460                4465                4470

Asn Thr Pro Glu Arg Ser Phe Ala Leu Pro Gly Thr Val Asn Val
    4475                4480                4485

Gly Ala Val Pro Val Ala Pro Thr Gly Thr Ser Arg Phe Asp Val
    4490                4495                4500

Ser Leu His Phe Val Glu Trp Gln Arg Glu Asp Gly Ala Ala Ser
    4505                4510                4515

Gly Leu Gly Gly Phe Val Glu Phe Ser Thr Asp Leu Phe Asp Arg
    4520                4525                4530

Val Ser Val Glu Val Val Leu Glu Arg Leu Arg Arg Val Leu Val
    4535                4540                4545

Ser Val Ala Ala Asp Pro Asp Val Thr Val Gly Ala Leu Pro Val
    4550                4555                4560

Leu Ser Gly Gln Glu Glu His Arg Leu Val Ala Glu Trp Asn Asp
```

```
              4565                4570                4575

Thr Val Leu Glu Val Pro Pro Ala Ser Leu Pro Glu Leu Phe Gln
         4580                4585                4590

Ala Gln Ala Ala Glu Ala Pro Glu Ala Thr Ala Val Val Phe Glu
         4595                4600                4605

Thr Glu Arg Leu Ser Tyr Arg Glu Leu Asn Glu Arg Ala Asn Arg
         4610                4615                4620

Leu Ala His Tyr Leu Ile Lys Gln Gly Ala Gly Pro Glu Arg Ile
         4625                4630                4635

Val Ala Leu Ala Leu Pro Arg Gly Thr Asp Leu Val Ile Ala Val
         4640                4645                4650

Leu Ala Val Leu Lys Ala Gly Ala Ala Tyr Leu Pro Val Asp Pro
         4655                4660                4665

Asp Tyr Pro Ala Glu Arg Ile Thr His Met Leu His Asp Ala Ala
         4670                4675                4680

Pro Ala Leu Met Val Thr Thr Ser Gly Val Ala Ala Gly Leu Pro
         4685                4690                4695

His Thr Glu Gly Val Thr Ser Val Leu Val Asp Ala Pro Ala Val
         4700                4705                4710

Val Glu Ala Val Ala Val Leu Ser Ala Asp Asp Pro Ser Asp Thr
         4715                4720                4725

Asp Arg Gly Val Val Leu Glu Gly Ser His Pro Ala Tyr Val Ile
         4730                4735                4740

Tyr Thr Ser Gly Ser Thr Gly Val Pro Lys Gly Val Leu Val Pro
         4745                4750                4755

His Ala Gly Leu Ala Asn Leu Thr Ala Ala Glu Arg Ala Ala Leu
         4760                4765                4770

Asp Leu Ser Ala Gly Ser Arg Val Leu Gln Leu Ala Ser Val Gly
         4775                4780                4785

Phe Asp Ala Ala Val Leu Glu Leu Ser Met Ala Phe Gly Ser Gly
         4790                4795                4800

Ala Thr Leu Val Ile Ala Pro Gln Gly Arg Leu Leu Gly Asp Asp
         4805                4810                4815

Leu Ala Ala Leu Leu Ala Arg Gln Glu Ile Thr His Thr Leu Ile
         4820                4825                4830

Thr Pro Ser Ala Leu Ala Thr Leu Pro Glu Thr Asp Leu Pro His
         4835                4840                4845

Leu Arg Thr Leu Leu Thr Gly Ala Glu Ala Cys Pro Pro Glu Leu
         4850                4855                4860

Val Ala Arg Trp Ser Pro Gly Arg Arg Phe Ile Asn Ala Tyr Gly
         4865                4870                4875

Pro Thr Glu Ala Ser Val Val Ala Thr Trp Ser Asp Pro Leu Thr
         4880                4885                4890

Gln Asp Thr Ala Pro Ile Gly Arg Pro Leu Pro Asn Thr Arg Val
         4895                4900                4905

Tyr Val Leu Asp Ala Gly Leu Arg Val Val Pro Val Gly Val Ala
         4910                4915                4920

Gly Glu Leu Tyr Val Ala Gly Ala Gly Leu Ala Arg Gly Tyr Val
         4925                4930                4935

Asn Arg Ala Gly Leu Thr Ala Ser Arg Phe Val Ala Asp Pro Tyr
         4940                4945                4950

Gly Pro Ala Gly Ser Arg Met Tyr Arg Thr Gly Asp Val Val Arg
         4955                4960                4965
```

-continued

```
Trp Asn Thr Ser Gly Glu Leu Glu Phe Val Gly Arg Ala Asp Asp
    4970            4975            4980

Gln Val Lys Ile Arg Gly Phe Arg Ile Glu Leu Gly Glu Ile Glu
    4985            4990            4995

Thr Thr Ala Ala Gly His Pro Ala Val Ala Gln Ala Ala Ala Thr
    5000            5005            5010

Val His Glu Asp Asp Thr Arg Gly Lys Gln Leu Ala Leu Tyr Ile
    5015            5020            5025

Val Pro Thr Gly Ile Thr Ser Gly Asp Val Pro Ala Ser Gly Gly
    5030            5035            5040

Val Val Asp Ala Gly Thr Val Arg Glu Tyr Leu Arg Thr Arg Leu
    5045            5050            5055

Pro Asp Tyr Met Val Pro Ala Ala Val Val Leu Glu Arg Leu
    5060            5065            5070

Pro Leu Thr Ala Ser Gly Lys Leu Asp Arg Arg Ala Leu Pro Thr
    5075            5080            5085

Pro Glu Phe Ala Ala Glu Pro Ala Gly Arg Thr Ala Arg Ser Pro
    5090            5095            5100

Arg Glu Glu Ile Leu Ala Gly Leu Phe Ala Glu Val Leu Gly Leu
    5105            5110            5115

Pro Ala Val Gly Ile Asp Asp Ser Phe Phe Asp Leu Gly Gly His
    5120            5125            5130

Ser Leu Leu Ala Thr Arg Leu Ile Ser Arg Ile Arg Ala Ile Leu
    5135            5140            5145

Gly Ala Glu Ile Pro Ile Arg Ala Leu Phe Glu Thr Pro Thr Val
    5150            5155            5160

Ala Gly Leu Ala Ala Leu Leu Glu Thr Ser Ser Glu Ser Val Arg
    5165            5170            5175

Ser Ala Leu Val Pro Val Thr Arg Pro Glu Arg Met Pro Leu Ser
    5180            5185            5190

Ser Ala Gln Ser Arg Leu Trp Phe Leu His Arg Leu Glu Gly Pro
    5195            5200            5205

Ser Ala Thr Tyr Asn Val Pro Met Ala Leu Arg Leu Thr Gly Pro
    5210            5215            5220

Val Met Pro Glu Val Leu Arg Leu Ala Leu Ala Asp Val Val Glu
    5225            5230            5235

Arg His Glu Ser Leu Arg Thr Val Phe Pro Glu Thr Asp Gly Ile
    5240            5245            5250

Pro His Gln Arg Ile Leu Thr Gly Ala Glu Ala Arg Pro Val Leu
    5255            5260            5265

Glu Val Ala Glu Val Gly Glu Asp Gly Leu Glu Glu Ala Leu Ala
    5270            5275            5280

Gly Ala Ala Arg Tyr Pro Phe Asp Leu Ser Ala Glu Leu Pro Val
    5285            5290            5295

Arg Ala Trp Leu Phe Ala Leu Ala Pro Glu Glu His Val Leu Val
    5300            5305            5310

Leu Val Val His His Ile Ala Gly Asp Gly Trp Ser Leu Ser Pro
    5315            5320            5325

Leu Phe Arg Asp Leu Thr Val Ala Tyr Ala Ala Arg Ala Asp Gly
    5330            5335            5340

Arg Thr Pro Gly Trp Ser Ala Leu Pro Val Gln Tyr Ala Asp Tyr
    5345            5350            5355
```

```
Thr Leu Trp Gln Asn Asp Leu Leu Gly Asp His Ser Asp Thr Gly
5360                5365                5370

Ser Leu Ile Ala Arg Gln Leu Glu Tyr Trp Arg Thr Thr Leu Thr
5375                5380                5385

Gly Leu Pro Glu Gln Val Thr Leu Pro Thr Asp Arg Pro Arg Pro
5390                5395                5400

Ala Thr Ala Thr Tyr Gln Gly Asp Ser Leu Tyr Phe Lys Trp Asp
5405                5410                5415

Ala Glu Leu His Gln Gly Leu Ile Asp Leu Ala Arg Ser Thr Gly
5420                5425                5430

Thr Thr Val Phe Met Val Leu Gln Ala Gly Leu Ala Ala Leu Met
5435                5440                5445

Ser Arg Leu Gly Ala Gly Asp Asp Ile Pro Leu Gly Ser Pro Ile
5450                5455                5460

Ala Gly Arg Thr Asp Glu Ala Leu Asp Asp Leu Val Gly Phe Phe
5465                5470                5475

Val Asn Thr Leu Val Leu Arg Thr Asp Thr Ser Gly Asn Pro Thr
5480                5485                5490

Phe Arg Glu Leu Leu Ala Arg Val Arg Glu Thr Asp Leu Ala Ala
5495                5500                5505

Tyr Ala His Gln Asp Val Pro Phe Glu His Leu Val Glu Ile Leu
5510                5515                5520

Asn Pro Glu Arg Ser Leu Ala His His Pro Leu Phe Gln Val Ser
5525                5530                5535

Val Thr Leu Asp Asn Thr Pro Gly His Arg Leu Glu Leu Asp Gly
5540                5545                5550

Leu Glu Ile Ser Val Glu Pro Val Gly Thr Arg Thr Ser Arg Phe
5555                5560                5565

Asp Leu Ala Leu Asn Phe Tyr Gly Leu Val Gly Asp Ser Gly Gly
5570                5575                5580

Pro Gly Gly Leu His Gly Ser Val Glu Phe Ser Thr Asp Leu Phe
5585                5590                5595

Asp Arg Val Ser Val Glu Val Val Leu Glu Arg Leu Arg Arg Val
5600                5605                5610

Leu Val Ser Val Ala Ala Asp Pro Asp Val Thr Val Gly Ala Leu
5615                5620                5625

Pro Val Leu Ser Gly Gln Glu Glu His Arg Leu Val Ala Glu Trp
5630                5635                5640

Asn Asp Thr Ala Leu Glu Val Pro Pro Ala Ser Leu Pro Glu Leu
5645                5650                5655

Phe Gln Ala Gln Ala Ala Ala Thr Pro Glu Ala Thr Ala Val Val
5660                5665                5670

Phe Glu Thr Glu Arg Leu Ser Tyr Arg Glu Leu Asn Glu Arg Ala
5675                5680                5685

Asn Arg Leu Ala His Tyr Leu Ile Gly Gln Gly Ala Gly Pro Glu
5690                5695                5700

Arg Ile Val Ala Leu Ala Leu Pro Arg Gly Thr Asp Leu Val Ile
5705                5710                5715

Ala Val Leu Ala Val Leu Lys Ala Gly Ala Ala Tyr Leu Pro Val
5720                5725                5730

Asp Pro Asp Tyr Pro Ala Glu Arg Ile Thr His Met Leu Thr Asp
5735                5740                5745

Thr Arg Pro Thr Leu Leu Leu Thr Thr Ser Asp Val Ala Ala Gly
```

-continued

```
            5750                5755                5760
Leu Pro Arg Thr Glu Gly Val Thr Ser Val Leu Leu Asp Asp Pro
    5765                5770                5775
Ala Val Thr Glu Thr Val Ala Leu Cys Ala Val Ser Asp Pro Thr
    5780                5785                5790
Asp Ser Glu Arg Gly Val Val Leu Glu Gly Ser His Pro Ala Tyr
    5795                5800                5805
Val Ile Tyr Thr Ser Gly Ser Thr Gly Val Pro Lys Gly Val Val
    5810                5815                5820
Met Pro Ser Gly Gly Leu Val Asn Leu Leu His Trp His Pro Ser
    5825                5830                5835
Val Ile Ala Gly Arg Ala Gly Ala Arg Thr Ala Gln Phe Thr Thr
    5840                5845                5850
Ile Ser Phe Asp Val Ser Ala Gln Glu Ile Leu Ser Ala Leu Val
    5855                5860                5865
Phe Gly Lys Glu Leu Trp Val Pro Gly Glu Glu Val Arg Arg Ser
    5870                5875                5880
Gly Glu Gly Leu Ala Arg Trp Leu Gln Glu His Ala Val Glu Glu
    5885                5890                5895
Leu Phe Ala Pro Ala Leu Val Ile Asp Ala Val Ala Gln Ala Ala
    5900                5905                5910
Gly Glu Leu Gly Leu Val Leu Pro Ala Leu Arg His Val Ala Gln
    5915                5920                5925
Gly Gly Glu Ala Leu Val Pro Gly Ala Ala Met Arg Arg Phe Phe
    5930                5935                5940
Arg Glu Arg Pro His Ile Arg Leu His Asn His Tyr Gly Pro Thr
    5945                5950                5955
Glu Thr His Ala Val Thr Ala Tyr Val Leu Pro Glu Arg Val Ala
    5960                5965                5970
Asp Trp Pro Val Ser Ala Ala Pro Val Gly Gly Pro Val Ala Asn
    5975                5980                5985
Asp Arg Val Tyr Val Leu Asp Ala Ala Leu Arg Ala Val Pro Val
    5990                5995                6000
Gly Val Ala Gly Glu Leu Tyr Val Ala Gly Ala Gly Leu Ala Arg
    6005                6010                6015
Gly Tyr Val Asn Arg Ala Gly Leu Thr Ala Ser Arg Phe Val Ala
    6020                6025                6030
Asp Pro Tyr Gly Pro Ala Gly Ser Arg Met Tyr Arg Thr Gly Asp
    6035                6040                6045
Val Val Arg Trp Asn Thr Ser Gly Glu Leu Glu Phe Val Gly Arg
    6050                6055                6060
Ala Asp Asp Gln Val Lys Ile Arg Gly Phe Arg Ile Glu Leu Gly
    6065                6070                6075
Glu Ile Glu Thr Thr Ala Ala Gly His Pro Ala Val Ala Gln Ala
    6080                6085                6090
Ala Ala Thr Val His Glu Asp Asp Thr Arg Gly Lys Gln Leu Ala
    6095                6100                6105
Leu Tyr Ile Val Pro Thr Gly Thr Gly Gly Val Val Asp Ala Gly
    6110                6115                6120
Thr Val Arg Glu Tyr Leu Arg Thr Lys Leu Pro Asp Tyr Met Val
    6125                6130                6135
Pro Ala Ala Val Val Val Leu Glu Gln Leu Pro Leu Thr Ala Ser
    6140                6145                6150
```

```
Gly Lys Leu Asp Arg Arg Ala Leu Pro Thr Pro Glu Phe Ala Ala
6155                6160                6165

Glu Pro Ala Gly Arg Thr Ala Arg Ser Pro Arg Glu Glu Ile Leu
6170                6175                6180

Ala Gly Leu Phe Ala Glu Val Leu Gly Leu Pro Ala Val Gly Ile
6185                6190                6195

Asp Asp Ser Phe Phe Asp Leu Gly Gly His Ser Leu Leu Ala Thr
6200                6205                6210

Arg Leu Ile Ser Arg Ile Arg Ala Ile Leu Gly Ala Glu Ile Pro
6215                6220                6225

Ile Arg Ala Leu Phe Glu Thr Pro Thr Val Ala Gly Leu Ala Ala
6230                6235                6240

Leu Leu Glu Thr Ser Ser Glu Ser Val Arg Ser Ala Leu Val Pro
6245                6250                6255

Val Thr Arg Pro Glu Arg Met Pro Leu Ser Ser Ala Gln Ser Arg
6260                6265                6270

Leu Trp Phe Leu His Arg Leu Glu Gly Pro Ser Ala Thr Tyr Asn
6275                6280                6285

Met Pro Met Ala Leu Arg Leu Ser Gly Arg Leu Asp Arg Glu Ala
6290                6295                6300

Leu His Thr Ala Leu Ala Asp Val Val Glu Arg His Glu Ser Leu
6305                6310                6315

Arg Thr Val Phe Pro Glu Thr Asp Gly Val Pro Cys Gln Gln Ile
6320                6325                6330

Leu Ala Gly Ala Glu Ala Gln Pro Val Leu Glu Val Ala Asp Ile
6335                6340                6345

Ala Glu Asp Gln Leu Asp Gln Ala Leu Ala Gly Ala Ala Arg Tyr
6350                6355                6360

Pro Phe Asp Leu Ser Val Glu Leu Pro Val Arg Ala Trp Leu Phe
6365                6370                6375

Ala Leu Ala Arg Glu Glu His Val Leu Val Leu Val Val His His
6380                6385                6390

Ile Ala Ser Asp Gly Trp Ser Leu Ala Pro Leu Ser Arg Asp Leu
6395                6400                6405

Val Thr Ala Tyr Ala Ala Arg Ala Asp Gly Arg Val Pro Gly Trp
6410                6415                6420

Ala Pro Leu Pro Val Gln Tyr Ala Asp Tyr Thr Leu Trp Gln Asn
6425                6430                6435

Asp Leu Leu Gly Asp His Ser Asp Thr Gly Ser Leu Ile Ala Arg
6440                6445                6450

Gln Leu Glu Tyr Trp Arg Thr Thr Leu Thr Gly Leu Pro Glu Gln
6455                6460                6465

Val Thr Leu Pro Thr Asp Arg Pro Arg Pro Ala Met Ala Ser Gln
6470                6475                6480

Arg Gly Glu Val Phe Glu Phe Ser Trp Asp Ala Glu Leu His Gln
6485                6490                6495

Gly Leu Val Asp Leu Ala Arg Ser Thr Gly Thr Thr Val Phe Met
6500                6505                6510

Val Leu Gln Ala Gly Leu Ala Ala Leu Met Ser Arg Leu Gly Ala
6515                6520                6525

Gly Asp Asp Ile Pro Leu Gly Ser Pro Ile Ala Gly Arg Thr Asp
6530                6535                6540
```

Glu Ala Leu Asp Asp Leu Val Gly Phe Phe Val Asn Thr Leu Val
    6545                6550                6555

Leu Arg Thr Asp Thr Ser Gly Asn Pro Thr Phe Arg Glu Leu Leu
    6560                6565                6570

Ala Arg Val Arg Glu Thr Asp Leu Ala Ala Tyr Ala His Gln Asp
    6575                6580                6585

Val Pro Phe Glu His Leu Val Glu Ile Leu Asn Pro Glu Arg Ser
    6590                6595                6600

Leu Ala His His Pro Leu Phe Gln Val Ser Val Thr Leu Asp Asn
    6605                6610                6615

Thr Pro Gly His Arg Leu Glu Leu Asp Gly Leu Glu Ile Ser Val
    6620                6625                6630

Glu Pro Val Gly Thr Arg Thr Ser Arg Phe Asp Leu Ala Leu Asn
    6635                6640                6645

Phe Tyr Gly Leu Val Gly Asp Ser Gly Pro Gly Gly Leu His
    6650                6655                6660

Gly Ser Val Glu Phe Ser Thr Asp Leu Phe Asp Arg Val Ser Val
    6665                6670                6675

Glu Val Val Leu Glu Arg Leu Arg Arg Val Leu Val Ser Val Ala
    6680                6685                6690

Ala Asp Pro Asp Val Thr Val Gly Ala Leu Pro Val Leu Ser Gly
    6695                6700                6705

Gln Glu His Arg Leu Val Ala Glu Trp Asn Asp Thr Ala Leu
    6710                6715                6720

Glu Val Pro Pro Ala Ser Leu Pro Glu Leu Phe Gln Ala Gln Ala
    6725                6730                6735

Ala Glu Ala Pro Glu Ala Thr Ala Val Val Phe Glu Thr Glu Arg
    6740                6745                6750

Leu Ser Tyr Arg Glu Leu Asn Glu Arg Ala Asn Arg Leu Ala His
    6755                6760                6765

Tyr Leu Ile Gly Gln Gly Ala Gly Pro Glu Arg Ile Val Ala Leu
    6770                6775                6780

Ala Leu Pro Arg Gly Thr Asp Leu Val Ile Ala Val Leu Ala Val
    6785                6790                6795

Leu Lys Ala Gly Ala Ala Tyr Leu Pro Val Asp Pro Asp Tyr Pro
    6800                6805                6810

Ala Glu Arg Ile Thr His Met Leu Thr Asp Thr Arg Pro Thr Leu
    6815                6820                6825

Leu Leu Thr Thr Ser Asp Val Ala Ala Gly Leu Pro Arg Thr Glu
    6830                6835                6840

Gly Val Thr Ser Val Leu Leu Asp Asp Pro Ala Val Thr Glu Thr
    6845                6850                6855

Val Ala Leu Cys Ala Val Ser Asp Pro Thr Asp Ser Glu Arg Gly
    6860                6865                6870

Val Val Leu Glu Gly Ser His Pro Ala Tyr Val Ile Tyr Thr Ser
    6875                6880                6885

Gly Ser Thr Gly Val Pro Lys Gly Val Leu Val Pro His Ala Gly
    6890                6895                6900

Leu Ala Asn Leu Thr Ala Ala Glu Arg Ala Ala Leu Asp Leu Ser
    6905                6910                6915

Ala Gly Ser Arg Val Leu Gln Leu Ala Ser Val Gly Phe Asp Ala
    6920                6925                6930

Ala Val Leu Glu Leu Ser Met Ala Phe Gly Ser Gly Ala Thr Leu

```
                6935                6940                6945
Val Ile Ala Pro Gln Gly Arg Leu Leu Gly Asp Asp Leu Ala Ala
        6950                6955                6960
Leu Leu Ala Arg Gln Glu Ile Thr His Thr Leu Ile Thr Pro Ser
        6965                6970                6975
Ala Leu Ala Thr Leu Pro Glu Thr Asp Leu Pro His Leu Arg Thr
        6980                6985                6990
Leu Leu Thr Gly Ala Glu Ala Cys Pro Pro Glu Leu Val Ala Arg
        6995                7000                7005
Trp Ser Pro Gly Arg Arg Phe Ile Asn Ala Tyr Gly Pro Thr Glu
        7010                7015                7020
Ala Ser Val Val Ala Thr Trp Ser Asp Pro Leu Thr Gln Asp Thr
        7025                7030                7035
Ala Pro Ile Gly Arg Pro Leu Pro Asn Thr Arg Val Tyr Val Leu
        7040                7045                7050
Asp Ala Gly Leu Arg Val Val Pro Val Gly Val Ala Gly Glu Leu
        7055                7060                7065
Tyr Val Ala Gly Ala Gly Leu Ala Arg Gly Tyr Val Asn Arg Ala
        7070                7075                7080
Gly Leu Thr Ala Ser Arg Phe Val Ala Asp Pro Tyr Gly Pro Ala
        7085                7090                7095
Gly Ser Arg Met Tyr Arg Thr Gly Asp Val Val Arg Trp Asn Thr
        7100                7105                7110
Ser Gly Glu Leu Glu Phe Val Gly Arg Ala Asp Asp Gln Val Lys
        7115                7120                7125
Ile Arg Gly Phe Arg Ile Glu Leu Gly Glu Ile Glu Thr Thr Ala
        7130                7135                7140
Ala Gly His Pro Ala Val Ala Gln Ala Ala Ala Thr Val His Glu
        7145                7150                7155
Asp Asp Thr Arg Gly Lys Gln Leu Ala Leu Tyr Ile Val Pro Thr
        7160                7165                7170
Gly Ile Thr Ser Gly Asp Val Pro Ala Ser Gly Gly Val Val Asp
        7175                7180                7185
Ala Gly Thr Val Arg Glu Tyr Leu Arg Thr Arg Leu Pro Asp Tyr
        7190                7195                7200
Met Val Pro Ala Ala Val Val Val Leu Glu Arg Leu Pro Leu Thr
        7205                7210                7215
Ala Ser Gly Lys Leu Asp Arg Arg Ala Leu Pro Thr Pro Glu Phe
        7220                7225                7230
Ala Ala Glu Pro Ala Gly Arg Thr Ala Arg Ser Pro Arg Glu Glu
        7235                7240                7245
Ile Leu Ala Gly Leu Phe Ala Glu Val Leu Gly Leu Pro Ala Val
        7250                7255                7260
Gly Ile Asp Asp Ser Phe Phe Asp Leu Gly Gly His Ser Leu Leu
        7265                7270                7275
Ala Thr Arg Leu Ile Ser Arg Ile Arg Ala Thr Leu Asn Thr Glu
        7280                7285                7290
Val Pro Val Arg Ala Leu Phe Glu Ala Pro Thr Val Ala Ala Leu
        7295                7300                7305
Thr Val Leu Leu Glu Thr Ser Asn Gly Glu Thr Val Arg Ser Thr
        7310                7315                7320
Leu Val Pro Ala Val Arg Pro Glu Arg Ile Pro Leu Ser Ser Ala
        7325                7330                7335
```

-continued

```
Gln Ser Arg Leu Trp Phe Leu His Arg Leu Glu Gly Pro Ser Ala
    7340                7345                7350

Thr Tyr Asn Ile Pro Met Ala Leu Arg Leu Ser Gly Arg Leu Asp
    7355                7360                7365

Arg Glu Ala Leu His Thr Ala Leu Thr Asp Val Val Glu Arg His
    7370                7375                7380

Glu Ser Leu Arg Thr Val Phe Pro Glu Thr Asp Ser Val Pro Tyr
    7385                7390                7395

Gln His Val Leu Ala Glu Val Glu Ala Arg Pro Val Leu His Val
    7400                7405                7410

Val Gln Thr Ser Glu Glu Gly Leu Ala Glu Ala Val Ser Ala Ala
    7415                7420                7425

Ser Gln Tyr Ala Phe Asp Leu Ser Ala Glu Leu Pro Val Arg Ala
    7430                7435                7440

Trp Leu Phe Ala Leu Ala Pro Glu Glu His Val Leu Val Leu Val
    7445                7450                7455

Val His His Ile Ala Gly Asp Gly Trp Ser Leu Ser Pro Leu Phe
    7460                7465                7470

Arg Asp Leu Thr Val Ala Tyr Ala Ala Arg Ala Asp Gly Arg Thr
    7475                7480                7485

Pro Gly Trp Ser Ala Leu Pro Val Gln Tyr Ala Asp Tyr Thr Leu
    7490                7495                7500

Trp Gln Asn Asp Leu Leu Gly Asp His Ser Asp Thr Gly Ser Leu
    7505                7510                7515

Ile Ala Arg Gln Leu Glu Tyr Trp Arg Thr Thr Leu Thr Gly Leu
    7520                7525                7530

Pro Glu Gln Val Thr Leu Pro Thr Asp Arg Pro Arg Pro Ala Thr
    7535                7540                7545

Ala Thr Tyr Gln Gly Asp Ser Leu Tyr Phe Lys Trp Asp Ala Glu
    7550                7555                7560

Leu His Gln Gly Leu Ile Asp Leu Ala Arg Ser Thr Gly Thr Thr
    7565                7570                7575

Val Phe Met Val Leu Gln Ala Gly Leu Ala Ala Leu Met Ser Arg
    7580                7585                7590

Leu Gly Ala Gly Asp Asp Ile Pro Leu Gly Ser Pro Ile Ala Gly
    7595                7600                7605

Arg Thr Asp Glu Ala Leu Asp Asp Leu Val Gly Phe Phe Val Asn
    7610                7615                7620

Thr Leu Val Leu Arg Thr Asp Thr Ser Gly Asn Pro Thr Phe Arg
    7625                7630                7635

Glu Leu Leu Ala Arg Val Arg Glu Thr Asp Leu Ala Ala Tyr Ala
    7640                7645                7650

His Gln Asp Val Pro Phe Glu His Leu Val Glu Ile Leu Asn Pro
    7655                7660                7665

Glu Arg Ser Leu Ala His His Pro Leu Phe Gln Val Met Leu Ala
    7670                7675                7680

Leu Gln Asn Thr Pro Glu Gly Gln Phe Lys Leu Pro Gly Leu Gln
    7685                7690                7695

Ala Arg Phe Glu Thr Thr His Thr Gln Thr Ala Lys Phe Asp Leu
    7700                7705                7710

Phe Phe Asn Phe Ser Glu Tyr Arg Ala Glu Asn Asn Ser Ala Arg
    7715                7720                7725
```

```
Gly Ile Asn Gly Val Ile Glu Tyr Asp Ser Ser Leu Phe Ser Val
    7730                7735                7740

Ala Thr Val Glu Lys Leu Thr Glu Arg Leu Leu Arg Val Leu Arg
7745                7750                7755

Glu Val Ile Ala Asn Pro Asp Lys Arg Leu Arg Arg Ile Glu Val
7760                7765                7770

Leu Thr Gln Gln Glu Arg Met Lys Leu Leu Asp Asn Leu Asn Lys
7775                7780                7785

Trp Ser Gly Gly Asp Ser
7790

<210> SEQ ID NO 10
<211> LENGTH: 110
<212> TYPE: PRT
<213> ORGANISM: Streptomyces 22643

<400> SEQUENCE: 10

Met Trp Cys Ala Arg Leu Ala Trp Ser Arg Phe Arg Val Val Ile Pro
1               5                   10                  15

Val Phe Glu Lys Ala Leu Pro Thr Ile Val Ala Cys Leu Asp Ala Thr
            20                  25                  30

Leu Arg Arg Ile Gly Gly Val Pro Ser Tyr Ala Leu Thr Asp Asn Glu
        35                  40                  45

Lys Ile Val Thr Thr Glu His Ile Ala Asn Ile Ala Val Arg Asn Pro
    50                  55                  60

Glu Ile Val Glu Val Gly Arg His Tyr Gly Ile Thr Ile His Thr Cys
65                  70                  75                  80

Leu Pro Ala Asp Pro Glu Ala Lys Gly Gly Ser Glu Ala Thr Val Arg
                85                  90                  95

Ile Ala Lys Ala Asp Leu Val Pro Thr Ser Ala Asn Arg Thr
            100                 105                 110

<210> SEQ ID NO 11
<211> LENGTH: 179
<212> TYPE: PRT
<213> ORGANISM: Streptomyces DSM 22643

<400> SEQUENCE: 11

Met Lys Gly Ala Gly Pro Pro Thr Pro Ala Gly Arg Ala Gly Cys Ser
1               5                   10                  15

Ala Glu Ala Glu Val Arg Thr Arg Gly Ala Leu Asp Trp Tyr Trp Ala
            20                  25                  30

Val Asp Val Leu Thr Glu Ala Gly Ala Val His Leu Thr His Pro
        35                  40                  45

Leu Gly Val Lys Ala Phe Ala Tyr Arg Arg Val Lys Asn Asp Glu Arg
    50                  55                  60

Asp Ala Ala Asp Leu Thr Asp Leu Leu Arg Leu Gly Arg Leu Pro Val
65                  70                  75                  80

Ala Gly Ser Met Leu Ala Val Tyr Val Arg Gln Cys Leu Lys Asn Gly
                85                  90                  95

Asp Thr Val Glu Val Ser Ala Ser Cys Trp Trp Lys Phe Ser Ala Asp
            100                 105                 110

Thr Ile Thr Gln His Gly Glu Tyr Leu Leu Ala Phe Val Asp Gly His
        115                 120                 125

Val Cys Val Gly Ala Phe Glu Ile Val Gly Ala Glu Pro Asp Glu Thr
    130                 135                 140
```

-continued

```
Glu Gly Glu Lys Tyr Val Phe Asp Leu Leu Arg Pro Ala Ala Arg Phe
145                 150                 155                 160

Gln Trp Ala Leu Gly Arg Lys Leu Pro Leu Pro Gly Arg Asn Pro
            165                 170                 175

Cys Ala Phe

<210> SEQ ID NO 12
<211> LENGTH: 186
<212> TYPE: PRT
<213> ORGANISM: Streptomyces DSM 22643

<400> SEQUENCE: 12

Val Ala Ser Leu Gly Ala Tyr His Leu Thr Gly Ser His Arg Ala Ala
1               5                   10                  15

Ala Glu Leu Ala Gly Val Asp His His Thr Val Ala Arg Tyr Val Lys
                20                  25                  30

Leu Arg Glu Ala Gly Glu Arg Pro Ala Glu Arg Gln His Arg Ala Arg
            35                  40                  45

Pro Ile Asp Glu Phe Met Asp Lys Ile Glu Glu Leu Leu Thr Ala Ser
    50                  55                  60

Lys Gly Arg Ile Gly Ala Asp Ile Val His Arg Ile Thr Ala Ala
65                  70                  75                  80

Gly Leu Thr Gly Gly Asp Arg Thr Thr Arg Arg Ala Val Val Lys Val
                85                  90                  95

Lys Ala Arg Met Arg Ser Arg His His Arg Val Pro Ser Ser Ser Pro
            100                 105                 110

Pro Ala Gln Pro Pro Gln Ile Pro Tyr Arg Gly Ser Asp Glu Glu Leu
        115                 120                 125

Ala Gln Gly Leu Ala Gln Asn Ala His Gly Leu Arg Pro Gly Gly
    130                 135                 140

Ser Gly Ser Phe Leu Pro Ser Ala His Trp Asn Arg Ala Ala Gly Arg
145                 150                 155                 160

Arg Arg Ser Lys Thr Tyr Phe Ser Pro Ser Val Ser Ser Gly Ser Ala
                165                 170                 175

Pro Thr Ile Ser Lys Ala Pro Thr His Thr
            180                 185

<210> SEQ ID NO 13
<211> LENGTH: 550
<212> TYPE: PRT
<213> ORGANISM: Streptomyces DSM 22643

<400> SEQUENCE: 13

Met Thr Pro Val Pro Gln Leu Arg Ile Pro Thr Ala Arg Leu Lys Ala
1               5                   10                  15

Lys Phe Asp Arg Ile Leu Pro His Leu Asp Glu Arg Arg Arg Phe
                20                  25                  30

Tyr Leu Ala Ser Glu Ala Val Ala Leu Gly His Gly Ile Ala Ala
            35                  40                  45

Val Ala Ala Ala Ser Gly Thr Ser Thr Ala Thr Ile Ala Arg Gly Ile
    50                  55                  60

Ala Glu Leu Asp Ala His Pro Ala Thr Thr Cys Arg Asn Arg Ala Leu
65                  70                  75                  80

Gly Ala Gly Arg Lys Pro Leu Thr Thr Thr Asp Thr Gly Leu Arg Pro
                85                  90                  95

Ala Leu Glu Ala Leu Ile Glu Pro Arg Thr Arg Gly Asp Pro Val Ser
```

```
                100                 105                 110
Pro Leu Arg Trp Thr Thr Leu Ser Leu Arg Thr Leu Ala Ser Thr Leu
            115                 120                 125
Thr Ala Gln Gly His Pro Val Gly Ala Thr Thr Val Gly Arg Leu Leu
        130                 135                 140
His Ala Met Gly Tyr Ser Leu Gln Gly Thr Ala Lys Thr Thr Glu Gly
145                 150                 155                 160
Ala Arg His Pro Asp Arg Asp Ala Thr Ala Thr Ala Phe Leu Asp Ser
                165                 170                 175
His Gln Pro Val Ile Ser Val Asp Thr Lys Ala Lys Glu Trp Ile Gly
            180                 185                 190
Asn Arg Asp Arg Pro Gly Arg Thr Trp Arg Pro Gly Lys Gly Pro Ile
        195                 200                 205
Lys Val Asp Cys His Thr Phe Val Thr Asp Glu Met Pro Val Ala Ile
210                 215                 220
Pro Tyr Gly Ile Tyr Asp Leu Ala Thr Asn Thr Gly Trp Val Asn Val
225                 230                 235                 240
Gly Thr Asp His Asp Thr Ala Glu Phe Ala Val Glu Ser Ile Arg Arg
                245                 250                 255
Trp Trp Arg Arg Arg Gly Arg Thr Asp His Pro Asn Ala Thr Arg Leu
            260                 265                 270
Leu Ile Thr Ala Asp Ala Gly Gly Ser Asn Asp Ala Arg Arg Trp Thr
        275                 280                 285
Trp Lys Lys Tyr Leu His Ala Phe Ala Gln Glu Ser Gly Leu Glu Ile
        290                 295                 300
Thr Val Cys His Phe Pro Pro Gly Thr Ser Lys Trp Asn Lys Ile Glu
305                 310                 315                 320
His Arg Met Phe Cys His Ile Thr Ala Asn Trp Arg Gly Gln Pro Leu
                325                 330                 335
Thr Ser Tyr Gln Val Val Glu Thr Ile Ala Ala Thr Thr Thr Ala
            340                 345                 350
Asn Gly Leu Ser Ile Gly Ala Glu Leu Asp Thr Gly Ser Tyr Pro Leu
            355                 360                 365
Gly Thr Thr Val Thr Pro Ala Glu Phe Gln Ala Leu Pro Ile Ala Pro
        370                 375                 380
Glu Ala Phe His Gly Asp Trp Asn Tyr Thr Leu Ala Pro Ala Pro Pro
385                 390                 395                 400
Ser Pro Ala Glu Ala Pro Thr Thr Arg Arg Pro Ile Asp Pro Ala Leu
                405                 410                 415
Thr Thr Met Leu Ile Asp Pro Ala Leu Thr Gly Met Pro Arg Ala Asp
                420                 425                 430
Phe Ala His Leu Ala Ala Val Ser Glu Pro Tyr Trp Asp Ala Leu Ala
            435                 440                 445
Glu Ala Ala Phe Gln Arg Arg Phe His Arg Pro Arg Ser Tyr Leu His
            450                 455                 460
Pro Gln Thr Ser Ser Leu Asp His Phe His Arg Leu Leu Thr Ala Leu
465                 470                 475                 480
Leu Arg Arg Arg Lys Ala Ala Thr Ser Thr Leu Leu Ala Gln Leu Leu
                485                 490                 495
Gly Val Thr Arg Thr Asn Leu Ser Asn Gln Phe Gln Asp Gly His Arg
            500                 505                 510
Ile Leu Asp Leu Tyr Arg Ile Ala Val Thr Pro Ile Pro Gly Ala Pro
            515                 520                 525
```

```
Ala Arg Thr Leu Glu Gln Leu Arg Ala Arg Leu Ala Ser Ala Glu Asp
            530                 535                 540

Asp Pro Thr Asp Gln Asp
545                 550

<210> SEQ ID NO 14
<211> LENGTH: 380
<212> TYPE: PRT
<213> ORGANISM: Streptomyces DSM 22643

<400> SEQUENCE: 14

Val Ala Glu Arg Asn Ser Leu Ala Gly Gln Val Glu Pro Ser Thr Pro
1               5                   10                  15

Leu Val Glu Val Gly Gln Asp Pro Ile Glu Leu Gly Leu Gln Pro Gly
            20                  25                  30

Cys Gly Asp Ala Lys Leu Arg Asn Arg Ser His Ala Pro Ala Ser His
        35                  40                  45

His Gly Ser Pro His Arg Ser Ser Leu Thr Val Ile His Val Gln Ala
    50                  55                  60

Leu Gly Gly Ile Gly Leu Cys Gln Val Ala Val His Leu Thr Tyr Ala
65                  70                  75                  80

Thr Pro Arg Gly His Ala Leu Ile Asp Arg Glu Leu Tyr Leu Pro Ala
                85                  90                  95

Ala Trp Ala Gln Asp Glu Arg Arg Leu Leu Arg His Val Pro Asp
            100                 105                 110

Glu Val Phe Phe Ala Thr Lys Pro Gln Leu Ala Ala Val Met Leu Thr
            115                 120                 125

Arg Ala Arg Glu Leu Gly Val Cys Ala Arg Trp Phe Ala Gly Asp Glu
        130                 135                 140

Val Tyr Gly Ser Leu Glu Leu Arg Arg Thr Ala Arg Met Leu Gly Phe
145                 150                 155                 160

Asp Tyr Ala Leu Ala Val Lys Ala Asp His Thr Ala Thr Thr Ser Ala
                165                 170                 175

Gly Arg Phe Thr Ala Ala Arg Leu Ala Ala Lys Val Pro Ala Lys Ser
            180                 185                 190

Trp Met Arg Met Arg Thr Gly His Gly Leu Lys Gly Asp Arg His Tyr
        195                 200                 205

Asp Trp Ala Leu Ile Glu Val Arg Pro Asp Asp Thr Pro Thr Asp Ser
    210                 215                 220

Glu Ala Gly Gly His Ala Phe Leu Val Ile Arg Arg His Arg Tyr Thr
225                 230                 235                 240

Arg Glu Leu Ser Phe Tyr Arg Cys His Ser Thr Thr Pro Ile Ser Leu
                245                 250                 255

Ala Asp Leu Val Asn Ile Ile Cys Thr Arg Trp Lys Ile Glu Glu Asp
            260                 265                 270

Phe Gln Gly Ala Lys Gly Leu Thr Gly Leu Asp Gln Gly Gln Val Ala
        275                 280                 285

Cys Trp Asn Ser Trp Met His Trp Ser Leu Ile Ser Leu Ile Ala Ala
    290                 295                 300

Ala Val Leu Ala Ile Thr Arg Ala Arg Thr Ala Pro Ala Ala Gly
305                 310                 315                 320

Ile Ala Leu Val Pro Ala Ser Pro Arg Glu Leu Leu Ala Val Leu Arg
                325                 330                 335

Ala Thr Ala Leu Pro Ala Pro Arg Arg His Leu Gly His Val Leu His
```

```
              340                 345                 350
Trp Ser Ala Trp Arg Arg His His Gln His Gln Ala Val Gln Ala His
        355                 360                 365

Arg Arg Trp Asn Asn Val Thr Ala Glu Ala Thr Arg
370                 375                 380

<210> SEQ ID NO 15
<211> LENGTH: 428
<212> TYPE: PRT
<213> ORGANISM: Streptomyces DSM 22643

<400> SEQUENCE: 15

Met Lys Cys Cys Ser Ala Gly Asp Tyr Pro Ala Arg Val Ala Asp Asp
1               5                   10                  15

Pro Trp Arg Leu Ala Pro Arg Gly Thr Ala Cys Gly Arg Cys Asp Ala
            20                  25                  30

Pro Tyr Trp Ala Ala Gly Gly Ala Asp Ser Val Ala Thr Cys Ser
        35                  40                  45

Lys Pro Ser Glu Ala Tyr Ser Met Arg Phe Gln Val Glu Arg Glu Val
    50                  55                  60

Leu Ala Glu Gly Ile Gly Trp Val Ala Arg Gly Leu Ala Val Arg Pro
65                  70                  75                  80

Ser Val Pro Ile Leu Ser Gly Val Val Asn Ala Glu Gly Asp Thr
                85                  90                  95

Leu Thr Leu Ser Gly Phe Asp Tyr Glu Val Ser Thr Arg Val Glu Leu
            100                 105                 110

Lys Ala Asn Val Glu Glu Ser Gly Thr Val Leu Ile Pro Gly Arg Arg
        115                 120                 125

Leu Ala Asp Ile Ala Lys Val Leu Pro Asp Val Pro Ile Glu Phe Asn
130                 135                 140

Val Asp Gln Thr Lys Val Tyr Val Gln Cys Asp Ser Asn Ser Phe Val
145                 150                 155                 160

Leu Asn Ala Leu Pro Leu Asp Glu Tyr Pro Thr Leu Pro Lys Leu Pro
                165                 170                 175

Thr Val Cys Gly Ser Val Glu Gly Asp Gln Phe Ala Arg Ala Val Ser
            180                 185                 190

Gln Val Ala Val Ala Ser Arg Asp Asp Ala Leu Pro Val Leu Thr
        195                 200                 205

Gly Ile Gly Val Asn Phe Asp Gly Glu Ile Met Lys Leu Asn Ala Thr
210                 215                 220

Asp Arg Tyr Arg Phe Ala Ile Arg Glu Leu Ala Trp Lys Pro Glu Gly
225                 230                 235                 240

Thr Pro Ser Ser Ser Val Leu Val Pro Ala Arg Thr Leu Leu Asp
                245                 250                 255

Phe Ala Lys Ser Leu Asn Lys Gly Asp Leu Val Lys Ile Ala Leu Ser
            260                 265                 270

Asp Glu Gly Asn Leu Leu Gly Leu His Ala Gly Thr Arg Gln Met Thr
        275                 280                 285

Cys Arg Leu Leu Glu Gly Thr Leu Pro Asp Tyr Glu Lys Leu Phe Pro
290                 295                 300

Lys Glu Phe Thr Ser Phe Gly Ala Val Glu Val Ser Arg Leu Val Glu
305                 310                 315                 320

Ala Leu Lys Arg Val Ser Leu Val Leu Glu Arg Asn Ser Ser Val Ala
                325                 330                 335
```

```
Leu Asp Phe Thr Asp Gly Glu Leu Val Gln Ala Gly Gly Ala Asp
            340                 345                 350

Asp Asp Arg Ala Thr Ser Arg Met Ala Ala Ser Leu Glu Gly Glu Ser
        355                 360                 365

Ile Asp Ile Ala Phe Asn Pro Ser Phe Leu Leu Asp Gly Leu Thr Asn
370                 375                 380

Leu Asp Ala Ser Trp Ala Gln Phe Ser Phe Thr Ser Ser Asn Gly Lys
385                 390                 395                 400

Ala Val Ile Met Gly Lys Ser Ser Val Asp Ala Glu Ala Asp Thr Ser
                405                 410                 415

Ala Arg Tyr Leu Val Met Pro Val Arg Phe His Arg
                420                 425

<210> SEQ ID NO 16
<211> LENGTH: 4168
<212> TYPE: PRT
<213> ORGANISM: Streptomyces DSM 22643
<220> FEATURE:
<221> NAME/KEY: DOMAIN
<222> LOCATION: (42)..(1066)
<223> OTHER INFORMATION: Module 7
<220> FEATURE:
<221> NAME/KEY: DOMAIN
<222> LOCATION: (42)..(500)
<223> OTHER INFORMATION: Module 7; domain A7'
<220> FEATURE:
<221> NAME/KEY: DOMAIN
<222> LOCATION: (501)..(938)
<223> OTHER INFORMATION: Module 7; domain MT7 in domain A7
<220> FEATURE:
<221> NAME/KEY: DOMAIN
<222> LOCATION: (939)..(979)
<223> OTHER INFORMATION: Module 7; domain A7''
<220> FEATURE:
<221> NAME/KEY: DOMAIN
<222> LOCATION: (1002)..(1066)
<223> OTHER INFORMATION: Module 7; domain T7
<220> FEATURE:
<221> NAME/KEY: DOMAIN
<222> LOCATION: (1088)..(2148)
<223> OTHER INFORMATION: Module 8
<220> FEATURE:
<221> NAME/KEY: DOMAIN
<222> LOCATION: (1088)..(1430)
<223> OTHER INFORMATION: Module 8; domain C8
<220> FEATURE:
<221> NAME/KEY: DOMAIN
<222> LOCATION: (1575)..(2061)
<223> OTHER INFORMATION: Module 8; domain A8
<220> FEATURE:
<221> NAME/KEY: DOMAIN
<222> LOCATION: (2084)..(2148)
<223> OTHER INFORMATION: Module 8; domain T8
<220> FEATURE:
<221> NAME/KEY: DOMAIN
<222> LOCATION: (2172)..(4160)
<223> OTHER INFORMATION: Module 9
<220> FEATURE:
<221> NAME/KEY: DOMAIN
<222> LOCATION: (2172)..(2513)
<223> OTHER INFORMATION: Module 9; domain C9
<220> FEATURE:
<221> NAME/KEY: DOMAIN
<222> LOCATION: (2658)..(3098)
<223> OTHER INFORMATION: Module 9; domain A9'
<220> FEATURE:
<221> NAME/KEY: DOMAIN
<222> LOCATION: (3099)..(3536)
<223> OTHER INFORMATION: Module 9; domain MT9 in domain A9
<220> FEATURE:
<221> NAME/KEY: DOMAIN
<222> LOCATION: (3537)..(3577)
<223> OTHER INFORMATION: Module 9; domain A9''
```

```
<220> FEATURE:
<221> NAME/KEY: DOMAIN
<222> LOCATION: (3600)..(3663)
<223> OTHER INFORMATION: Module 9; domain T9
<220> FEATURE:
<221> NAME/KEY: DOMAIN
<222> LOCATION: (3679)..(4160)
<223> OTHER INFORMATION: Module 9; domain E9

<400> SEQUENCE: 16
```

| | | | | | | | | | | | | | | | |
|---|---|---|---|---|---|---|---|---|---|---|---|---|---|---|---|
| Val | Phe | Asp | Arg | Ile | Ser | His | Asp | Asn | Arg | Lys | Ile | Pro | Thr | Ala | Gly |
| 1 | | | | 5 | | | | | 10 | | | | | 15 | |
| Thr | Leu | Pro | Gly | Leu | Phe | Glu | Val | Cys | Ala | Ala | Ser | Val | Pro | Gly | Ala |
| | | | 20 | | | | | 25 | | | | | 30 | | |
| Thr | Ala | Val | Val | Phe | Gly | Asp | Val | Arg | Val | Ser | Tyr | Gly | Val | Leu | Asn |
| | | | 35 | | | | | 40 | | | | | 45 | | |
| Glu | Arg | Ala | Asn | Arg | Leu | Ala | His | Trp | Leu | Leu | Gly | Arg | Gly | Val | Gly |
| | 50 | | | | | 55 | | | | | 60 | | | | |
| Pro | Glu | Arg | Val | Val | Ala | Leu | Ala | Leu | Pro | Arg | Gly | Val | Asp | Leu | Val |
| 65 | | | | | 70 | | | | | 75 | | | | | 80 |
| Val | Ala | Val | Leu | Ala | Val | Val | Lys | Ala | Gly | Ala | Ala | Tyr | Leu | Pro | Val |
| | | | | 85 | | | | | 90 | | | | | 95 | |
| Asp | Pro | Asp | Tyr | Pro | Ala | Glu | Arg | Val | Ala | Tyr | Met | Leu | Glu | Asp | Ser |
| | | | | 100 | | | | | 105 | | | | | 110 | |
| Arg | Pro | Val | Leu | Ala | Leu | Thr | Ser | Ser | Ala | Val | Ala | Gly | Leu | Pro | |
| | | | 115 | | | | | 120 | | | | | 125 | | |
| Val | Val | Asp | Asp | Val | Glu | Tyr | Val | Ser | Leu | Asp | Asp | Pro | Ala | Val | Leu |
| | | | 130 | | | | | 135 | | | | | 140 | | |
| Gly | Glu | Leu | Ala | Gly | Cys | Gly | Val | Ser | Asp | Pro | Ser | Asp | Ala | Asp | Arg |
| 145 | | | | | 150 | | | | | 155 | | | | | 160 |
| Gly | Ala | Val | Leu | Ser | Pro | Ala | His | Pro | Val | His | Val | Ile | Tyr | Thr | Ser |
| | | | | 165 | | | | | 170 | | | | | 175 | |
| Gly | Ser | Thr | Gly | Arg | Pro | Lys | Gly | Val | Met | Thr | Ser | His | Gly | Asn | Val |
| | | | 180 | | | | | 185 | | | | | 190 | | |
| Val | Arg | Leu | Phe | Asp | Val | Gly | Glu | Gly | Gly | His | Trp | Phe | Gly | Phe | Ala |
| | | | 195 | | | | | 200 | | | | | 205 | | |
| Pro | Asp | Asp | Val | Trp | Ala | Leu | Phe | His | Ser | Tyr | Thr | Phe | Asp | Phe | Ser |
| | 210 | | | | | 215 | | | | | 220 | | | | |
| Val | Phe | Glu | Leu | Trp | Gly | Ala | Leu | Leu | His | Gly | Gly | Cys | Leu | Val | Val |
| 225 | | | | | 230 | | | | | 235 | | | | | 240 |
| Val | Pro | His | Leu | Thr | Ser | Arg | Ser | Pro | Val | Glu | Leu | Arg | Leu | Leu | |
| | | | | 245 | | | | | 250 | | | | | 255 | |
| Val | Ala | Glu | Gln | Val | Thr | Val | Leu | Cys | Gln | Thr | Pro | Ser | Ala | Phe | Asp |
| | | | 260 | | | | | 265 | | | | | 270 | | |
| Ala | Leu | Ala | Gly | Val | Val | Ala | Gln | Asp | Pro | Ala | Gly | Ala | Glu | Gly | Leu |
| | | | | 275 | | | | | 280 | | | | | 285 | |
| Val | Leu | Arg | Arg | Val | Val | Phe | Gly | Gly | Glu | Ala | Leu | Pro | Ala | Arg | Thr |
| | | | 290 | | | | | 295 | | | | | 300 | | |
| Ala | Glu | Leu | Ala | Ser | Gly | Leu | Val | Pro | Gly | Val | Arg | Val | Val | Asn | Ile |
| 305 | | | | | 310 | | | | | 315 | | | | | 320 |
| Tyr | Gly | Pro | Thr | Glu | Thr | Thr | Val | His | Ala | Thr | Thr | Cys | His | Val | Asp |
| | | | | 325 | | | | | 330 | | | | | 335 | |
| Ser | Val | Ser | Gly | Gly | Asn | Pro | Val | Val | Ser | Ile | Gly | Arg | Pro | Val | Asp |
| | | | 340 | | | | | 345 | | | | | 350 | | |
| Lys | Ala | Arg | Ala | Tyr | Val | Leu | Asp | Asp | Glu | Leu | Phe | Pro | Val | Ala | Pro |
| | | | | 355 | | | | | 360 | | | | | 365 | |

-continued

```
Gly Val Ala Gly Glu Leu Tyr Val Ala Gly Ala Gly Leu Ala Arg Gly
    370                 375                 380
Tyr Val Asn Arg Ala Gly Leu Thr Ala Ser Arg Phe Val Ala Asp Pro
385                 390                 395                 400
Tyr Gly Pro Ala Gly Ser Arg Met Tyr Arg Thr Gly Asp Val Val Arg
                405                 410                 415
Trp Asn Thr Ser Gly Glu Leu Glu Phe Val Gly Arg Ala Asp Asp Gln
                420                 425                 430
Val Lys Ile Arg Gly Phe Arg Ile Glu Leu Gly Glu Ile Glu Thr Thr
                435                 440                 445
Ala Ala Gly His Pro Ala Val Ala Gln Ala Ala Thr Val His Glu
    450                 455                 460
Asp Asp Thr Arg Gly Lys Gln Leu Ala Leu Tyr Val Val Pro Thr Gly
465                 470                 475                 480
Leu Thr Ser Gly Asp Val Ser Gly Ser Val Ser Gly Asp Gly Ala Val
                485                 490                 495
Pro Asp Gly Gly Val Ser Gly Val Val Asp Glu Gln Val Gly Glu Trp
                500                 505                 510
Arg Glu Ile Tyr Asp Ser Leu Tyr Gly Gly Pro Gly Ser Ser Val Phe
    515                 520                 525
Gly Glu Asp Phe Ser Gly Trp Asp Ser Ser Tyr Asp Gly Ala Ala Ile
    530                 535                 540
Pro Leu Glu Glu Met Arg Glu Trp Arg Asp Ala Thr Val Glu Arg Ile
545                 550                 555                 560
Arg Gly Leu Gly Gly Arg Arg Val Leu Glu Ile Val Gly Thr Gly
                565                 570                 575
Leu Leu Met Ser Arg Leu Ala Ala Gly Cys Glu Glu Tyr Trp Ala Thr
                580                 585                 590
Asp Leu Ser Gly Val Val Ile Asp Ala Leu Asp Gly His Val Gln Ala
                595                 600                 605
Asp Pro Val Leu Arg Glu Arg Val Arg Leu Ala Cys Gln Arg Ala Asp
    610                 615                 620
Asp Thr Arg Gly Leu Pro Glu Gly Tyr Phe Asp Thr Val Val Ile Asn
625                 630                 635                 640
Ser Val Val Gln Tyr Phe Pro Gly Ala Gln Tyr Leu Ala Ser Val Ile
                645                 650                 655
Glu Ala Ala Val Ser Arg Leu Ala Pro Gly Gly Arg Val Phe Ile Gly
                660                 665                 670
Asp Val Arg Asp Leu Arg Thr Leu Arg Ala Phe His Thr Ala Val Gln
    675                 680                 685
Leu Thr Arg Thr Thr Gly Gly Arg Ala Gly Asp Gly Met Asp Ala Gly
    690                 695                 700
Gly Leu Arg Arg Ala Val Glu Gln Gly Leu Leu Glu Asn Glu Leu
705                 710                 715                 720
Leu Leu Asp Pro Glu Phe Phe Thr Ala Val Gly Arg Thr Leu Pro Ala
                725                 730                 735
Val Ser Ala Val Glu Val Arg Leu Lys His Gly Gln Ala His Asn Glu
                740                 745                 750
Leu Thr Arg His Arg Tyr Asp Val Ile Leu His Thr Thr Asn Thr Glu
    755                 760                 765
Thr Asp Thr Ala Thr Glu Glu Glu Ala Glu Ala Ala Arg Pro Thr Lys
    770                 775                 780
```

```
Ala Glu Ala Glu Thr Pro Ala Leu Val Glu Arg Ile Ser Trp Asn Thr
785                 790                 795                 800

Leu Ser Gly Gly Leu Asp Gly Leu Asp Asp Leu Leu Arg Ser Arg Gly
            805                 810                 815

Ala Ala Pro Leu Arg Val Thr Gly Ile Pro Asn Ala Arg Leu Ala Gly
            820                 825                 830

Glu Tyr Ala Ala Leu Arg Val Leu Glu Asn Gly Gly Thr Leu Thr Glu
            835                 840                 845

Ala Val Thr Ala Leu Ala Gly Pro Arg Gly Ile Asp Pro Glu His Leu
            850                 855                 860

His Gln Leu Ala Ala Ala Thr Gly Tyr His Ala Val Leu Gln Pro Ala
865                 870                 875                 880

Pro Ala Pro Asp Thr Tyr Asn Thr Leu Leu Leu Pro Leu Asp Ile Phe
                885                 890                 895

Asp Gly Thr Ala Trp Ser Ala Thr Ala Thr Ala Thr Ala Thr Asp Leu
                900                 905                 910

Arg Glu Thr Ser Ala Pro Asp His Thr Ala Glu Thr Ser Phe Gln Ala
            915                 920                 925

Leu Ala Asn Asn Pro Ala Ala Ser Arg Asp Thr Ser Thr Leu Ile Thr
930                 935                 940

Gln Val Arg Asp His Leu Arg Thr Lys Leu Pro Asp His Met Val Pro
945                 950                 955                 960

Ala Ala Ile Val Val Leu Glu Arg Leu Pro Leu Thr Ala Ser Gly Lys
                965                 970                 975

Leu Asp Arg Arg Ala Leu Pro Ala Pro Asp Leu Gly His Thr Thr
            980                 985                 990

Gly Arg Ala Pro Arg Ser Pro Arg Glu Glu Ile Leu Ala Gly Leu Phe
            995                 1000                1005

Ala Glu Val Leu Gly Leu Pro Ala Val Gly Ile Asp Asp Ser Phe
    1010                1015                1020

Phe Asp Leu Gly Gly His Ser Leu Leu Ala Thr Arg Leu Ile Ser
    1025                1030                1035

Arg Ile Arg Ala Ile Leu Gly Val Glu Ile Pro Ile Arg Asp Leu
    1040                1045                1050

Phe Glu Ala Pro Thr Val Ala Gly Leu Ala Thr Leu Leu Asp Glu
    1055                1060                1065

Asn Arg Ala Val Arg Pro Thr Leu Thr Pro Ala Ala Arg Pro Glu
    1070                1075                1080

Arg Ile Pro Leu Ser Ser Ala Gln Asn Arg Leu Trp Phe Leu His
    1085                1090                1095

Arg Leu Glu Gly Met Gly Ala Ala Ala Tyr Asn Val Pro Met Ala
    1100                1105                1110

Leu Arg Leu Thr Gly Ser Val Met Pro Glu Val Leu Arg Leu Ala
    1115                1120                1125

Leu Ala Asp Val Val Glu Arg His Glu Ser Leu Arg Thr Val Phe
    1130                1135                1140

Pro Glu Thr Asp Gly Val Pro Cys Gln His Ile Leu Ser Val Val
    1145                1150                1155

Glu Ala Arg Pro Val Leu His Val Val Gln Thr Ser Glu Glu Gly
    1160                1165                1170

Leu Ala Glu Ala Val Ser Thr Ala Ser Gln Tyr Ala Phe Asp Leu
    1175                1180                1185

Ser Ala Glu Leu Pro Val Arg Ala Trp Leu Phe Ala Leu Ala Pro
```

```
           1190                1195                1200
Glu Glu His Val Leu Val Leu Val Val His His Ile Ala Gly Asp
   1205                1210                1215
Gly Trp Ser Leu Ser Pro Leu Phe Arg Asp Leu Thr Thr Ala Tyr
   1220                1225                1230
Ala Ala Arg Ala Asp Gly Arg Thr Pro Gly Trp Ala Pro Leu Pro
   1235                1240                1245
Val Gln Tyr Ala Asp Tyr Thr Leu Trp Gln Asn Asp Leu Leu Gly
   1250                1255                1260
Asp His Ser Asp Thr Gly Ser Leu Ile Ala Arg Gln Leu Glu Tyr
   1265                1270                1275
Trp Arg Thr Thr Leu Thr Gly Leu Pro Glu Gln Val Thr Leu Pro
   1280                1285                1290
Thr Asp Arg Pro Arg Pro Ala Thr Ala Thr Tyr Gln Gly Ala Leu
   1295                1300                1305
His Asp Phe Ala Trp Asp Ala Glu Leu His Gln Gly Leu Ile Asp
   1310                1315                1320
Leu Ala Arg Ser Thr Gly Thr Thr Val Phe Met Val Leu Gln Ala
   1325                1330                1335
Gly Leu Ala Ala Leu Met Ser Arg Leu Gly Ala Gly Asp Asp Ile
   1340                1345                1350
Pro Leu Gly Ser Pro Ile Ala Gly Arg Thr Asp Glu Ala Leu Asp
   1355                1360                1365
Asp Leu Val Gly Phe Phe Val Asn Thr Leu Val Leu Arg Thr Asp
   1370                1375                1380
Thr Ser Gly Asn Pro Thr Phe Arg Glu Leu Leu Ala Arg Val Arg
   1385                1390                1395
Glu Thr Asp Leu Ala Ala Tyr Ala His Gln Asp Val Pro Phe Glu
   1400                1405                1410
His Leu Val Glu Ile Leu Asn Pro Glu Arg Ser Leu Ala His His
   1415                1420                1425
Pro Leu Phe Gln Val Met Leu Ala Leu Gln Asn Ala Pro Glu Gly
   1430                1435                1440
Gln Phe Lys Leu Pro Gly Leu Gln Ala Arg Phe Glu Thr Thr His
   1445                1450                1455
Thr Gln Thr Ala Lys Phe Asp Leu Phe Phe Asn Val His Glu Tyr
   1460                1465                1470
Arg Ala Thr Asp Gly Gly Pro Gly Gly Leu Tyr Gly Ser Val Glu
   1475                1480                1485
Phe Ser Thr Asp Leu Phe Asp Arg Val Ser Val Glu Val Val Leu
   1490                1495                1500
Glu Arg Leu Arg Arg Val Leu Val Ser Val Ala Ala Asp Pro Asp
   1505                1510                1515
Val Thr Val Gly Ala Leu Pro Val Leu Ser Gly Gln Glu Glu His
   1520                1525                1530
Arg Leu Val Ala Glu Trp Asn Asp Thr Ala Leu Glu Val Pro Pro
   1535                1540                1545
Ala Ser Leu Pro Glu Leu Phe Gln Ala Gln Ala Ala Ala Thr Pro
   1550                1555                1560
Glu Ala Thr Ala Val Val Phe Glu Asp Val Arg Ile Ser Tyr Gly
   1565                1570                1575
Glu Leu Asn Glu Arg Ala Asn Arg Leu Ala His Tyr Leu Ile Gly
   1580                1585                1590
```

```
Gln Gly Ala Gly Pro Glu Arg Ile Val Ala Leu Ala Leu Pro Arg
1595                1600                1605

Gly Thr Asp Leu Val Ile Ala Val Leu Ala Val Leu Lys Ala Gly
1610                1615                1620

Ala Ala Tyr Leu Pro Val Asp Pro Asp Tyr Pro Ala Glu Arg Ile
1625                1630                1635

Thr His Met Leu Thr Asp Thr Arg Pro Thr Leu Leu Leu Thr Thr
1640                1645                1650

Ser Asp Ala Thr Ala Gly Leu Pro His Thr Glu Gly Ile Pro Gln
1655                1660                1665

Val Leu Leu Asp Asp Ser Ala Val Ile Glu Thr Val Ala Val Leu
1670                1675                1680

Ser Ala Asp Asp Pro Ser Asp Thr Asp Arg Gly Val Val Leu Glu
1685                1690                1695

Gly Ser His Pro Ala Tyr Val Ile Tyr Thr Ser Gly Ser Thr Gly
1700                1705                1710

Val Pro Lys Gly Val Val Met Pro Ser Gly Gly Leu Val Asn Leu
1715                1720                1725

Leu His Trp His His Ser Val Ile Ala Gly Arg Ala Gly Ala Arg
1730                1735                1740

Thr Ala Gln Phe Thr Thr Ile Ser Phe Asp Val Ser Ala Gln Glu
1745                1750                1755

Ile Leu Ser Ala Leu Val Phe Gly Lys Glu Leu Trp Val Pro Gly
1760                1765                1770

Glu Glu Val Arg Arg Ser Gly Glu Gly Leu Ala Arg Trp Leu Gln
1775                1780                1785

Glu His Ala Val Glu Glu Leu Phe Ala Pro Ala Leu Val Ile Asp
1790                1795                1800

Ala Val Ala Gln Ala Ala Gly Glu Leu Gly Leu Val Leu Pro Ala
1805                1810                1815

Leu Arg His Val Ala Gln Ala Gly Glu Ala Leu Val Pro Gly Ala
1820                1825                1830

Ala Met Arg Arg Phe Phe Arg Glu Arg Pro His Ile Arg Leu His
1835                1840                1845

Asn His Tyr Gly Pro Ala Glu Thr His Val Val Thr Ala His Pro
1850                1855                1860

Leu Pro Asn Arg Ile Ala Asp Trp Ala Thr Ser Val Pro Ile Gly
1865                1870                1875

Arg Pro Leu Pro Asn Thr Arg Val Tyr Val Leu Asp Ala Gly Leu
1880                1885                1890

Arg Val Val Pro Val Gly Val Ala Gly Glu Leu Tyr Val Ala Gly
1895                1900                1905

Ala Gly Leu Ala Arg Gly Tyr Val Asn Arg Ala Gly Leu Thr Ala
1910                1915                1920

Ser Arg Phe Val Ala Asp Pro Tyr Gly Pro Ala Gly Ser Arg Met
1925                1930                1935

Tyr Arg Thr Gly Asp Val Val Arg Trp Asn Thr Ser Gly Glu Leu
1940                1945                1950

Glu Phe Val Gly Arg Ala Asp Asp Gln Val Lys Ile Arg Gly Phe
1955                1960                1965

Arg Ile Glu Leu Gly Glu Ile Glu Thr Thr Ala Ala Glu His Pro
1970                1975                1980
```

```
Ala Val Ala Gln Ala Ala Ala Thr Val His Glu Asp Asp Thr Arg
    1985            1990                1995

Gly Lys Gln Leu Ala Leu Tyr Val Val Pro Thr Gly Ile Thr Ser
    2000            2005                2010

Gly Asp Val Pro Ala Ser Gly Gly Val Val Asp Ala Gly Thr Val
    2015            2020                2025

Arg Glu Tyr Leu Arg Thr Lys Leu Pro Asp Tyr Met Val Pro Ala
    2030            2035                2040

Ala Val Val Val Leu Glu Gln Leu Pro Leu Thr Ala Ser Gly Lys
    2045            2050                2055

Leu Asp Arg Arg Ala Leu Pro Thr Pro Glu Phe Ala Ala Glu Pro
    2060            2065                2070

Ala Gly Arg Thr Ala Arg Ser Pro Arg Glu Glu Ile Leu Ala Gly
    2075            2080                2085

Leu Phe Ala Glu Val Leu Gly Leu Pro Ala Val Gly Ile Asp Asp
    2090            2095                2100

Ser Phe Phe Asp Leu Gly Gly His Ser Leu Leu Ala Thr Arg Leu
    2105            2110                2115

Ile Ser Arg Ile Arg Ala Thr Leu Asn Thr Glu Val Pro Val Arg
    2120            2125                2130

Ala Leu Phe Glu Ala Pro Thr Val Ala Ala Leu Thr Val Leu Leu
    2135            2140                2145

Glu Ala Gly Ser Ser Asp Val Val Arg Arg Lys Leu Thr Pro Ala
    2150            2155                2160

Ala Arg Pro Glu Arg Ile Pro Leu Ser Ser Ala Gln Ser Arg Leu
    2165            2170                2175

Trp Phe Leu His Arg Leu Glu Gly Pro Ser Ala Thr Tyr Asn Met
    2180            2185                2190

Pro Met Ala Leu Arg Leu Thr Gly Pro Val Met Pro Glu Val Leu
    2195            2200                2205

Arg Leu Ala Leu Ala Asp Val Val Glu Arg His Glu Ser Leu Arg
    2210            2215                2220

Thr Val Phe Pro Glu Thr Asp Gly Val Pro Cys Gln His Ile Leu
    2225            2230                2235

Ala Gly Ala Glu Ala Gln Pro Val Leu Glu Val Val Glu Val Gly
    2240            2245                2250

Glu Asp Gly Leu Glu Glu Ala Leu Ala Gly Ala Ala Arg Tyr Pro
    2255            2260                2265

Leu Asp Leu Ser Ala Glu Leu Pro Val Arg Gly Trp Leu Phe Gly
    2270            2275                2280

Leu Gly Pro Thr Glu His Val Leu Val Leu Val Val His His Ile
    2285            2290                2295

Ala Gly Asp Gly Trp Ser Leu Ala Pro Leu Ser Arg Asp Leu Val
    2300            2305                2310

Thr Ala Tyr Ala Ala Arg Ala Asp Gly Arg Thr Pro Gly Trp Ala
    2315            2320                2325

Pro Leu Pro Val Gln Tyr Ala Asp Tyr Thr Leu Trp Gln Asn Asp
    2330            2335                2340

Leu Leu Gly Asp Gln Ser Asp Gly Asp Ser Leu Val Ala Arg Gln
    2345            2350                2355

Leu Glu Tyr Trp Arg Thr Thr Leu Thr Gly Leu Pro Glu Gln Val
    2360            2365                2370

Thr Leu Pro Thr Asp Arg Pro Arg Pro Ala Thr Ala Thr Tyr Gln
```

```
                2375                2380                2385
Gly Ala Leu His Asp Phe Ala Trp Asp Ala Glu Leu His Gln Gly
            2390                2395                2400
Leu Ile Asp Leu Ala Arg Ser Thr Gly Thr Thr Val Phe Met Val
            2405                2410                2415
Leu Gln Ala Gly Leu Ala Ala Leu Met Ser Arg Leu Gly Ala Gly
            2420                2425                2430
Asp Asp Ile Pro Leu Gly Ser Pro Ile Ala Gly Arg Thr Asp Glu
            2435                2440                2445
Ala Leu Asp Asp Leu Val Gly Phe Phe Val Asn Thr Leu Val Leu
            2450                2455                2460
Arg Thr Asp Thr Ser Gly Asn Pro Thr Phe Arg Glu Leu Leu Ala
            2465                2470                2475
Arg Val Arg Glu Thr Asp Leu Ala Ala Tyr Ala His Gln Asp Val
            2480                2485                2490
Pro Phe Glu His Leu Val Glu Ile Leu Asn Pro Glu Arg Ser Leu
            2495                2500                2505
Ala His His Pro Leu Phe Gln Val Ala Leu Ala Leu His Asn Thr
            2510                2515                2520
Pro Pro Gly Asn Phe Thr Leu Pro Asp Ile Asn Ile His Gly Gln
            2525                2530                2535
Arg Leu Ser Thr Gly Thr Ser Arg Phe Asp Val Ser Leu His Phe
            2540                2545                2550
Val Glu Trp Gln Arg Glu Asp Gly Ala Ala Ser Gly Leu Gly Gly
            2555                2560                2565
Phe Val Glu Phe Ser Thr Asp Leu Phe Asp Arg Val Ser Val Glu
            2570                2575                2580
Val Val Leu Glu Arg Leu Arg Arg Val Leu Val Ser Val Ala Ala
            2585                2590                2595
Asp Pro Asp Val Thr Val Gly Ala Leu Pro Val Leu Ser Gly Gln
            2600                2605                2610
Glu Glu His Arg Leu Val Ala Glu Trp Asn Asp Thr Val Leu Glu
            2615                2620                2625
Val Pro Pro Ala Ser Leu Pro Glu Leu Phe Gln Ala Gln Ala Ala
            2630                2635                2640
Glu Ala Pro Glu Ala Thr Ala Val Val Phe Glu Thr Glu Arg Leu
            2645                2650                2655
Ser Tyr Arg Glu Leu Asn Glu Arg Ala Asn Arg Leu Ala His Tyr
            2660                2665                2670
Leu Ile Lys Gln Gly Ala Gly Pro Glu Arg Ile Val Ala Leu Ala
            2675                2680                2685
Leu Pro Arg Gly Thr Asp Leu Val Ile Ala Val Leu Ala Val Leu
            2690                2695                2700
Lys Ala Gly Ala Ala Tyr Leu Pro Val Asp Pro Asp Tyr Pro Ala
            2705                2710                2715
Glu Arg Ile Thr His Met Leu His Asp Ala Ala Pro Ala Leu Met
            2720                2725                2730
Val Thr Thr Ser Gly Val Ala Ala Gly Leu Pro His Thr Glu Gly
            2735                2740                2745
Val Thr Ser Val Leu Val Asp Ala Pro Ala Val Val Glu Ala Val
            2750                2755                2760
Ala Val Leu Ser Ala Asp Asp Pro Ser Asp Thr Asp Arg Gly Val
            2765                2770                2775
```

```
Val Leu Glu Gly Ser His Pro Ala Tyr Val Ile Tyr Thr Ser Gly
2780                2785                2790

Ser Thr Gly Val Pro Lys Gly Val Leu Val Pro His Ala Gly Leu
    2795                2800                2805

Ala Asn Leu Thr Ala Ala Glu Arg Ala Ala Leu Asp Leu Ser Ala
    2810                2815                2820

Gly Ser Arg Val Leu Gln Leu Ala Ser Val Gly Phe Asp Ala Ala
    2825                2830                2835

Val Leu Glu Leu Ser Met Ala Phe Gly Ser Gly Ala Thr Leu Val
    2840                2845                2850

Ile Ala Pro Gln Gly Arg Leu Leu Gly Asp Asp Leu Ala Ala Leu
    2855                2860                2865

Leu Ala Arg Gln Glu Ile Thr His Thr Leu Ile Thr Pro Ser Ala
    2870                2875                2880

Leu Ala Thr Leu Pro Glu Thr Asp Leu Pro His Leu Arg Thr Leu
    2885                2890                2895

Leu Thr Gly Ala Glu Ala Cys Pro Pro Glu Leu Val Ala Arg Trp
    2900                2905                2910

Ser Pro Gly Arg Arg Phe Ile Asn Ala Tyr Gly Pro Thr Glu Ala
    2915                2920                2925

Ser Val Val Ala Thr Trp Ser Asp Pro Leu Thr Gln Asp Thr Ala
    2930                2935                2940

Pro Ile Gly Arg Pro Leu Pro Asn Thr Arg Val Tyr Val Leu Asp
    2945                2950                2955

Ala Gly Leu Arg Val Val Pro Val Gly Val Ala Gly Glu Leu Tyr
    2960                2965                2970

Val Ala Gly Ala Gly Leu Ala Arg Gly Tyr Val Asn Arg Ala Gly
    2975                2980                2985

Leu Thr Ala Ser Arg Phe Val Ala Asp Pro Tyr Gly Pro Ala Gly
    2990                2995                3000

Ser Arg Met Tyr Arg Thr Gly Asp Val Val Arg Trp Asn Thr Ser
    3005                3010                3015

Gly Glu Leu Glu Phe Val Gly Arg Ala Asp Asp Gln Val Lys Ile
    3020                3025                3030

Arg Gly Phe Arg Ile Glu Leu Gly Glu Ile Glu Thr Thr Ala Ala
    3035                3040                3045

Gly His Pro Ala Val Ala Gln Ala Ala Thr Val His Glu Asp
    3050                3055                3060

Asp Thr Arg Gly Lys Gln Leu Ala Leu Tyr Val Val Pro Thr Gly
    3065                3070                3075

Leu Thr Ser Gly Asp Val Ser Gly Ser Val Ser Gly Asp Gly Ala
    3080                3085                3090

Val Pro Asp Gly Gly Val Ser Gly Val Val Asp Glu Gln Val Gly
    3095                3100                3105

Glu Trp Arg Glu Ile Tyr Asp Ser Leu Tyr Gly Gly Pro Gly Ser
    3110                3115                3120

Ser Val Phe Gly Glu Asp Phe Ser Gly Trp Asp Ser Ser Tyr Asp
    3125                3130                3135

Gly Ala Ala Ile Pro Leu Glu Glu Met Arg Glu Trp Arg Asp Ala
    3140                3145                3150

Thr Val Glu Arg Ile Arg Gly Leu Gly Gly Arg Val Leu Glu
    3155                3160                3165
```

```
Ile Gly Val Gly Thr Gly Leu Leu Met Ser Arg Leu Ala Ala Gly
3170            3175                3180

Cys Glu Glu Tyr Trp Ala Thr Asp Leu Ser Gly Val Val Ile Asp
3185            3190                3195

Ala Leu Asp Gly His Val Gln Ala Asp Pro Val Leu Arg Glu Arg
3200            3205                3210

Val Arg Leu Ala Cys Gln Arg Ala Asp Asp Thr Arg Gly Leu Pro
3215            3220                3225

Glu Gly Tyr Phe Asp Thr Val Val Ile Asn Ser Val Val Gln Tyr
3230            3235                3240

Phe Pro Gly Ala Gln Tyr Leu Ala Ser Val Ile Glu Ala Ala Val
3245            3250                3255

Ser Arg Leu Ala Pro Gly Gly Arg Val Phe Ile Gly Asp Val Arg
3260            3265                3270

Asp Leu Arg Thr Leu Arg Ala Phe His Thr Ala Val Gln Leu Thr
3275            3280                3285

Arg Thr Thr Gly Gly Arg Ala Gly Asp Gly Met Asp Ala Gly Gly
3290            3295                3300

Leu Arg Arg Ala Val Glu Gln Gly Leu Leu Glu Asn Glu Leu
3305            3310                3315

Leu Leu Asp Pro Glu Phe Phe Thr Ala Val Gly Arg Thr Leu Pro
3320            3325                3330

Ala Val Ser Ala Val Glu Val Arg Leu Lys His Gly Gln Ala His
3335            3340                3345

Asn Glu Leu Thr Arg His Arg Tyr Asp Val Ile Leu His Thr Thr
3350            3355                3360

Asn Thr Glu Thr Asp Thr Ala Thr Glu Glu Ala Glu Ala Ala
3365            3370                3375

Arg Pro Thr Lys Ala Glu Ala Glu Thr Pro Ala Leu Val Glu Arg
3380            3385                3390

Ile Ser Trp Asn Thr Leu Ser Gly Gly Leu Asp Gly Leu Asp Asp
3395            3400                3405

Leu Leu Arg Ser Arg Gly Ala Ala Pro Leu Arg Val Thr Gly Ile
3410            3415                3420

Pro Asn Ala Arg Leu Ala Gly Glu Tyr Ala Ala Leu Arg Val Leu
3425            3430                3435

Glu Asn Gly Gly Thr Leu Thr Glu Ala Val Thr Ala Leu Ala Gly
3440            3445                3450

Pro Arg Gly Ile Asp Pro Glu His Leu His Gln Leu Ala Ala Ala
3455            3460                3465

Thr Gly Tyr His Ala Val Leu Gln Pro Ala Pro Ala Pro Asp Thr
3470            3475                3480

Tyr Asn Thr Leu Leu Leu Pro Leu Asp Ile Phe Asp Gly Thr Ala
3485            3490                3495

Trp Ser Ala Thr Ala Thr Ala Thr Ala Thr Asp Leu Arg Glu Thr
3500            3505                3510

Ser Ala Pro Asp His Thr Ala Glu Thr Ser Phe Gln Ala Leu Ala
3515            3520                3525

Asn Asn Pro Ala Ala Ser Arg Asp Thr Ser Thr Leu Ile Thr Gln
3530            3535                3540

Val Arg Asp His Leu Arg Thr Lys Leu Pro Asp His Met Val Pro
3545            3550                3555

Ala Ala Ile Val Val Leu Glu Arg Leu Pro Leu Thr Ala Ser Gly
```

```
            3560                3565                3570
Lys Leu Asp Arg Arg Ala Leu Pro Ala Pro Asp Leu Gly Thr His
    3575                3580                3585
Thr Thr Gly Arg Ala Pro Arg Ser Pro Arg Glu Glu Ile Leu Ala
    3590                3595                3600
Gly Leu Phe Ala Glu Val Leu Gly Leu Pro Ala Val Gly Ile Asp
    3605                3610                3615
Asp Ser Phe Phe Asp Leu Gly Gly Asp Ser Ile Ile Ser Ile Gln
    3620                3625                3630
Leu Val Ser Arg Ala Arg Lys Ala Gly Leu Lys Val Ser Ala Gly
    3635                3640                3645
Asp Val Leu Arg Tyr Lys Thr Val Ser Ala Leu Ala Ala Val Ala
    3650                3655                3660
Gln Asp Leu His Ala Glu Ala Ser Tyr Ile Ser Asp Asp Gly Leu
    3665                3670                3675
Gly Asp Val Pro Gln Thr Pro Ile Met Arg Trp Ala Phe Lys Gln
    3680                3685                3690
Glu Asp Leu Val His Gly Leu His Gln Ala Met Leu Leu Glu Thr
    3695                3700                3705
Pro Ala Gly Leu Gln Gln Ala Gln Leu Val Ala Ile Thr Gln Thr
    3710                3715                3720
Leu Leu Asp His His Glu Met Leu Arg Ala Arg Leu Val Val Arg
    3725                3730                3735
Arg Gly Glu Glu Ser Val Leu Arg Val Ala Glu Ala Gly Ala Val
    3740                3745                3750
Arg Ala Asp Asp Leu Ile Gln Gln Val Ala Val Ala Ala Asn Ser
    3755                3760                3765
Gly Glu Asn Leu Arg Asp Ser Ile Ser Ala Glu Phe Ser Ala Ala
    3770                3775                3780
Arg Asp Arg Leu Ser Pro Glu Ser Gly Ser Met Leu Gln Leu Val
    3785                3790                3795
Trp Phe Asn Ser Gly Pro Asn His Ala Gly Arg Leu Leu Ile Val
    3800                3805                3810
Ile His His Leu Val Val Asp Gly Val Ser Trp Arg Ile Leu Leu
    3815                3820                3825
Ser Asp Val Ala Asp Ala Trp Glu Asp Ile Ser Ala Gly Arg Ala
    3830                3835                3840
Pro Val Leu Glu Pro Arg Arg Thr Ser Phe Lys Arg Trp Ala Asn
    3845                3850                3855
Ala Leu Ile Ser Glu Ala His Ala Pro Lys Arg Val Glu Glu Met
    3860                3865                3870
Pro Leu Trp Met Gly Thr Leu Thr Asp Ser Gly Trp Glu Phe Ala
    3875                3880                3885
Ser Lys Pro Lys Asp Glu Lys Glu Ala Ser Thr Ser Ala Gln Leu
    3890                3895                3900
Thr Leu Thr Leu Ser Pro Glu Lys Thr Ile Pro Ile Leu Thr Glu
    3905                3910                3915
Val Pro Ala Val Phe His Gly Lys Ile Asn Asp Val Leu Leu Thr
    3920                3925                3930
Ala Phe Thr Ile Ala Ala Val Glu Trp Arg Arg Val His Arg Ala
    3935                3940                3945
Thr Tyr Ala Gly Thr Asp Val Leu Leu Asn Leu Glu Gly His Gly
    3950                3955                3960
```

```
Arg Glu His Phe Ala Glu Gly Phe Asp Val Ser Arg Thr Val Gly
    3965            3970            3975

Trp Phe Thr Ser Met Phe Pro Val Arg Leu Asp Pro Gly Glu Tyr
    3980            3985            3990

Asp Arg Asp Glu Val Arg Ile Gly Gly Pro Ala Leu Gly Lys Val
    3995            4000            4005

Leu Lys Thr Val Lys Glu Gln Leu Arg Ser Gln Pro Asp Asn Gly
    4010            4015            4020

Leu Gly Phe Gly Leu Leu Arg Tyr Leu Asn Thr Glu Thr Ala Thr
    4025            4030            4035

Lys Leu Cys Gly Leu Ala Val Pro Gln Val Ser Phe Asn Tyr Leu
    4040            4045            4050

Gly Arg Phe Gly Ala Ser Gly Gly Ala Gly Trp Val Gln Ala Pro
    4055            4060            4065

Glu Ser Asp Ile Val Ala Asn Gly Gln His Gly Pro Leu Ala His
    4070            4075            4080

Leu Leu Glu Val Asn Ala Leu Thr Arg Asp Gly Val Asp Gly Pro
    4085            4090            4095

Glu Leu Ile Ala Thr Trp Ser Trp Thr Pro Gly Arg Phe Thr Glu
    4100            4105            4110

Ala Glu Val Leu Asp Phe Ala Glu Arg Trp Phe Ser Val Leu Gly
    4115            4120            4125

Ser Leu Thr Ile His Ala Ser Ala Pro Asp Ala Gly Gly Tyr Thr
    4130            4135            4140

Pro Ser Asp Val Pro Leu Val Ser Leu Ser Gln Glu Gln Ile Glu
    4145            4150            4155

Leu Leu Glu Ser Glu Trp Arg Ala Ser Glu
    4160            4165

<210> SEQ ID NO 17
<211> LENGTH: 1324
<212> TYPE: PRT
<213> ORGANISM: Streptomyces DSM 22643
<220> FEATURE:
<221> NAME/KEY: DOMAIN
<222> LOCATION: (13)..(1312)
<223> OTHER INFORMATION: Module 10
<220> FEATURE:
<221> NAME/KEY: DOMAIN
<222> LOCATION: (13)..(343)
<223> OTHER INFORMATION: Module 10; domain C10
<220> FEATURE:
<221> NAME/KEY: DOMAIN
<222> LOCATION: (484)..(951)
<223> OTHER INFORMATION: Module 10; domain A10
<220> FEATURE:
<221> NAME/KEY: DOMAIN
<222> LOCATION: (974)..(1038)
<223> OTHER INFORMATION: Module 10; domain T10
<220> FEATURE:
<221> NAME/KEY: DOMAIN
<222> LOCATION: (1060)..(1312)
<223> OTHER INFORMATION: Module 10; domain TE10

<400> SEQUENCE: 17

Met Lys Asp Pro Gly Leu Glu Asp Ile Leu Pro Leu Thr Pro Leu Gln
1               5                   10                  15

Glu Gly Ile Leu Phe His Ala Ala Phe Asp Ala Glu Gly Gln Asp Pro
                20                  25                  30

Tyr Val Ile Gln Leu Thr Leu Glu Phe Gln Gly Pro Leu Lys Ala Lys
            35                  40                  45
```

```
Asp Leu Arg Ser Ala Ala Gln Ser Leu Leu Glu Arg His Ser Asn Leu
 50                  55                  60

Arg Ala Ser Phe Arg Tyr His Gly Leu Asp Arg Pro Val Gln Leu Ile
 65                  70                  75                  80

Pro Arg His Ala Glu Ala Pro Trp Glu Ile Asp Leu Ser Asn Leu
                 85                  90                  95

Ser Ala Ala Leu Arg Asp Gln Glu Val Ser Lys Ala Val Ala Ala Asp
                100                 105                 110

Leu Gln Arg Arg Phe Asp Leu Thr Lys Gly Pro Ser Ile Arg Phe Thr
                115                 120                 125

Leu Val Arg Leu Ala Glu Asp Leu His Lys Phe Val Ile Thr Ser His
                130                 135                 140

His Ile Leu Met Asp Gly Trp Ser Ile Pro Val Leu Phe Arg Glu Leu
145                 150                 155                 160

Phe Ala Cys Tyr Ala Ala Gly Gly Ala Thr Ser Met Leu Pro Pro Ala
                165                 170                 175

Gln Pro Phe Arg Asn Tyr Leu Ala Trp Ser Ala Lys Gln Asp Arg Ser
                180                 185                 190

Ser Ala Glu Gln Ala Trp Lys Glu Ala Leu Ser Gly Leu Asp His Pro
                195                 200                 205

Thr Arg Leu Ala Pro His Ser Pro Ala Arg Ser Val Leu Leu Pro Gln
                210                 215                 220

Gln Val Ser Leu Ser Leu Gly Glu Asp Leu Thr Glu Gln Leu Gly Ala
225                 230                 235                 240

Trp Ala Arg Ser Arg Asp Phe Thr Leu Ser Gln Val Val Gln Gly Ala
                245                 250                 255

Trp Gly Val Leu Leu Gly Arg Leu Thr Gly Gln Ser Asp Val Val Phe
                260                 265                 270

Gly Ala Thr Val Ala Gly Arg Pro Pro Glu Val Ala Gly Val Glu Ser
                275                 280                 285

Met Ile Gly Leu Phe Ile Asn Thr Leu Pro Val Arg Leu Arg Ile Val
                290                 295                 300

Pro Asp Glu Ser Phe Thr Val Leu Leu Arg Arg His Gln Arg Asp Gln
305                 310                 315                 320

Glu Arg Leu Phe Pro His His His Leu Gly Leu Thr Asp Ile Gln His
                325                 330                 335

Ala Ala Gly Val Gly Gln Leu Phe Asp Ser Ile Val Ile Phe Glu Asn
                340                 345                 350

Tyr Pro Thr Lys Ile Gly Ser Glu Lys Thr Gly Ser Gly Ser Leu Arg
                355                 360                 365

Val Thr Gly Phe Glu Ala His Asp Ala Thr His Tyr Pro Ile Thr Leu
                370                 375                 380

Phe Val Ile Pro Gly Lys Arg Leu Asn Phe Arg Leu Asp Tyr Asn Ala
385                 390                 395                 400

Glu Tyr Phe Asp His Ala Thr Val Gln Thr Met Leu Glu Arg Leu Arg
                405                 410                 415

Arg Leu Leu Ala Ser Val Val Ser Asp Pro Glu Pro Gln Leu Ser Gly
                420                 425                 430

Leu Thr Leu Leu Gly Thr Glu Glu His Arg Ile Leu Thr Glu Trp
                435                 440                 445

Asn Asp Thr Arg Leu Glu Val Pro Ala Ala Ser Leu Phe Glu Leu Phe
450                 455                 460
```

```
Gln Ala Gln Ala Val Ser Thr Pro Asp Ala Thr Ala Val Val Phe Glu
465                 470                 475                 480

Asp Thr Ser Val Thr Tyr Glu Glu Leu Asn Ala Arg Ala Asn Arg Leu
            485                 490                 495

Ala His Trp Leu Ile Gly Glu Gly Val Gly Pro Glu Arg Val Val Ala
            500                 505                 510

Leu Ala Ile Pro Arg Ser Val Asp Leu Val Ala Val Leu Ala Val
            515                 520                 525

Leu Lys Ala Gly Ala Ala Tyr Leu Pro Ile Asp Pro Glu Tyr Pro Pro
530                 535                 540

Glu Arg Ile Ala His Met Leu Thr Asp Ser Arg Pro Thr Met Leu Val
545                 550                 555                 560

Thr Ser Ser Lys Ala Ala Gln Asp Leu Pro Thr Val Ser Gly Thr Arg
            565                 570                 575

Ser Val Cys Leu Asp Gly Pro Ala Leu Met Trp Ser Leu Gly Thr Ser
            580                 585                 590

Lys Ala Thr Asn Pro Thr His Val Asp Arg Gly Lys Ala Val Asp Ala
            595                 600                 605

Arg His Pro Ala Tyr Val Ile Tyr Thr Ser Gly Ser Thr Gly Arg Pro
610                 615                 620

Lys Gly Val Val Val Pro Thr Gly Ser Val Val Asn Leu Leu Thr Ala
625                 630                 635                 640

Met Gly Asp Trp Phe Pro Val Thr Gly Lys Asp Cys Leu Leu Ala Val
            645                 650                 655

Thr Thr Phe Ala Phe Asp Ile Ala Thr Leu Glu Leu Leu Leu Pro Leu
            660                 665                 670

Leu Asn Gly Ala Arg Leu Val Leu Thr Asn Arg Glu Thr Val Leu Glu
            675                 680                 685

Ser Ser Ala Leu Ala Glu Val Ile Ala Arg His Ser Val Thr Ile Met
            690                 695                 700

Gln Ala Thr Pro Thr Phe Trp Asn Glu Phe Ala Ala Asn Glu Pro Glu
705                 710                 715                 720

Ala Leu Thr Gly Ile Arg Ile Leu Thr Gly Gly Glu Ala Leu Ser Glu
            725                 730                 735

Gly Leu Ala Gly Arg Leu Gln Ala Leu Ala Asp Asp Val Thr Asn Val
            740                 745                 750

Tyr Gly Pro Thr Glu Thr Thr Ile Trp Ser Thr Ala Ala Ala Ile Thr
            755                 760                 765

Ala Ala Thr Gly Val Pro Pro Ile Gly Arg Pro Leu Ala Asn Thr Gln
            770                 775                 780

Ala Tyr Val Leu Asp Glu Ser Leu Arg Pro Val Pro Pro Gly Val Pro
785                 790                 795                 800

Gly Asp Leu Tyr Leu Ala Gly Ala Gly Val Ala Gln Gly Tyr His Asn
            805                 810                 815

Arg Pro Gly Leu Thr Ala Gln Arg Phe Val Ala Asn Pro Tyr Gly Pro
            820                 825                 830

Ile Gly Ala Arg Met Tyr Gln Thr Gly Asp Val Val Arg Trp Asp Leu
            835                 840                 845

Asp Gly Tyr Leu Glu Phe Leu Gly Arg Ser Asp Asn Gln Ile Lys Ile
            850                 855                 860

Arg Gly Phe Arg Ile Glu Pro Gly Glu Ile Val Ala Ala Leu Glu Arg
865                 870                 875                 880

His Pro His Val Ala Glu Ala Ala Val Ala Val Gln Glu Arg Lys Arg
```

```
                    885                 890                 895
Asn Gln Lys Gly Leu Val Ala Tyr Val Thr Ala Ser Asp Gly Gln Glu
                900                 905                 910

Ile Asp Thr Thr Glu Leu Arg Asn His Leu Ser Asp Ile Leu Ala Arg
        915                 920                 925

His Ala Ile Pro Ser Ala Phe Val Val Met Ser Glu Leu Pro Arg Thr
    930                 935                 940

Ser Asn Gly Lys Leu Asp Ser Ser Ala Leu Pro Ala Pro Thr Gln Glu
945                 950                 955                 960

Ala Thr Ala Gln Gly Arg Ala Pro Arg Ser Pro Gln Glu Glu Ile Leu
                965                 970                 975

Cys Glu Leu Phe Ala Glu Val Leu Glu Ile Pro Arg Val Gly Val Asp
            980                 985                 990

Asp Asp Phe Phe Glu Leu Gly Gly His Ser Leu Leu Ala Ile Arg Leu
        995                 1000                1005

Ile Ser Arg Ile Arg Asp Ala Leu Gly Ser Asn Leu Thr Ile Arg
    1010                1015                1020

Ser Leu Phe Glu Ala Pro Thr Val Leu Ala Leu Ala Gln Arg Leu
    1025                1030                1035

Asp Met Asp Thr Ala Asp Asn Ala Phe Asp Val Met Leu Pro Met
    1040                1045                1050

Lys Ser Asn Gly Ser Asn Pro Pro Ile Phe Cys Ile His Pro Gly
    1055                1060                1065

Gly Gly Ile Gly Trp Ile Tyr Ala Arg Leu Ile Ala Phe Leu Gly
    1070                1075                1080

His Glu Gln Pro Val Tyr Ala Ile Gln Ala Arg Gly Leu Ala Lys
    1085                1090                1095

Glu Glu Pro Leu Pro Glu Thr Ile Glu Glu Met Ala Glu Asp Tyr
    1100                1105                1110

Val Arg Glu Ile Arg Ser Ile Gln Ala Ser Gly Pro Tyr His Leu
    1115                1120                1125

Val Gly Tyr Ser Phe Gly Gly Leu Val Ala Gln Ala Ile Ala Thr
    1130                1135                1140

Arg Leu Gln Gln Asp Gly Asp Lys Val Gly Val Leu Gly Leu Ile
    1145                1150                1155

Glu Ala Tyr Pro Ala Glu Gly Met Ala Gly Ser Glu Arg Pro Glu
    1160                1165                1170

Ile Ser Glu Gln Glu Ile Leu Glu Val Ile Ala Glu Ser Ile Asp
    1175                1180                1185

Lys Ala Glu Glu Ile Lys Ala Lys Asp Arg Ala Phe Glu Arg Met
    1190                1195                1200

Glu Thr Glu Gly Ile Thr Phe Glu Gln Leu Ile Glu Gly Ala Arg
    1205                1210                1215

Ala Arg Gly Ser Val Leu Ser Ala Leu Asp Arg Arg His Val Thr
    1220                1225                1230

Ala Met Ala Asp Ile His Ala Asn Cys Leu His Leu Arg His Asn
    1235                1240                1245

Phe Thr Pro Ser Cys Tyr Asp Gly Asp Ala Leu Leu Phe Arg Ser
    1250                1255                1260

Thr Leu Thr Pro Asn Thr Pro Ser Pro Asp Thr Trp Arg Pro Phe
    1265                1270                1275

Ile Gly Gly Arg Ile Glu Thr Arg Glu Ile Ala Ala Leu His His
    1280                1285                1290
```

```
Gln Met Leu His Pro Glu Pro Leu Ala Ala Ile Gly Lys Ile Leu
    1295                1300                1305

Ala Glu Glu Leu Arg Lys Thr His His Glu Tyr Glu Glu Lys Ser
1310                1315                1320

Lys

<210> SEQ ID NO 18
<211> LENGTH: 72
<212> TYPE: PRT
<213> ORGANISM: Streptomyces DSM 22643

<400> SEQUENCE: 18

Met Asn Asn Pro Phe Glu Asp Pro Glu Gly Thr Tyr Lys Val Leu Ile
1               5                   10                  15

Asn Gly Glu Ala Gln Tyr Ser Leu Trp Pro Thr Ser Ile Asp Val Pro
            20                  25                  30

Ala Gly Trp Thr Ile Val His Gly Pro Asp Ser Gln Gln Ala Cys Leu
        35                  40                  45

Asp Phe Val Glu Glu Asn Trp Thr Asp Met Arg Pro Lys Ser Leu Ile
    50                  55                  60

Glu Ala Met Asn Asp Thr Val Ser
65                  70

<210> SEQ ID NO 19
<211> LENGTH: 270
<212> TYPE: PRT
<213> ORGANISM: Streptomyces DSM 22643

<400> SEQUENCE: 19

Met Gln Leu Thr Ala Asp Gln Val Glu Lys Tyr Lys Ser Asp Gly Tyr
1               5                   10                  15

Val Leu Leu Glu Gly Ala Phe Ser Pro Glu Glu Val His Val Met Arg
            20                  25                  30

Gln Ala Leu Lys Lys Asp Gln Glu Val Gln Gly Pro His Arg Ile Leu
        35                  40                  45

Glu Glu Asp Gly Arg Thr Val Arg Ala Leu Tyr Ala Ser His Thr Arg
    50                  55                  60

Gln Ser Val Phe Asp Gln Leu Ser Arg Ser Asp Arg Leu Leu Gly Pro
65                  70                  75                  80

Ala Thr Gln Leu Leu Glu Cys Asp Leu Tyr Ile His Gln Phe Lys Ile
            85                  90                  95

Asn Thr Lys Arg Ala Phe Gly Gly Asp Ser Trp Ala Trp His Gln Asp
            100                 105                 110

Phe Ile Val Trp Arg Asp Thr Asp Gly Leu Pro Ala Pro Arg Ala Val
        115                 120                 125

Asn Val Gly Val Phe Leu Ser Asp Val Thr Glu Phe Asn Gly Pro Val
    130                 135                 140

Val Phe Leu Ser Gly Ser His Gln Arg Gly Thr Val Glu Arg Lys Ala
145                 150                 155                 160

Arg Glu Thr Ser Arg Ser Asp Gln His Val Asp Pro Asp Asp Tyr Ser
            165                 170                 175

Met Thr Pro Ala Glu Leu Ser Gln Met Val Glu Lys His Pro Met Val
        180                 185                 190

Ser Pro Lys Ala Ala Ser Gly Ser Val Met Leu Phe His Pro Glu Ile
    195                 200                 205
```

```
Ile His Gly Ser Ala Pro Asn Ile Ser Pro Phe Ala Arg Asp Leu Leu
    210                 215                 220

Ile Ile Thr Tyr Asn Asp Val Ala Asn Ala Pro Lys Pro Ala Gly Glu
225                 230                 235                 240

Pro Arg Pro Glu Tyr Val Ile Gly Arg Asp Thr Thr Pro Leu Val Ser
                245                 250                 255

Arg Ser Gly Pro Leu His Glu Ala Ala Glu Ser Arg Leu Ala
                260                 265                 270

<210> SEQ ID NO 20
<211> LENGTH: 391
<212> TYPE: PRT
<213> ORGANISM: Streptomyces DSM 22643

<400> SEQUENCE: 20

Met Ser Asp Arg Ser Pro Ser Val Val Thr Pro Gly Val Ala Ser Gly
1               5                   10                  15

Gly Ile Thr Ala Arg Ala Ala Val Leu Glu Ser Phe Gln Lys Pro Leu
                20                  25                  30

Thr Val Arg Gln Phe Pro Val Pro Ala Pro Ser Pro Gly Glu Ile Leu
            35                  40                  45

Val Asp Val Arg Tyr Gly Gly Ile Cys Gly Thr Asp Leu His Leu Gln
50                  55                  60

Leu Gly His Leu Pro Ile Pro Val Pro Leu Val Leu Gly His Glu Gly
65                  70                  75                  80

Leu Gly Ser Ile Arg Arg Leu Gly Thr Glu Gly Leu Thr Asp Ala Asn
                85                  90                  95

Gly Thr Glu Leu Arg Ile Gly Asp Thr Val Met Trp Ala Ser Ser Ile
            100                 105                 110

Ala Cys Gly Ser Cys Gly Pro Cys Arg Gln His Arg Glu Pro Thr Leu
        115                 120                 125

Cys Glu Ser Arg Arg Thr Tyr Gly Val Asn Arg Gln Val Glu Gly Asp
130                 135                 140

Ser Gly Leu Phe Gly Ala Trp Ser Glu Thr Ile Leu Leu His Pro Gly
145                 150                 155                 160

Ala Thr Val Val Arg Leu Pro Gln Ser Val Asp Pro Leu Ala Ala Met
                165                 170                 175

Ser Leu Ala Cys Ala Gly Pro Thr Leu Ile His Ala Leu Tyr Glu Arg
            180                 185                 190

Arg Pro Val Arg Val Gly Glu Thr Val Ile Val Gln Gly Ser Gly Pro
        195                 200                 205

Val Gly Met Ala Ala Ala Ala Leu Ala Gln Leu Ser Gly Ala Ala Met
210                 215                 220

Val Ile Leu Leu Gly Pro Gln Gln Arg Leu Asp Leu Ala Arg Gln
225                 230                 235                 240

Cys Gly Ile Gly Asp Val His Leu Asn Ile Ala Asp Arg Ser Asp Thr
                245                 250                 255

Thr Ser Ala Leu Asn Glu Ala Arg Glu Met Thr Arg Gly Gly Leu Gly
            260                 265                 270

Ala Asp Leu Val Ile Glu Cys Ala Gly Val Pro Glu Ala Val Ala Gln
        275                 280                 285

Gly Val Tyr Leu Ala Arg Arg Gly Gly Ser Tyr Leu Val Val Gly Gln
290                 295                 300

Tyr Thr Asp Ser Gly Glu Thr Leu Phe Asn Pro His Gln Leu Val Tyr
305                 310                 315                 320
```

```
Arg Gln Leu Glu Val Val Gly Ser Trp Ala Phe Thr Gly Ala His Leu
                325                 330                 335

Val His Tyr Val Asn Leu Leu Pro Ser Leu Leu Glu Arg Phe Asp Leu
            340                 345                 350

Arg Arg Leu Val Thr Glu Phe Pro Leu Gly Glu Val Asn Asp Ala Met
            355                 360                 365

Val Ala Val Gly Thr Gly Glu Val Val Lys Ala Val Leu Glu Ser Arg
370                 375                 380

His Leu Pro Thr Val Asp Thr
385                 390

<210> SEQ ID NO 21
<211> LENGTH: 266
<212> TYPE: PRT
<213> ORGANISM: Streptomyces DSM 22643

<400> SEQUENCE: 21

Met Pro Ile Ala Thr Val Asn Glu Thr Gln Leu Arg Tyr Asp Ile His
1               5                   10                  15

Gly Ser Gly Glu Pro Val Val Met Val Gly Ser Gly Ser Gly Gly
                20                  25                  30

Arg Val Trp Glu Met His Gln Val Pro Ala Leu Val Ala Asp Gly Tyr
            35                  40                  45

Gln Val Val Thr Phe Asp Asp Arg Gly Val Ser Gln Pro Glu Asp Ile
50                  55                  60

Glu Pro Tyr Gly Leu Asp Asp Met Val Ala Asp Val Ala Leu Val
65                  70                  75                  80

Asp His Leu Ser Leu Gly Pro Cys Arg Phe Val Gly Thr Ser Leu Gly
                85                  90                  95

Ala Leu Thr Val Gln Glu Leu Ala Ile Arg Arg Pro Asp Leu Val Ser
            100                 105                 110

Glu Ser Val Leu Met Ala Thr Arg Gly Arg Thr Asp Thr Leu Ser Gly
            115                 120                 125

Ala Ile Ser Lys Ala Glu Ile Asp Leu Ile Asp Glu Ser Ala Lys Ile
130                 135                 140

Pro Val Arg Tyr Gln Ala Val Val Gln Ala Leu Leu Asn Leu Ser Arg
145                 150                 155                 160

Lys Thr Leu Arg Asn Glu Gln Glu Leu Arg Asp Trp Ile Asp Ile Leu
                165                 170                 175

Glu Met Ser Gly Pro Gln Pro Ser Gly Leu Arg Ser Gln Leu Glu Ala
            180                 185                 190

Ser Leu Ile Glu Asp Arg Leu Glu Ala Leu Arg Ser Thr Arg Ala Gln
            195                 200                 205

Thr Leu Val Ile Gly Phe Gln Asp Asp Leu Ile Thr Pro Pro His Leu
210                 215                 220

Asn Arg Gln Val Ala Glu Ala Ile Pro Gly Ser Thr Tyr Ile Glu Val
225                 230                 235                 240

Ala Asp Cys Gly His Tyr Gly Tyr Leu Glu Gln Pro Asp Val Val Asn
                245                 250                 255

Lys His Ile Leu Asp Phe Phe Ser Lys Gly
                260                 265

<210> SEQ ID NO 22
<211> LENGTH: 299
<212> TYPE: PRT
```

<213> ORGANISM: Streptomyces DSM 22643

<400> SEQUENCE: 22

Met Thr Arg Arg Met Arg Tyr Gly Val Val Ile Leu Pro Glu His Ser
1               5                   10                  15

Trp Ala Arg Ala Gln Asp Leu Trp Arg Asn Val Glu Asp Leu Gly Phe
            20                  25                  30

Asp His Ala Trp Thr Tyr Asp His Leu Gln Trp Arg Trp Leu Ser Asp
        35                  40                  45

Arg Pro Trp Phe Gly Ala Ile Pro Thr Leu Thr Ala Ala Val Val
    50                  55                  60

Thr Ser Arg Ile Gly Leu Gly Thr Leu Val Ala Ser Thr Lys Leu Arg
65                  70                  75                  80

Asp Pro Val Met Leu Ala Lys Glu Ile Met Thr Leu Asp Asp Ile Ser
                85                  90                  95

Gly Gly Arg Met Leu Cys Gly Val Gly Ser Gly Gly Pro Asp Arg Asp
            100                 105                 110

Leu Leu Gln Ala Tyr Glu Leu Thr Arg Arg Gln Leu Thr Ala Arg Tyr
        115                 120                 125

Gly Glu Phe Ile Glu Leu Leu Asp Ser Leu Leu Arg Gln Glu Pro Val
    130                 135                 140

Val Phe Glu Gly Thr Tyr Tyr Thr Cys Arg Asn Thr Leu Leu Gln Pro
145                 150                 155                 160

Ala Cys Leu Gln Arg Pro Arg Ala Pro Leu Cys Val Ala Ala Gly
                165                 170                 175

Pro Gln Gly Met Arg Leu Ala Ala Arg Phe Ala Asp Ile Trp Val Thr
            180                 185                 190

Met Gly Ala Pro Asn Met Phe Asp Glu Ala Pro Tyr Ala Asp Ser Ala
        195                 200                 205

Met Leu Ile Lys Asp Gln Val Ala Ala Leu Glu Gln Thr Cys His Glu
    210                 215                 220

Val Gly Arg Asp Pro Ala Ser Leu Arg Arg Leu Val Thr Gly Pro
225                 230                 235                 240

Ser Ile Gly Gly Val Leu Asp Ser Val Gly Ser Phe Gln Asp Ala Ala
                245                 250                 255

Gly Thr Phe Gln Glu Val Gly Ile Thr Asp Leu Val Val His Trp Pro
            260                 265                 270

Arg Pro Asp Phe Pro Tyr Arg Gly Asp Pro Ala Val Met Glu Asp Ile
        275                 280                 285

Ala Ser Ile Leu Pro Thr Ala Pro Gly Lys Leu
    290                 295

<210> SEQ ID NO 23
<211> LENGTH: 178
<212> TYPE: PRT
<213> ORGANISM: Streptomyces DSM 22643

<400> SEQUENCE: 23

Val Arg Ile Ser Pro Arg His Gly Leu Ala Gly Arg Cys Val Glu Glu
1               5                   10                  15

Val Thr Ser Ala Pro Ile Cys Ala Val Val Arg Val Thr Leu Thr Gly
            20                  25                  30

Met Pro Ser Asp Ile Phe Ser Gln Ile Pro Glu Tyr Ser Ala Phe Trp
        35                  40                  45

Asn Glu Tyr His Leu Cys Thr Leu Thr Thr Leu Arg Ser Asp Gly Ser

```
                    50                  55                  60

Pro His Val Val Pro Val Gly Val Thr Leu Asp Val Asp Ala Gly Val
 65                  70                  75                  80

Ala Arg Val Ile Thr Arg Lys Ser Ser Arg Lys Val Ala Asn Ile Gln
                 85                  90                  95

Ala Ser Arg Pro Gly Glu Ala Arg Ala Ala Val Cys Gln Val Asp Gly
                100                 105                 110

Gly Arg Trp Ala Thr Leu Glu Gly Thr Ala Glu Val Leu Thr Asp Ala
            115                 120                 125

Ala Ala Val Ala Asp Ala Val Ala Arg Tyr Ala Asp Arg Tyr Gly Arg
130                 135                 140

Thr Pro Ala Pro Asp Pro Glu Arg Val Val Ile Glu Ile Thr Ile Asp
145                 150                 155                 160

Arg Ala Met Gly Gln Val Asn Ala Ala Arg Pro Lys Ala Ala Ser Thr
                165                 170                 175

Ala Ala
```

<210> SEQ ID NO 24
<211> LENGTH: 216
<212> TYPE: PRT
<213> ORGANISM: Streptomyces DSM 22643

<400> SEQUENCE: 24

```
Met Ser Pro Gly Asp Ser Arg Arg Val Ala Ala Glu Ser Thr Val Pro
  1               5                  10                  15

Ala Arg Glu Lys Val Ser Cys Arg Arg Leu Gly Arg Trp Arg Thr Ala
                 20                  25                  30

Ala Arg Arg Thr Val Glu Arg Asp Leu His Arg Arg Leu Arg Gln Glu
             35                  40                  45

Leu Arg Asp Leu Gly Ile His Pro Leu Asp Val Glu Glu Leu Ala
 50                  55                  60

Lys Ala Leu Gly Glu Arg Gly Arg Pro Ile Val Leu Arg Pro Phe
 65                  70                  75                  80

Pro Leu Glu Lys Pro Gly Pro Ser Gly Leu Trp Ile Asp Thr Pro Gln
                 85                  90                  95

Met Asp Val Ile Leu Tyr Gln Gln Glu Thr Thr Arg Leu His Gln Arg
                100                 105                 110

Gln Ile Ile Leu His Glu Ile Leu His Ile Leu Val Ala Glu Trp Glu
            115                 120                 125

Glu Asp Gln Ala Glu Ala Pro Glu Glu Ser Pro Asp Asp Phe Val
130                 135                 140

Glu Gly Trp Ala Thr Leu Ile Pro Val Leu Asp Pro Lys Leu Ile Arg
145                 150                 155                 160

Arg Val Ala Arg Arg Cys Ser Tyr Glu Asp Glu Glu Cys Ser Val
                165                 170                 175

Glu Leu Ala Ala Thr Ile Ile Leu Glu Trp Ser Ser Val Leu Asp Glu
            180                 185                 190

Leu Pro Pro Leu Ser Glu Asp Pro Glu Val Arg Val Gln Ser Ala
            195                 200                 205

Leu Gly Asp Arg Arg Gly Trp Leu
            210                 215
```

<210> SEQ ID NO 25
<211> LENGTH: 371
<212> TYPE: PRT

<213> ORGANISM: Streptomyces DSM 22643

<400> SEQUENCE: 25

| | | | | | | | | | | | | | | |
|---|---|---|---|---|---|---|---|---|---|---|---|---|---|---|
| Val | Ser | Glu | Ile | Leu | Leu | Val | Ile | Ala | Ala | Val | Val | Trp | Arg |
| 1 | | | | 5 | | | | | 10 | | | | | 15 |
| Leu | Tyr | Leu | Trp | Ser | Arg | Ala | Pro | His | Asp | Ala | Pro | Thr | Arg | Ser | Val |
| | | | 20 | | | | | 25 | | | | | 30 | | |
| Ala | Leu | Cys | Leu | Leu | Ser | Ala | Gly | Leu | Ser | Tyr | Pro | Val | Ala | Met | Pro |
| | | 35 | | | | | 40 | | | | | 45 | | | |
| Gly | Gly | Thr | Thr | Gly | Ile | Asp | Thr | Val | Ala | Gly | His | Gly | Thr | Ala | Lys |
| 50 | | | | | 55 | | | | | 60 | | | | | |
| Leu | Leu | Gln | Asn | Val | Leu | Leu | Leu | Thr | Val | Tyr | Phe | Leu | Met | Cys |
| 65 | | | | 70 | | | | | 75 | | | | | 80 |
| Phe | Tyr | Leu | Tyr | Ser | Ala | Asp | Gly | Ser | Val | Ala | Arg | Arg | Ala | Arg |
| | | | | 85 | | | | | 90 | | | | | 95 |

Trp Glu Ala Val Val Ser Val Val Ala Val Ala Ile Ile Leu Ala
            100                 105                 110
Ala Val Thr Val Pro His Glu Asp Phe Ala Gly Ser Phe Ser Thr Ala
            115                 120                 125
Asp Met Thr Ile Pro Gln Ile Ala Phe Phe Tyr Ala Gly Ala Gly Leu
130                 135                 140
Tyr Leu Met Tyr Ala Leu Gly Ala Ala Gly Arg Trp Thr Val Arg Tyr
145                 150                 155                 160
Ala Arg Met Ser Ser Arg Pro His Ala Thr Gly Leu Trp Met Thr Ala
            165                 170                 175
Ile Gly Leu Gly Ala Met Ala Val Ala Cys Ala Val Arg Ala Val Phe
            180                 185                 190
Val Ala Val Arg Trp Ser Gly Gly Thr Val Pro Asp Arg Leu Met Ala
            195                 200                 205
Gly Val Ala Phe Trp Leu Val Val Ser Ile Leu Leu Phe Val Ala Gly
            210                 215                 220
Val Thr Tyr Ser Ala Thr Arg Ser Arg Ile Thr Ala Thr Arg Leu Trp
225                 230                 235                 240
Leu Arg Arg Arg Asp His Arg Arg Leu Ser Pro Leu Trp Gln Leu
            245                 250                 255
Leu Ala Glu Val Tyr Pro Glu Asn Gly Leu Arg Pro Ala Ser Arg Gly
            260                 265                 270
Leu Trp Asp Arg Trp Arg Ala Arg Gly Val His Arg Arg Tyr His Arg
            275                 280                 285
Arg Ile Val Glu Cys Arg Asp Gly Leu Val Asp Ile Ser Pro Tyr Leu
            290                 295                 300
Val Asp Glu Asn Gly Asp Ala Asp Leu Leu Arg Leu Glu Pro Ala Glu
305                 310                 315                 320
Leu Ala Ser Arg Leu Arg Gln Ala Ala Asp Met Ile Arg Gln Gly Ser
            325                 330                 335
Pro Ala Pro Gly Gln Ala Val Pro Leu Ala Val Pro Lys Glu Asp Asp
            340                 345                 350
Arg Asp Ala Asp Val Arg Gln Leu Ile Ala Val Ser Glu Ala Leu Arg
            355                 360                 365
Leu Thr Ala
            370

<210> SEQ ID NO 26
<211> LENGTH: 398

<212> TYPE: PRT
<213> ORGANISM: Streptomyces DSM 22643

<400> SEQUENCE: 26

```
Met Leu Ile Thr Ala Ser Arg Val Leu Thr Gly Ser Gly Thr His Leu
1               5                   10                  15

Glu Asp Gly Ala Val Leu Val Glu Gly Asp Ser Ile Ala Ala Val Gly
            20                  25                  30

Arg Arg Ala Glu Leu Ala Asp Arg Val Gly Ala Asp Gly Lys His Leu
        35                  40                  45

Ala Phe Pro Asp Ala Thr Leu Leu Pro Gly Leu Ile Asp Ala His Val
    50                  55                  60

His Leu Ala Phe Asp Gly Gly Asp Pro Val Ala Thr Leu Asp Glu
65                  70                  75                  80

Ser Ser Asp Glu Lys Leu Leu Glu Asp Met Arg Arg Ala Glu Gln
                85                  90                  95

Leu Leu Ser Ser Gly Val Thr Thr Val Arg Asp Leu Gly Asp Arg His
            100                 105                 110

Gly Leu Ala Leu Arg Leu Asp Glu Glu Ile Ser Gln Gly Gly Thr Ser
        115                 120                 125

Gly Pro Arg Ile Val Ala Ala Gly Thr Pro Ala Thr Pro Pro Gly Gly
    130                 135                 140

His Cys His Phe Leu Gly Gly Glu Val Ser Gly Val Asp Gln Val Arg
145                 150                 155                 160

Asp Leu Val Arg Arg Asn Ile Ala Ala Gly Ala Gly Val Ile Lys Ala
                165                 170                 175

Met Val Thr Gly Gly Gly Leu Thr Lys Asp Gly Pro Lys Ser Trp Gln
            180                 185                 190

Ser Gln Phe Ser Pro Asp Glu Leu Gln Ala Leu Val Asp Glu Ala His
        195                 200                 205

Gln Ala Asp Val Pro Val Ala Ala His Ala His Gly Thr Asp Gly Ile
    210                 215                 220

Thr Ala Ala Val Glu Ala Gly Val Asp Thr Ile Glu His Cys Thr Trp
225                 230                 235                 240

Met Thr Ala Asp Gly Phe Asp Leu Arg Gln Asp Val Leu Lys Gln Ile
                245                 250                 255

Ile Asp Arg Asp Ile Ala Val Cys Pro Ala Val Ser Pro His Trp Glu
            260                 265                 270

Met Leu Pro Arg Phe Phe Gly Glu Glu Arg Ala Ala Ala Met Phe Asp
        275                 280                 285

Leu Val Arg Gln Met Ala Glu Ala Gly Ala Lys Leu Ile Ala Gly Thr
    290                 295                 300

Asp Ala Gly Val Gln Arg Ala Gly Phe Asp Gly Leu Val Pro Ala Leu
305                 310                 315                 320

Ser Phe Tyr Ala His Leu Gly Leu Ser Asn Ser Arg Ile Leu Asp Met
                325                 330                 335

Ala Thr Ala Asp Ala Ala Gly Ala Leu Gly Leu Gly Glu Thr Thr Gly
            340                 345                 350

Arg Ile Ala Pro Arg Phe Arg Ala Asp Leu Leu Val Ile Asp Gly Asp
        355                 360                 365

Pro Leu Glu Asp Leu Ser Ala Leu Lys Met Val Arg Ala Val Val Ala
    370                 375                 380

Ala Gly Arg Leu Leu Glu Pro Gly Arg Thr Ala Glu Gln Gln
385                 390                 395
```

<210> SEQ ID NO 27
<211> LENGTH: 300
<212> TYPE: PRT
<213> ORGANISM: Streptomyces DSM 22643

<400> SEQUENCE: 27

Met Ser Ala Arg His Phe Asp Arg Ser Arg Leu Arg Thr Val Arg Arg
1               5                   10                  15

Ala Ala Glu Lys Ser Gln Ala Ala Val Gly Glu Val Leu Gly Val Ser
            20                  25                  30

Asp Ser Ala Val Ala Ser Trp Glu Ser Gly Ala Gln Thr Pro Asp Pro
        35                  40                  45

Glu Lys Leu Pro Ala Leu Ala Arg Ala Val Gly His Asp Val Asp Asp
    50                  55                  60

Leu Phe Pro Arg Ser Gly Pro Pro Asp Leu Thr Asp Leu Arg Cys Asp
65                  70                  75                  80

Ala Gly Tyr Tyr Gln Tyr Glu Thr Ala Thr Leu Ile Gly Thr Lys Ser
                85                  90                  95

Ala Gly Pro Val Ala Gly Ala Glu Arg Gly Glu Arg Arg Leu Lys Asp
            100                 105                 110

Lys Tyr Ile Pro Ala Leu Ala Ala Ala Tyr Gly Val Ser Glu Val Glu
        115                 120                 125

Leu Arg Arg Ala Glu Asp Arg Ser Ile Ala Lys Ala Gln Gly Met Pro
    130                 135                 140

Val Glu Gly Ser Ala Pro Ser Glu Ala Lys Arg Ala Pro Ala Ala Asp
145                 150                 155                 160

Ala Ala Pro Gly Ser Leu Thr Glu Lys Ile Thr Leu Leu Leu Asn Ser
                165                 170                 175

Ser Tyr Pro Ser Pro Pro Gly Pro Pro Ser Asp Ala Glu Met Ala Ser
            180                 185                 190

Ala Val Asn Ala Ser Ala Gly Glu Gln Ile Leu Thr Glu Glu Gly Phe
        195                 200                 205

Arg His Leu Arg Thr Gly Val Ala Glu Thr Ala Ala Pro Glu Val Leu
    210                 215                 220

Asp Ala Leu Ala Asp Val Ile Gly Val Ser Arg Met Tyr Phe Lys Pro
225                 230                 235                 240

Asp Asp Ala Val Ala Ala Gln Val Tyr Glu Gly Leu Gln Leu Leu Ala
                245                 250                 255

Ala Ala Lys Lys Gly Ala Val Gly Arg Val Lys Ala Arg Gly Leu Gly
            260                 265                 270

Ala Gln Gly Leu Ser Pro Lys Ala Met Ala Leu Val Asn Glu Leu Val
        275                 280                 285

Ala Glu Leu Glu Glu Lys Glu Thr Gly Ala Asn Glu
    290                 295                 300

<210> SEQ ID NO 28
<211> LENGTH: 29
<212> TYPE: DNA
<213> ORGANISM: Artificial sequence
<220> FEATURE:
<223> OTHER INFORMATION: Description of Artificial Sequence: Primer for
      amplification of the mps-1 gene

<400> SEQUENCE: 28
gccgccatat gatgcagctc acggccgat                                              29

```
<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Primer for
      amplification of the mps-1 gene

<400> SEQUENCE: 29
ggtcaggatc ctcatgccag cctcgattc                                          29

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Primer for
      amplification of A domains A2, A5 and A8

<400> SEQUENCE: 30
ccgaccatat ggatccggat gtgacggtgg g                                       31

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Primer for
      amplification of A domains A2, A5 and A8

<400> SEQUENCE: 31
accgggaatt cgccgacggc gggcaggccg a                                       31
```

GENE CLUSTER FOR BIOSYNTHESIS OF GRISELIMYCIN AND METHYLGRISELIMYCIN

CROSS-REFERENCE TO RELATED APPLICATIONS

This application is a 371 National Phase Entry application of co-pending International Application No. PCT/EP2012/070213, filed Oct. 11, 2012, which claims the benefit of priority of European Patent Application No. 11306400.0, filed Oct. 28, 2011 and European Patent Application No. 11306321.8, filed Oct. 12, 2011, each of which is hereby incorporated by reference in its entirety.

SEQUENCE LISTING

The instant application contains a Sequence Listing which has been submitted in ASCII format via EFS-Web, and is hereby incorporated by reference in its entirety. Said ASCII copy, created on Apr. 3, 2014, is named DE2011-234USPCT_20140411_SeqList.txt and is 272150 bytes in size.

The present invention relates to the field of antibiotics and more specifically to genes and proteins involved in the biosynthesis of (methyl)griselimycin. The present invention provides recombinant methods for producing (methyl)griselimycin by recombinant DNA technology.

BACKGROUND OF THE INVENTION

Griselimycin is a naturally occurring antibiotic produced by microorganism of the genus *Streptomyces* which is the largest genus of the *Actinobacteria* and the type genus of the family Streptomycetaceae. *Streptomycetes* are Gram-positive and have genomes with high GC-content. *Streptomycetes* are characterized by a complex secondary metabolism. They produce over two-thirds of the clinically useful antibiotics of natural origin. Griselimycin is an antibiotic which was first described by Terlain and Thomas, 1971. It is composed of ten amino acids being in this order L-N-methylvaline, which is N-acetylated, L-trans-4-methylproline, L-N-methylthreonine, L-leucine, L-trans-4-methylproline, L-leucine, L-N-methylvaline, L-proline, D-N-methylleucine and glycine. The peptide chain is cyclised between glycine and L-N-methylthreonine via an ester bond resulting in a non-cyclised tail consisting of the amino acids L-N-methylvaline, which is N-acetylated, and L-trans-4-methylproline.

Griselimycin belongs to the group of non-ribosomally synthesized microbial peptides which group of peptides shows a remarkable structural diversity and comprises a wide-spread class of the most potent antibiotics and other important pharmaceuticals. Although structurally diverse, non-ribosomally synthesized microbial peptides share a common mode of synthesis, the multienzyme thiotemplate mechanism. Thereby, peptide bond formation takes place on large multi-enzyme complexes, which simultaneously represent template and biosynthesis machinery. These multienzyme complexes are designated non-ribosomal peptide synthetases (NRPSs). Sequencing of genes encoding NRPS revealed a modular organization. A module is a section of the NRPS polypeptide chain that is responsible for the incorporation of one defined monomer into the growing polypeptide chain. Thus, NRPSs are used simultaneously as template because the amino acid to be incorporated is determined by the module and as biosynthetic machinery because it is the module that harbors all necessary catalytic functions. Modules can be further dissected into catalytic domains. These domains catalyse at least the steps of substrate activation, covalent binding and peptide bond formation. Domains of equal function share a number of highly conserved sequence motifs. They can be modified for activity changes within the polypeptide chain which opens up prospects for manipulation of the NRPS machinery.

Within each module, the selection of a specific substrate (amino acid) is mediated by an adenylation domain (A-domain). This A-domain is responsible for the selection of the amino acids that make up the product and thus controls its primary sequence. A-domains activate amino and also some carboxy substrates as amino acyl adenylate while ATP is consumed. This reactive intermediate is further transported onto the terminal cysteamine thiol moiety of the Ppan prosthetic group that is attached to the peptidyl carrier protein (PCP) domain which is also referred to as thiolation (T) domain located downstream of the A-domain in the same module. It represents the transport unit that accepts the activated amino acid that is covalently tethered to its 4'PP cofactor thioester. This cofactor acts as a flexible arm to allow the bound amino acyl and peptidyl substrate to travel between different catalytic centers. The combination of A-domain and T-domain is defined as an initiation module since both domains are required to activate and covalently tether the first building block for subsequent peptide synthesis. The initiation modules of lipopeptide pathways harbor an additional N-terminal C domain for condensation of an acyl side chain with the amino group of the first amino acid. The condensation or C-domain is the central entity of non-ribosomal peptides synthesis because it is responsible for peptide bond formation between amino acyl substrates bound to the T-domain of adjacent modules. The enzyme catalyses the nucleophilic attack of the amino (or imino, hydroxyl) group of the activated amino acid bound to the downstream (with respect to the C-domain) module onto the acyl group or the amino acid tethered to the upstream module. The resulting peptidyl intermediate is then translocated down the assembly line for subsequent condensation and further modification steps. During synthesis, the growing peptide chain is handed over from one module to the next module until it reaches the final modul's T-domain. This module contains in most cases a TE (thioesterase)-domain that is important for the liberation of the product. Product release is achieved by a two-step process that involves an acyl-O-TE-enzyme intermediate that is subsequently attacked by either a peptide-internal nucleophile or water, which results in a macrocyclic product or a linear peptide, respectively.

An especially striking feature of non-ribosomal peptides is the occurrence of D-amino acids. One way to incorporate a D-amino acid is to use a D-amino acid selective A domain. The more common way is, however, through the use of E (epimerization)-domains that occur at the C-terminal end of modules responsible for the incorporation of D-amino acids. The enzyme catalyses the epimerisation of T-domain bound L-amino acid of the growing peptide chain. Discrimination of the T-domain bound L-amino acid through enantioselectivity of the downstream condensation domain donor site leads to a clean D-configurated product.

A number of NRPS contain methyltransferases (MT domain) that are responsible for the N- or C-methylation of amino acid residues thus making the peptide less susceptible to proteolytic breakdown. Both types of methyltransferases (N- or C-methyltransferases or abbreviated N-MT or C-MT) use S-adenosyl methionine as the methyl donor. The MT domains are often found as insertions in the A-domains (Finking et Marahiel, 2004; Marahiel, 2009). Even more striking is the incorporation of unnatural amino acids such as methylproline which are usually biosynthesized in advance to their use in the assembly line. Alternatively, incorporated amino acids can be modified enzymatically post assembly by the NRPS.

Griselimycin is naturally produced by microorganisms of the genus *Streptomyces*. However, although the production of griselimycin by *Streptomyces* has been known in the art, the genetic locus responsible for the biosynthesis of griselimycin has not been identified so far. Consequently, targeting and modification of the biosynthesis of griselimycin were still limited. Accordingly, there is a need for genetic information regarding the biosynthesis of griselimycin.

SUMMARY OF THE INVENTION

Besides griselimycin, *Streptomycetes* also produce a variant form of griselimycin, termed methylgriselimycin. Methylgriselimycin contains L-trans-4-methylproline instead of L-proline. Methylgriselimycin possesses some advantages, such as e.g different antibacterial specificity, in its use as an anti-bacterial agent over griselimycin, however, is produced by *Streptomycetes* as a side-component only. Accordingly, there is a need for genetic information regarding the biosynthesis of methylgriselimycin.

The production of the methylproline moiety as comprised by griselimycin and methylgriselimycin, namely L-trans-4-methylproline, was completely unknown. Accordingly, there is a need for genetic information regarding the biosynthesis of L-trans-4-methylproline.

The genetic locus encoding the polypeptides involved in the biosynthetic pathway of (methyl)griselimycin has now been identified. The present inventors succeeded in isolating and cloning the entire griselimycin biosynthetic gene cluster from the genomic DNA of *Streptomyces* DSM 26643. The present inventors also succeeded in elucidating the open reading frames (ORFs) that encode the polypeptides involved in the (methyl)griselimycin biosynthetic pathway including such responsible for the formation of L-trans-4-methylproline. This allows the identification and influencing of the distinct biosynthesis steps on the molecular level.

Thus, in one aspect, the present invention provides a nucleic acid comprising at least one nucleic acid selected from:

(a) a nucleic acid comprising at least one of the Open Reading Frames (ORFs) 1 to 26 as comprised by SEQ ID NO: 1 encoding proteins of SEQ ID Nos: 2 to 27 or a variant or fragment thereof whereby the variant or fragment encodes a functionally active variant or fragment of a protein of SEQ ID Nos: 2 to 27, (b) a nucleic acid encoding at least one of the proteins of SEQ ID Nos: 2 to 27 or a functionally active variant or fragment thereof, I a nucleic acid encoding a protein that is at least 70%, 80%, 90%, 95% or 97% identical in amino acid sequence to a protein or fragment thereof encoded by the nucleic acid of (a) or (b), (d) a nucleic acid which hybridizes under stringent conditions with a nucleic acid of (a) to (c), (e) a nucleic acid which hybridizes under stringent conditions with a nucleic acid of (a) to (d) and consists of 10 to 50 nucleotides in length, or (f) a nucleic acid which is complementary to a nucleic acid of (a) to (f).

DETAILED DESCRIPTION

The nucleic acid as comprised by the present invention is, in one embodiment, a nucleic acid comprising or consisting of SEQ ID NO: 1 being the part of the genome of *Streptomyces* DSM 26643 comprising the griselimycin biosynthesis gene cluster with a length of 66.868 nucleotides. This newly discovered gene cluster contains at least 26 ORFs designated ORF 1 to ORF 26 (ORF 1, 2, 3, 4, 5, 6, 7, 8, 9, 10, 11, 12, 13, 14, 15, 16, 17, 18, 19, 20, 21, 22, 23, 24, 25, 26) or designated with the gene names orf-1, orf-2, orf-3, orf-4, orf-5, orf-6, orf-7, nrps-1, int-1, tnp-1, int-2, tnp-2, tnp-3, dna, nrps-2, nrps-3, mbtH, mps-1, mps-2, mps-3, mps-4, orf-8, orf-9, orf-10, orf-11, orf-12, respectively, from nucleotides 837 to 66.108 of SEQ ID NO: 1 with a length of 65.272 nucleotides. These ORFs encode proteins of SEQ ID Nos: 2 to 27 (SEQ ID NO: 2, 3, 4, 5, 6, 7, 8, 9, 10, 11, 12, 13, 14, 15, 16, 17, 18, 19, 20, 21, 22, 23, 24, 25, 26, 27), respectively, involved in the biosynthesis of (methyl)griselimycin. Structural and functional characterization of the proteins encoded by the griselimycin biosynthesis gene cluster is provided below.

In the context of the present invention, the term "(methyl)griselimycin" refers to griselimycin as well as to methylgriselimycin. Griselimycin is an antibiotic which is composed of ten amino acids being L-N-methylvaline, which is acetylated (1), L-trans-4-methylproline (2), L-N-methylthreonine (3), L-leucine (4), L-trans-4-methylproline (5), L-leucine (6), L-N-methylvaline (7), L-proline (8), D-N-methyl-D-leucine (9) and glycine (10). The structural formula of griselimycin and methylgriselimycin is given in FIG. 1. Griselimycin and its variant methylgriselimycin are produced in different amounts by the same biosynthesis pathway involving the same genes of the (methyl)griselimycin biosynthesis gene cluster as identified herein. Methylgriselimycin differs from griselimycin by the presence of L-trans-4-methylproline instead of L-proline at position 8. The multidomain-enzyme responsible for the incorporation of L-trans-4-methylproline into methylgriselimycin and of L-proline into griselimycin is the same enzyme, namely NRPS-2, and is the protein product of the gene nrps-2, as identified herein.

In the context of the present invention the term "gene cluster" refers to a set of several genes which are located on a contiguous stretch of the genome and which direct the synthesis of (methyl)griselimycin. Some of the genes belonging to the gene cluster are genes which are related and are grouped to a gene family. They encode proteins which are similar in structure and function. The remainder of the genes are unrelated in structure and encode proteins which have different structure and function. The encoded proteins are either enzymes which catalyse reactions or are involved inter alia in regulation or transport. Altogether, the genes as comprised by the gene cluster encode proteins that serve the purpose of the biosynthesis of (methyl)griselimycin.

The term "nucleic acid" encompasses nucleic acids which are defined by ORFs 1 to 26 coding for the proteins of SEQ ID Nos: 2 to 27, respectively, as well as naturally occurring and non-naturally occurring variants or fragments thereof (as defined herein). The nucleic acid may be any macromolecule composed of chains of monomeric nucleotides carrying genetic information or form structures within cells. The most common (and therefore preferred) nucleic acids are deoxyribonucleic acid (DNA) and ribonucleic acid (RNA). The nucleic acid can be a DNA molecule such as a genomic DNA molecule such as SEQ ID NO: 1 or a cDNA molecule which can be single- or double-stranded such as a nucleic acid representing an ORF and encoding a protein as well as a synthetic DNA such as a synthesized single-stranded polynucleotide such as a primer or probe. The nucleic acid of the present invention can also be an RNA molecule. Preferably, the term also relates to non-coding regions of a gene, wherein these sections are of a relevant size in order to be specific for that gene. Examples of those regions are regulatory elements such as a promoter. Most preferably, the term "nucleic acid" relates to gene, ORF, promoter, DNA, cDNA or mRNA. The nucleic acid encoding the desired genetic information, preferably DNA, may comprise the gene of interest, a promoter region, a start codon and a stop codon and possibly further regions which may be used for regulation of expression of the gene. The regulatory regions may be heterologous to the respective gene or may be associated therewith in nature. The genetic information may be expressed permanently or under the control of a repressor and/or a promoter region in a cell into which the nucleic acid of the present invention is introduced. The obtained cells may be either used directly or used for tissue cultures or the cells may be harvested and samples comprising the respective protein are obtained by disrupting the cells. Alternatively, DNA or RNA may be used either in cells or in cell-free expression systems such as, e.g., microarray systems in which the DNA or RNA is immobilized and is translated and/or transcribed by the addition of functional cell lysate, comprising the factors required for transcription and/or translation (enzymes, ribosomes, tRNA, amino acids, nucleotides, ATP etc.). Also included are artificial nucleic acids which include peptide nucleic acid (PNA), morpholino and locked nucleic acid (LNA), as well as glycol nucleic acid (GNA) and threose nucleic acid (TNA). Each of these is distinguished from naturally-occurring DNA or RNA by changes to the backbone of the molecule.

The term "comprising" as used herein is meant to "include or encompass" the desired feature and further features which must not be specifically mentioned. The term "comprising" is also meant to "consist of" the desired feature and not to include further features except the desired feature. Thus, the nucleic acid or protein referred to herein may be defined by additional features in addition to the definition as indicated, e.g. in addition to the definition by an ORF or SEQ ID number, or may consist of such indicated feature only.

The term "heterologous" as it relates to nucleic acid sequences such as coding or control sequences denotes sequences that are normally not associated with a region of a recombinant construct and/or a particular cell. A "heterologous" region is an identifiable segment of a nucleic acid within or attached to another nucleic acid that is not found in association with the other molecule in nature. For example, a heterologous region of a construct could be a regulatory region not found to be associated with a gene as identified herein in nature. Similarly, a heterologous sequence could be a coding sequence which is itself not found in nature as it contains e.g. synthetic sequences with codons different from the native gene. Moreover, a host cell transformed with a construct which is not normally present in the host cell would be considered heterologous for the purposes of the present invention. A homologous nucleic acid sequence is a variant sequence as defined herein. The term "homologous" may be used interchangeably with variant. The term "homologous" may also refer to an identical sequence.

In an embodiment of the present invention the nucleic acid comprises a nucleic acid molecule which encodes at least one distinct protein as comprised by the sequence of SEQ ID Nos: 2 to 27. In a particular embodiment, the entire sequence of the (methyl)griselimycin gene cluster as comprised by SEQ ID NO: 1 is comprised by a nucleic acid of the present invention. In another embodiment, the nucleic acids are variants or fragments of ORFs 1 to 26 encoding functionally active variants or fragments of at least one of the proteins of SEQ ID Nos: 2 to 27. The most preferred nucleic acid codes for a naturally occurring variant protein of ORFs 1 to 26 as detailed below, more preferably, a naturally occurring *Streptomyces* protein, still more preferably a protein of SEQ ID Nos: 2 to 27, which is involved in the synthesis of (methyl)griselimycin.

The term "nucleic acid" may comprise full length ORFs 1 to 26 as disclosed herein or may comprise fragments or partial sequences of ORFs 1 to 26. Such fragments or partial sequences of ORFs 1 to 26 encode fragments of the proteins with the amino acid sequences shown in SEQ ID Nos: 2 to 27, respectively. This may include fragmental proteins with short internal and/or C- and/or N-terminal deletions whereby the activity of the resulting proteins as identified herein is maintained to an extent of more than 5%, more than 10%, more than 20%, more than 30%, more than 40%, more than 50%, more than 60%, more than 70%, more than 80%, more than 90%, more than 95%, more than 97% or more than 100%, e.g. more than 150%, 200%, 300% 400% or 500%, of the activity of the wild-type proteins as encoded by the ORFs 1 to 26. Consequently, the respective nucleic acid encoding such fragments contains deletions within and/or at the 5' and/or 3' termini of ORFs 1 to 26, e.g., deletions of at the most 50%, 45%, 40%, 35%, 30%, 25%, 20%, 15%, 10%, 5%, or less. In the context of the present invention, a fragmental nucleic acid sequence encoding a functionally active fragment of a protein of SEQ ID Nos: 2 to 27 means a sequence encoding a fragment which directs synthesis of (methyl)griselimycin and/or which can be substituted for the respective ORF encoding the protein of SEQ ID Nos: 2 to 27 to direct synthesis of (methyl)griselimycin.

The term "nucleic acid" may refer to variants of ORFs 1 to 26 as disclosed herein encoding functionally active variants of the proteins of SEQ ID Nos: 2 to 27 as defined herein. Such functionally active variants have a sequence identity with SEQ ID Nos: 2 to 27 of more than 50%, of more than 60%, preferably more than 70%, more preferably of more than 80%, still more preferably more than 85%, even more preferably more than 90%, even more preferably more than 95%, most preferably more than 97% and/or have an activity of more than 5%, more than 10%, more than 20%, more than 30%, more than 40%, more than 50%, more than 60%, more than 70%, more than 80%, more than 90%, more than 95%, more than 97% or more than 100%, e.g. more than 150%, 200%, 300% 400% or 500% of the activity of the proteins of SEQ ID Nos: 2 to 27. Consequently, the nucleic acid encoding such variants contains deletions, insertions, substitutions and/or additions within and/or at the 5' and/or 3' termini of ORFs 1 to 26 and show an identity to the sequences of ORFs 1 to 26 of more than 50%, more than 60%, more than 70%, preferably more than 80%, more preferably more than 85%, even more preferably more than 90%, even more preferably more than 95%, most preferably more than 97%. In the context of the present invention, a variant nucleic acid sequence encoding a functionally active variant of the protein of SEQ ID Nos: 2 to 27 means a sequence encoding a variant which directs synthesis of (methyl)griselimycin and/or which can be substituted for the respective ORF encoding the protein of SEQ ID Nos: 2 to 27 to direct synthesis of (methyl)griselimycin.

It is noted that the above mentioned modifications may be combined. For example, a nucleic acid as comprised by the present invention may be a fragment comprising one or more variations of ORFs 1 to 26. It should also be noted that fragments or variants include fragments or variants, as defined herein, of promoter or regulatory sequences with which ORFs 1 to 26 or fragments or variants thereof are associated in nature. These variants are functionally active in that they regulate the transcription or translation of the genes associated therewith.

An ORF is an open reading frame which is a DNA sequence that could potentially encode a protein. In the context of the present invention, the term "ORF" stands for open reading frame in the (methyl)griselimycin biosynthetic gene cluster as isolated from *Streptomyces* DSM 22643 (ORFs 1 to 26). The present inventors succeeded in identifying the griselimycin biosynthesis gene cluster of *Streptomyces* DSM 22643 and identified 26 ORFs over a stretch of 65272 nucleotides. These ORFs were designated orf-1, orf-2, orf-3, orf-4, orf-5, orf-6, orf-7, nrps-1, int-1, tnp-1, int-2, tnp-2, tnp-3, dna, nrps-2, nrps-3, mbtH, mps-1, mps-2, mps-3, mps-4, orf-8, orf-9, orf-10, orf-11 or orf-12, respectively. The whole griselimycin biosynthesis gene cluster of *Streptomyces* DSM 22643 is 66868 nucleotides in length comprising ORFs 1 to 26 and additional nucleotides located 5' and 3' to ORF 1 and ORF 26, respectively.

The 26 ORFs comprised by SEQ ID NO: 1 extend from nucleotide 837 to nucleotide 66108 of SEQ ID NO: 1 of *Streptomyces* DSM 26643. Table 1 shows a list of the specific putative ORFs, the designation of the corresponding genes, the start and stop nucleotides within SEQ ID NO: 1, the lengths of the genes in nucleotides (nt), the strandedness, the number of amino acids (aa) of the putative proteins encoded thereby, the protein designation and the SEQ ID numbers of the proteins. Table 2 shows proteins which are designated by their GenBank accession numbers as available from the NCBI (National Centre for Biotechnology Information; National Library of Medicine 38A, Bethesda, Md. 20894; USA; www.ncbi.nih.gov). These proteins have been identified, based on homology searches, as showing the highest identity/similarity to the proteins of SEQ ID Nos: 2 to 27. These proteins are defined by their function, their accession number and their origin. Table 2 moreover shows the e-value and the degree of identity and similarity between the proteins of SEQ ID Nos: 2 to 27 and the proteins as identified by the homology searches. The e-value relates to the expected number of chance alignments with an alignment score of at least equal to the observed alignment score. An e-value of 0.00 indicates a perfect homolog. The e-value is calculated as described in Altschul S. F. et al. 1997. The e-value assists in the determination of whether two sequences display sufficient similarity to justify an inference of homology. Identity indicates that identical amino acids are present in the compared proteins at the respective sites whereas similarity indicates that conservative amino acids substitutions as defined herein below are present at the respective sites. Moreover, the putative function of the proteins encoded by ORFs 1 to 26 is indicated.

The substitution of a variant nucleic acid for ORFs 1 to 26 to direct synthesis of (methyl)griselimycin means that this variant nucleic acid can be inserted into the genome of *Streptomyces* DSM 22643 instead of the ORF to which it is a variant thereby expressing a variant protein which takes over the function of the respective protein of SEQ ID Nos: 2 to 27 and directs, i.e. participates in, the synthesis of (methyl)griselimycin. The extent to which the variant takes over the function is as defined herein.

In another embodiment, the nucleic acid encodes a protein of SEQ ID Nos: 2 to 27. The nucleic acid may comprise the sequences of ORFs 1 to 26 as comprised by SEQ ID NO: 1 with the start and stop nucleotides (nt) as indicated in Table 1. The nucleic acid may also encode a protein with the same amino acids as the proteins of SEQ ID Nos: 2 to 27, however, which differs in its nucleotide composition due to the degeneracy of the genetic code.

In a further embodiment, the nucleic acid hybridizes under stringent conditions to a nucleic acid which is comprised by the (methyl)griselimycin gene cluster as identified by SEQ ID NO: 1 or which constitutes ORFs 1 to 26 or which encodes proteins with SEQ ID NO: 2 to 27 or functionally active variants or fragments thereof. In the present invention, the term "hybridise(s)(ing) under stringent conditions" refers to the formation of a hybrid between two nucleic acid molecules under conditions which allow the formation of a so-called specific hybrid, while a non-specific hybrid is substantially not formed. An example of such conditions includes conditions under which a complementary strand of a highly identical nucleic acid, namely, a DNA composed of a nucleotide sequence having 70% or more, preferably 80% or more, more preferably 85% or more, still more preferably 90% or more and even more preferably 95% or more identity with the nucleotide sequence of SEQ ID NO. 1 or shown in ORFs 1 to 26, hybridizes, while a less complementary strand of a nucleic acid less identical than the above does not hybridize. More specifically, such conditions refer to conditions in which the sodium salt concentration is 15 to 750 mM, preferably 50 to 750 mM, and more preferably 300 to 750 mM, the temperature is 25 to 70° C., preferably 50 to 70° C., and more preferably 55 to 65° C., and the formamide concentration is 0 to 50%, preferably 20 to 50%, and more preferably 35 to 45%. Furthermore, under stringent conditions, conditions for washing a filter after hybridization normally comprise the following: the sodium salt concentration is 15 to 600 mM, preferably 50 to 600 mM, and more preferably 300 to 600 mM, and the temperature is 50 to 70° C., preferably 55 to 70° C., and more preferably 60° C. Stringency, and thus specificity, can e.g. be increased by increasing the reaction temperature and/or lowering the ion strength of the reaction buffer. For example, low stringent conditions comprise hybridization in 3×SSC at room temperature to 65° C. and highly stringent conditions comprise hybridization in 0.1×SSC at 68° C. Exemplary moderately stringent conditions (nucleic acids hybridize under moderately stringent conditions, if they are maximally degenerate with respect to their codon composition) comprise 50% formamide, 5×SSC and 1% SDS at 42° C. and washing in 1×SSC at 45° C. Highly stringent conditions comprise incubation at 42° C., 50% formamide, 5×SSC and 1% SDS (e.g. 50% formamide, 5×SSC and 1% SDS, 50 mM sodium phosphate, 5×Denhardt's solution, 10× dextran sulphate, 20 mg/ml sheared salmon sperm DNA) or 5×SSC and 1% SDS at 65° C. and washing in 0.2×SSC and 0.1% SDS at about 65° C. (1×SSC stands for 0.15 M sodium chloride and 0.015 M trisodium citrate buffer). Preferred in the present invention are moderately or highly stringent conditions, most preferred are highly stringent conditions. In the context of the present invention, a "hybridizing" sequence means a sequence which encodes a protein which directs synthesis of (methyl)griselimycin and/or which can be substituted for the ORF to which it specifically hybridizes to direct synthesis of (methyl)griselimycin.

In a further preferred embodiment of the present invention, a nucleic acid which hybridizes under stringent conditions with a nucleic acid as identified above and consists of 5 to 100 nucleotides in length is provided. The sequence information provided in the present application enables the design of specific nucleotide probes and primers that are useful for identifying and isolating microorganisms producing (methyl) griselimycin and harboring any of the proteins of SEQ ID Nos: 2 to 27 or variants thereof. Thus, the nucleotide probe has a sequence found in or derived by the degeneracy of the genetic code from a sequence within the (methyl)griselimycin gene cluster as comprised by SEQ ID NO: 1 or a variant thereof or encoding any of SEQ ID Nos: 2 to 27 or functionally active variants thereof. The term "probe" refers to DNA, preferably single-stranded, or RNA molecules or modifications or combinations thereof, that hybridize under stringent conditions, as defined above, to nucleic acid molecules comprised within the (methyl)griselimycin gene cluster identified by SEQ ID NO: 1 or variants thereof or encoding any of the proteins of SEQ ID Nos: 2 to 27 or functionally active variants thereof, or their complementary or sense sequences. Generally, probes are significantly shorter than full-length sequences. They may contain from 5 to 100, preferably 10 to 80 nucleotides, more preferably 10 to 50 nucleotides, still more preferably 10 to 40 nucleotides and still more preferably 15 to 25 nucleotides. In particular, such probes may have sequences that are at least 70%, at least 75%, preferably at least 85%, more preferably at least 95% and most preferably 100% homologous to a coding (ORFs 1 to 26) or non-coding sequence as comprised by SEQ ID NO: 1 or that are, to the above extents, complementary thereto. They may contain modified bases such as inosine, methyl-5-deoxycytidine, deoxyuridine, dimethylamino-5-deoxyuridine or diamino-2, 6-purine. Sugar or phosphate residues may also be modified or substituted as is known in the art. For example, a deoxyribose residue may be replaced by a polyamide and a phosphate residue may be replaced by ester groups such as diphosphate, alky, arylphosphonate or phosphorothioate esters. Alternatively or in addition, the 2'-hydroxyl group on ribonucleotides may be modified by including such groups as alkyl, O-alkyl or halogen groups. Probes of the invention are used in any conventional hybridization technique such as dot blot, Southern blot, northern blot or sandwich technique which is a technique using specific capture and/or detection probes with nucleotide sequences that at least differ partially from each other (Sambrook et al., Molecular cloning: A laboratory manual. Cold Spring Harbor, N.Y.: Cold Spring Harbor Laboratory Press, 2001). A primer is used to initiate enzymatic polymerization of DNA in an amplification (e.g. PCR), elongation or reverse transcription method. Primers used in diagnostic methods involving PCR are labeled by methods known in the art. They can also be used as probes. In principle, primers may have the same characteristics as probes. They may contain from 5 to 100, preferably 10 to 80 nucleotides, more preferably 10 to 50 nucleotides, still more preferably 10 to 40 nucleotides and still more preferably 15 to 25 nucleotides. In the context of the present invention, the primer or probe can be used for detecting, identifying and/or isolating a microorganism which produces (methyl)griselimycin, in particular which comprises any of the proteins of SEQ ID Nos: 2 to 27 or functionally active variants thereof, for detecting, identifying and/or isolating DNA or RNA encoding proteins of SEQ ID Nos: 2 to 27 or functionally active variants thereof and and/or for amplifying DNA or RNA encoding proteins of SEQ ID Nos: 2 to 27 or functionally active variants thereof. Thus, in an embodiment of the present invention a reagent is comprised comprising a primer or probe for the purposes of detection, identification and/or purification as outlined above.

Alternatively, identification of a nucleic acid encoding a protein which has activity in the (methyl)griselimycin biosynthetic pathway may be achieved by screening for reactivity or cross-reactivity with an antibody raised against the protein having an amino acid sequence of SEQ ID Nos: 2 to 27 or a functionally active variant or fragment thereof. The procedure is as follows: an antibody is specifically raised against a protein of SEQ ID Nos: 2 to 27 or a functionally active variant or fragment thereof, a fusion polypeptide (for example, an expression product of MBP, GST, or His-tag systems), or a synthetic peptide derived from the protein of SEQ ID Nos: 2 to 27 or a known variant or fragment thereof. Specific antigenicity can be determined according to a number of methods, including Western blot, dot blot, and ELISA. Once a specific antibody has been raised this antibody can be used to identify nucleic acids encoding proteins harbouring the immunogenic peptide against which the antibody has been raised thus identifying proteins which are proteins of SEQ ID Nos: 2 to 27 or functionally active fragments or variants thereof as defined herein. Specific antigenicity or specific antibody as used herein means that the antibody binds only to the immunogenic peptide against which the antibody was raised.

In a further embodiment, the nucleic acid is complementary to a nucleic acid sequence as comprised by SEQ ID NO: 1 or encoding a protein with SEQ ID Nos: 2 to 27 or functionally active fragments or variants thereof.

In one embodiment, the nucleic acid comprises at least one, at least two, at least three, at least four, at least five or more ORFs selected from ORFs 1 to 26 encoding polypeptides shown in SEQ ID Nos: 2 to 27 of the griselimycin biosynthesis gene cluster or functionally active fragments or variants thereof. In a preferred embodiment, the nucleic acid comprises a specific ORF or a combination of specific ORFs which is/are involved in and function together in defined steps during the biosynthesis of (methyl)griselimycin. In a more preferred embodiment, a combination of ORFs selected from ORFs 1 to 27 is provided which encodes polypeptides which manage the biosynthesis of (methyl)griselimycin. In a still more preferred embodiment, the ORF is ORF 8, 15 or 16 or the combination comprises at least two of ORFs 8, 15 or 16 designated nrps-1, nrps-2 and nrps-3, respectively, encoding subunits of the non-ribosomal protein synthetase (NRPS). In another embodiment, the nucleic acid comprises ORF 18, 19 or 21 or a combination of at least two of ORFs 18 to 21 constituting genes designated mps-1, mps-2, mps-3 and mps-4, respectively, or at least two of ORFs 18, 19 and 21 constituting genes designated mps-1, mps-2 and mps-4, respectively, which are necessary for the biosynthesis of L-trans-4-methylproline. In another embodiment, ORFs 8, 15 and/or 16 may be combined with ORFs 18, 19, 20 and/or 21 or with ORFs 18, 19 and/or 21 to enhance production of L-trans-4-methylproline and of (methyl)griselimycin, in particular of methylgriselimycin. Thereby, any of ORFs 1 to 26 may be combined with any of a variant or fragment of ORFs 1 to 26 to direct synthesis of (methyl)griselimycin. In another embodiment of this invention, the ORFs may be unchanged, but the control elements (e.g. promoters, ribosome binding sites, terminators, enhancers etc.) may be modified.

In another embodiment, a nucleic acid is provided comprising or consisting of the griselimycin gene cluster having the sequence of SEQ ID NO: 1 or having a variant sequence of SEQ ID NO: 1 harboring a variant or fragment of at least one of ORFs 1 to 26 whereby the variant or fragment encodes a functionally active variant or fragment of a protein of SEQ ID Nos: 2 to 27. Variant or fragmental sequences of any of ORFs 1 to 26 within the (methyl)griselimycin gene cluster of SEQ ID NO: 1 in an otherwise unmodified state may result in one or more variant proteins of SEQ ID Nos: 2 to 27, which modify a specific step of the synthesis pathway of (methyl)griselimycin. This may result in an enhanced production of (methyl)griselimycin or L-trans-4-methylproline or in a modified structure of (methyl)griselimycin with enhanced antibiotic activity. As an example, any of the ORFs 8, 15 and 16 and/or 18, 19, 20 and 21 may be modified within the griselimycin cluster as comprised by SEQ ID NO: 1 as referred to above, whereas the remaining ORFs remain unmodified. Alternatively or additionally, the control elements may be modified resulting in a modified expression of at least one of the ORFs 1 to 26.

Thus, the present invention provides in one embodiment a nucleic acid comprising at least one ORF being involved in the biosynthesis of (methyl)griselimycin such as ORFs 18, 19, 20 and 21 or otherwise designated ORFs 18 to 21 or ORFs 18, 19 and/or 21 and/or ORFs 8, 15 and/or 16 or functionally active variants or fragments of these ORFs as defined herein. One or a combination of ORFs may be expressed or overexpressed in a heterologous cell in order to allow production of the respective proteins which may, e.g., be used as a fermentative aid to enhance the production of griselimycin and especially methygriselimycin in an organism endogenously or heterologously producing griselimycin and/or methygriselimycin. Alternatively, an ORF or a combination of ORFs as comprised by the invention is expressed or overexpressed in a cell or organism producing (methyl)griselimycin in order to enhance the production of the respective protein(s) in order to enhance production of (methyl)griselimycin and/or to favor the production of methylgriselimycin. For example, ORFs 18 to 21 or ORFs 18, 19 and 21 may be concomitantly expressed to allow synthesis of L-trans-4-methylproline. Enhanced production of L-trans-4-methylproline may serve to enhance production of methylgriselimycin versus the production of griselimycin as could be demonstrated by feeding 4-methyl proline whereby five fold higher amounts of methylgriselimycin were obtained. Thus, in a preferred embodiment of the present invention, the yield of methylgriselimycin can be enhanced in Streptomyces DSM 22643 or another organism producing (methyl)griselimycin by introducing a nucleic acid comprising genes involved in the biosynthesis of L-trans-4-methylproline, in particular ORFs 18 to 21, more particularly ORFs 18, 19 and 21, according to methods as known in the art or as described herein and allowing expressing said genes and the genes of the (methyl)griselimycin gene cluster. Alternatively or additionally, at least one nrps nucleic acid (ORFs 8, 15 and/or 16) may be expressed for the synthesis of (methyl)griselimycin in a heterologous organism or in an organism endogenously expressing (methyl)griselimycin for enhancing expression thereof. Alternatively or additionally, variant nucleic acids may be expressed which modulate the synthesis of (methyl)griselimycin in order to enhance the synthesis of (methyl)griselimycin, to favor the synthesis of methylgriselimycin or to generate derivatives of (methyl)griselimycin with a composition of amino acids different from that of (methyl)griselimycin which are, for example, more efficient antibiotics. For example, the amino acid specificity of the A-domains of NRPS proteins may be altered by mutagenesis or by domain swapping between peptide synthetases thereby allowing the selection of different amino acids and generating derivatives of a natural (methyl)griselimycin. Alternatively, the nucleic acid encoding the A-domain of module 8 of NRPS2 may be mutated to produce a variant nucleic acid which results in the enhanced insertion of L-trans-4-methylproline into the nascent polypeptide chain, thus resulting in an enhanced production of methylgriselimycin compared to the wild-type. Alternatively, the complete module 8 may be swapped or the C-domain of module 8 may be swapped or mutated to preferably condense methylproline.

L-trans-4-methylproline is comprised by griselimycin at positions 2 and 5 and by methylgriselimycin at positions 2, 5 and 8. L-trans-4-methylproline can be chemically produced, however, the chemical production is cost-intensive and time-consuming Thus, the present invention provides in one aspect a nucleic acid comprising genes being involved in the biosynthesis of L-trans-4-methylproline, in particular ORFs 18 to 21 or ORFs 18, 19 and 21 or functionally active variants or fragments of these ORFs as defined herein. The combination of these ORFs may be expressed or overexpressed in a heterologous cell in order to allow production of L-trans-4-methylproline for use, e.g., as a fermentative aid to enhance the production of griselimycin and especially methygriselimycin in an organism endogenously or heterologously producing griselimycin and/or methylgriselimycin. Alternatively, the combination of these genes is expressed or overexpressed in a cell or organism naturally producing (methyl)griselimycin in order to enhance the production of L-trans-4-methylproline in order to favor the production of methylgriselimycin. Thus, in a preferred embodiment of the present invention, the yield of methylgriselimycin can be enhanced in Streptomyces DSM 22643 by introducing a nucleic acid comprising genes involved in the biosynthesis of L-trans-4-methylproline, in particular ORFs 18 to 21, more particularly ORFs 18, 19 and 21, into in an organism endogenously or heterologously producing griselimycin and/or methylgriselimycin, e.g. Streptomyces DSM 22643 according to methods as known in the art or as described herein and allowing expressing said genes and the genes of the griselimycin biosynthesis gene cluster.

The nucleic acid of the present invention may be provided by any methods known in the art. Using the sequence information provided herein, primers suitable for amplification/isolation of one or more ORFs can be determined according to standard methods well known to those of skill in the art. Primers suitable for amplification/isolation of any one or more of the ORFs as defined herein are designed according to the nucleotide sequence information provided in the sequence listing. The procedure is as follows: a primer is selected which may consist of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. Typically such amplifications will utilize the DNA or RNA of an organism containing the requisite genes (e.g. Streptomyces, in particular Streptomyces DSM 22643) as a template. A standard PCR reaction will be performed which typically contains 0.5 to 5 Units of Taq DNA polymerase per 100 µl, 20 to 200 µM deoxynucleotide each, preferably at equivalent concentrations, 0.5 to 2.5 mM magnesium over the total deoxynucleotide concentration, 105 to 106 target molecules, and about 20 pmol of each primer. About 25 to 50 PCR cycles are performed. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for denaturation of G+C-rich targets. The number of cycles performed depends on the starting concentration of target molecules, though typically more than 40 cycles are not recommended as non-specific background products tend to accumulate. An alternative method for retrieving polynucleotides encoding variant polypeptides as defined herein is by hybridization screening of a DNA or RNA library using the primers and probes as defined herein. Hybridization procedures are well-known and are described in the art and herein.

Alternatively or additionally to the above the nucleic acid may be provided by cloning and thereby introducing it into and amplifying it in a cell. Thus, in a further aspect of the present invention, a vector comprising a nucleic acid as defined herein and a host cell transformed with the expression vector are provided. The procedure of introducing a gene into a recipient cell is called transformation. The genes can be introduced into the cells by a variety of means known in the art and adapted to each cell type. The term "cell" or "host cell" refers to the cell in which the gene is expressed irrespective of whether it is a prokaryotic cell or a eukaryotic cell and of whether the cell naturally expresses the respective genes or not. Thereby the cell may be, in a preferred embodiment, a cell which naturally harbors the gene expressing the protein as comprised by the present invention, e.g., *Streptomyces* DSM 22643. Recombinant DNA cloning techniques well known in the art for introducing and expressing a nucleic acid molecule can be used to introduce and express the gene which is either endogenous if the cell harbours the respective gene or is heterologous if the gene is not endogenous to the cell. Cells can be transformed using any appropriate means, including viral or bacteriophage based vectors, chemical agents, electroporation, calcium phosphate co-precipitation or direct diffusion of DNA. Vectors are agents that transport an endogenous or heterologous gene into the cell and may include appropriate transcriptional and translational control signals such as a promoter. Vectors can be a plasmid, a virus (e.g. bacteriophage) or others as known in the art. Vectors are able to autonomously replicate in a host cell or can be incorporated into chromosomal DNA. The term "vectors" includes those that function primarily for insertion of a nucleic acid into a cell, those that function primarily for replication of a nucleic acid (replication vector) in a cell or those that function primarily for transcription and/or translation of DNA or RNA in a cell. Examples of vectors include pBTrp2, pBTac1, pBTac2 (all of which are manufactured by Boehringer Mannheim), pKK263-2 (manufactured by Pharmacia), pGEX (manufactured by Pharmacia), pSE280 (manufactured by Invitrogen), pGEMEX-1 (manufactured by Promega), pQE-8 (manufactured by Qiagene), pET-3 (manufactured by Novagen), pBluescriptII SK+ (manufactured by Stratagene), pBluescript II SK (−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pSTV28 (manufactured by Takara Bio Inc.), pUC118 (manufactured by Takara Bio Inc.), pHW1520 (manufactured by MoBiTec), pSET152, pOJ436 and pOJ446 (Bierman M, et al., 1992), pSH19 (Herai S, et al., 2004), pUWL199, pUWL218 and pUWL219 (Wehmeier U. F., 1995) and pIJ6021 (Takano E. et al., 1995).

The promoter can be inducible or constitutive, general or cell specific, nuclear or cytoplasmic specific, heterologous or associated with the gene in nature. Any type of promoter can be used, as long as it functions in host cells. Examples of the promoter include promoters derived from *Escherichia coli* or phage, such as a tip promoter (Ptrp), a lac promoter (Plac), a PL promoter, a PR promoter or a PSE promoter, a SPO1 promoter, a SPO2 promoter, and a penP promoter. In addition, artificially designed or modified promoters such as a promoter formed by placing two Ptrp in series (Ptrp*2), a tac promoter, a lacT7 promoter or a let I promoter, can also be used. Moreover, a xylA promoter for expression in the bacteria of the genus *Bacillus*, or a P54-6 promoter for expression in the bacteria of the genus *Corynebacterium* can also be used. Further useful promoters are PermE (Bibb et al., 1985, PermE* (Bibb et al., 1994), PtipA (Murakami et al., 1989), PnitA-NitR expression system (Herai et al., 2004) and actII-ORF4/PactI activator-promoter system (Ferna'ndez-Moreno et al., 1991). Selection of promoters, vectors and other elements is a matter of routine design. Many such elements are described in literature and are available through commercial suppliers. A single gene can be introduced into a cell. Also, more than one gene can be introduced into a cell and expressed therein. Where large clusters are to be expressed, it is preferable that phagemids, cosmids, P1s, YACs, BACs, PACs, HACs, or similar cloning vectors are used. If more than one gene is introduced into a cell, then the genes may be under the regulation of the same promoter and/or regulatory elements. Alternatively, the genes may be under the regulation of different promoter and/or regulatory elements. Usually, the method of transfer includes transfer of a selectable marker to the cells. In general, a cell line is transformed by any of the means mentioned above wherein the transgene is operatively linked to a selectable marker. Following transformation, cells are grown for an adapted period of time. Transformed cells exhibit resistance to the selection and are able to grow, whereas non-transformed cells die in general. Examples for selective markers include puromycin, zeocin, neomycin and hygromycin B which confer resistance to puromycin, zeocin, aminoglycoside G-418 and hygromycin B, respectively.

Examples of host cells suitable in the context of the present invention are derived from any organism with the capability of harboring and expressing a recombinant griselimycin biosynthesis gene cluster or one or more genes of the griselimycin biosynthesis gene cluster. Examples include bacteria, yeasts, filamentous fungi, animal cells and plant cells, such as, without limitation, cells of *E. coli* strains, of the order Actinomycetales such as a *Streptomyces* species such as *Streptomyces* DSM 22643 or *Streptomyces coelicolor*, of yeast strains such as *Saccharomyces cerevisiae*, of the insect cell line Lepidoptera such as from *Spodoptera frugiperda*, of plant cells or of mammal cells such as L6 cells, 3T3 adipocytes, HEK 293, 745-A, A-431, atrial myocytes, BxPC3, CSN, Caco-2, Capan-1, CC531, CFPAC, CHO, CHO K1, COS-1, COS-7, CV-1, EAHY, EAHY 926. Preferred embodiments are bacterial cells such as cells of the order Actinomycetales such as *Streptomyces* DSM 26643 or *Streptomyces coelicolor* or cells of *E. coli* strains. Particularly preferred embodiments are cells of the order Actinomycetales, in particular *Streptomyces* DSM 26643.

As stated above, preferred host cells for harboring and expressing genes as comprised by the present invention are bacterial cells. Other host cells suitable for harboring and expressing genes as comprised by the present invention are established or immortalized cell lines which have acquired the ability to proliferate indefinitely either through random mutation or deliberate modification, such as artificial expression of the telomerase gene. There are numerous well established cell lines representative of particular cell types and it is within the knowledge of the skilled person to select a suitable cell line. A cell line is a population of cells propagated in culture that are derived from, and therefore genetically identical to, a single common ancestor cell. Suitable cell lines for the present invention are HEK 293 cells (primary human embryonic kidney), 3T3 cells (murine embryonic fibroblasts), CHO cells (Chinese hamster ovary), COS-7 cells (African green monkey cell line), HeLa cells (human epithelioid cervical carcinoma), JURKAT cells (human T-cell leukemia), BHK 21 cell (hamster normal kidney, fibroblast), and MCF-7 cells (human breast cancer).

Alternatively, the nucleic acids as defined herein may be cloned and expressed in a tissue culture. The term "tissue culture" refers to a method in which a group of cells forming a three dimensional network is cultivated. The tissue can be formed in culture by the cells themselves or may be formed by an extracellular matrix produced by the cells, the culture may be cultivated on a natural or an artificial extracellular matrix (e.g. collagen, elastin, polystyrene, nylon, polylysine) or the tissue may be obtained from an animal including human. The tissue culture may be cultivated in culture medium and at suitable temperature. The culture medium may contain nutrients (e.g. sugars, salts, amino acids, and lipids), a buffer system (often comprising one or more chemical buffer substances such as phosphates, hydrogen phosphates and/or Tris with low or no toxicity and/or carbon dioxide ($CO_2$) gassing)

and/or optionally one or more antibiotics. In order to provide sufficient amounts of nutrients and/or to remove metabolites the medium may be changed when required. Optionally, the tissue culture may be perfused with medium. The perfusion may be a permanent or pulsed perfusion.

Variations may be introduced into a nucleic acid by design, for example, by modification of a nucleotide within a nucleic acid in a specific way, e.g. by replacing a single substituent by another and thereby resulting in a partly or complete artificelle biosynthesis gene cluster for griselimycin. As a further example, the skilled person knows the field of the art termed "synthetic biology" which deals with the design and construction of new biological functions and systems not found in nature. For example, the skilled person is capable of designing a DNA sequence in silico and synthesizing it having no similarity to the nucleic acid level of the wildtype sequence, however, coding for the same protein(s) as the wildtype sequence. Alternatively, variations can be made randomly, for example, by making a library of molecular variants of (methyl)griselimycin by systematically or haphazardly replacing one or more ORFs in the biosynthetic pathway. Moreover, useful variants and fragments of a nucleic acid that do not occur naturally are designed using known methods. Such variation may be any modification as outlined above, e.g. replacement of a single substituent by another. For example, regions of a polypeptide that are likely to tolerate amino acid sequence changes and/or deletions are identified. As an example, variant polypeptides involved in the synthesis of (methyl)griselimycin from different species producing (methyl)griselimycin are compared; conserved sequences are identified. The more divergent sequences are the most likely to tolerate sequence changes. Homology among sequences may be analyzed using methods known in the art. Mutation introduction methods into a nucleic acid include error-prone PCR, site-directed mutagenesis, a method using hydroxylamine or a method of allowing a mutation agent such as UV to act on cells having the nucleic acid of interest. When an error-prone PCR is used, e.g. a plasmid into which the nucleic acid of interest has been incorporated is used as a template, the PCR reaction is carried out in a reaction solution wherein a manganese (Mn) salt concentration is higher than in a usual PCR reaction.

Using the information provided herein other approaches to cloning the desired sequences will be apparent to those of skill in the art, for example, at least one of the ORFs 1 to 26 including the total griselymcin biosynthesis gene cluster comprising ORFs 1 to 26 and/or optionally nucleic acids encoding NRPS modules or enzymatic domains of interest can be obtained from an organism that expresses such, using recombinant methods, such as by screening cDNA or genomic libraries derived from cells expressing the gene(s) or by deriving the gene(s) from a vector known to include the same. The gene(s) or cluster can then be isolated and combined with other desired biosynthetic elements using standard techniques. If the gene(s) or cluster in question is(are) already present in a suitable expression vector, it(they) can be combined in situ with, e.g. other domains or subunits, as desired. The gene(s) of interest can be produced synthetically, rather than cloned. The nucleotide sequence can be designed with the appropriate codons for the particular amino acid sequence desired. In general, one will select preferred codons for the intended host in which the sequence will be expressed. In addition, it is noted that custom gene synthesis is commercially available.

In another aspect, the present invention is directed to a protein, comprising at least one amino acid sequence selected from SEQ ID Nos: 2 to 27 or functionally active fragments or variants thereof or encoded by a nucleic acid as referred to above. The protein may be a single protein or may be a mixture of proteins or may be a fusion protein of at least two proteins of SEQ ID Nos: 2 to 27. The protein may be isolated which means that it is substantially pure and not associated with components with which it is associated in nature or the protein is present in a lysate of a cell producing the protein. The proteins of SEQ ID Nos: 2 to 27 are encoded by the putative ORFs 1 to 26, respectively. These ORFs belong to and constitute the griselimycin biosynthesis gene cluster. Based on sequence analysis and homology searches, the present inventors succeeded in identifying the griselimycin biosynthesis gene cluster, in identifying specific putative ORFs within the gene cluster and in assigning the identified ORFs to either a specific protein function and/or to a specific homologous nucleotide sequence coding for a known or hypothetical protein.

The proteins as comprised by the present invention encompass proteins of SEQ ID Nos: 2 to 27 as encoded by the griselimycin biosynthesis gene cluster of *Streptomyces* DSM 26643 of the sequence of SEQ ID NO: 1 and encompass proteins as they occur in other *Streptomyces* species and strains and non-*Streptomyces* species which produce (methyl)griselimycin which are orthologs or homologs whereby these orthologs or homologs have the same function as the proteins of SEQ ID NO: 2 to 27 of *Streptomyces* DSM 26643. Preferably, orthologs or homologs thereof differ from the sequences of SEQ ID Nos: 2 to 27 e.g. by addition, deletion, substitution and/or insertion of amino acids and have a sequence identity with SEQ ID Nos: 2 to 27 of more than 50%, of more than 60%, more than 70%, preferably of more than 80%, more preferably more than 85%, even more preferably more than 90%, even more preferably more than 95%, most preferably more than 97% and/or have an enzyme activity of more than 5%, more than 10%, more than 20%, more than 30%, more than 40%, more than 50%, more than 60%, more than 70%, more than 80%, more than 90%, more than 95%, more than 97% or more than 100%, e.g. more than 150%, 200%, 300% 400% or 500% of the activity of the proteins of SEQ ID Nos: 2 to 27.

In the context of the present invention the naturally or non-naturally occurring variant of the proteins of SEQ ID Nos: 2 to 27 as comprised by the present invention is a functionally active protein in that it maintains the biological function of the reference protein of SEQ ID Nos: 2 to 27, i.e. the involvement in a reaction in which the reference protein is involved under natural conditions (in case of a non-natural variant, the biological function of the reference protein) as referred to in the respective chapters disclosing the function of the protein of SEQ ID Nos: 2 to 27, and can be substituted therefor, as defined herein. Non-naturally occurring variants of the proteins of SEQ ID Nos: 2 to 27 or of naturally occurring variants thereof may be obtained by a limited number of amino acid deletions, insertions and/or substitutions, particularly deletions, insertions and/or substitutions of, e.g., at most 10, 9, 8, 7, 6, 5, 4, 3, 2 or 1 amino acid(s) thereby obtaining a sequence identity or activity of the respective wild-type proteins, e.g. with respect to SEQ ID Nos: 2 to 27, as mentioned above.

The variant may be a modified protein or a modified protein variant which comprises a further component. Accordingly, the variant may be a molecule having a domain composed of a naturally occurring protein of SEQ ID Nos: 2 to 27 or a variant thereof as detailed herein and at least one further component. In one preferred embodiment the variant may be a fusion protein comprising (i) a protein of SEQ ID Nos: 2 to 27 or functionally active variant and (ii) a further protein or peptide component. For example, the protein may be coupled to a marker, such as a tag used for purification purposes (e.g. 6 His (or HexaHis) tag, Strep tag, HA tag, c-myc tag or glutathione S-transferase (GST) tag). If e.g. a highly purified protein of SEQ ID Nos: 2 to 27 or variant should be required, double or multiple markers (e.g. combinations of the above markers or tags) may be used. In this case the proteins are purified in two or more separation chromatography steps, in each case utilizing the affinity of a first and then of a second tag. Examples of such double or tandem tags are the GST-His-tag (glutathione-S-transferase fused to a polyhistidine-tag), the 6xHis-Strep-tag (6 histidine residues fused to a Strep-tag), the 6xHis-tag100-tag (6 histidine residues fused to a 12-amino-acid protein of mammalian MAP-kinase 2), 8xHisHA-tag (8 histidine residues fused to a hemagglutinin-epitope-tag), His-MBP (His-tag fused to a maltose-binding protein, FLAG-HA-tag (FLAG-tag fused to a hemagglutinin-epitope-tag), and the FLAG-Strep-tag. The marker could be used in order to detect the tagged protein, wherein specific antibodies could be used. Suitable antibodies include anti-HA (such as 12CA5 or 3F10), anti-6 His, anti-c-myc and anti-GST. Furthermore, the protein could be linked to a marker of a different category, such as a fluorescence marker such as green fluorescent protein, to a binding protein such as steptavidin, one or more small molecular dyes such as Cy dye, or a radioactive marker, which allows for the detection of a protein as comprised by the present invention. In a further embodiment, the proteins of SEQ ID Nos: 2 to 27 could be part of a fusion protein, wherein the second part could be used for detection, such as a protein component having enzymatic activity.

In another embodiment of the present invention, the variant of the proteins of SEQ ID Nos: 2 to 27 could be a fragment, wherein the fragment is still functionally active. This may include proteins of SEQ ID Nos: 2 to 27 or variants thereof as detailed above with short internal and/or C- and/or N-terminal deletions (e.g. deletions of at most 20, 19, 18, 17, 16, 15, 14, 13, 12, 11, 10, 9, 8, 7, 6 5, 4, 3, 2, or 1 amino acids within the variant and/or at the C- and/or N-termini or total deletions of 5%, 10%, 20%, 30%, 40%, 50%, 60% 70% amino acids or any values in between these values). Additionally, the fragment may be further modified as detailed above for the proteins of SEQ ID NO: 2 to 27.

Alternatively or additionally, the proteins of SEQ ID Nos: 2 to 27 or variants thereof as described above may comprise one or more amino acid substitution(s). However, semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative substitution |
| --- | --- | --- |
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |

-continued

| Amino acid | Conservative substitution | Semi-conservative substitution |
| --- | --- | --- |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure. The proteins of SEQ ID Nos: 2 to 26 or fragments or variants thereof with substitution may be modified as detailed above for the proteins of SEQ ID Nos: 2 to 27 or fragments or variants thereof.

It is noted that the above modifications of the protein of SEQ ID Nos: 2 to 27 may be combined. The variants of the present invention may be e.g. a fragment of a protein of SEQ ID Nos: 2 to 27 having a marker fused to it or comprising one or more amino acid substitutions. It is furthermore noted that any of the proteins of SEQ ID Nos: 2 to 27 may be combined with any of a variant or fragment of the proteins of SEQ ID Nos: 2 to 27.

The proteins as comprised by the present invention may be provided by any means, e.g., by obtaining the proteins from a natural source, by biotechnological methods well-known in the art and/or by synthetic methods. Herein the term "providing" may be understood in the widest sense and may include but may not be limited to any biochemical or biotechnological means as known in the art that may be used to obtain the protein or other product. Consequently, the protein may be obtained by extraction from a natural source such as a microorganism containing the proteins, such as a *Streptomyces* species, in particular *Streptomyces* DSM 26643. The skilled person will know methods of how to isolate the protein. Cells naturally harbouring a protein as comprised by the present invention may be disrupted by any means known in the art but not limited to sonication, hypotonic buffer, detergents, UltraTurrax, French press, freeze-thaw cycles, mechanical homogenization and scratching. The protein of interest may then be isolated by known methods, e.g., a solvent extraction method, a salting-out method, a solvent precipitation method, a dialysis method, an ultrafiltration method, a gel electrophoresis method, a gel filtration chromatography, an ion exchange chromatography, a reverse phase chromatography, and an affinity chromatography, either alone or in combination as appropriate.

Alternatively, the proteins as comprised by the present invention may be proteins which are produced by recombinant methods, e.g. by cloning and expressing a nucleic acid encoding a protein as comprised by the present invention or a functional fragment or variant thereof and isolating the protein. Procedures of cloning nucleic acids and of isolating the expressed proteins are as disclosed above.

The proteins may be expressed with a convenient marker to facilitate isolation. A marker (or tag or label) is any kind of substance which is able to indicate the presence of another substance or complex of substances. The marker can be a substance that is linked to or introduced in the substance to be detected. Detectable markers are used in molecular biology and biotechnology to detect e.g. a protein, a product of an enzymatic reaction, a second messenger, DNA, interactions of molecules etc. Examples of suitable marker or labels include a fluorophore, a chromophore, a radiolabel, a metal colloid, an enzyme, or a chemiluminescent or bioluminescent molecule. Examples of fluorophores include fluorescein, rhodamine, and sulfoindocyanine dye Cy5. Examples of radiolabels include $^3$H, $^{14}$C, $^{32}$P, $^{33}$P, $^{35}$S, $^{99m}$Tc or $^{125}$I. Examples of enzymes include horseradish peroxidase, alkaline phosphatase, glucose oxidase, and urease.

The proteins of the present invention including functionally active variants and fragments thereof can be singly expressed in a cell or several proteins including functionally active variants and fragments thereof as comprised by the present invention such as at least two, three, four, five or more proteins can be simultaneously expressed in a cell. Also, the whole griselimycin biosynthesis gene cluster may be heterologously expressed. Thereby, any combination of variant and non-variant protein is comprised. In one embodiment, several proteins which contribute to a certain aspect of the synthesis pathway of (methyl)griselimycin such as those which belong to a same family of proteins such as the nonribosomal protein synthetases encoded by the nrps-1, nrps-2 and/or nrps-3 genes or such as the proteins encoded by the methylproline synthesis genes mps-1, mps-2, mps-3 and mps-4 or mps-1, mps-2 and mps-4 may be expressed together in a cell. Thereby, a specific step of the synthesis of (methyl) griselimycin is especially favored so that production of (methyl)griselimycin and in particular of methylgriselimycin is enhanced. Alternatively, variants may be produced which influence a specific aspect of the synthesis pathway of (methyl)griselimycin and thus the synthesis of (methyl)griselimycin. Examples are variants of one or more of the proteins of SEQ ID Nos: 9, 16 and 17, in particular SEQ ID NO: 16, more particularly module 8 of SEQ ID NO: 16 which promote insertion of L-trans-4-methylproline into methylgriselimycin and/or SEQ ID Nos: 19, 20 and 22 and possibly SEQ ID NO: 21 which enhance the synthesis of L-trans-4-methylproline so that methylgriselimycin is produced at higher yield than if not using such variants. One or more of the variants may be combined with one or more non-variant proteins of SEQ ID Nos: 2 to 27.

In a further aspect of the present invention an antibody against at least one of the proteins of SEQ ID Nos: 2 to 27 or a functionally active fragment or variant thereof is provided. The detection of protein often involves the use of specific antibodies. Accordingly, the detection of at least one of the proteins of SEQ ID Nos: 2 to 27 or a functional variant or fragment thereof may include a specific antibody. Antibodies can be raised using well established techniques for immunizing animals with prepared forms of the antigen. A variety of reagents is available to assist in antibody production and purification, and various companies specialize in antibody production services. Depending on the application to be performed, different levels of purity and types of specificity are needed in a supplied primary antibody. To name just a few parameters, antibodies may be monoclonal or polyclonal, supplied as antiserum or affinity-purified solution, and validated for native protein or denatured protein detection. They may be chimeric, humanized, multifunctional, bispecific or oligospecific antibodies. Antibodies as comprised by the present invention may include whole antibodies or antibody fragments such as Fab, F(ab)$_2$ or sc (single chain) Fv.

An antibody that recognizes the target antigen, here the proteins of SEQ ID Nos: 2 to 27 or a functional variant or fragment thereof, is called the "primary antibody." If this antibody is labeled with a tag, direct detection of the antigen is possible. Usually, however, the primary antibody is not labeled for direct detection. Instead a "secondary antibody" that has been labeled with a detectable tag is applied in a second step to probe for the primary antibody, which is bound to the target antigen. Thus, the antigen is detected indirectly. Another form of indirect detection involves using a primary or secondary antibody that is labeled with an affinity tag such as biotin. Then a secondary (or tertiary) probe, such as streptavidin that is labeled with the detectable enzyme or fluorophore tag, can be used to probe for the biotin tag to yield a detectable signal. Several variants of these probing and detection strategies exist. However, each one depends on a specific probe (e.g., a primary antibody) whose presence is linked directly or indirectly to some sort of measurable tag (e.g., an enzyme whose activity can produce a colored product upon reaction with its substrate).

In a further aspect of the present invention, the use of the nucleic acid or the protein as defined herein including fragments and variants, of an expression vector harboring the nucleic acid or of a host cell harboring said expression vectors for the production of (methyl)griselimycin is provided. Particularly, the use of at least one of the nucleic acids comprising ORFs 8, 15 and 16 or of at least one of the proteins of SEQ ID Nos: 9, 16 and 17 including fragments and variants for the production of (methyl)griselimycin is provided. Preferably, a combination of the nucleic acids comprising ORFs 8, 15 and 16 or of the proteins of SEQ ID Nos: 9, 16 and 17 is provided. With respect to the terms "nucleic acid", "protein", "ORFs 8, 15 and 16" and "proteins of "SEQ ID Nos: 9, 16 and 17," it is referred to the definitions provided in the context of the nucleic acids and proteins of the invention.

In a further aspect of the present invention, the use of at least one of the nucleic acids comprising ORFs 18, 19 and 21 or of at least one of the proteins of SEQ ID Nos: 19, 20 and 22 including fragments and variants for the production of L-trans-4-methylproline is provided. Preferably, a combination of the nucleic acids comprising ORFs 18, 19 and 21 or of the proteins of SEQ ID Nos: 19, 20 and 22 is provided. With respect to ORFs 18, 19 and 21 and the proteins of SEQ ID Nos: 19, 20 and 22 it is referred to the definitions provided in the context of the nucleic acids and proteins of the invention. With respect to the method of producing (methyl)griselimycin or L-trans-4-methylproline reference is made to the definition thereof in the context of determining a variant of ORFs 1 to 26.

In another aspect of the invention, a method for producing at least one of the proteins or a functionally active variant or fragment thereof as defined herein comprising expressing the nucleic acid including variant forms and fragments as defined herein, and optionally isolating the protein or functionally active variant or fragment thereof is provided. Methods of cloning and expressing a nucleic acid and of isolating a protein are known in the art and are disclosed herein.

The present invention refers in a preferred embodiment to the above mentioned nucleic acid or protein which is isolated. The term "isolated" as used herein with respect to nucleic acids, such as DNA or RNA, refers to a nucleic acid which is not associated with all or a portion of a polynucleotide in which the isolated nucleic acid is found in nature. The term "isolated" as used herein with respect to proteins refers to a protein which is not associated with all or a portion of compounds in which or with which the isolated protein is found in nature. The isolated nucleic acid or the isolated protein is separated from other cellular components which naturally accompany a native human sequence or protein, e.g., ribosomes, polymerases, many other human genome sequences and proteins and any other kind of cellular material. The term embraces a nucleic acid sequence or protein which has been removed from its naturally occurring environment and includes recombinant or cloned DNA isolates or proteins derived therefrom and chemically synthesized analogs or analogs biologically synthesized by heterologous systems. An "isolated nucleic acid" is meant to include nucleic acid fragments which have been removed from its natural surroundings or which are not naturally occurring as fragments and would not be found in nature. The term "isolated" also refers to proteins which are isolated from other cellular proteins and is meant to also encompass recombinant proteins. The term "isolated" does not mean "purified" which means that the nucleic acid or polypeptide or protein is purified from its natural requirement by only separating out impurities.

In another aspect of the invention a method of determining a variant of ORFs 1 to 26 or of the proteins of SEQ ID Nos: 2 to 27 which modulates production of griselimycin and/or methylgriselimycin is provided. The method comprises producing a variant of any of ORFs 1 to 26, expressing the variant into a protein, allowing the production of griselimycin and/or methylgriselimycin or of a derivative thereof using said variant protein and determining the amount of griselimycin and/or methylgriselimycin, wherein an increase of the amount of griselimycin and/or methylgriselimycin compared to the amount produced if the variant protein is not present, but the corresponding invariant form of the protein is present is indicative that the variant is capable of increasing the production of griselimycin and/or methylgriselimycin, or determining the antibiotic activity of the derivative of griselimycin and/or methylgriselimycin, wherein an increase in the antibiotic activity compared to the antibiotic activity if the variant protein is not present, but the corresponding invariant form of the protein is present is indicative that the variant is capable of producing a derivative of griselimycin and/or methylgriselimycin with increased antibiotic activity and wherein the derivative differs in amino acid composition from griselimycin and/or methylgriselimycin and exhibits an enhanced antibiotic activity over griselimycin and/or methylgriselimycin. In a further aspect the invention comprises a method of determining a variant of ORFs 1 to 26 or of the proteins of SEQ ID Nos: 2 to 27 which enhances production of L-trans-4-methylproline comprising producing a variant of any of ORFs 1 to 26, expressing the variant into a protein, allowing the production of L-trans-4-methylproline using said variant protein and determining the amount of L-trans-4-methylproline, wherein an increase of the amount of L-trans-4-methylproline compared to the amount if the variant protein is not present, but the corresponding invariant form of the protein is present is indicative that the variant is capable of increasing the production of L-trans-4-methylproline.

As used herein, the term "method", or "assay" may be understood in the widest sense as an experimental activity or procedure. It will be understood as all means that may be used to determine a variant of ORFs 1 to 26 or of a protein of SEQ ID Nos: 2 to 27 that is able to modulate or enhance the production of (methyl)griselimycin or L-trans-4-methylproline. The term "variant of ORFs 1 to 26" may be understood in the sense as defined herein, namely variants of ORFs 1 to 26 with substitutions, additions, insertions and/or deletions of one or more nucleic acids encoding variants of one or more proteins of SEQ ID Nos: 2 to 27 as long as the variant encodes a protein which is capable of increasing the yield of griselimycin and/or methylgriselimycin, in particular methylgriselimycin, or of L-trans-4-methylproline by the cell harboring the variant or of changing the composition of (methyl)griselimycin so that the (methyl)griselimycin with the changed composition shows enhanced antibiotic activity. Suitable variants are those which increase the yield of griselimycin and/or methylgriselimycin, in particular methylgriselimycin, or of L-trans-4-methylproline by at least 5%, at least 10%, least 20%, least 30%, least 40%, least 50%, at least 100%, at least 200%, at least 300, at least 400% or at least 500%. Alternatively, suitable variants are those which change the composition of (methyl)griselimycin so that the antibiotic activity is increased by at least 5%, at least 10%, least 20%, least 30%, least 40%, least 50%, at least 100%, at least 200%, at least 300, at least 400% or at least 500%. The term "modulates the production of griselimycin and methylgriselimycin" means enhancing the amount of griselimycin and/or methylgriselimycin produced or varying the composition of griselimycin and/or methylgriselimycin. Thus, one or two amino acids or even more amino acids (e.g. three or four amino acids) or one or two or more domains or one or two or more modules may be replaced by different amino acids or domains or modules, respectively, whereby the resulting derivatives of griselimycin and/or methylgriselimycin show an enhanced antibiotic activity. For example, variants of nucleic acids coding for the A-domain of any of the modules of the NRPS proteins may result in the incorporation of different amino acids which may result in a derivative of (methyl)griselimycin which may possess enhanced antibiotic activity. The term "producing a variant" means the production by any method known in the art or as described herein. The method includes intentionally mutated nucleic acids by introducing targeted mutations or randomly mutated nucleic acids. Once a variant nucleic acid has been produced, the variant nucleic acid is introduced into a cell. Alternatively, the variant is produced inside the cell by applying mutating treatments on the cell. The cell may naturally harbor the genes for production of griselimycin and/or methylgriselimycin or of L-trans-4-methylproline or the cell may comprise a heterologous system for the production of griselimycin and/or methylgriselimycin or of L-trans-4-methylproline. The gene, of which a variant is to be expressed in the cell, is preferably inactive by deletion or any other kind of mutation or is comprised by the cell in an active state. For example, the cell may harbor each of the nucleic acid of ORFs 1 to 26 including one or more variant nucleic acids to be tested or a set of nucleic acids out of ORFs 1 to 26 such as the nrps genes including a variant nrps gene or another variant gene other than a variant nrps gene or the mps genes including a variant mps gene or another variant gene other than a variant mps gene. The cell harboring nucleic acids coding for proteins for synthesis of (methyl)griselimycin or L-trans-4-methylproline and one or more variant nucleic acids is incubated under appropriate conditions to allow synthesis of (methyl)griselimycin or a derivative thereof or L-trans-4-methylproline. Preferably, the production of (methyl)griselimycin or L-trans-4-methylproline is carried out in an aqueous buffer of neutral pH, more preferably in a buffer with a pH around pH 7, even more preferably in a buffer of pH 7 comprising the amino acids such as L-N-methylvaline, L-leucine, L-N-methylthreonine, L-proline, L-N-methylleucine and glycine to be incorporated into (methyl)griselimycin or L-leucine for production of L-trans-4-methylproline. Preferably, the proteins of SEQ ID Nos: 2 to 27 and the variant proteins maintain their activity in the used buffer and preferably protein and substrate precipitation is prohibited. Optionally, the samples may be incubated at a temperature suitable for the protein activity, preferably at temperatures between 0 and 50° C., more preferably at temperatures between 10 and 40° C., even more preferably at temperatures between 20 and 40° C., most preferably at 37°

C. Alternatively, the variant nucleic acid is expressed, e.g., by a cell-free expression system, and the resulting protein is then added to a cell harboring the proteins for producing (methyl) griselimycin or L-trans-4-methylproline.

In another embodiment the method for determining a variant of any of the ORFs 1 to 26 which enhances the yield of (methyl)griselimycin or L-trans-4-methylproline or changes the composition of (methyl)griselimycin may be performed in vitro. A procedure performed in vitro (Latin: within the glass) is performed not in a living organism but in a controlled environment, such as in a test tube or Petri dish. In the in vitro assay, the components participating in a reaction are combined in a test tube, the reaction is allowed to proceed and the product is determined. For this to occur, the variant nucleic acids produced as described herein are transcribed and translated into the respective variant proteins, either by a cell or in a cell free translation method, the proteins are purified or cell lysates (crude, fractionated or purified) are used and the proteins are used in the assay together with non-variant proteins as comprised by SEQ ID Nos: 2 to 27. An in vitro assay is useful if the variant proteins are involved in defined steps within the (methyl)griselimycin synthesis pathway, such as for example if the variant protein belongs to the proteins directly performing the synthesis of (methyl)griselimycin such as the NRPS proteins and only NRPS proteins including the variant form participate in the synthesis of (methyl)griselimycin or of L-trans-4-methylproline such as the proteins encoded by the mps genes and only these proteins including the variant form participate in the synthesis of L-trans-4-methylproline. In an in vitro assay, the components participating in the reaction such as amino acids such as L-N-methylvaline, L-leucine, L-N-methylthreonine, L-proline, L-N-methylleucine and glycine and at least one of the proteins of SEQ ID Nos: 2 to 27 including the variant to be tested are combined under defined definitions of time, amounts of components, compositions of reaction buffers, temperature etc. to allow the synthesis of (methyl)griselimycin or a derivative thereof or L-trans-4-methylproline. The measurements may be carried out in a molecular environment suitable for the activity of the participating proteins. Suitable conditions are as outlined above.

For the in vitro synthesis of L-trans-4-methylproline, three subsequent assays using Mps1, Mps-2 and Mps-3 are performed. In the Mps-1 assay L-leucine is converted to 5-hydroxyleucine, in the Msp-2 assay 5-hydroxyleucine is converted to γ-methylglutamic acid γ-semialdehyde and in the Msp-4 assay 3-methyl-$\Delta^1$-pyrroline-5-carboxylic acid is converted to 4-methylproline. It is assumed that the cyclisation of γ-methylglutamic acid γ-semialdehyde to 3-methyl-$\Delta^1$-pyrroline-5-carboxylic acid occurs spontaneously. Possibly, Mps-3 participates in this cyclisation reaction. Preferably, for the production of 5-hydroxyleucine the Mps-1 assay is carried out in an aqueous buffer of neutral pH, more preferably in a buffer with a pH around pH 7, even more preferably in a buffer of pH 7 comprising the substrate, leucine or related compounds, and the Mps-1 protein. Preferably, the Mps-1 protein maintains its activity in the used buffer and preferably protein and substrate precipitation is prohibited. Optionally, the samples may be incubated at a temperature suitable for the protein activity, preferably at temperatures between 0 and 50° C., more preferably at temperatures between 10 and 40° C., even more preferably at temperatures between 20 and 40° C., most preferably at 37° C. Typically, the reaction duration is between several minutes and several hours, preferably 30 minutes to two hours and more preferably one hour. Preferably, for the production of γ-methylglutamic acid γ-semialdehyde the Mps-2 assay is carried out in an aqueous buffer of basic pH, more preferably in a buffer with a pH around pH 10, even more preferably in a buffer of pH 10 comprising the substrate, 5-hydroxyleucine, and the Mps-2 protein. Preferably, the Mps-2 protein maintains its activity in the used buffer and preferably protein and substrate precipitation is prohibited. Optionally, the samples may be incubated at a temperature suitable for the protein activity, preferably at temperatures between 0 and 50° C., more preferably at temperatures between 10 and 45° C., even more preferably at temperatures between 30 and 42° C. Typically, the reaction duration is between several minutes and several hours, preferably 30 minutes to four hours and more preferably one to three hours. Preferably, for the production of 4-methylproline the Mps-4 assay is carried out in an aqueous buffer of neutral pH, more preferably in a buffer with a pH of 7 to 8, even more preferably in a buffer of pH 7.5 to 8 comprising the substrate, 3-methyl-$\Delta^1$-pyrroline-5-carboxylic acid or related compounds, and the Mps-4 protein. Preferably, the Mps-4 protein maintains its activity in the used buffer and preferably protein and substrate precipitation is prohibited. Optionally, the samples may be incubated at a temperature suitable for the protein activity, preferably at temperatures between 0 and 50° C., more preferably at temperatures between 10 and 45° C., even more preferably at temperatures between 30 and 42° C. and still more preferably at 30° C. Typically, the reaction duration is between several minutes and several hours, preferably 30 minutes to four hours and more preferably one to three hours.

Preferably, for the production of griselimycin the assay is carried out in an aqueous buffer of neutral pH, more preferably in a buffer with a pH of 7 to 8, even more preferably in a buffer of pH 8 comprising the substrates acetyl-CoA, L-valine, (2S,4R)-4-methylproline (or related compounds), L-leucine, L-proline, L-threonine, L-glycine and the proteins NRPS-1, NRPS-2, NRPS-3 (Non Ribosomal Peptide Synthetase) and MtbH and, as necessary, SAM and ATP. Preferably, the proteins maintain their activity in the used buffer and preferably proteins and substrates precipitation is prohibited. Optionally, the samples may be incubated at a temperature suitable for the protein activity, preferably at temperatures between 0 and 50° C., more preferably at temperatures between 10 and 45° C., even more preferably at temperatures between 20 and 40° C. and still more preferably at 30° C. Typically, the reaction duration is between one hour and 100 hours, preferably two to 72 hours. Preferably, for the production of methylgriselimycin the assay is carried out as the assay for griselimycin. However, L-proline is not necessary and therefore, must not be contained in the reaction.

A variety of assays is known in the art by which the skilled person may determine the concentration of a compound and thus measure of whether the concentration of a compound is changed versus a control reaction. Explicitly mentioned are radiometric assays which measure the incorporation of radioactivity into substances or its release from substances. The radioactive isotopes most frequently used in these assays are $^{14}C$, $^{32}P$, $^{35}S$ and $^{125}I$. The concentration may also be determined by Western analysis or an ELISA assay using an antibody or antiserum against the tested compound. Chromatographic assays measure product formation by separating the reaction mixture into its components by chromatography. This is usually done by high-performance liquid chromatography (HPLC), but one can also use the simpler technique of thin layer chromatography. Although this approach can need a lot of material, its sensitivity can be increased by labeling the substrates/products with a radioactive or fluorescent tag. A preferred method is quantification is by HPLC/MS. Liquid chromatography-mass spectrometry (LC-MS, or alternatively HPLC-MS) is an analytical chemistry technique that combines the physical separation capabilities of liquid chromatography (or HPLC) with the mass analysis capabilities of mass spectrometry. LC-MS is a powerful technique used for many applications which has very high sensitivity and specificity. The term "mass spectrometry" refers to the use of a ionization source to generate gas phase ions from a sample on a surface and detecting the gas phase ions with a mass spectrometer. The term "laser desorption mass spectrometry" refers to the use of a laser as a ionization source to generate gas phase ions from a sample on a surface and detecting the gas phase ions with a mass spectrometer. A preferred method of mass spectrometry for biomolecules such as acylated acyl acceptor is matrix-assisted laser desorption/ionization mass spectrometry or MALDI. Another preferred method is surface-enhanced laser desorption/ionization mass spectrometry or SELDI. In mass spectrometry the "apparent molecular mass" refers to the molecular mass (in Daltons)-to-charge value, m/z, of the detected ions. In combination with HPLC the analyte is ionized by diverse API techniques such as ESI (elektrospray ionization) or APCI (atmospheric pressure chemical ionization). In the analysator, the ions are separated according to their mass-to-charge m/z ratio. Alternatively, the amount of (methyl)griselimycin may be measured by determining its antibiotic activity using assays well-known in the art. In another embodiment the antibiotic activity of a derivative of (methyl)griselimycin may be measured using assays well-known in the art. The skilled person thereby knows of how to differentiate of whether an increased antibiotic activity is due to an increased amount of (methyl)griselimycin or of whether a derivative of (methyl)griselimycin with enhanced antibiotic activity is generated, e.g. by determining of whether the generated antibiotic agent is (methyl)griselimycin or not. Such methods are listed above.

Antibiotic testing can e.g. be disk diffusion antibiotic sensitivity testing which is a test which uses antibiotic-impregnated wafers. A known quantity of bacteria is grown on agar plates in the presence of thin wafers containing the antibiotics. An area of clearing surrounds the wafer where bacteria are not capable of growing (called a zone of inhibition). This along with the rate of antibiotic diffusion is used to estimate the effectiveness of a particular antibiotic. In general, larger zones correlate with smaller minimum inhibitory concentration (MIC) of the antibiotic. This information can be used to evaluate the effectiveness of a derivative of (methyl)griselimycin versus (methyl)griselimycin. MIC is the lowest concentration of an antimicrobial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. MIC is generally regarded as the most basic laboratory measurement of the activity of an antimicrobial agent against an organism. MICs can be determined by agar or broth dilution methods usually following the guidelines of a reference body such as the Clinical and Laboratory Standards Institute (CLSI) or the British Society for Antimicrobial Chemotherapy (BSAC). There are several commercial methods available, including the well established Etest strips. The Etest system comprises a predefined and continuous concentration gradient of different antimicrobial agents, which when applied to inoculated agar plates and incubated, create ellipses of microbial inhibition. The MIC is determined where the ellipse of inhibition intersects the strip, and is easily read off the MIC reading scale on the strip.

Controls are a part of the test methods, since they can eliminate or minimize unintended influences (such as background signals). Controlled experiments are used to investigate the effect of a variable on a particular system. In a controlled experiment one set of samples has been (or is believed to be) modified and the other set of samples is either expected to show no change (negative control) or expected to show a definite change (positive control). The control can be determined in one test run together with the test substance. It may be determined before or after determining the effect of the test compound or it may be a known value. A possible control experiment may be an experiment in which the same conditions are used for the production of (methyl)griselimycin, a derivative thereof or L-trans-4-methylproline as in the test experiment, however, the variant nucleic acid is replaced by the nucleic acid which was the starting nucleic acid for producing the variant, e.g. the control nucleic acid is the wildtype nucleic acid. Examples are ORFs 1 to 26 being in an unmodified state in the control experiment, however, being modified in the test experiment.

The nucleic acid sequence of the variant may be determined by sequencing methods as known in the art whereby any mutation in any of ORFs 1 to 26 may be responsible for a modulation of the resulting protein resulting in an increased production of (methyl)griselimycin or L-trans-4-methylproline or in the production of a derivative of (methyl)griselimycin.

In another aspect of the invention, a method of producing griselimycin and/or methylgriselimycin is provided comprising providing at least one protein or a functionally active variant or fragment thereof as defined herein or a variant protein obtained by a method for identifying variants and incubating the at least one protein or variant or fragment thereof with L-N-methylvaline, L-leucine, L-N-methylthreonine, L-proline, L-N-methylleucine, glycine and possibly L-methylproline to produce griselimycin and/or methylgriselimycin. Preferably the at least one protein comprises at least NRPS-1, NRPS-2 and NRPS-3. In a further aspect, the present invention provides a method of producing L-trans-4-methylproline comprising providing at least one protein or a functionally active variant or fragment thereof as defined herein or a variant protein obtained by a method for identifying variants and incubating the at least one protein or variant or fragment thereof with L-leucine, 5-hydroxyleucine, γ-methylglutamic acid γ-semialdehyde or 3-methyl-$\Delta^1$-pyrroline-5-carboxylic acid, preferably L-leucine, to produce L-trans-4-methylproline. Preferably, the at least one protein comprises at least Mps-1, Mps-2 and Mps-4. With respect to the terms "providing" and "protein or a functionally active variant or fragment thereof" it is referred to the definitions provided in the context of nucleic acids and proteins of the invention. With respect to the term "obtainable by the method" it is referred to the definitions provided in the context of determining a variant of SEQ ID Nos: 2 to 27. The term "incubating" means maintaining the protein and other components at particular conditions in order to allow production of griselimycin and/or methylgriselimycin or L-trans-4-methylproline. With respect to the particular conditions reference is made to the definitions in the context of determining a variant of SEQ ID Nos: 2 to 27.

Thus, the present invention refers in one embodiment to an isolated nucleic acid sequence comprising at least one nucleic acid selected from the group consisting of:
(a) a nucleic acid comprising at least one of Open Reading Frames (ORFs) 1 to 26 of SEQ ID NO: 1 that encodes proteins of SEQ ID NOs: 2 to 27 respectively, or a variant or fragment thereof whereby the variant or fragment encodes a functionally active variant or fragment of a protein of SEQ ID NOs: 2 to 27;

(b) a nucleic acid encoding at least one of the proteins of SEQ ID NOs: 2 to 27, or a functionally active variant or fragment thereof;

(c) a nucleic acid encoding a protein that is at least 70%, 80%, 90%, 95% or 97% identical in amino acid sequence to a protein or fragment thereof encoded by the nucleic acid of step (a) or (b);

(d) a nucleic acid that hybridizes under stringent conditions with a nucleic acid of any of steps (a) to (c);

(e) a nucleic acid that hybridizes under stringent conditions with a nucleic acid of any of steps (a) to (d) and consists of 10 to 50 nucleotides in length; and (f) a nucleic acid that is complementary to a nucleic acid of any of steps (a) to (f).

In a further embodiment the nucleic acid mentioned before comprises at least two ORFs encoding any of the proteins of SEQ ID NOs: 2 to 27, or a functionally active variant or fragment thereof as referred to in any of steps (a) to (d).

In yet another embodiment said nucleic acid comprises at least one of ORFs 18, 19, 20 and 21 that encodes proteins of SEQ ID NO: 19, 20, 21 and 22, respectively, or a functionally active variant or fragment thereof in any of steps (a) to (d).

In yet another embodiment said nucleic acid comprises at least one of ORFs 8, 15 and 16 that encodes proteins of SEQ ID NO: 9, 16 and 17, respectively, or a functionally active variant or fragment thereof in any of steps (a) to (d).

In yet another embodiment said nucleic acid comprises the griselimycin biosynthesis gene cluster having the nucleic acid sequence of SEQ ID NO: 1, or having a variant sequence of SEQ ID NO: 1 harboring a variant or fragment of at least one of ORFs 1 to 26 whereby the variant or fragment encodes a functionally active variant or fragment of a protein of SEQ ID NOs: 2 to 27.

In another embodiment the present invention encompasses an expression vector comprising any of the before mentioned nucleic acids.

In another embodiment the present invention encompasses a host cell transformed with the before mentioned expression vector.

In yet another embodiment the present invention encompasses a protein comprising at least one amino acid sequence selected from the group consisting of SEQ ID NOs: 2 to 27, or a functionally active variant or fragment thereof.

In yet another embodiment the present invention encompasses an antibody specifically directed against at least one of the before mentioned proteins or a functionally active variant or fragment thereof.

This application also encompasses an invention regarding to a method for producing griselimycin and/or methylgriselimycin comprising producing at least one of the proteins of SEQ ID NOs: 9, 16 and 17.

In one embodiment the invention encompasses a method for producing L-trans-4-methylproline comprising producing at least one of the proteins of SEQ ID NOs: 19, 20, 21 and 22.

In another embodiment the invention encompasses a method for producing at least one of above mentioned proteins or a functionally active variant or fragment thereof comprising:

a) expressing any of above mentioned nucleic acids, and b) optionally, isolating the above mentioned protein or a functionally active variant or fragment thereof.

In yet another embodiment the invention encompasses a method for determining a variant of one or more of ORFs 1 to 26 of SEQ ID NO: 1 that encodes the proteins of SEQ ID NOs: 2 to 27 respectively that modulates the production of griselimycin and/or methylgriselimycin comprising the steps:

a) producing a variant of any one or more of ORFs 1 to 26, b) expressing the variant into a protein, c) producing griselimycin and/or methylgriselimycin or of a derivative thereof using the protein of step b), and d1) determining the amount of griselimycin and/or methylgriselimycin produced, wherein an increase of the amount of griselimycin and/or methylgriselimycin produced as compared to the amount produced if the protein of step b) is not present, but the corresponding invariant form of the protein is present is indicative that the variant is capable of increasing the production of griselimycin and/or methylgriselimycin, or d2) determining the antibiotic activity of the derivative of griselimycin and/or methylgriselimycin, wherein an increase in the antibiotic activity in step d2) compared to the antibiotic activity if the protein of step b) is not present, but the corresponding invariant form of the protein is present is indicative that the variant is capable of producing a derivative of griselimycin and/or methylgriselimycin with increased antibiotic activity, and wherein the derivative differs in amino acid composition from griselimycin and/or methylgriselimycin and exhibits an enhanced antibiotic activity over griselimycin and/or methylgriselimycin.

In another embodiment the invention encompasses a method for determining a variant of one or more of ORFs 1 to 26 of SEQ ID NO: 1 that encodes the proteins of SEQ ID NOs: 2 to 27 respectively that enhances production of L-trans-4-methylproline comprising the steps of:

a) producing a variant of any one or more of ORFs 1 to 26, b) expressing the variant into a protein, c) producing L-trans-4-methylproline using the protein of step b), and d) determining the amount of L-trans-4-methylproline produced, wherein an increase in the amount of L-trans-4-methylproline produced in step c) compared to the amount produced if the protein of step b) is not present, but the corresponding invariant form of the protein is present is indicative that the variant is capable of increasing the production of L-trans-4-methylproline.

In another embodiment the invention encompasses a method for producing griselimycin and/or methylgriselimycin comprising the steps of:

a) providing at least one protein of claim 8 or a functionally active variant or fragment thereof, and b) incubating the at least one protein of step a) with L-N-methylvaline, L-leucine, L-N-methylthreonine, L-proline, L-N-methylleucine and glycine to produce griselimycin and/or methylgriselimycin.

In another embodiment the invention encompasses a method for producing L-trans-4-methylproline comprising the steps of:

a) providing at least one protein of claim 8 or a functionally active variant or fragment thereof, and b) incubating the at least one protein of step a) with L-leucine, 5-hydroxyleucine, γ-methylglutamic acid γ-semialdehyde and/or 3-methyl-$\Delta^1$-pyrroline-5-carboxylic acid to produce L-trans-4-methylproline.

In yet another embodiment the invention encompasses the *Streptomyces* strain deposited with the Deutsche Sammlung von Mikroorganismen and Zellkulturen Gmbh (DSMZ) under deposit number DSM 22643.

A. Complementation of the mps mutant by feeding 20 μg/ml (2S,4R)-4-methylproline once at day 0 to the production medium. At days 1 to 4 the (methyl)griselimycin production was analysed (grey bar: griselimycin production, black bar: methylgriselimycin production). Only in the complement medium the mps-mutant is able to produce (methyl) griselimycin. The experiment that is exhibiting an increase of methylgriselimycin versus griselimycin when methyl-prolin was feeded is mentioned in example 9 and on page 15.

B. Schematical drawing of the relevant aspects for genetic complementation of the mps-mutant: The mps-operon (mps-1, mps-2, mps-3 and mps-4 genes) is under expression control of the 5' inserted constitutive ermE-promotor.

C. Genetic complementation of the mps-mutant. After integration of the P(ermE)-mps-operon into the attB site of the mps mutant, the capability of griselimycin production is restored (grey bar: griselimycin production, black bar: methylgriselimycin production).

Figure 8:
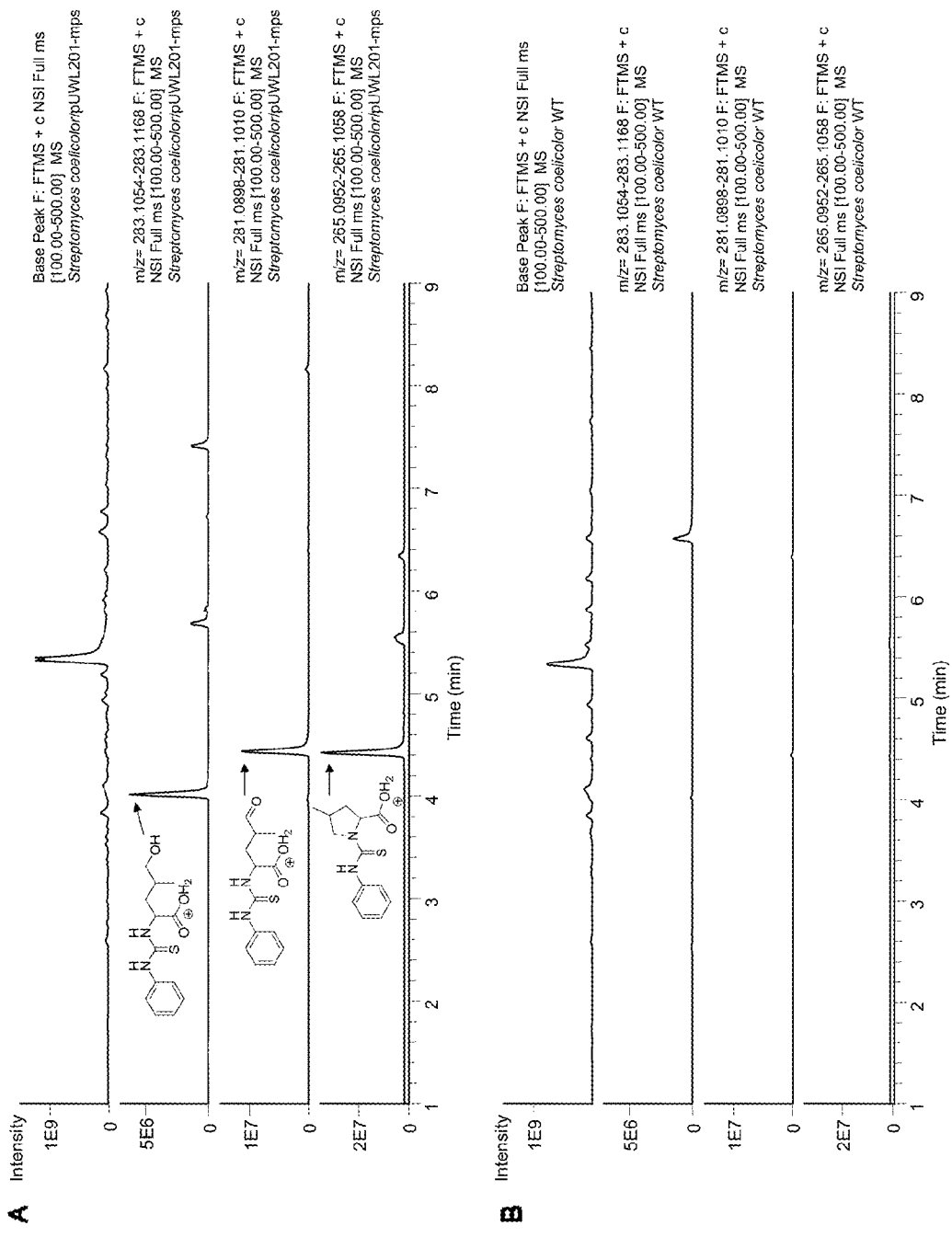
Figure 9:
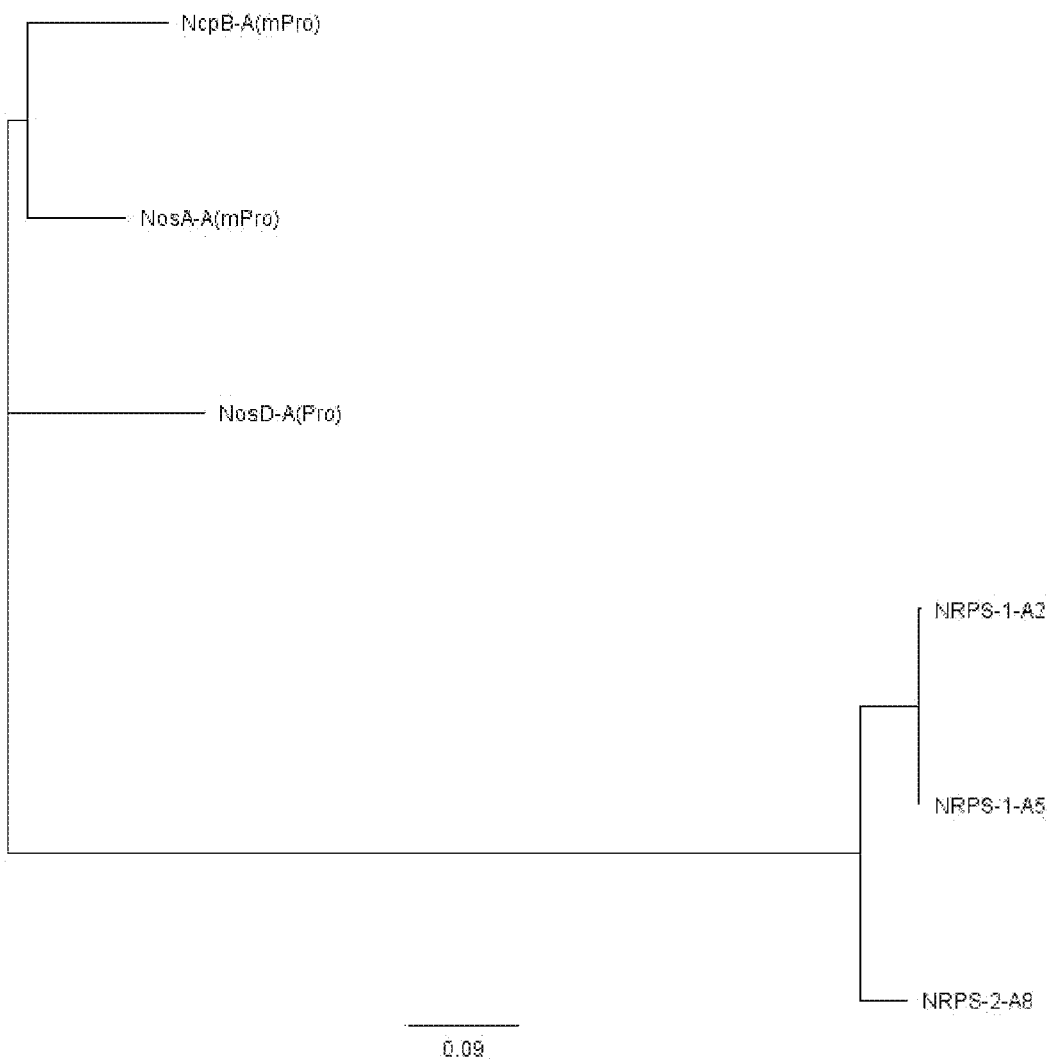

FIG. 8 shows an HPLC-MS analysis of derivatized extracts from an mps expression culture (*Streptomyces coelicolor*/pUWL201-mps; FIG. 8A) and the negative control (*Streptomyces coelicolor* WT; FIG. 8B). The PITC derivatives of the expected product (2S,4R)-4-methylproline ($4^{th}$ chromatogram of FIGS. 8A and B) as well as PITC derivatives of two biosynthetic intermediates 5-hydroxyleucine ($2^{nd}$ chromatogram of FIGS. 8A and B) and γ-methylglutamic acid γ-semialdehyde ($3^{rd}$ chromatogram of FIGS. 8A and B) could be detected in the extract of the mps expression culture, but not in *Streptomyces coelicolor* WT. The $1^{st}$ chromatogram of FIGS. 8A and B corresponds to leucine FIG. 9 shows a phylogenetic tree indicating the relationship between NosA-A(mPro), NcpB-A(mPro) and NosD-A (pro) and NRPS-1-A2, NRPS-1-A5 and NRPS-2-A8. The scale bar represents 0.09 substitutions per amino acid site.

Figure 10:
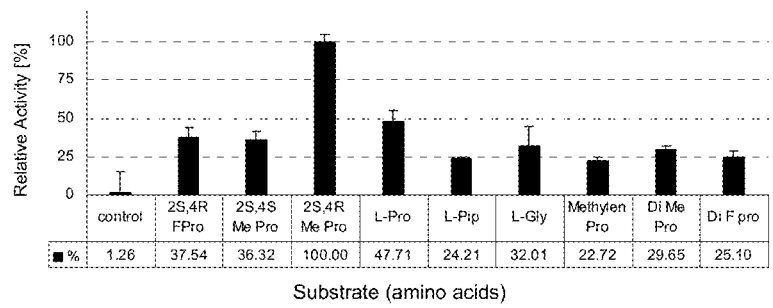
Figure 10:
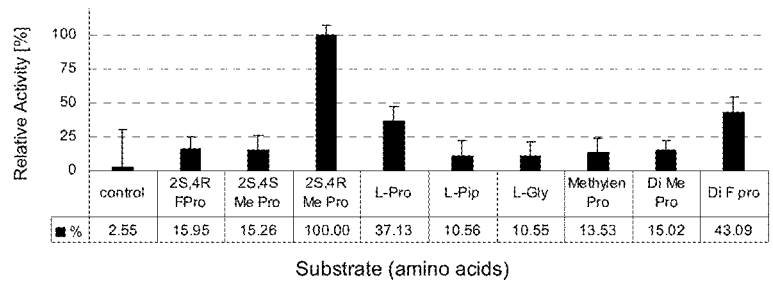
Figure 10:
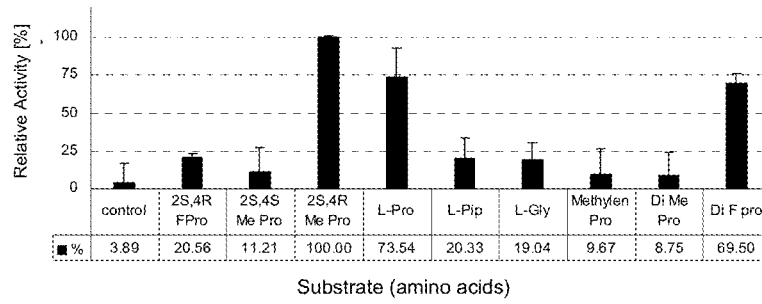

FIG. 10 shows an analysis of substrate specificity of the A domains of module 2 (A2; upper panel), module 5 (A5; middle panel) and module 8 (A8; lower panel) by in vitro ATP-Ppi-exchange experiments. For A5 and A8 experiments were performed in triplicate, for A2 in duplicate. Highest activities were scaled up to 100%. The following substrates were tested: (2S,4R)-4-fluoroproline (2S,4R Fpro), (2S,4S)-4-methylproline (2S,4S MePro), (2S,4R)-4-methylproline (2S,4R MePro), L-proline (L-Pro), L-pipecolic acid (L-Pip), L-glycine (L-Gly), 4-methylenproline (Methylen Pro), 4,4-Dimethylproline (Di Me Pro) and 4,4-difluoroproline (Di F Pro). Relative activities are indicated on the Y axis. Below each substrate activities as compared to highest activities which are given as 100% are indicated in percent. In the control experiment, no amino acid was present.

Figure 11:
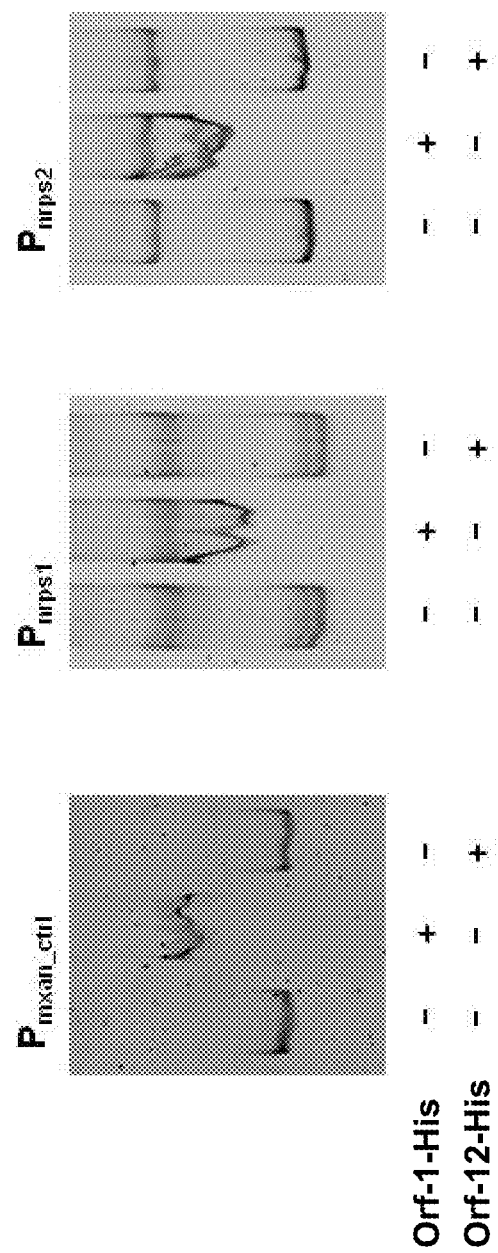

FIG. 11: Binding of full length regulators Orf-1 and Orf-12 to DNA fragments Pnrps1, Pnrps2 and Pmxan_ctrl. Scanned pictures of the EMSA assays are shown. Pnrps1 and Pnrps2: EMSA assay using DNA fragments comprising promoter regions of genes nrps1 or nrps2. Pmxan_ctrl: EMSA assay using Hex labeled DNA fragment comprising the dual promoter system in an intergenic region of *Myxococcus xanthus* DK1622 flanked by mxan_3950 and mxan_3951. Orf-1-His and Orf-12-His: C-terminal 6xHis tagged Orf-1 and Orf-12. +: With regulator. −: without regulator.

Figure 12:
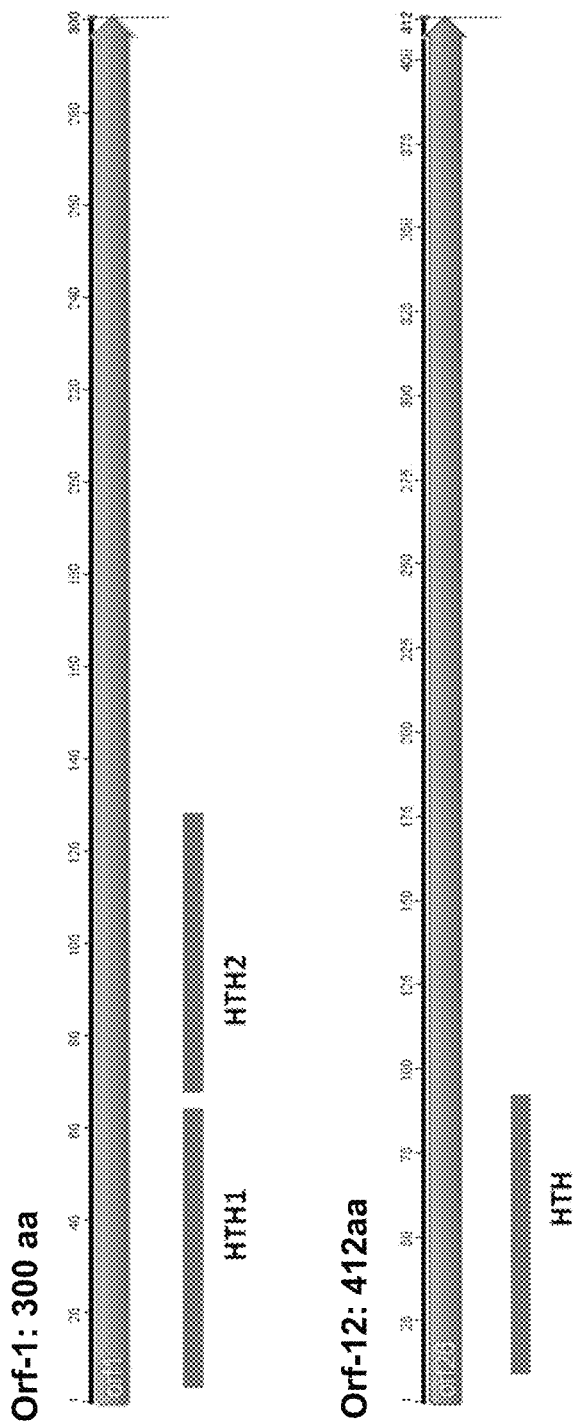

FIG. 12 shows the predicted domain organization of regulators Orf-1 and Orf-12. Domains predicted by the SMART tool at http://smart.embl-heidelberg.de/ are shown. HTH: helix-turn-helix motif, aa: amino acids.

Figure 13:
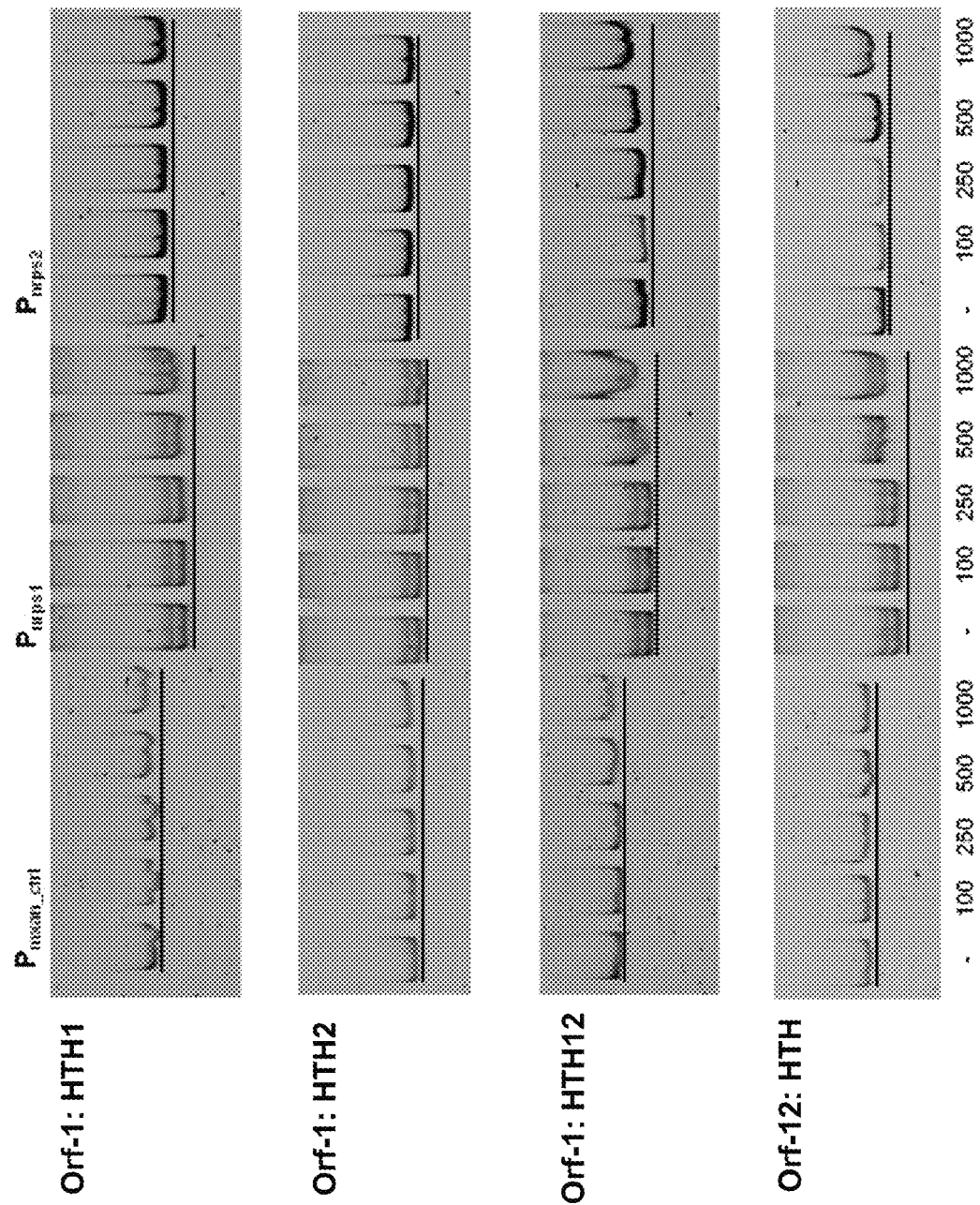

FIG. 13 shows the binding of shortened versions of regulators Orf-1 and Orf-12 to DNA fragments Pnrps1, Pnrps2 and Pmxan_ctrl. Scanned pictures of the EMSA assays are shown. In the assays derivatives of Orf-1 and Orf-12 were used only comprising the predicted HTH domains. Pnrps1 & Pnrps2: EMSA assay using DNA fragments comprising promoter regions of genes nrps1 or nrps2. Pmxan_ctrl: EMSA assay using Hex labeled DNA fragment comprising the dual promoter system in an intergenic region of *Myxococcus xanthus* DK1622 flanked by mxan_3950 and mxan_3951. Orf-1-HTH1, Orf-1-HTH2, Orf1-HTH12 and Orf-12-HTH: C-terminal 6xHis tagged Orf-1 and Orf-12 only comprising HTH domains. –: without regulator. Numbers depict the molar excess of regulator protein compared to the quantity of DNA fragment.

DESCRIPTION OF THE EXAMPLES

Example 1

Identification of the Griselimycin Biosynthesis Locus in *Streptomyces* DSM 22643

Figure 1:
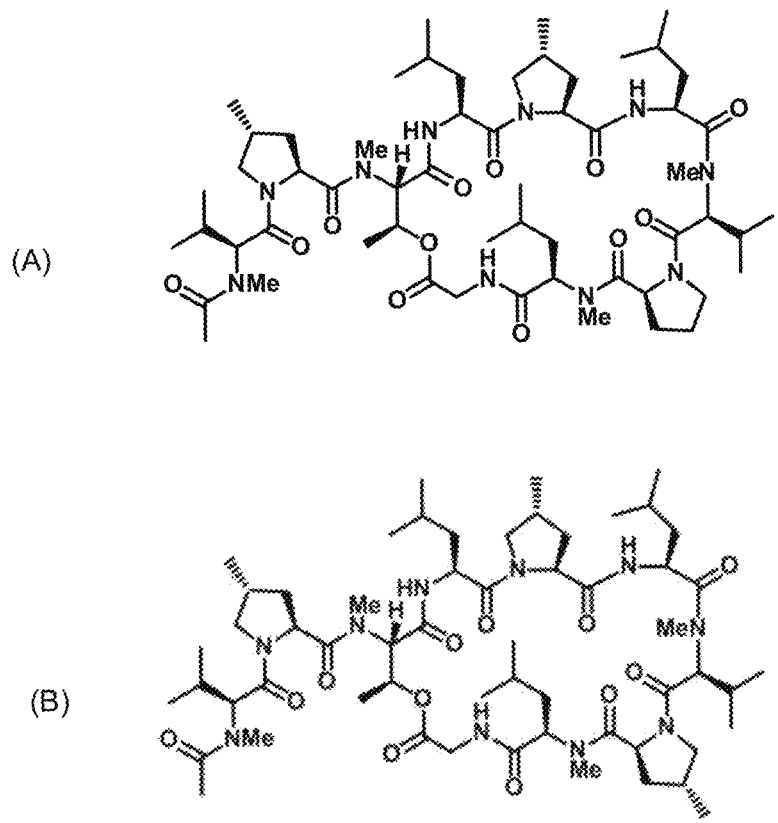
FIG. 1 shows the structure of griselimycin (A) and methylgriselimycin (B).
Figure 2:
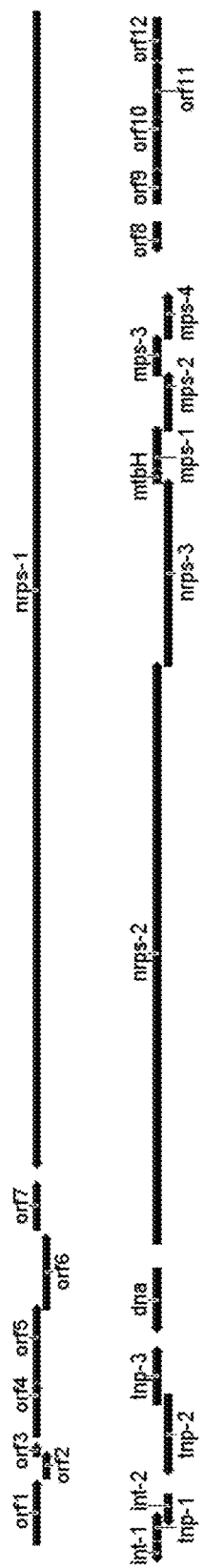
FIG. 2 shows the map and gene arrangement of the griselimycin biosynthesis gene cluster of *Streptomyces* DSM 22643 as comprised by SEQ ID NO: 1. The putative ORFs are indicated by black block arrows designated by the respective gene names. Transcription directions and relative sizes are indicated.

*Streptomyces* DSM 22643 naturally produces the antibiotics griselimycin and methylgriselimycin. However, the genetic locus involved in the biosynthesis of these antibiotic substances was not previously identified. For the identification of the griselimycin locus, *Streptomyces* DSM 22643 was cultured according to standard microbiological techniques. DNA was extracted according to standard procedures and the total sequence was determined according to standard procedures. Analysis of the genes comprised by the DNA of *Streptomyces* DSM 22643 and proteins encoded by the genes was performed in silico. Table 1 lists the genes identified by ORF numbers which were determined by homology searches. Specific gene designations were assigned to the ORF numbers. The location of the genes and their arrangement within the griselimycin biosynthesis gene cluster is schematically indicated in FIG. 2.

TABLE 1

| ORF number | gene designation | start nt | stop nt | gene length (nt) | strandedness | protein length (aa) | protein designation | SEQ ID NO: protein |
|---|---|---|---|---|---|---|---|---|
| 1 | orf-1 | 837 | 2075 | 1269 | positive | 412 | Orf-1 | 2 |
| 2 | orf-2 | 2185 | 2625 | 441 | positive | 146 | Orf-2 | 3 |
| 3 | orf-3 | 2625 | 2819 | 195 | positive | 64 | Orf-3 | 4 |
| 4 | orf-4 | 3033 | 4037 | 1005 | positive | 334 | Orf-4 | 5 |
| 5 | orf-5 | 4110 | 5630 | 1521 | positive | 506 | Orf-5 | 6 |
| 6 | orf-6 | 5627 | 7066 | 1440 | positive | 479 | Orf-6 | 7 |
| 7 | orf-7 | 7240 | 8133 | 894 | positive | 297 | Orf-7 | 8 |
| 8 | nrps-1 | 31885 | 8501 | 26385 | negative | 7794 | NRPS-1 | 9 |
| 9 | int-1 | 33102 | 32770 | 333 | negative | 110 | Int-1 | 10 |
| 10 | tnp-1 | 33187 | 33726 | 540 | positive | 179 | Tnp-1 | 11 |
| 12 | tnp-2 | 36300 | 34648 | 1653 | negative | 550 | Tnp-2 | 13 |
| 13 | tnp-3 | 36172 | 37314 | 1143 | positive | 380 | Tnp-3 | 14 |
| 14 | dna | 39032 | 37746 | 1287 | negative | 428 | Dna | 15 |
| 15 | nrps-2 | 39643 | 52149 | 12507 | positive | 4168 | NRPS-2 | 16 |
| 16 | nrps-3 | 52146 | 56120 | 3975 | positive | 1324 | NRPS-3 | 17 |
| 17 | mbtH | 56117 | 56335 | 219 | positive | 72 | MbtH | 18 |
| 18 | mps-1 | 56434 | 57246 | 813 | positive | 270 | Mps-1 | 19 |
| 19 | mps-2 | 57243 | 58418 | 1176 | positive | 391 | Mps-2 | 20 |
| 20 | mps-3 | 58445 | 59245 | 801 | positive | 266 | Mps-3 | 21 |
| 21 | mps-4 | 59242 | 60141 | 900 | positive | 299 | Mps-4 | 26 |
| 26 | orf-8 | 61680 | 61144 | 537 | negative | 178 | Orf-8 | 26 |
| 26 | orf-9 | 62170 | 62820 | 651 | positive | 216 | Orf-9 | 24 |
| 24 | orf-10 | 62824 | 63939 | 1116 | positive | 371 | Orf-10 | 25 |
| 25 | orf-11 | 63969 | 65165 | 1197 | positive | 398 | Orf-11 | 26 |
| 26 | orf-12 | 66108 | 65206 | 903 | negative | 300 | Orf-12 | 27 |

Example 2

Genes and Proteins Involved in the Biosynthesis of Griselimyin and Methylgriselimycin By in silico analysis it was determined that the griselimycin biosynthesis gene cluster comprises 26 genes encoding 26 proteins. The biological function of the 26 (methyl)griselimycin biosynthetic proteins was assessed by computer comparison of each identified protein with proteins found at the NCBI. Table 2 identifies the proteins as comprised by the griselimycin biosynthesis gene cluster and the corresponding GenBank proteins found by the homology searches.

TABLE 2

| | | best blast hit | | | | |
|---|---|---|---|---|---|---|
| ORF number | Best blast hit | GenBank Accession number | nearest homologue in | e-Value | identity/ similarity (%) | putative function |
| 1 | TlmR2 | ABL74963.1 | *Streptoalloteichus hindustanus* | 2E−55 | 35/53 | Xre family transcriptional regulator |
| 2 | Hypothetical protein SSOG_02153 | ZP_07294072 | *Streptomyces hygroscopicus* ATCC 53653 | 5E−11 | 41/47 | Hypothetical protein |

TABLE 2-continued best blast hit

| ORF number | Best blast hit | GenBank Accession number | nearest homologue in | e-Value | identity/ similarity (%) | putative function |
|---|---|---|---|---|---|---|
| 3 | Conserved hypothetical protein | ZP_06583961 | Streptomyces roseosporus NRRL 15998 | 3E−15 | 61/86 | Conserved hypothetical protein |
| 4 | Conserved hypothetical protein | CBG69271.1 | Streptomyces scabiei 87.26 | 1.00E−140 | 81/87 | Conserved hypothetical protein |
| 5 | Putative transporter | CBG69272.1 | Streptomyces scabiei 87.26 | 0.0 | 91/94 | Transporter |
| 6 | Putative glutamine synthetase | CBG69273.1 | Streptomyces scabiei 87.26 | 0.0 | 81/87 | Glutamine synthetase |
| 7 | Hypothetical protein | CBG69274.1 | Streptomyces scabei 87.26 | 8E−120 | 73 81 | Hypothetical protein |
| 8 | Amino acid adenylation domain-containing protein | YP_001539321.1 | Salinispora arenicola CNS-205 | 0.0 | 51/63 | NRPS |
| 9 | Integrase catalytic region | YP_004330163 | Pseudonocardia dioxanivorans CB1190 | 1E−43 | 75/92 | Integrase catalytic region |
| 10 | Putative transposase for insertion sequence element | YP_001509642 | Frankia sp. EAN1pec | 3E−15 | 76/78 | Transposase for insertion sequence element |
| 11 | Integrase catalytic region | YP_004330974 | Pseudonocardia dioxanivorans CB1190 | 4E−33 | 67/81 | Integrase catalytic region |
| 12 | Rhodopirellula transposase family protein | ZP_07610914 | Streptomyces violaceusniger Tu 4113 | 0.0 | 74/80 | Transposase |
| 13 | Putative IS4 family Transposase | ZP_06418432.1 | Frankia sp. EUN1f | 9E−60 E−60 | 43/55 | Transposase |
| 14 | DNA polymerase III, beta subunit | ZP_06824689 | Streptomyces sp. SPB74 | 4E−110 | 53/70 | DNA polymerase III, beta subunit |
| 15 | putative pristinamycin I peptide synthase 3 and 4 | CBH31051.1 | Streptomyces pristinaespiralis | 0.0 | 51/62 | NRPS |
| 16 | Putative NRPS | ZP_04685020.1 | Streptomyces ghanaensis ATCC 14672 | 0.0 | 45/61 | NRPS |
| 17 | MbtH domain protein | ZP_06476953 | Frankia symbiont of Datisca glomerata | 9E−26 | 72/81 | MbtH domain protein |
| 18 | Phytanoyl-CoA dioxyposase | YP_001539320.1 | Salinispora arenicola CNS-205 | 8E−91 | 60/76 | Leucine hydroxylase |
| 19 | Alcohol dehydrogenase | YP_707358.1 | Rhodococcus jostii RHA1 | 6E−102 | 51/67 | Alcohol dehydrogenase |
| 20 | Alpha/beta hydrolase fold protein | ZP_04702845.1 | Streptomyces albus J1074 | 3E−77 | 56/71 | Alpha/beta hydrolase |
| 21 | LmbY | ABX00626.1 | Streptomyces lincolnensis | 5E−131 | 76/88 | Oxidoreductase |
| 26 | Hypothetical protein SclaA2_13611 | ZP_08216838 | Streptomyces clavuligerus ATCC 27064 | 1E−42 | 65/78 | PNPOx-like superfamily protein |
| 26 | Hypothetical protein SACTEDRAFT_3210 | ZP_06272665.1 | Streptomyces sp. ACTE | 3E−38 | 64/74 | Hypothetical protein |
| 24 | Hypothetical protein SACTEDRAFT_3209 | ZP_06272664.1 | Streptomyces sp. ACTE | 2E−112 | 67/78 | Hypothetical protein |
| 25 | Amidohydrolase | ZP_06272663.1 | Streptomyces sp. ACTE | 1E−148 | 70/80 | Amidohydrolase |
| 26 | Hypothetical protein SACTEDRAFT_3207 | ZP_06272662.1 | Streptomyces sp. ACTE | 2E−64 | 52/69 | Xre family trans criptional regulator |

Between the individual modules and domains, there are linker regions, namely inter-module linker and inter-domain linker. At the N-terminus and C-terminus of the proteins, there are COM or docking domains which are necessary for interaction of the individual NRPS proteins. Communication-mediating (COM) domains facilitate the selective interaction between nonribosomal peptide synthetases by short communication-mediating domains (Hahn M. and Stachelhaus T.; 2004).

Figure 3:
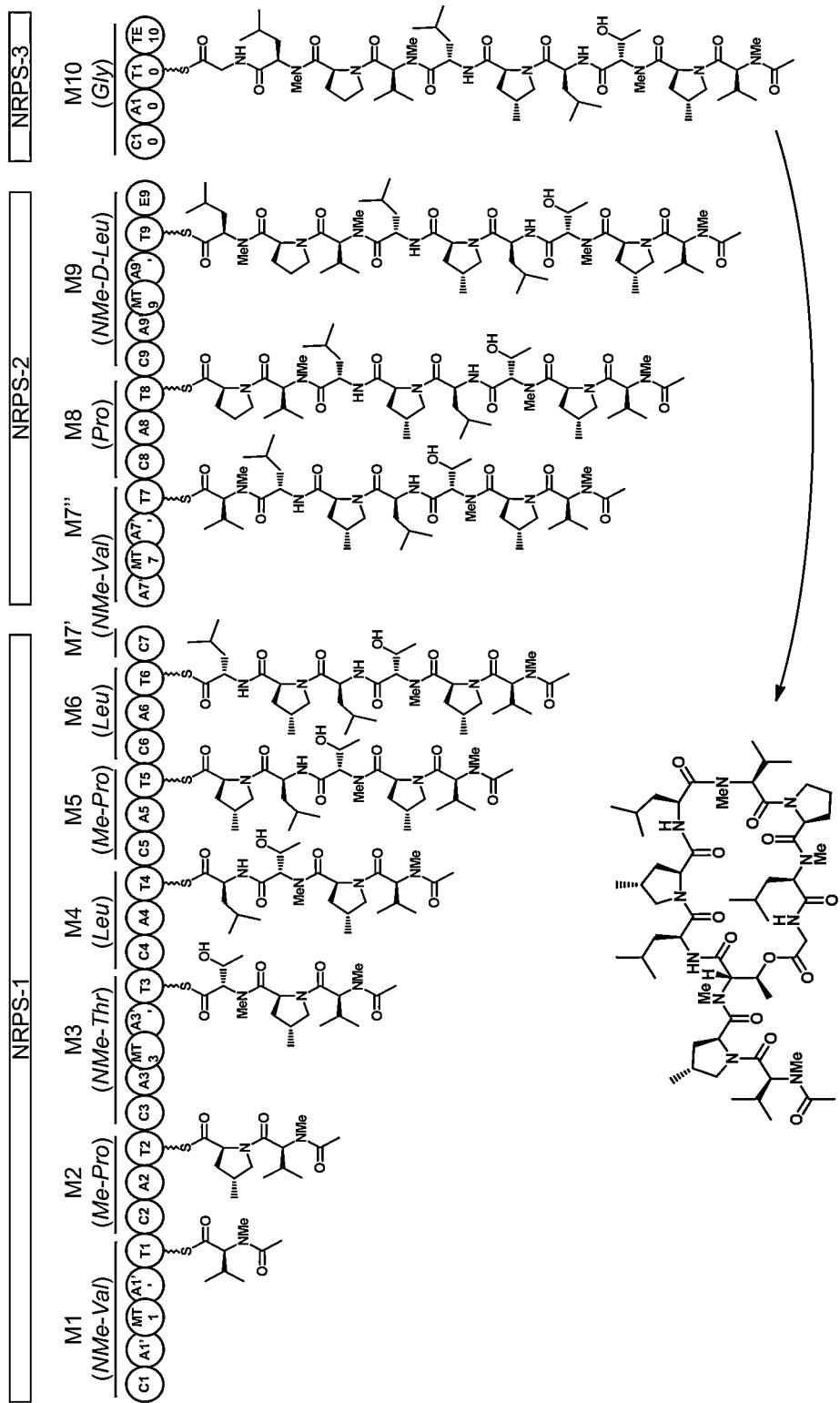
FIG. 3 shows a model of the griselimycin biosynthesis. The putative NRPS proteins, NRPS-1, NRPS-2, NRPS-3, are indicated by white blocks. The modules designated M1 to M10 are indicated below each block. Each module is dissected in domains designated C for condensation domain, A for adenylation domain, MT for methyltransferase domain, T for thiolation domain, E for epimerisation domain and TE for thioesterase domain, whereby the number behind each domain designation indicates the number of the module to which this domain is assigned. The arrangement A'-MT-A" indicates that the MT domains are integrated into the A domains. Below each module designation stands the amino acid which is introduced by the respective module into griselimycin. Nme-Val represents L-N-methylvaline, Me-Pro represents L-trans-4-methylproline, Nme-Thr represents L-N-methylthreonine, Leu represents L-leucine, Pro represents L-proline, Nme-D-Leu represents D-N-methylleucine and Gly represents glycine. Below the modules, the biosynthetic role of each module is presented by the presentation of the structure of the respective amino acids and their incorporation into griselimycin. By each module, one amino acid is condensed to the foregoing one resulting in an elongation of the growing peptide chain. Product release involves the TE10 domain with the subsequent cyclisation of the peptide to result in the macrocyclic product. The N-terminal C domain of module 1 is assumed to catalyze the acetylation of valine.

Based on homology searches the genes designated nrps-1, nrps-2 and nrps-3 encode subunits of the nonribosomal protein synthetase (NRPS) synthesizing griselimycin and methylgriselimycin (see FIG. 3). The nrps-1 gene has a length of about 26.4 kb and encodes 6 modules that are necessary for the incorporation of (1) L-N-methylvaline (M1), (2) L-trans-4-methylproline (M2), (3) L-N-methylthreonine (M3), (4) L-leucine (M4), (5) L-trans-4-methylproline (M5) and (6) L-leucine (M6), respectively, into (methyl)griselimycin. Module 1 or M1 and module 3 or M3 each encode a C-domain, an A-domain which is interrupted by a MT-domain and a T-domain, whereas module 2 or M2, module 4 or M4, module 5 or M5 and module 6 or M6 each encode a C-domain, an A-domain and a T-domain. Furthermore it contains the condensation domain of module 7 or M7. The condensation domain of M1, C1, is responsible for N-acetylation. The nrps-2 gene has a length of about 12.5 kb and encodes part of module 7 and modules 8 and 9 that are necessary for the incorporation of (7) L-N-methylvaline (M7), (8) L-proline (griselimycin) or L-trans-4-methylproline (methylgriselimycin) (M8) and (9) D-N-methylleucine (M9). The part of module 7 comprises an A-domain which is interrupted by a MT-domain and a T-domain, module 8 or M8 comprises a C-domain, an A-domain and a T-domain and module 9 or M9 comprises a C-domain, an A-domain which is interrupted by a MT-domain, a T-domain and an E-domain. The presence of a D-amino acid at position 9 of (methyl)griselimycin coincides with the presence of an E-domain in module 9 which catalyses the insertion of D-N-methylleucine. The nrps-3 gene has a length of about 4 kb and codes for module 10 which incorporates glycine into the molecule and manages the cyclisation of the linear peptide chain between glycine and L-N-methylthreonine via an ester bond. Module 10 comprises a C-domain, an A-domain, a T-domain and a TE-domain.

Homology searches allowed the assignment of a biosynthesis role to the repeating units, the modules, of the NRPS proteins. FIG. 3 shows the assignment of modules 1 to 10 to the NRPS proteins, the dissection into the domains and the biosynthesis activity by indicating the amino acids and their incorporation into the growing griselimycin chain. Module 10 releases the chain from the NRPS-3 protein, followed by chain cyclisation. In Table 3, the approximate boundaries of the modules and domains on the protein and DNA level with respect to their location within the individual NRPS proteins are indicated. Thereby, C represents a condensation domain, A represents an adenylation domain, MT represents a methyltransferase domain, and T represents a thiolation domain. The MT domains are integrated into the A domains. This is indicated by the arrangement "A'-MT-A".

TABLE 3

| Protein | Modules/Domains | Location within the protein sequence (aa) | Location within the gene cluster sequence (SEQ ID NO: 1) (nt) |
|---|---|---|---|
| NRPS-1 (SEQ ID NO: 9) | Module 1 | 9-1493 aa | 31861-27407 nt |
| | C1 | 9-336 aa | 31861-30878 nt |
| | A1' | 481-939 aa | 30445-29069 nt |
| | MT | 940-1365 aa | 29068-27791 nt |
| | A1" | 1366-1406 aa | 27790-27668 nt |
| | T1 | 1429-1493 aa | 27601-27407 nt |
| | Module 2 | 1517-2569 aa | 27337-24179 nt |
| | C2 | 1517-1858 aa | 27337-26312 nt |
| | A2 | 2003-2482 aa | 25879-24440 nt |
| | T2 | 2505-2569 aa | 24373-24179 nt |
| | Module 3 | 2591-4102 aa | 24115-19580 nt |
| | C3 | 2591-2932 aa | 24115-26090 nt |
| | A3' | 3077-3536 aa | 26657-21278 nt |
| | MT3 | 3537-3974 aa | 21277-19964 nt |
| | A3" | 3975-4015 aa | 19963-19841 nt |
| | T3 | 4038-4102 aa | 19774-19580 nt |
| | Module 4 | 4124-5170 aa | 19516-16376 nt |
| | C4 | 4124-4465 aa | 19516-18491 nt |
| | A4 | 4612-5083 aa | 18052-16637 nt |
| | T4 | 5106-5170 aa | 16570-16376 nt |
| | Module 5 | 5193-6245 aa | 16309-13151 nt |
| | C5 | 5193-5534 aa | 16309-15284 nt |
| | A5 | 5679-6158 aa | 14851-13412 nt |
| | T5 | 6181-6245 aa | 13345-13151 nt |
| | Module 6 | 6268-7312 aa | 13084-9950 nt |
| | C6 | 6268-6609 aa | 13084-12059 nt |
| | A6 | 6754-7265 aa | 11626-10211 nt |
| | T6 | 7248-7312 aa | 10144-9950 nt |
| | Module 7' | 7336-7677 aa | 9880-8855 nt |
| | C7 | 7336-7677 aa | 9880-8855 nt |
| NRPS-2 (SEQ ID NO: 16) | Module 7" | 42-1066 aa | 39766-42840 nt |
| | A7' | 42-500 aa | 39766-41142 nt |
| | MT7 | 501-938 aa | 41143-42456 nt |
| | A7" | 939-979 aa | 42457-42579 nt |
| | T7 | 1002-1066 aa | 42646-42840 nt |
| | Module 8 | 1088-2148 aa | 42904-46086 nt |
| | C8 | 1088-1430 aa | 42904-43932 nt |
| | A8 | 1575-2061 aa | 44365-45825 nt |
| | T8 | 2084-2148 aa | 45892-46086 nt |
| | Module 9 | 2172-4160 aa | 46156-52126 nt |
| | C9 | 2172-2513 aa | 46156-47181 nt |
| | A9' | 2658-3098 aa | 47614-48936 nt |
| | MT9 | 3099-3536 aa | 48937-50250 nt |
| | A9" | 3537-3577 aa | 50251-50373 nt |
| | T9 | 3600-3663 aa | 50440-50631 nt |
| | E9 | 3679-4160 aa | 50677-52126 nt |
| NRPS-3 (SEQ ID NO:. 17) | Module 10 | 13-1312 aa | 52182-56081 nt |
| | C10 | 13-343 aa | 52182-53174 nt |
| | A10 | 484-951 aa | 53595-54998 nt |
| | T10 | 974-1038 aa | 55065-55259 nt |
| | TE10 | 1060-1312 aa | 55326-56081 nt | nt: nucleotide, aa: amino acid

Figure 4:
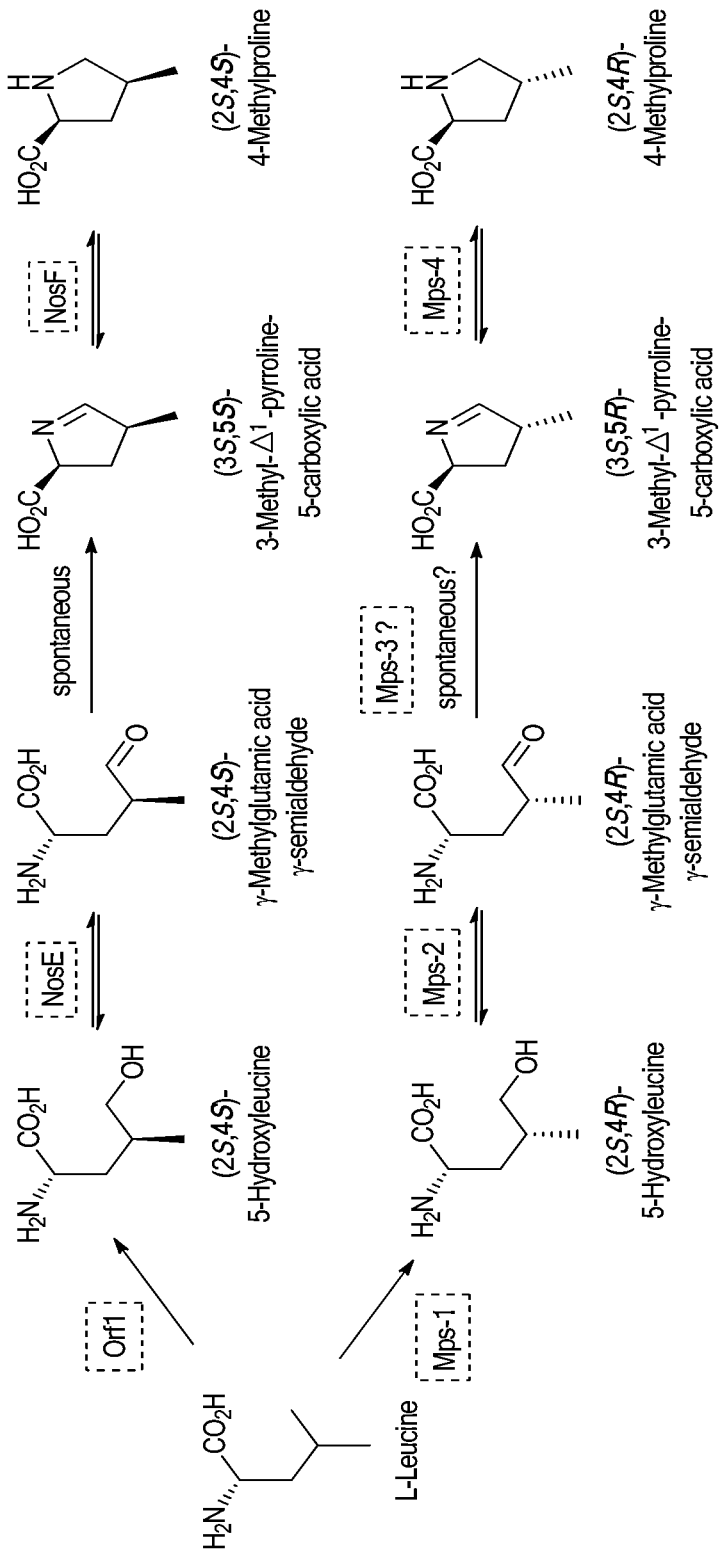
FIG. 4 shows the synthesis of 4-methylproline within the nostopeptolide biosynthesis gene cluster (Hoffmann et al., 2003; upper pathway) and the griselimycin biosynthesis gene cluster (lower pathway). In both biosynthesis pathways L-leucine is converted by the enzymes Orf1 (nostopeptolide) or Mps-1 ((methyl)griselimycin) to 5-hydroxyleucine, which is converted by NosE (nostopeptolide)) or Mps-2 ((methyl) griselimycin) to γ-methylglutamic acid γ-semialdehyde which spontaneously forms 3-methyl-$\Delta^1$-pyrroline-5-carboxylic acid. This is converted to 4-methylproline by NosF (nostopeptolide) or Mps4 ((methyl)griselimycin). The products of each step of the 4-methylproline synthesis of the (nostopeptolide) or ((methyl)griselimycin) pathways differ by their configuration with respect to the methyl group at position 4 of 5-hydroxyleucin, γ-methylglutamic acid γ-semialdehyde and 4-methylproline and at position 5 of 3-methyl-$\Delta^1$-pyrroline-5-carboxylic acid, in that in the nostopeptolide biosynthesis the methyl group is in the S configuration, whereas in the ((methyl)griselimycin) biosynthesis the methyl group is in the R configuration. Possibly, Mps-3 plays a role in the conversion of γ-methylglutamic acid γ-semialdehyde to 3-methyl-$\Delta^1$-pyrroline-5-carboxylic acid

Based on homology searches and biochemical analysis the genes designated mps-1, mps2- and mps-4 encode proteins necessary for the biosynthesis of L-trans-4-methylproline. L-trans-4-methylproline is contained at positions 2 and 5 of griselimycin and at positions 2, 5 and 8 of methylgriselimycin. The mps-1 gene encodes a protein with highest homology to 4-proline hydroxylases (41% identity/57% similarity) and phytanoyl-CoA dioxygenase but by biochemical analysis it could be shown that the mps-1 gene codes for a leucine hydroxylase which hydroxylates L-leucine to (2S,4R)-5-hydroxyleucine. The gene mps-2 codes for an alcohol dehydrogenase that has 34% identity/55% similarity to the nosE gene of the nostopeptolide gene cluster which is involved in synthesis of L-cis-4-methylproline (Luesch et al. 2003). Mps-2 catalyses the dehydrogenation of (2S,4R)-5-hydroxyleucine to (2S,4R)-γ-methylglutamic acid γ-semialdehyde. After spontaneous ring formation the protein encoded by mps-4 probably catalyses the reduction of (3S,5R)-3-methyl-$\Delta^1$-pyrroline-5-carboxylic acid to (2S,4R)-4-methylproline. The mps-4 gene shows the highest homology to Sib (55% identity/70% similarity) and LmbY, that both code for flavin dependent monoxygenases and catalyse a similar reaction (Li et al. 2009; Peschke et al. 1995). The mps-3 gene shows highest homology to α,β-hydrolase with highest homology to the lipE gene product (50% identity/68% similarity) in the friulimycin biosynthetic gene cluster (Müller et al. 2007). The encoded protein might act as type II thioesterase with a function in regeneration of misprimed NRPS. Possibly, the mps-3 gene product is involved in the cyclisation of the pyrroline derivative in the biosynthesis pathway of 4-methylproline. Based on these results, the present inventors succeeded to elucidate the biosynthetic pathway of L-trans-4-methylproline for the biosynthesis of griselimycin or methylgriselimycin. FIG. 4 shows a comparison of the biosynthesis pathways of 4-methylproline including the proteins involved therein within the nostopeptolide biosynthesis pathway of the cyanobacterium Nostoc sp. GSV264 (Hoffmann et al. 2003) and within the (methyl)griselimycin biosynthesis pathway as identified by the present invention. Based on sequence analysis the genes designated mps-1 to mps4 are probably transcribed as an operon.

Furthermore, based on homology searches, the following genes were identified. There are two genes orf-1 and orf-12 with homology to proteins of the Xre-family transcriptional regulators in the gene cluster. The encoded proteins play a role in regulation of (methyl)griselimycin biosynthesis. It could be shown that inactivation of both genes results in a significant loss of production of (methyl)griselimycin, which proves their function as direct or indirect regulators. Orf-5 encodes a protein with homology to a putative transport molecule and might be involved in export of (methyl)griselimycin. Orf-6 encodes a protein with the putative function of a glutamine synthetase. Int-1 and int-2 encode proteins with homology to integrase catalytic regions, so that it is assumed that these proteins have integrase functionality. Tnp-1, tnp-2 and tnp-3 between the genes nrps-1 and nrps-3 encode proteins with homology to putative transposase proteins and are assumed to have transposase activity. A further open reading frame has the putative function as a subunit β of the DNA polymerase III. This orf was designated dna. A small 219 bp ORF directly downstream of nrps-3 encodes a MbtH like protein and was therefore designated mbtH. The MbtH protein is needed for correct function of the NRPS (Barry & Challis, 2009). Orf-8 has homology to the hypothetical protein Scla2_13611 and is assumed to belong to the PNPOx-like superfamily. Orf-11 encodes a putative protein of the amidohydrolase superfamily. The proposed genes orf-2, orf-3, orf-4, orf-7, orf-9 and orf-10 all encode different conserved hypothetical proteins.

Example 3

In Vitro-Synthesis of L-trans-4-methylprolin

In vitro-synthesis of L-trans-4-methylproline can be performed by coupling three subsequent assays, namely the Mps-1 assay, the Mps-2 assay and the Mps-3 assay. Cyclisation of γ-methylglutamic acid γ-semialdehyde to 3-methyl-$\Delta^1$-pyrroline-5-carboxylic occurs spontaneously or may involve Mps-3. FIG. 4 shows the conversion of L-leucine to (2S,4R)-4-methylproline using Mps-1, Mps-2, possibly Mps-3 and Mps-4.

(a) Leucine Hydroxylase Assay

Based on in silico analysis it was found that the mps-1 gene encodes a leucine hydroxylase. The following experimental procedure was performed which confirms that the Mps-1 protein encodes a leucine hydroxylase.

The putative leucine hydroxylase encoding gene mps-1 was amplified using the primers Gri3_for (5'-GCCGC-CATATGATGCAGCTCACGGCCGAT-3') (SEQ ID NO: 28) and Gri3_rev (5'-GGTCAGGATCCTCATGCCAGCCTC-GATTC-3') (SEQ ID NO: 29) from genomic DNA from Streptomyces DSM 26643 with Phusion polymerase and cloned into the pJET 2.1 vector (Fermentas) by blunt end ligation. After sequence verification the DNA fragment was subcloned into pET28b(+) via the introduced NdeI/BamHI restriction sites. The resulting construct pGris3 was transformed into E. coli Rosetta BL21 (DE3) pLysS/RARE for protein expression. Fresh transformants harboring the constructs were grown in LB-medium (1 l batches started with 0.1% inocula from a 10-ml culture grown for 5 h at 37° C.) supplemented with kanamycin (50 µg/ml) and chloramphenicol (34 µg/ml). All cells were grown at 37° C. to an OD600 of approximately 0.8. The cells were then induced with 1 M isopropyl-b-D-thiogalactopyranoside (IPTG) to an end concentration of 0.2 mM and then grown at 16° C. overnight. The cells were harvested by centrifugation (6000 rpm, 10 min, 4° C.) and resuspended in buffer A (20 mM Tris-HCl, pH 7.8, 200 mM NaCl, and 10% [v/v] glycerol). The cells were then lysed (2 passes at 700 psi, French press, SLM Aminco), and the cell debris was removed by centrifugation (21,000 rpm, 10 min. 4° C.). Prepacked HisTrap™ HP columns were used for preparative purification of histidine-tagged recombinant proteins by immobilized metal ion affinity chromatography (IMAC) on the Äkta Prime™ plus system (Ge Healthcare). 15 ml protein lysates were filtered through a sterile filter and loaded onto a 1 ml HisTrap column. Purification was performed as recommended in the GE Healthcare manual (HisTrap HP, Instructions 71-5027-68 AF). The desired protein was eluted from the column in a stepwise imidazole gradient with buffer B (20 mM Tris-HCl, pH 7.8, 200 mM NaCl, and 10% [v/v] glycerol and 60, 100, 200, 300 and 500 mM imidazole, 10 ml fractions). Fractions containing the pure target protein, as determined by SDS-polyacrylamide gel electrophoresis (PAGE), were combined and concentrated to approximately 200 µl by using Amicon Ultra PL-10 centricons. Then 800 µl of storage buffer (50 mM Tris-HCl, pH 7.5, 50 mM NaCl, and 10% [v/v] glycerol) was added to the concentrated protein before flash-freezing in liquid nitrogen and storage at −80° C. Protein concentrations were determined using the Bradford assay (Bio-Rad, Hercules, Calif., USA). 1-3 mg/ml purified protein were obtained per liter of culture.

Figure 5:
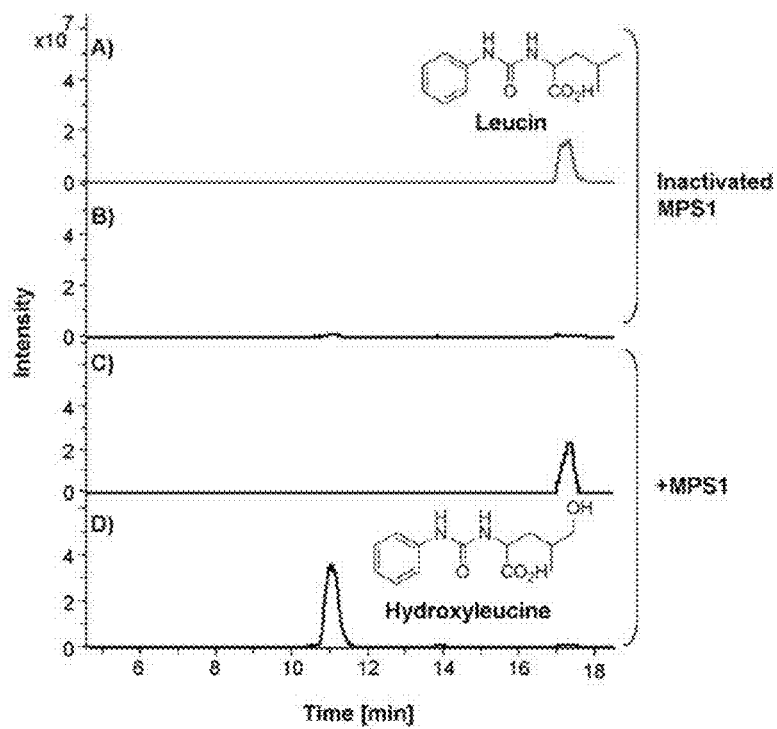
FIG. 5 shows the results of an HPLC-MS analysis of the Mps-1 or Leucine-hydroxylase assay. The diagram shows that in the enzyme assay performed with inactivated Mps-1 (chromatograms A) and B)) hydroxyleucine is not produced whereas in the assay performed with active Mps-1 (chromatograms C) and D)) hydroxyleucine is produced. A) and C): Extracted ion chromatograms for m/z=273.1 ([M+Na]$^+$ of PTC-leucine). B) and D): Extracted ion chromatograms for m/z=289.1 ([M+Na]$^+$ of PTC-hydroxyleucine).

Assays with leucine as substrate were conducted in MOPS (50 mM), pH7.0, and included substrate (1 mM), α-ketoglutarat (1 mM), FeSO$_4$ (25 µM), DTT (0.5 mM), ascorbate (0.1 mM) and Mps1 (1 µM) in a total volume of 200 µl. Reactions were initiated by the addition of Mps1 and incubated at 30° C. for 1 hour. Protein was precipitated with cold ethanol and the supernatant was decanted and used for derivatization. The solution was dried by rotary evaporation and resuspended in 200 µl coupling buffer (acetonitrile:pyridine:triethylamine:H$_2$O 10:5:2:3). 50 µl of PITC solution were added to this solution and after a 5 min reaction at room temperature 50 µl H$_2$O were added to stop the reaction. The solution was evaporated to dryness by speedvac evaporation. The resulting PTC amino acids were dissolved in 1 ml water:acetonitrile (7:2), centrifuged and the supernatant was dried by speed vac evaporation again. The amino acids were then dissolved in 100 µl water/acetonitrile and used for HPLC/MS analysis. PITC-leucine and PITC-hydroxyleucine were detected in the positive ionization mode (Leucine: [M+H]$^+$=272.9 and hydroxyleucine: [M+H]$^+$=288.9). It was shown that Msp-1 catalyses the reaction from leucine to 5-hydroxyleucine (FIG. 5).

(b) Mps-2 Assay

The conversion of 5-hydroxyleucine to γ-methylglutamic acid γ-semialdehyde can be performed by the Mps-2 or alcohol dehydrogenase assay according to Luesch et al., 2003 who performed the assay with the functionally similar protein NosE. Typical reaction mixtures with 5-hydoxyleucine or related compounds as substrate may contain 100 mM glycine (pH 10), 2 mM β-NAD, substrate (0.1-10 mM), 1 mM ZnSO$_4$, and approximately 3 µg of Mps-2. Typical reaction volumes may be 500 µl, reactions may be initiated by the addition of Mps-2 and incubated at 30-42° C. for 1-3 h.

(c) Mps-4 Assay

The conversion of 3-methyl-$\Delta^1$-pyrroline-5-carboxylic acid to 4-methylproline can be performed in the Mps-4 assay according to Luesch et al., 2003 who performed the assay with the functionally similar protein NosF. Typical reaction mixtures may contain 200 mM Tris (pH 8), substrate, 0.2 mM β-NADH or β-NADPH, and approximately 5 µg of Mps-4. Reaction volumes are usually 1 ml, reactions may be initiated by the addition of Mps-4 and incubated at 30-42° C. for 1-3 h. An alternative Mps-4 assay according to Becker et al., 1997 comprises 3-methyl-$\Delta^1$-pyrroline-5-carboxylic acid or related compounds as substrate and may be conducted in 50 mM Tris/HCl, pH 7.5, and include substrate (0.1-10 mM), 0.2 mM FAD, 0.5 mM NADH and an appropriate dilution of Mps-4 (e.g. 1 µg final concentration in a total volume of 100-500 µl. Reactions may be initiated by the addition of Mps-4 and incubated at 30° C. for 1-3 hours.

Example 4

In Vitro-Synthesis of Griselimycin and Methylgriselimycin

In vitro-synthesis of griselimycin and methylgriselimycin can be performed according to reaction conditions as disclosed in Gaitatzis N. et al., 2001. Incubations of 1 ml each may contain 25 mM Tris HCl (pH 8.0), 50 mM NaCl, 1 mM acetyl-CoA (or 1 mM acetyl-SNAC), 2 mM L-valine, 2 to 3 mM (2S,4R)-4-methylproline (or related compounds), 3 mM L-leucine, 1 mM L-proline (or no L-proline for the methylgriselimycin synthesis), 1 mM L-threonine, 4 mM S-adenosyl-L-methionine, 1 mM glycine, 10 mM ATP, 0.5-5 mM NRPS-1, NRPS-2, NRPS-3 and MtbH. The reactions may be incubated at 30° C. after starting the reaction with ATP for 2-72 hours.

Example 5

Inactivation of the Genes nrps-1 and nrps-3 and of the Mps Operon

Insertional mutants of Streptomyces DSM 22643 were created according to standard procedures. Fragments of about 3000 bp in length which are homologues to parts of the mps-operon, the nrps-1 and the nrps-3 gene, respectively, were amplified from chromosomal DNA of DSM 26643 by PCR using the primers listed in Table 4. These fragments were cloned in the *E. coli* cloning vector pBluescript SK+ giving the plasmids pMPS, pNRPS-1, pNRPS-3. Subsequently, an AprR-oriT cassette, created as described in Gust et al., 2003, was amplified with the primers listed in Table 5 and integrated into the plasmids pMPS, pNRPS-1 and pNRPS-3 with the RedET technology (Genebridges) to give conjugational plasmids. The created plasmids were then transferred into DSM 22643 and conjugants were analysed for correct genetic integration into the mps-operon, the nrps-1 and the nrps-3 gene, respectively, before being tested for (methyl) griselimycin production.

TABLE 4

Primer for amplification of homologous DNA-fragments

| Mutant | Primer | Sequence | SEQ ID NO |
|---|---|---|---|
| Nrps-1 | Nrps-1_for | GCTCTAGAGTCATGCAGATCAACTCG | 30 |
|  | Nrps-1_rev | GCTCTAGATGGTCACGGACCTGTG | 31 |
| Nrps-3 | Nrps-3_for | GCTCTAGAATGGAGGGCATCGGAAT | 32 |
|  | Nrps-3_rev | GCTCTAGAAGCTCTTCCGCCAGGAT | 33 |
| mps | Mps_for1 | CGGGGTACCCATCTGGTCCGTACCAT | 34 |
|  | Mps_rev1 | TCGCGTCGTTTACCTCA | 35 |
|  | Mps_for2 | GCCTTCACCGGAGCTCA | 36 |
|  | Mps_rev2 | GCTCTAGATCCTGAACTCTCGCATA | 37 |

Underlined: sequences for restriction sites

TABLE 5

Primer for insertion of AprR-oriT-cassette

| Mutant | Primer | Sequence | SEQ ID NO |
|---|---|---|---|
| Nrps-1 | Nrps-1_for2 | TGAGGTGTGTGCTGCGTCTGTTCCGGGGGCGACTGCGGTATTCCGGGGATCCGTCGACC | 38 |
|  | Nrps-1_rev2 | TGACACGTCGTTGGCGTGCACCGTCGTCTCCGTCGGCCCGTGTAGGCTGGAGCTGCTTC | 39 |
| Nrps-3 | Nrps-3_for2 | TCCGGATGCGACGGCAGTCGTCTTTGAGACACGAGCGTATTCCGGGGATCCGTCGACC | 40 |
|  | Nrps-3_rev2 | AGCATCACGTCGAACGATTGTCTGCGGTGTCCATGTCTTGTAGGCTGGAGCTGCTTC | 41 |
| mps | Mps_for3 | ATGAGCGTAGGTCTCCGTCTGTGGTAACCCTGGTGTGATTCCGGGGATCCGTCGACC | 42 |
|  | Mps_rev3 | TCAGGTATCACCGTGGGAAGGTGCCGGCTTTCCAGTACTGTAGGCTGGAGCTGCTTC | 43 |

Underlined: sequences homologous to the AprR-oriT cassette

To verify griselimycin production in the wild type and to test the insertional mutants for the ability of griselimycin synthesis, the different strains were cultured in medium NL5645 (composition (amount in percentage): lactose 2.0, soy meal 2.5, NaCl 0.5, $CaCO_3$ 0.1 and yeast extract 0.5, pH 6.8) in shaking flasks. At different time points the culture supernatant was collected, filtered and mixed 1:1 with ethanol. After precipitation and separation of unsolved substances the supernatant was analysed by UHPLC (Ultra High Performance Liquid Chromatography) for (methyl)griselimycin production.

Figure 6:
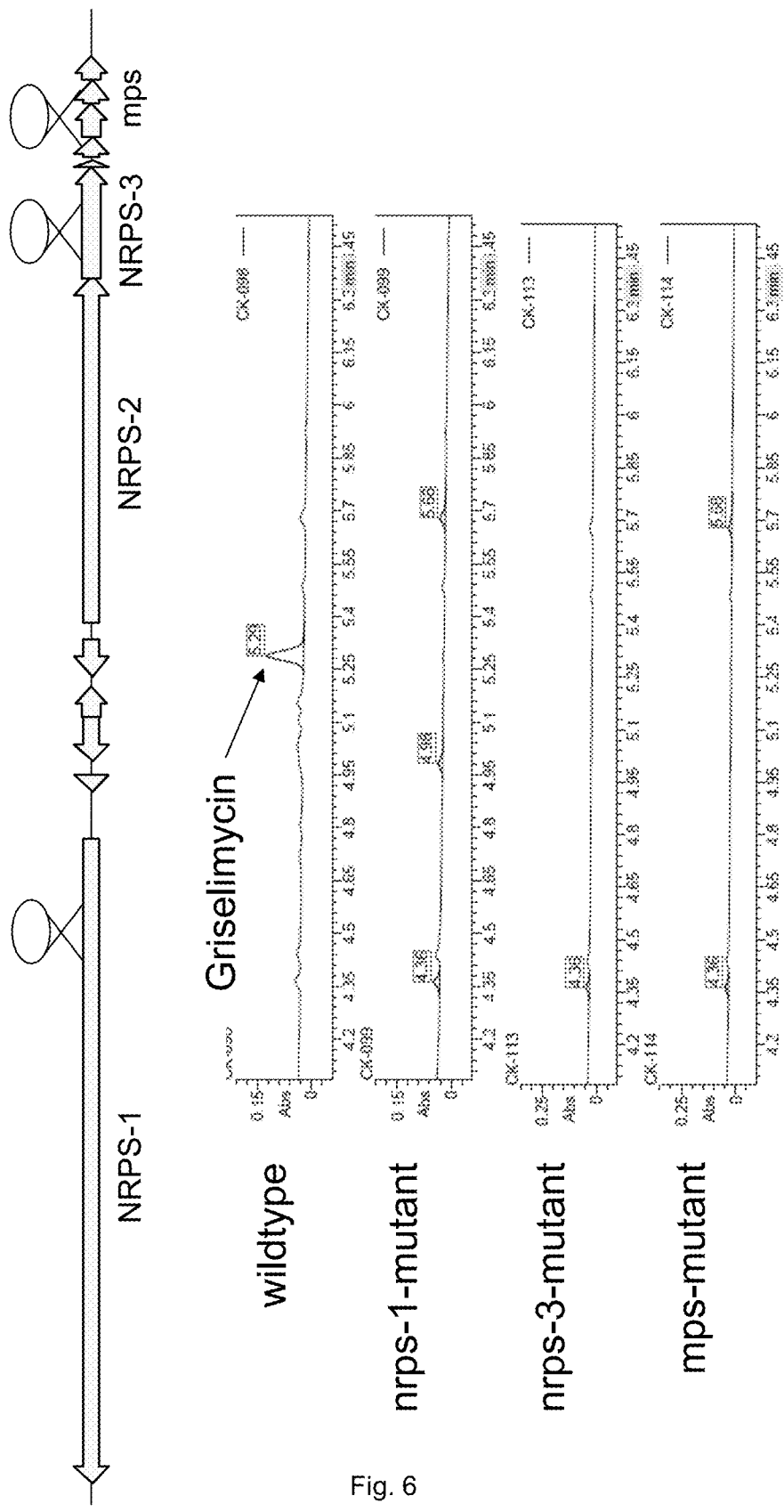
FIG. 6 shows results obtained with mutant nrps-1 and nrps-3 genes and a mutant mps operon. The nrps and mps genes are indicated by block arrows. The approximate location of the insertional mutations is indicated by the circle-cross symbol. Below the presentation of the nrps and mps genes are the relevant UHPLC chromatograms (UV 210 nm) of the supernatant from cultures of the wildtype, the nrps-1 mutant, the nrps-3 mutant and the mps-mutant. In the wildtype the peak at 5.29 min shows the presence of griselimycin. In contrast no griselimycin can be detected in the culture supernatants of the three mutants.

As can be taken from FIG. 6 the wildtype strain DSM 22643 produces griselimycin (see "griselimycin" marked peak at 5.29 min in the UHPLC chromatogram (UV210 nm)), whereas the nrps-1, the nrps-3 and the mps-mutants of DSM 22643 do not produce griselimycin (absence of the peark at 5.29 min) This experiment confirms the importance of the NRPS proteins and Mps proteins for the synthesis of griselimycin and methylgriselimycin.

Example 6

Complementation of Mps-Mutants

To demonstrate that the genes of the mps-operon are relevant for synthesis of (2S,4R)-4-methylproline the mps-mutant was complemented (1) by feeding (2S,4R)-4-methylproline and (2) by genetic complementation due to the chromosomal integration of an expression construct, where the mps operon is expressed from the constitutive ermE-promoter.

In the feeding experiment 20 μg/ml (2S,4R)-4-methylproline were fed to cultures of the mps-mutant and (methyl) griselimycin production was analysed in the culture supernatant as described in Example 5. Whereas in the normal culture medium without (2S,4R)-4-methylproline feeding the mps-mutant does not produce any (methyl)griselimycin), feeding of 20 μg leads to (methyl)griselimycin production (FIG. 7A; also example 9).

Figure 7:
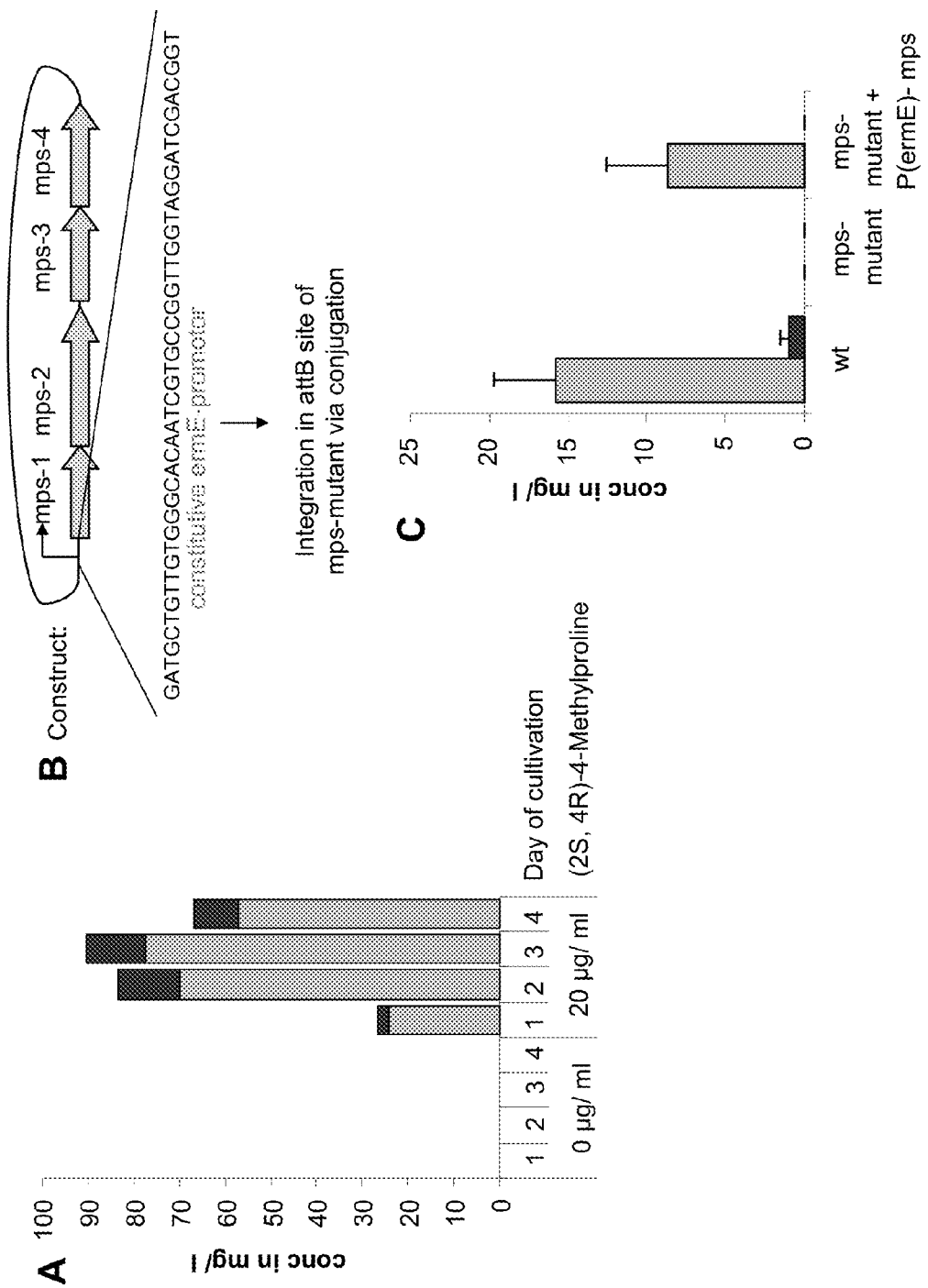
FIG. 7 shows complementation of the mps-mutant obtained in Example 5.

For the genetic complementation of the mps-mutant, a construct, P(ermE)-mps, comprising the mps operon with the genes mps-1, mps-2, mps-3 and mps-4 under the control of the constitutive ermE promoter was created in a conjugational vector with an attP attachment site for integrase mediated integration into the chromosomal attB site (see FIG. 7B for the sequence of the ermE-promoter). After integration of this P(ermE)-mps construct into the mps-mutant created in Example 5 the complemented mps-mutant was tested for griselimycin production. As shown in FIG. 7C griselimycin production could be restored in the complemented mps-mutant.

Both experiments clearly indicate that the mps operon is necessary for the synthesis of (2S,4R)-4-methylproline, that is then used for methylgriselimycin synthesis.

Example 7

Heterologous Production of Methylproline by Expression of the Mps1-4 Gene Set in *Escherichia coli* and *Streptomyces coelicolor*

To confirm that the gene set mps1-4 encodes the enzymatic machinery for 4-methylproline biosynthesis constructs for the expression in *E. coli* (pET28-mps) and *S. coelicolor* (pUWL201-mps) were generated.

(a) Generation of pUWL201-Mps and Heterologous Expression in *Streptomyces coelicolor*

A ~5.8 kb EcoRI fragment from Cosmid B:L23 harbouring the 3' end from the griselimycin biosynthetic gene cluster (54283-60163 nt from SEQ ID NO:1) was subcloned into the replicative *E. coli/Streptomyces* shuttle vector pUWL201 under control of the constitutive PermE* promotor. The resulting expression construct pUWL201-mps was subsequently transformed into the host strain *Streptomyces coelicolor* A3(2) using the protoplast method (Kieser et al., 2000). The transformants (*S. coelicolor*/pUWL201-mps) were cultivated in parallel to the wildtype strain in 50 ml TSB medium for 4 days at 30° C. in baffled shaking flasks (mutant cultures were supplemented with thiostreptone 20 μg/ml final concentration). Cells were harvested by centrifugation and extracted with 50 ml methanol (15 min sonication and 30 min stirring). After filtration the extract was evaporated to dryness and derivatized as described below.

(b) Generation of pET28-mps and Heterologous Expression in *Escherichia coli*

A ~3.7 kb XbaI/EcoRI fragment from the Cosmid B:L23-CmR was subcloned into the expression vector pET28b (Novagen) linearized with NheI/EcoRI under control of the inducible T7 promotor. The cloned 3.7 kb DNA fragment harbors the genes mps1-4 (56434-60163 nt from SEQ ID NO:1 extended with the sequence CTAGA at the 5' end). The resulting expression construct pET28-mps as well as the empty expression vector pET28b were subsequently transformed into the host strain *Escherichia* coli BL21 (DE3)/Codonplus/pL1SL2 by electroporation. The transformants (*E. coli* BL21 (DE3)/Codonplus/pL1SL2/pET28-mps or pET28b) were cultivated in 50 ml LB medium containing 0.2% glucose supplemented with kanamycin (50 μg/ml final concentration), ampicillin (50 μg/ml final concentration) and chloramphenicol (25 μg/ml final concentration) at 30° C. Cultures were grown until $OD_{600}$=0.6, expression was induced with IPTG (0.3 mM final concentration) and incubation was continued for additional 4 hours at 30° C. Cells were harvested by centrifugation and extracted with 50 ml methanol (15 min sonication and 20 min stirring). After filtration the extract was evaporated to dryness and derivatized as described below.

(c) Derivatization of the Extracts and HPLC-MS Analysis

The dried cell extracts as well as (2S,4R)-4-methylproline (as reference standard for retention time and fragmentation spectra) were resuspended in 200 μl coupling buffer (acetonitrile:pyridine:triethylamine:$H_2O$). 50 μl of PITC (phenyl-isothiocyanat) solution were added and after 5 min reaction at room temperature 50 μl $H_2O$ were added to stop the reaction. The solution was evaporated to dryness by speedvac evaporation. The resulting PITC amino acids were dissolved in 1 ml water:acetonitrile (7:2), centrifuged and the supernatant was dried by speedvac evaporation. The derivatized extracts and the derivatized (2S,4R)-4-methylproline reference were then dissolved in 100 μl water/acetonitrile for HPLC/MS analysis.

All measurements were performed on a Dionex Ultimate 3000 RSLC system using a Waters BEH C18, 50×2.1 mm, 1.7 μm dp column. Two μl of sample was injected unless otherwise stated. Separation was achieved by a linear gradient with (A) $H_2O$+0.1% FA to (B) ACN+0.1% FA at a flow rate of 600 μl/min and 45° C. The gradient was initiated by a 0.33 min isocratic step at 5% B followed by an increase to 95% B in 9 min to end up with a 1.6 min flush step at 95% B before re-equilibration with initial conditions. UV and MS detection were performed simultaneously. Coupling the HPLC to a MS was supported by an Advion Triversa Nanomate nano-ESI system attached to a Thermo Fisher Orbitrap. Mass spectra were acquired in centroid mode ranging from 100-500 m/z at a resolution of R=30000. Single reaction monitoring using collision induced dissociation was performed on 247.11, 249.12, 265.12, and 267.12 m/z. All parent ions were isolated within a 2 m/z window and fragmented at 35% CID energy.

The expected derivative of 4-methylproline could be detected in the derivatized extracts from the cultures harboring the mps expression constructs (pUWL201-mps and pET28-mps), but not in the derivatized extracts of the negative controls as shown in FIG. 8 exemplified with the heterologous expression in *S. coelicolor* (*S. coelicolor*/pUWL201-mps compared to *S. coelicolor* WT). By comparison of the retention times and high resolution mass data (including fragmentation data) with the derivatized PITC-(2S,4R)-4-methylproline reference substance, this compound could be clearly identified in the extracts of mps expression cultures.

This unambiguously proofs that the gene set mps1-4 encodes all necessary enzymatic activities required for the biosynthesis of the griselimycin precursor 4-methylproline. In addition, derivatives of two proposed intermediates of the pathway (5-hydroxyleucine and γ-methylglutamic acid γ-semialdehyde, see FIG. 8) could be detected providing further proof of the postulated enzymatic activities. The function of the putative leucine hydroxylase could be further verified by in vitro studies using the purified enzyme (as described above in Example 5). A derivative of the third postulated intermediate 3-methyl-$\Delta^1$-pyrroline-5-carboxylic acid could not be detected as this compound cannot be derivatized with the applied method.

The successful heterologous expression of the mps genes in two different host strains (*E. coli* and *S. coelicolor*) also shows that this strategy can be applied to generate 4-methylproline, e.g. for organic synthesis approaches towards griselimycin or to feed the precursor to griselimycin/methylgriselimycin production cultures to enhance the methylgriselimycin yield.

Example 8

In Silico Analysis of a Domain Specificity

An in silico analysis of the amino acid specificity of the A domains of the NRPS proteins was performed according to Challis et al., 2000. Briefly the A domain sequences were aligned with the sequence of the phenylalanine-activating A domain (PheA) of the gramicidin S synthetase GrsA. Based on this alignment, the eight amino acids lining the binding pocket were identified and compared with the specificity-conferring amino acids from A domains with known substrate specificity. In the following Table 6 the specificity of the A domains of NRPS-1, NRPS-2 and NRPS-3 for substrates as predicted in silico is presented. In comparison, the actual substrates as they are activated for introduction into (methyl) griselimycin are listed.

"Residue position" are the eight amino acids of the individual A domains, which are thought to be important for substrate recognition ('specificity-conferring amino acids' or 'specificity-conferring code'). These residues were compared with the 'specificity-conferring codes' of A domains with known substrate specificity (http://nrps.igs.umaryland.edu/nrps/blast.html).

TABLE 6

| A domain | Activated substrate(s)[a] | In silico substrate prediction[b] | Residue position[c] | | | | | | | |
|---|---|---|---|---|---|---|---|---|---|---|
| | | | 265 | 266 | 269 | 278 | 299 | 301 | 326 | 330 |
| NRPS-1-A1 | Valine | Threonine | D | F | F | C | V | G | I | V |
| NRPS-1-A2 | (4R)Me- | Proline | D | V | Q | F | A | G | H | A |

TABLE 6-continued

| A domain | Activated substrate(s)[a] | In silico substrate prediction[b] | Residue position[c] | | | | | | | |
|---|---|---|---|---|---|---|---|---|---|---|
| | | | 265 | 266 | 269 | 278 | 299 | 301 | 326 | 330 |
| | Proline | | | | | | | | | |
| NRPS-1-A3 | Threonine | Threonine | D | F | W | N | V | G | M | V |
| NRPS-1-A4 | Leucine | Phenylalanine/ Tryptophane | D | A | L | L | L | G | A | V |
| NRPS-1-A5 | (4R)Me-Proline | Proline | D | V | Q | F | A | G | H | A |
| NRPS-1-A6 | Leucine | Phenylalanine/ Tryptophane | D | A | L | L | L | G | A | V |
| NRPS-2-A7 | Valine | Threonine | D | F | F | C | V | G | I | V |
| NRPS-2-A8 | Proline/ (4R)Me-Pro | Proline | D | V | Q | F | A | A | H | V |
| NRPS-2-A9 | Leucine | Phenylalanine/ Tryptophane | D | A | L | L | L | G | A | V |
| NRPS-3-A10 | Glycine | Glycine | D | I | L | Q | L | G | V | I |
| NosA-A3[d] | (4S)Me-Pro | Proline | D | V | Q | F | I | A | H | L |
| NcpB-A3[e] | (4S)Me-Pro | Proline | D | V | Q | F | I | A | H | V |
| NosD-A2[f] | Pro | Proline | D | V | Q | F | I | A | H | V |

[a]According to griselimycin and methylgriselimycin primary structures
[b]According to the comparison of the specificity conferring code of other A domains (http://nrps.igs.umaryland.edu/nrps/blast.html)
[c]The residues correspond to the gramicidin S synthetase PheA numbering (Challis et al., 2000)
[d]Accession number: AF204805_1 (Hoffmann et al., 2003)
[e]Accession number: AAO26334 (Luesch et al., 2003)
[f]Accession number: AAF17281 (Hoffmann et al., 2003)

The results for the A3 domain, the A10 domain and partially the A8 domain are consistent with the amino acids which are actually incorporated into (methyl)griselimycin. The remaining results do not seem to be in alignment with the actually incorporated amino acids, which may be due to the method applied. Based on the eight amino acid residues of the synthetases which were believed to be essential for the specificity of the substrate amino acid to be incorporated into griselimycin, it is not possible to differ between proline and methylproline specific A domains.

Example 9

Phylogenetic Analysis of Methylproline and Proline Specific Domains

Phylogenetic analysis as presented in FIG. 9 of A domains which are specific for methylproline and proline demonstrate that A domains from methylproline incorporating NRPS modules (NRPS-1-A2 and NRPS-1-A5 and NcpB8(mPro) and NosA-A(mPro)) are more closely related to each other than to the A domains of proline incorporating domains (NRPS-2-A8 and NosD(mPro)). This suggests, that the specificity is not only determined by the eight amino acid residues as presented in Table 6.

The analysis was performed using the Geneious Tree Builder function from the Geneious Pro 5.4.3 software (Tree Alignment Options: Cost Matrix (Blosum 62), Gap open penalty (12), Gap extension penalty (3) and Alignment type (Global alignment); Tree Builder Options: Genetic distance model (Jukes-Cantor), Tree build method (Neighbor-Joining), Outgroup (No outgroup)). The scale bar represents 0.09 substitutions per amino acid site.

Example 10

Specificity of A Domains of Modules 2, 5 and 8

In order to gain insight into the specificity of the A domains of modules 2, 5 and 8, the domains were recombinantly produced and their specificity analysed via an ATP/PPi exchange assay in vitro. Results are shown in FIG. 10. As expected, specificity of the domains A2 and A5 is highest for (2S,4R)-4-methylproline. Interestingly, this is also the case for domain A8, although L-proline is preferably incorporated by module 8 during the biosynthesis of griselimycin. It is shown that there is also a high specificity for L-proline. It is assumed that the C domain of module 8 preferably condenses proline and introduces it into the growing peptide chain. Availability of methylproline during (methyl)griselimycin biosynthesis seems also to play a role as could be shown by feeding experiments. Feeding of 4-methylproline in concentrations from 0.025 to 1.0 g/l shows an increase of methylgriselimycin up to fivefold higher than the control. The experiments show also that the incorporation rate is not linear but reaches a saturation at about 0.5 g/l. Also the feeding with trans-hydroxyproline and trans-fluoroproline shows significant incorporation.

(a) Production of Recombinant A2, A5 and A8 Domains

In order to directly investigate A domain substrate specificity, we aimed to express A domains A2, A5 and A8 from the griselimycin pathway as N-terminally $His_6$-tagged proteins from pET28b (+). DNA fragments coding for the adenylation domains of A2, A5 and A8 were amplified from genomic DNA from the *Streptomyces* DSM 22643 using the oligos A2_for 5'-CCGACCATATGGATCCGGATGTGACG-GTGGG-3' (SEQ ID NO: 44) and A2_rev 5'-ACCGGGAAT-TCGCCGACGGCGGGCAGGCCGA-3' (SEQ ID NO: 45) (due to the high homology, all three A domains can be amplified by using the same primer pair), and cloned into pJET2.1 vector by blunt end ligation.

Sequencing revealed that all of the A domains were correct. According to the molecular structure of griselimycin and the in silico analysis A domains A2 and A5 were expected to incorporate 2S,4R-methylproline. A domain A8 was expected to show a broader substrate specificity and either incorporate L-proline or 2S, 4R-methylproline. To determine this in vitro we expressed the A domains in *E. coli* Rosetta pLys(RARE) at 16° C. overnight. All three A domains could be obtained in the soluble fractions.

The proteins were then purified with Ni$^+$-affinity chromatography using a stepwise imidazol gradient. Pure protein could be obtained in fraction 8 for all A domains. Although the amount of protein was very low (0.2 mg/ml), it could be used in the ATP-PP$_i$ exchange assay to determine substrate specificity.

Substrate specificity of the 3 purified adenylation domains was evaluated using the established ATP-PP$_i$ exchange assay (Mootz and Marahiel. 1997, Thomas et al., 2002). Briefly, each protein was incubated with a panel of different amino acids, including the anticipated substrate of each domain. As a control, each protein was incubated in the absence of added amino acid, to determine the radioactivity background reaction. Nine different substrates were tested (see FIG. 10).

(b) Determination of Substrate Specificity by ATP-[$^{32}$P]PP$_i$ Exchange Assay To determine substrate specificity, ATP-[$^{32}$P]PPi reactions (100 μl) containing Tris-HCl (pH 7.5, 75 mM), MgCl$_2$ (10 mM), dATP (5 mM), amino acid (5 mM), and protein (2 μg) were performed at 30° C. $^{32}$P-tetrasodium pyrophosphate was obtained from Perkin Elmer (NEN #NEX019). The reactions were started by the addition of [$^{32}$P]PPi (0.1 μCi final amount) for up to 30 min before quenching with charcoal suspensions (500 μl, 1.6% [w/v] activated charcoal, 0.1 M Na$_4$P$_2$O$_7$, and 0.35 M perchloric acid in H$_2$O). The charcoal was pelleted by centrifugation prior to being washed twice with the washing solution 0.1 M Na$_4$P$_2$O$_7$ and 0.35 M perchloric acid in H$_2$O), resuspended in H$_2$O (500 μl), and counted by liquid scintillation (Beckman LS6500).

Example 11

Transcriptional Regulators of the Xre-Type Encoded by Orf-1 and Orf-12 of the Griselimycin Biosynthetic Cluster To elucidate an involvement of two putative transcriptional regulators encoded by orf-1 and orf-12 in production of griselimycin inactivation mutants of the respective ORFs were generated. Subsequently, effects on production of griselimycin were determined by HPLC/MS analysis of extracts of the wild type strain ST105671 and the mutant strains ST105671-orf-1 and ST105671-orf-26, respectively. In order to determine whether effects on production observed in the inactivation mutants are due to direct regulation by the transcription regulators encoded by orf-1 and orf-12, the regulators were heterologously expressed and purified. The purified proteins were used in electrophoretic mobility shift assays (EMSA) to examine direct interaction to putative promoter regions of the griselimycin biosynthetic cluster.

(a) Inactivation of Orf-1 and Orf-12

The genes orf-1 and orf-12 were disrupted using derivatives of the pKC1132 plasmid integrating in orf-1 and orf-12 by homologous recombination. Two derivatives of pKC1132 (pKC1132-orf-1 and pKC1132-orf-26, respectively) were constructed carrying the central part of the coding region of either orf-1 or orf-12. Therefore, a 623 bp DNA fragment of orf-1 and a 1139 bp DNA fragment of orf-12 were amplified by PCR reactions using the primer combinations dxregrise_for/dxregrise_rev and dxreIIgrise_for/dxreIIgrise_rev, respectively (primer sequences see Table 8). EcoRI restriction sites were thereby attached to both ends of the fragments by the used primers. The DNA fragments and plasmid pKC1132 were digested using EcoRI and subsequently subjected to ligation. The ligations containing the desired plasmids pKC1132-orf-1 and pKC1132-orf-26, respectively, were transformed into electrocompetent *E. coli* DH10B cells. Transformants were selected on LB agar plates containing 60 μg/ml apramycin. Single colonies were grown in liquid LB medium in the presence of 60 μg/ml apramycin and plasmids were prepared. Plasmids carrying the correct inserts (pKC1132-orf-1 and pKC1132-orf-26) were identified by analytical digestion using EcoRI. *E. coli* ET12567 cells harboring the non-permissive plasmid pUZ8002 were then transformed using the correct plasmids pKC1132-orf-1 and pKC1132-orf-26. Transformants were selected on LB agar plates containing 60 μg/ml apramycin to yield strains *E. coli* ET12567pUZ8002pKC1132-orf-1 and *E. coli* ET12567pUZ8002pKC1132-orf-26. These strains were used to deliver the derivatives of plasmid pKC1132 into strain ST105671 by conjugation. The procedure was performed as follows. 2 ml of 2 day old liquid cultures of *Streptomyces* strain ST105671 grown in griselimycin production medium 5288 and in TSB medium at 30° C. and 2 ml of the respective *E. coli* strains harboring plasmids pKC1132-orf-1 or pKC1132-orf-26 (grown in LB containing 25 μg/ml kanamycin, 25 μg/ml chloramphenicol and 60 μg/ml apramycin) were pelleted, washed with sterile water and resuspended in 500 μl TSB each. 250 μl of *Streptomyces* strain ST105671 and the respective *E. coli* strain were mixed and incubated overnight under aeration at 30° C. 1 ml of TSB containing 60 μg/ml apramycin and 25 μg/ml nalidixic acid was added and further incubated overnight at 30° C. under aeration. After incubation cells were pelleted, washed once with TSB and plated out on MS-agar containing 60 μg/ml apramycin and 25 μg/ml nalidixic acid, followed by further incubation at 30° C. until conjugants became visible. Correct integration of the plasmids pKC1132-orf-1 or pKC1132-orf-26 in the coding regions of orf-1 or orf-12, respectively, was verified by performing PCR using genomic DNA of the conjugants and combinations of primers lacZ1, lacZ2 and grixreI_g1, grixreI_g2 in case of disruption of orf-1 or grixreII_g1, grixreII_g2 in case of disruption of orf-12, respectively. The inactivation mutants of ST105671-orf-1 and ST105671-orf-26 generated by this procedure were used to determine effects on griselimycin production compared to the ST105671 predecessor.

(b) HPLC/MS Analysis of Extracts of ST105671-orf-1 and ST105671-orf-26

Liquid cultures of four independent inactivation mutants of orf-1 and of two independent inactivation mutants of orf-12 were grown for two days in TSB liquid medium containing 60 μg/ml apramycin. Using these cultures, 100 ml of fresh TSB medium without antibiotic were inoculated 1:50 in duplicates each and grown for 3 days. Wild type ST105671 cells were treated equally without using apramycin in the preculture. Cells were pelleted by centrifugation and the supernatant was used for ethylacetate extraction. To monitor effects on griselimycin production the extracts were subsequently analyzed by HPLC/MS analysis. Quantities of griselimycin of each mutant and the wild type strain ST105671 relative to the total protein amount of each culture were determined. Therefore, the respective peak areas were integrated and the counts were set relative to the total protein amount of the pelleted cells. Mean values and standard deviations were calculated. Inactivation of orf-1 led to a more than 200 fold decrease in griselimycin production. No griselimycin could be detected in the inactivation mutant of orf-12 (see Table 7). The observations show an involvement of the Xre-type transcriptional regulators encoded by orf-1 and orf-12 in regulation of griselimycin production. Whether these effects are a result of direct regulation of promoters within the griselimycin biosynthetic cluster by binding of the Xre-type regulators or depict an indirect effect should be elucidated by performing DNA protein interaction studies (electrophoretic mobility shift assays, EMSA).

TABLE 7

Table 7: Effects on griselimycin production in mutants ST105671-orf-1 and ST105671-orf-26.

| strain | no. of replicates | mean (rel. intensity) | std dev |
|---|---|---|---|
| ST105671 | 4 | $7.38 * 10^9$ | $4.59 * 10^9$ |
| ST105671-orf-1 | 8 | $3.19 * 10^7$ | $1.41 * 10^7$ |
| ST105671-orf-26 | 8 | — | — |

Quantities of griselimycin of each mutant and the wild type strain ST105671 are shown as mean values of counts of extracts obtained relative to the whole protein content from independently grown replicate cultures.

(c) Verification of Specific Binding of the Transcription Regulators Orf-1 and Orf-12 to the Promoter Regions of nrps1 and nrps2

To examine a direct transcriptional regulation of griselimycin biosynthetic genes by regulators Orf-1 and Orf-12, possible binding to the putative promoter regions upstream of genes nrps1 and nrps2 was determined Therefore, the coding regions of orf-1 and orf-12 were first amplified in PCR reactions with primer combinations xreI-NdeI-for/xreI-HindIII-rev and xreII-NdeI-for/xreII-HindIII-rev using genomic DNA of strain ST105671 as a template. NdeI restriction sites were thereby attached to the 5' ends and HindIII restriction sites attached to the 3' ends of the resulting DNA fragments. Plasmid pET22b and the amplified DNA fragments carrying genes orf-1 and orf-12 were digested with NdeI and HindIII. Subsequently, NdeI/HindIII digested orf-1 and orf-12 were ligated with NdeI/HindIII digested pET22b in two separate attempts. Ligations were transformed into E. coli DH10B and transformants selected on LB agar plates containing 200 µg/ml ampicillin. Plasmids were prepared and correct integration of the inserts (orf-1 and orf-12, respectively) into the plasmids was verified by HindIII/NdeI digests. Plasmids carrying the inserts were finally subjected to DNA sequencing in order to exclude mutations in the DNA sequence. Due to the cloning strategy, the resulting plasmids pET22b-orf-1 and pET22b-orf-26 encoded for C-terminally 6 fold His tagged (6xHis) Orf-1 and Orf-12, respectively. Both plasmids were transformed into E. coli BL21(DE3) by electroporation and transformants were selected on LB agar plates containing 200 µg/ml ampicillin. Expression of the C-terminal 6xHis tag fusion proteins Orf-1-His and Orf-12-His was performed in LB liquid medium containing 200 µg/ml ampicillin in the presence of 0.1 mM IPTG at 16° C. overnight. Cells were lysed by sonication and purification of Orf-1-His (~33 kDa) and Orf-12-His (~47 kDa) was achieved by using $Ni^{2+}$ affinity columns. Putative promoter region of genes nrps1 (581 bp region upstream of nrps1) and nrps2 (632 bp region upstream of nrps2) were amplified in PCR reactions using primer combinations prom4hex2_rev/prom4hex3_for and prom5hex2_rev/prom5hex3_for, respectively, to yield DNA fragments carrying 18 bp linker regions on both ends. In a second PCR reaction these DNA fragments were labeled with a Hex fluorophor at the 5' end of each strand. At this, primers (Hex2 and Hex3) carrying a 5' Hex fluorophor and being reverse complementary to the 18 bp linker regions attached in the first PCR reactions were used. Hex labeled DNA fragments spanning the above mentioned upstream regions of genes nrps1 and nrps2 were thereby generated and referred to as Pnrps1 and Pnrps2. In a parallel attempt, a 696 bp intergenic region flanked by genes mxan_3950 and mxan_3951 of the annotated genome of *Myxococcus xanthus* DK1622 comprising a dual promoter system was amplified with primers EH33951_rev/EH33950_rev using genomic DNA of the respective strain. As the primers carried the same 18 bp linker regions like mentioned above, the DNA fragment could subsequently be labeled with the Hex fluorophor at both 5' ends like described before. As specific binding of regulators Orf-1-His and Orf-12-His to this promoter region out of the genome of *Myxococcus xanthus* DK1622 cannot be expected, the resulting DNA fragment referred to as Pmxan_ctrl served as a negative control in the EMSA assays.

These DNA fragments as well as both purified regulators (Orf-1-His and Orf-12-His) were subsequently used in EMSA assays. In brief, the assays were performed as follows. 4% native PAA-gels were prepared in 1× buffer HG (25 mM HEPES, 192 mM glycin, pH 7.3 with KOH). Pockets of the gel were rinsed and electrophoresis was performed for 30 min at 120 V without samples in 1× buffer HG. Samples (100 fMol of each DNA-fragment Pnrps1, Pnrps2 and Pmxan_ctrl with and without 500 fold molar excess of either Orf-1-His or Orf-12-His and 2.5 µg high molecular weight salmon sperm DNA as competitor DNA) were prepared and incubated for 10 min at 30° C. Samples were loaded on the gel and electrophoresis was performed for 2 h at 120 V. Detection of the DNA fragments was done using a Typhoon 9410 imager (Amersham) at the respective wavelength. In the presence of Orf-1-His, a retardation of each Hex labeled DNA fragment compared to the attempts without Orf-1-His could be observed in electrophoresis indicating a non specific binding of regulator Orf-1-His to DNA comprising a promoter region (FIG. 11). On the other hand, Orf-12-His exhibited no ability to interact with any of the DNA fragments demonstrating no specificity towards the Hex labeled DNA used in the assays. Taken together these results suggested that neither Orf-1-His nor Orf-12-His are direct transcriptional regulators of the promoters Pnrps1 and Pnrps2.

Xre-type regulators Orf-1 and Orf-12 show remarkable aspects regarding their predicted domain organization which was determined using the SMART tool at http://smart.embl-heidelberg.de/ (FIG. 12). As expected, both regulators possess an N-terminal Xre-type helix-turn-helix (HTH) motif whereby Orf-1 obviously contains a second domain of this kind (HTH2). In addition to this, both regulators are characterized by an extended C-terminus with unknown function.

As it was possible, that these extraordinary features are part of regulatory mechanisms which influence affinity and thereby specificity towards distinct DNA sequences of regulators Orf-1 and Orf-12 the EMSA assays were repeated using C-terminally shortened versions of the regulators. In case of Orf-1, these versions only comprised HTH1, HTH2 or both predicted HTH domains. The respective proteins were named ORF1-HTH1 (~9.6 kDa), ORF1-HTH2 (~9.8 kDa) and ORF1-HTH12 (16.4 kDa). In case of Orf-12, the shortened version only contained the N-terminal HTH domain named ORF26-HTH (~9.9 kDa). Regulatory effects (e.g. binding of unknown cofactors or protein-protein interactions) resulting in conformational changes of the C-terminus or the whole protein and thereby influencing DNA binding affinity of the regulators should be excluded.

The shortened versions of Orf-1 and Orf-12 were obtained by cloning of the respective 5' regions of orf-1 and orf-12 as NdeI/HindIII fragments into NdeI/HindIII digested pET22b to yield the encoded C-terminal 6xHis tagged fusion proteins. Cloning was performed as described in case of the full length Orf-1 and Orf-12. Primer pairs used for amplification of the inserts to be cloned were xreI-NdeI-for/xreIhth1rev (Orf-1-HTH1), xreI-hth2for/xreIhth12rev (Orf-1-HTH2), xreI-NdeI-for/xreIhth12rev (Orf-1-HTH12) and xreII-NdeI-for/ xreIIhthrev (Orf-12-HTH). Heterologous expression, purification and subsequent verification of binding to the above mentioned promoter regions of genes nrps1 and nrps2 was performed as described for the full length proteins. The EMSA assays performed using these shortened versions of the regulators revealed a specific binding of ORF1-HTH12 to promoter Pnrps1 and of Orf-12-HTH to both promoter regions Pnrps1 and Pnrps2 (FIG. 13).

Only by co-incubation of Orf-1-HTH12 and Pnrps1 a significant retardation in electrophoresis of the DNA could be achieved. This retardation could not be observed using the negative control Pmxan_ctrl. Co-incubation with Pnrps2 gave a less clear result whereby no distinct statement can be made about direct binding of Orf-1-HTH12 to promoter region Pnrps2. Orf-12-HTH co-incubated with Pnrps1 or Pnrps2 resulted in clear distinct retardations of the DNA fragments whereas in case of the negative control Pmxan_ctrl a shift was completely absent.

Based on theses experimental results, roles of the C-termini of both regulators remain to be elucidated but seem to be related to modification of DNA binding specificity of Orf-1 and Orf-12.

Nevertheless, based on the effects observed after inactivation of orf-1 or orf-12 on production of griselimycin, the direct specific binding of Orf-1-HTH12 to promoter Pnrps1 and of Orf-12-HTH to promoters Pnrps1 and Pnrps2, the Xre-type transcriptional regulators encoded by orf-1 and orf-12 are clearly functionally related to griselimycin biosynthesis and can be considered as a part of the secondary metabolite cluster.

TABLE 8

Table 8: List of primers used in the experiments. Name and DNA sequence in 5' to 3' orientation of oligonucleotides are shown.

| primer name | sequence 5' -> 3' | SEQ ID NO |
| --- | --- | --- |
| dxregrise_for | cgGAATTCTGAGAAGCTGCCTGCAC | 46 |
| dxregrise_rev | cgGAATTCCTCATAGACCTGAGCGGC | 47 |
| dxreIIgrise_for | cgGAATTCCGTAGGACACGGAAACTGTC | 48 |
| dxreIIgrise_rev | cgGAATTCGCATCCATCCTGAGCAG | 49 |
| EH33950_rev | GGAATGGGCCGGGTACTGCAGCCTGCTATTTCTCAGAATC | 50 |
| EH33951_rev | GGAATGGGCCGGGTACTGAGAGCACGGGGTGTG | 51 |
| grixreI_g1 | ATCGCCTTCGGCGACAG | 52 |
| grixreI_g2 | GCTGGGCGTATCCGACTC | 53 |
| grixreII_g1 | GAAGGGACAGGTCCACCG | 54 |
| grixreII_g2 | GGTGTCCTGCACGGACAG | 55 |
| hex2 | GCTCTCGGTGCCCTTGTG | 56 |
| hex3 | GGAATGGGCCGGGTACTG | 57 |
| lacZ1 | CTTGGGCTGCAGGTCGAC | 58 |
| lacZ2 | GTGTGGAATTGTGAGCGG | 59 |
| prom4hex2_rev | GCTCTCGGTGCCCTTGTGTTCACTATCCCCATGTTGTTTCC | 60 |
| prom4hex3_for | GGAATGGGCCGGGTACTGCTGCTGACTGAACCAGATCTCAC | 61 |
| prom5hex2_rev | GCTCTCGGTGCCCTTGTGGATCGAACACGGCTCAGCTC | 62 |
| prom5hex3_for | GGAATGGGCCGGGTACTGGCAGCACTTCATGGTCGC | 63 |
| xreI-HindIII-rev | cgtAAGCTTCTCGTTCGCGCCCGTTTC | 64 |
| xreIhth12rev | cgtAAGCTTGGCGATCGACCGGTCTTC | 65 |
| xreIhth1rev | cgtAAGCTTATCAGTCAGATCGGGCGG | 66 |
| xreIhth2for | gtaaggCATATGGATCTGTTCCCGCGGTCC | 67 |
| xreII-HindIII-rev | cgtAAGCTTGGTTGTGCTAATGCCCGTCC | 68 |
| xreIIhthrev | cgtAAGCTTCTCCGCTTCCGGCTCAC | 69 |
| xreII-NdeI-for | gtaaggCATATGAGTGAAAACCTGACGCTGGGAG | 70 |
| xreI-NdeI-for | gtaaggCATATGTCTGCTCGTCACTTCGACCG | 71 |

Letters with simple underlining: Restriction sites attached to the primers.
Letters with double underlining: 5' linker regions attached to the respective sequence.
Small letters: Nucleotides attached to enhance restriction efficiency.

Example 12

*Streptomyces* DSM 22643

*Streptomyces* DSM 22643 was deposited at 6 Apr. 2009 according to the Budapest Treaty on the International Recognition of the Deposit of Microorganisms for the Purposes of Patent Procedure with the Deutsche Sammlung von Mikroorganismen and Zellkulturen GmbH (DSMZ), Inhoffenstraße 7B, 38124 Braunschweig, Germany on Jun. 4, 2009 by Sanofi-Aventis Deutschland GmbH, Industriepark Hochst, 65926 Frankfurt/Main, Germany.

References
Altschul S. F. et al., Nucleic Acids Res., 1997, 25, 3389-3402
Barry S. M. and Challis G. L., Curr. Opin. Chem. Biol., 2009, 13, 205-215
Becker D. et al., Eur. J. Biochem. 1997, 249, 739-747
Bibb, M. J. et al., Gene 1985, 38, 215-266
Bibb, M. J. et al., Molecular Microbiology 1994, 14, 533-545
Bierman M. et al., Gene 1992, 116, 43-49
Challis G. L. et al., Chem. Biol. 2000, 7, 211-264
Eriko T. et al., Gene, 1995, 66, 133-137
Ferna'ndez-Moreno M. A. et al., Cell, 1991, 66, 769-780
Finking R. and Marahiel M. A., Annu. Rev. Microbiol., 2004; 58, 453-488
Gaitatzis N. et al., Proc. Natl. Acad. Sci. USA, 2001, 98, 11136-11141
Gust B et al., Proc. Natl. Acad. Sci. USA, 2003, 100, 1541-1546
Hahn M. and Stachelhaus T.; Proc. Natl. Acad. Sci. USA, 2004, 101, 15585-15590; Epub 2004 Oct. 21
Herai S. et al., Proc. Natl. Acad. Sci. USA 2004, 101, 14031-14035

Hoffmann D. et al., Gene, 2003, 311, 171-180
Kieser et al., *Practical Streptomyces Genetics*, The John Innes Foundation, Norwich 2000
Li W. et al., Appl. Environ. Microbiol., 2009, 75, 2869-2878
Luesch H. et al., J. Org. Chem., 2003, 68, 83-91
Marahiel M. A., J. Pept. Sci., 2009, 15, 799-807
Mervyn J. et al., Molecular Microbiology, 1994, 14(3), 533-545
Mootz H. D. and Marahiel M. A., J. Bacteriol., 1997, 179, 6843-6850
Müller C. et al., Antimicrob. Agents Chemother., 2007, 51, 1028-1037
Murakami, T. et al., J. Bacteriol., 1989, 171, 1459-1466
Peschke U. et al., Mol. Microbiol., 1995, 16, 1137-1156
Sambrook et al., Molecular cloning: A laboratory manual. Cold Spring Harbor, N.Y.: Cold Spring Harbor Laboratory Press, 2001
Takano, E. et al., Gene, 1995, 166, 133-137
Terlain B. and Thomas J.-P., Bulletin de la Sociétié Chemique de France, 1971, 6, 2657-2662
Thomas M. G. et al., Chem. Biol. 2002, 9, 171-184.
Wehmeier U. F:, Gene, 1995, 165, 149-150
Yin X. et al., Chem. Biol. Chem. 2004, 5, 1274

The invention claimed is:

1. A method of producing griselimycin and/or methylgriselimycin comprising
   a) providing at least one protein comprising an amino acid sequence selected from SEQ ID NOs:9, 16, 17, 19, 20, 21 and 22,
      or a functionally active fragment thereof that directs synthesis of griselimycin and/or methylgriselimycin,
      or a functionally active variant thereof having more than 80% identity to the amino acid sequence selected from SEQ ID NO: 9, 16, 17, 19, 20, 21 and 22 that directs synthesis of griselimycin and/or methylgriselimycin and
   b) incubating the at least one protein or functionally active variant or fragment thereof with L-N-methylvaline, L-leucine, L-N-methylthreonine, L-proline, L-trans-4-methylproline, L-N-methylleucine and glycine to produce griselimycin and/or methylgriselimycin.

2. The method of claim 1, wherein the method comprises providing the proteins comprising amino acid sequences SEQ ID NOs: 9, 16 and 17.

3. The method of claim 1, wherein the at least one protein comprises SEQ ID NO: 9.

4. The method of claim 1, wherein the at least one protein comprises SEQ ID NO: 16.

5. The method of claim 1, wherein the at least one protein comprises SEQ ID NO: 17.

6. The method of claim 1, wherein the method comprises providing the proteins comprising amino acid sequences SEQ ID NOs: 19, 20, 21, and 22.

7. The method of claim 1, wherein the method comprises providing the proteins comprising amino acid sequences SEQ ID NOs: 19, 20, and 22.

8. The method of claim 1, wherein the at least one protein comprises SEQ ID NO: 19.

9. The method of claim 1, wherein the at least one protein comprises SEQ ID NO: 20.

10. The method of claim 1, wherein the at least one protein comprises SEQ ID NO: 21.

11. The method of claim 1, wherein the at least one protein comprises SEQ ID NO: 22.

12. The method of claim 1, wherein the method is performed in a host cell.

13. The method of claim 1, wherein the functionally active variant thereof comprises any combination of a deletion, insertion, substitution and/or addition of an amino acid.

14. The method of claim 13, wherein the substitution is a semi-conservative substitution or a conservative substitution.

15. The method of claim 1, wherein step b) comprises incubating the at least one protein or functionally active variant or fragment thereof with L-proline to produce griselimycin.

16. The method of claim 1, wherein step b) comprises incubating the at least one protein or functionally active variant or fragment thereof with L-trans-4-methylproline to produce methylgriselimycin.

17. A method of producing griselimycin and/or methylgriselimycin comprising
   a) providing at least one protein comprising an amino acid sequence SEQ ID NO:16, or a functionally active fragment thereof that directs synthesis of griselimycin and/or methylgriselimycin,
      or a functionally active variant thereof having more than 80% identity to the amino acid sequence of SEQ ID NO:16 that directs synthesis of griselimycin and/or methylgriselimycin and b) incubating the at least one protein or functionally active variant or fragment thereof with L-N-methylvaline, L-leucine, L-N-methylthreonine, L-proline, L-trans-4-methylproline, L-N-methylleucine and glycine to produce griselimycin and/or methylgriselimycin.

18. The method of claim 17, wherein the functionally active variant thereof comprises any combination of a deletion, insertion, substitution and/or addition of an amino acid.

19. The method of claim 18, wherein the substitution is a semi-conservative substitution or a conservative substitution.

20. The method of claim 17, wherein step b) comprises incubating the at least one protein or functionally active variant or fragment thereof with L-proline to produce griselimycin.

21. The method of claim 17, wherein step b) comprises incubating the at least one protein or functionally active variant or fragment thereof with L-trans-4-methylproline to produce methylgriselimycin.

22. A method of producing griselimycin and/or methylgriselimycin comprising
   a) providing at least one protein comprising an amino acid sequence SEQ ID NO:16,
      or a functionally active fragment thereof that directs synthesis of griselimycin and/or methylgriselimycin, or a functionally active variant thereof having more than 80% identity to the amino acid sequence of SEQ ID NO:16 that directs synthesis of griselimycin and/or methylgriselimycin and
   b) incubating the at least one protein or functionally active variant or fragment thereof with one or both of L-proline and L-trans-4-methylproline to produce griselimycin and/or methylgriselimycin.

23. The method of claim 22, wherein the functionally active variant thereof comprises any combination of a deletion, insertion, substitution and/or addition of an amino acid.

24. The method of claim 23, wherein the substitution is a semi-conservative substitution or a conservative substitution.

25. The method of claim 22, wherein step b) comprises incubating the at least one protein or functionally active variant or fragment thereof with L-proline to produce griselimycin.

26. The method of claim 22, wherein step b) comprises incubating the at least one protein or functionally active variant or fragment thereof with L-trans-4-methylproline to produce methylgriselimycin.

* * * * *